United States Patent
Shiraishi et al.

(10) Patent No.: US 6,350,749 B1
(45) Date of Patent: Feb. 26, 2002

(54) AMINOGUANIDINE HYDRAZONE DERIVATIVES, PROCESS FOR PRODUCING THE SAME AND DRUGS THEREOF

(75) Inventors: Mitsuru Shiraishi, Amagasaki; Shoji Fukumoto, Kobe; Keiji Kusumoto, Osaka, all of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/601,866

(22) PCT Filed: Feb. 18, 1999

(86) PCT No.: PCT/JP99/00703

§ 371 Date: Aug. 8, 2000

§ 102(e) Date: Aug. 8, 2000

(87) PCT Pub. No.: WO99/42442

PCT Pub. Date: Aug. 26, 1999

(30) Foreign Application Priority Data

Feb. 20, 1998 (JP) .......................... 10-038720
Oct. 20, 1998 (JP) .......................... 10-298383

(51) Int. Cl.[7] .................... C07D 209/08; C07D 215/38; C07D 231/56; A61K 31/343; A61K 31/403
(52) U.S. Cl. ................. 514/248; 546/171; 546/167; 548/503; 548/360.1; 548/241; 594/462; 594/468; 594/57; 544/235; 514/311; 514/314; 514/415; 514/405; 514/379; 514/469; 514/443
(58) Field of Search ............... 546/171, 167; 514/311, 314, 415, 405, 379, 469, 443, 248; 548/503, 360.1, 241; 549/462, 468, 57; 544/235

(56) References Cited

U.S. PATENT DOCUMENTS 5,395,855 A 3/1995 Stanek .................. 514/632
5,591,754 A 1/1997 Lang .................... 514/331
6,093,729 A 7/2000 Schwark et al. ........... 514/307

FOREIGN PATENT DOCUMENTS

| EP | 0825187 A | 2/1998 |
| JP | 60-239454 | 11/1985 |
| JP | 10-114744 | 5/1998 |

*Primary Examiner*—Richard L. Raymond
*Assistant Examiner*—Hoang Liu
(74) *Attorney, Agent, or Firm*—Mark Chao; Elaine M. Ramesh

(57) ABSTRACT

The present invention is to provide a compound of the formula:

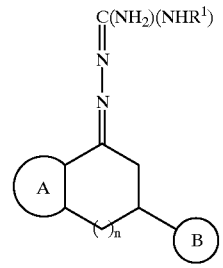

wherein the ring A is an optionally substituted 5- to 6-membered aromatic heterocyclic ring, the ring B an optionally substituted 5- to 6-membered aromatic homocyclic ring or an optionally substituted 5- to 6-membered aromatic heterocyclic ring, $R^1$ is a hydrogen atom, a hydroxy group or a lower alkyl group, and n is 0 or 1, or a salt thereof, which is effective for the prevention or treatment of ischemic cardiac disease, etc., and which is useful as an agent for preventing or treating ischemic cardiac disease, etc. such as myocardial infarction, arrhythmia, etc.

23 Claims, No Drawings

AMINOGUANIDINE HYDRAZONE DERIVATIVES, PROCESS FOR PRODUCING THE SAME AND DRUGS THEREOF

This application is the National Stage of International Application No. PCT/JP99/00703, filed Feb. 18, 1999.

TECHNICAL FIELD

The present invention relates to aminoguanidinehydrazone derivatives which are useful as a medicine, their production and use.

Sodium-proton (Na—H) exchange inhibitor comprising the aminoguanidinehydrazone derivative of the present invention is effective for the prevention and treatment of myocardial infarction and insufficiency accompanying therewith, arrhythmia, unstable angina, cardiac hypertrophy, restenosis after PTCA (percutaneous transluminal coronary angioplasty), hypertension and tissue injury accompanying therewith, etc.

BACKGROUND ART

On the other hand, Na—H exchange inhibitors, assumed to exhibit ameliorating and cell-protecting action in cell disorders under ischemic conditions, especially on the myocardium, are drawing attention in the field of therapeutic drugs for ischemic diseases.

Amiloride, an acylguanidine derivative and potassium-retaining diuretic, possesses weak activities for inhibiting Na—H exchange and potent activities for inhibiting sodium channel opening.

As Na—H exchange inhibitors, various kinds of acylguanidine derivatives are disclosed in Japanese Patent Unexamined Publication No. 228082/1994, WO 96/04241, EP 708091 and EP 708088, etc.

On the other hand, in EP456133, it is disclosed that a compound of the formula:

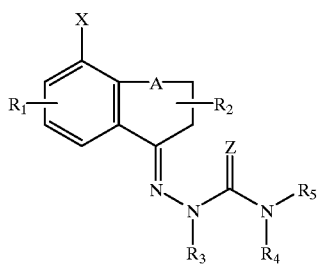

wherein A is a chemical bond or —CH$_2$—, X is a group of the formula: —C(=Y)—NR$_6$R$_7$, Y and Z are NH, R$_1$ is hydrogen, lower alkyl, hydroxy group, lower alkoxy or halogen atom, R$_2$ is hydrogen or lower alkyl, R$_3$, R$_4$ and R$_6$ are hydrogen, and R$_5$ and R$_7$ are independently hydrogen, lower alkyl or hydroxy group; is useful as anti-cancer agent or agent for treating protozoiasis.

In addition, in Japanese Patent Publication No. 239454/1985, it is disclosed that a compound of the formula:

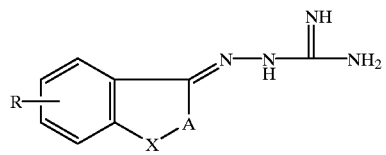

wherein R is hydrogen, halogen atom, etc., A is a chemical bond, CR$^4$R$^5$, CR$^6$R$^7$—CR$^8$R$^9$, CR$^{10}$R$^{11}$—CR$^{12}$R$^{13}$—CR$^{14}$R$^{15}$, etc., X is CR$^1$R$^2$, O, S(O)n (n=0,1,2), NR$^3$, etc., and R$^1$ to R$^{15}$ are independently hydrogen, an optionally substituted aromatic or hetero-aromatic group, etc.; shows digitalis agonistic or antagonistic activity.

Amiloride causes hypotension and salt excretion, which activities are undesirable for the treatment of heart rate disorder, by its potent activities for inhibiting sodium channel opening.

DISCLOSURE OF INVENTION

The present invention is to provide a Na—H exchange inhibitor which is effective for the prevention and treatment of myocardial infarction and insufficiency accompanying therewith, arrhythmia, unstable angina, cardiac hypertrophy, restenosis after PTCA, hypertension and tissue injury accompanying therewith, etc.

The present inventors studied various compounds having activities for inhibiting Na—H exchange, and as a result, for the first time synthesized a novel compound of the formula (I):

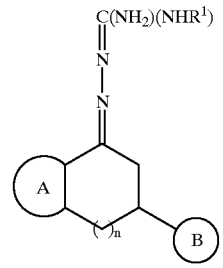

wherein the ring A is an optionally substituted 5- to 6-membered aromatic heterocyclic ring, the ring B an optionally substituted 5- to 6-membered aromatic homocyclic ring or an optionally substituted 5- to 6-membered aromatic heterocyclic ring, R$^1$ is a hydrogen atom, a hydroxy group or a lower alkyl group, and n is 0 or 1, or a salt thereof [hereinafter referred to as Compound (I)], and found that said Compound (I) unexpectedly exhibits excellent activities for inhibiting Na—H exchange. The present inventors accomplished the present invention based on this finding.

Accordingly, the present invention relates to (1) Compound (I);
(2) a pro-drug of Compound (I);
(3) a compound of the formula:

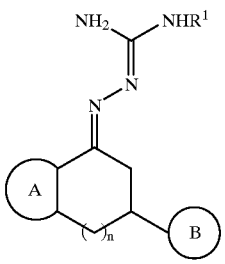

wherein each symbol is as defined in the above (1) or a salt thereof;

(4) a compound of the formula:

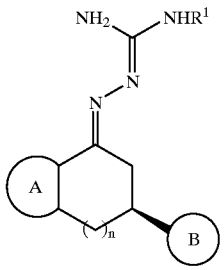

wherein each symbol is as defined in the above (1) or a salt thereof;

(5) Compound (I) as described in the above (1), wherein the aromatic heterocyclic ring is an aromatic heterocyclic ring containing 1 to 3 hetero-atoms selected from the class consisting of oxygen atom, sulfur atom and nitrogen atom;

(6) Compound (I) as described in the above (1), wherein the ring A is pyridine ring, pyridazine ring, pyrrole ring, pyrazole ring, furan ring, thiophene ring, isoxazole ring or pyrimidine ring, each of which may be substituted;

(7) Compound (I) as described in the above (1), wherein the ring B is pyridine ring, pyrrole ring, furan ring, thiophene ring or benzene ring, each of which may be substituted;

(8) Compound (I) as described in the above (1), wherein $R^1$ is a hydrogen atom;

(9) Compound (I) as described in the above (1), wherein n is 1;

(10) (S)-(−)-7-(2,5-dichlorothiophen-3-yl)-5-guanidinoimino-4-methyl-5,6,7,8-tetrahydroquinoline or a salt thereof;

(11) (±)-7-(2,5-dichlorothiophen-3-yl)-5-guanidinoimino-4-methyl-5,6,7,8-tetrahydroquinoline or a salt thereof;

(12) (S)-(−)-7-(2-chlorophenyl)-5-guanidinoimino-4-methyl-5,6,7,8-tetrahydroquinoline or a salt thereof;

(13) (±)-7-(2-chlorophenyl)-5-guanidinoimino-4-methyl-5,6,7,8-tetrahydroquinoline or a salt thereof;

(14) (±)-7-(2,5-dichlorophenyl)-5-guanidinoimino-4-methyl-5,6,7,8-tetrahydrocinnoline or a salt thereof;

(15) (±)-7-(5-chloro-2-methylphenyl)-5-guanidinoimino-4-methyl-5,6,7,8-tetrahydroquinoline or a salt thereof;

(16) (±)-7-(5-fluoro-2-methylphenyl)-5-guanidinoimino-4-methyl-5,6,7,8-tetrahydroquinoline or a salt thereof;

(17) (±)-7-(2-chloro-5-fluorophenyl)-5-guanidinoimino-4-methyl-5,6,7,8-tetrahydroquinoline or a salt thereof;

(18) (±)-7-(5-chloro-2-fluorophenyl)-5-guanidinoimino-4-methyl-5,6,7,8-tetrahydroquinoline or a salt thereof;

(19) (±)-7-(5-fluoro-2-methylphenyl)-5-guanidinoimino-4-methyl-5,6,7,8-tetrahydrocinnoline or a salt thereof;

(20) (±)-7-(5-chloro-2-fluorophenyl)-5-guanidinoimino-4-methyl-5,6,7,8-tetrahydrocinnoline or a salt thereof;

(21) a pharmaceutical composition comprising Compound (I) as described in the above (1) or a salt thereof;

(22) a composition of the above (21), which is for Na—H exchange inhibitor;

(23) a composition of the above (21), which is for the prevention or treatment of ischemic cardiac disease;

(24) a composition of the above (23), wherein the ischemic cardiac disease is myocardial infarction, unstable angina or arrhythmia;

(25) a composition of the above (21), which is for the prevention or treatment of cardiac insufficiency;

(26) use of Compound (I) as described in the above (1) or a salt thereof for manufacturing Na—H exchange inhibitor;

(27) use of Compound (I) as described in the above (1) or a salt thereof for manufacturing a pharmaceutical composition for the prevention or treatment of ischemic cardiac disease;

(28) use of Compound (I) as described in the above (1) or a salt thereof for manufacturing a pharmaceutical composition for the prevention or treatment of cardiac insufficiency;

(29) a method for inhibiting Na—H exchange in a mammal which comprises administering to said mammal an effective amount of Compound (I) as described in the above (1) or a salt thereof;

(30) a method for preventing or treating ischemic cardiac disease in a mammal which comprises administering to said mammal an effective amount of Compound (I) as described in the above (1) or a salt thereof;

(31) a method for preventing or treating cardiac insufficiency in a mammal which comprises administering to said mammal an effective amount of Compound (I) as described in the above (1) or a salt thereof; and

(32) a method for producing a compound of the formula (I):

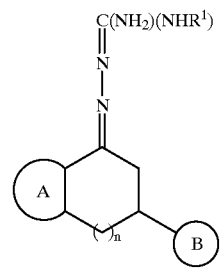

wherein each symbol is as defined below, or a salt thereof, which comprises reacting a compound of the formula (II):

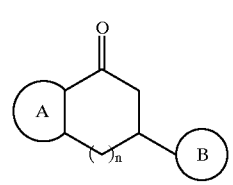

(II)

wherein the ring A is an optionally substituted 5- to 6-membered aromatic heterocyclic ring, the ring B an optionally substituted 5- to 6-membered aromatic homocyclic ring or an optionally substituted 5- to 6-membered aromatic heterocyclic ring, and n is 0 or 1, or a salt thereof with a compound of the formula (III):

wherein $R^1$ is a hydrogen atom, a hydroxy group or a lower alkyl group, or a salt thereof; etc.

In the above formula (I), the ring A is an optionally substituted 5- to 6-membered aromatic heterocyclic ring.

Examples of the aromatic heterocyclic ring in the "optionally substituted 5- to 6-membered aromatic heterocyclic ring" represented by A include, for example, an aromatic heterocyclic ring containing at least one hetero-atom (preferably 1 to 3 hetero-atoms, more preferably 1 to 2 hetero-atoms) consisting of 1 to 3 kinds (preferably 1 to 2 kinds) of hetero-atoms selected from an oxygen atom, a sulfur atom, a nitrogen atom, etc., as an atom constituting ring structure (ring atom).

Examples of said "aromatic heterocyclic ring" include, for example, a 5- to 6-membered aromatic heterocyclic ring, etc. such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, pyridine, pyridazine, pyrimidine, pyrazine, triazine, etc.), etc.

Among others, a 5- to 6-membered aromatic heterocyclic ring containing 1 to 3 hetero-atoms (preferably 1 to 2 hetero-atoms) selected from an oxygen atom, a sulfur atom and a nitrogen atom is preferable, and preferred examples of the ring A include a pyridine ring, a pyridazine ring, a pyrrole ring, a pyrazole ring, a furan ring, a thiophene ring, an isoxazole ring, a pyrimidine ring (preferably, a 5- to 6-membered nitrogen-containing aromatic heterocyclic ring which contains 1–2 nitrogen atoms, etc. such as a pyridine ring, a pyridazine ring, a pyrrole ring, a pyrazole ring, etc.).

In the above formula (I), the ring B is an optionally substituted 5- to 6-membered aromatic homo- or heterocyclic ring.

Examples of the "optionally substituted 5- to 6-membered aromatic homocyclic ring" represented by B include an optionally substituted benzene ring, etc.

Examples of the aromatic heterocyclic ring in the "optionally substituted 5- to 6-membered aromatic heterocyclic ring" represented by B include, for example, an aromatic heterocyclic ring containing at least one hetero-atom (preferably 1 to 3 hetero-atoms, more preferably 1 to 2 hetero-atoms) consisting of 1 to 3 kinds (preferably 1 to 2 kinds) of hetero-atoms selected from an oxygen atom, a sulfur atom, a nitrogen atom, etc., as an atom constituting ring structure (ring atom).

Examples of said "aromatic heterocyclic ring" include, for example, a 5- to 6-membered aromatic heterocyclic ring, etc. such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, pyridine, pyridazine, pyrimidine, pyrazine, triazine, etc.), etc. Among others, a 5- to 6-membered aromatic heterocyclic ring containing 1 to 3 hetero-atoms (preferably 1 to 2 hetero-atoms) selected from an oxygen atom, a sulfur atom and a nitrogen atom is preferable.

Preferred examples of the ring B include a 5- to 6-membered aromatic homo- or hetero-cyclic ring which may contain one hetero-atom selected from an oxygen atom, a sulfur atom and a nitrogen atom, etc. such as a benzene ring, a pyrrole ring, a furan ring, a thiophene ring, a pyridine ring (preferably a benzene ring, a furan ring, a thiophene ring, etc.), etc.

Both of the ring A and the ring B may be substituted with 1 to 4 (preferably 1 to 2) identical or different substituents selected from, for example, (1) a halogen atom, (2) a hydroxy group, (3) a nitro group, (4) a cyano group, (5) an optionally substituted lower alkyl group, (6) an optionally substituted lower alkenyl group, (7) an optionally substituted lower alkynyl group, (8) an optionally substituted lower aralkyl group, (9) an optionally substituted lower alkoxy group, (10) an optionally substituted mercapto group, (11) an optionally substituted amino group, (12) a carboxyl group optionally esterified or amidated, (13) an optionally substituted sulfonyl group, (14) an optionally substituted acyl group and (15) an optionally substituted phenyl group, at any possible position; and (16) adjoining two of these substituents may bind to each other to form a divalent hydrocarbon group; and a nitrogen atom of the ring A and the ring B may be oxidized.

In addition, when the ring A or the ring B is a nitrogen-containing aromatic heterocyclic ring having a hydroxy group as a substituent such as 2-oxypyridine, etc., the ring A or the ring B may be a nitrogen-containing aromatic heterocyclic ring having a oxo group such as α-pyridone, etc. (which is equivalent to a nitrogen-containing aromatic heterocyclic ring having a hydroxy group as a substituent, in chemical structure), and when the ring A or the ring B is a nitrogen-containing aromatic heterocyclic ring having a oxo group, the ring A or the ring B may have a substituent similar to that for the above-mentioned ring A or ring B, on the nitrogen atom.

Examples of the halogen atom as (1) include, for example, chlorine, bromine, fluorine, iodine, etc.

Examples of the lower alkyl group in the optionally substituted lower alkyl group as (5) include, for example, a $C_{1-6}$ alkyl group (for example, methyl, ethyl, propyl, isopropyl, butyl, isobutyl, t-butyl, s-butyl, pentyl, hexyl, etc.), etc.

Said lower alkyl group may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the lower alkenyl group in the optionally substituted lower alkenyl group as (6) include, for example, a $C_{2-6}$ alkenyl group, etc. such as vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, etc.

Said lower alkenyl group may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2$), etc.), etc., at any possible position.

Examples of the lower alkynyl group in the optionally substituted lower alkynyl group as (7) include, for example, a $C_{2-6}$ alkynyl group such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, etc.

Said lower alkynyl group may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the lower aralkyl group in the optionally substituted lower aralkyl group as (8) include, for example, a $C_{7-10}$ aralkyl group (preferably, phenyl-$C_{1-6}$ alkyl group, etc.), etc. such as benzyl, phenethyl, etc.

Said lower aralkyl group may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkyl group (for example, methyl, ethyl, propyl, isopropyl, butyl, isobutyl, s-butyl, t-butyl, pentyl, hexyl, etc.), a halogeno lower ($C_{1-6}$) alkyl group (for example, $CF_3$, $CF_2CF_3$, $CH_2F$, $CHF_2$, etc.), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the lower alkoxy group in the optionally substituted lower alkoxy group as (9) include, for example, a $C_{1-6}$ alkoxy group (for example, methoxy, ethoxy, propoxy, isopropoxy, butoxy, s-butoxy, t-butoxy, pentyloxy, isopentyloxy, neopentyloxy, hexyloxy, etc.), etc.

Said lower alkoxy group may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the optionally substituted mercapto group as (10) include, for example, an optionally substituted $C_{1-6}$ alkylthio group (for example, methylthio, ethylthio, propylthio, isopropylthio, butylthio, s-butylthio, t-butylthio, pentylthio, isopentyloxy, neopentylthio; hexylthio, etc.), etc.

Said $C_{1-6}$ alkylthio group may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the optionally substituted amino group as (11) include, for example, amino groups which may be substituted with 1 or 2 identical or different substituents selected from lower ($C_{1-6}$) alkyl (for example, methyl, ethyl, propyl, isopropyl, butyl, isobutyl, s-butyl, t-butyl, pentyl, hexyl, etc.), lower ($C_{1-6}$) alkoxy (for example, methoxy, ethoxy, propoxy, isopropoxy, butoxy, isobutoxy, s-butoxy, t-butoxy, pentyloxy, hexyloxy, etc.), halogeno lower ($C_{1-6}$) alkyl (for example, $CF_3$, $CF_3CF_2$, $CH_2F$, $CHF_2$, etc.), lower ($C_{3-6}$)cycloalkyl (for example, cyclopropyl, cyclobutyl, cyclopentyl, cyclohexyl, etc.), hydroxy group, carbamoyl, phenyl, phenyl-lower ($C_{1-6}$) alkyl (for example, benzyl, phenethyl, 3-phenylpropyl, 4-phenylbutyl, etc.), lower ($C_{1-6}$) alkanoyl (for example, formyl, acetyl, propionyl, butyryl, isobutyryl, valeryl, pivaloyl, etc.), $C_{3-6}$ cycloalkyl-carbonyl (for example, cyclopropylcarbonyl, cyclobutylcarbonyl, cyclopentylcarbonyl, cyclohexylcarbonyl, etc.), benzoyl, phenyl-$C_{2-6}$ alkanoyl (for example, phenylacetyl, phenylpropionyl, etc.), lower ($C_{1-6}$) alkoxy-carbonyl (for example, methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, etc.), phenoxycarbonyl, phenyl-$C_{1-6}$ alkoxy-carbonyl (for example, benzyloxycarbonyl, phenylethoxycarbonyl, etc.), lower ($C_{1-6}$) alkylsulfinyl (for example, methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, hexylsulfinyl, etc.), $C_{3-6}$ cycloalkylsulfinyl (for example, cyclopropylsulfinyl, cyclobutylsulfinyl, cyclopentylsulfinyl, cyclohexylsulfinyl, etc.), phenylsulfinyl, lower ($C_{1-6}$) alkyl-sulfonyl (for example, methylsulfonyl, ethylsulfonyl, propylsulfonyl, isopropylsulfonyl, butylsulfonyl, isobutylsulfonyl, t-butylsulfonyl, s-butylsulfonyl, pentylsulfonyl, hexylsulfonyl, etc.), $C_{3-6}$ cycloalkylsulfonyl (for example, cyclopropylsulfonyl, cyclobutylsulfonyl, cyclopentylsulfonyl, cyclohexylsulfonyl, etc.), lower ($C_{1-6}$) alkoxysulfonyl (for example, methoxysulfonyl, ethoxysulfonyl, propoxysulfonyl, isopropoxysulfonyl, butoxysulfonyl, isobutoxysulfonyl, s-butoxysulfonyl, t-butoxysulfonyl, pentyloxysulfonyl, hexyloxysulfonyl, etc.), phenylsulfonyl, etc.

Also, two of the substituents may form a cyclic amino group in cooperation with a nitrogen atom, and examples of the cyclic amino group include, for example, pyrrolidino, piperidino, morpholino, thiomorpholino, etc.

Each of the optionally substituted amino groups as exemplified above may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkyl group (for example, methyl, ethyl, propyl, isopropyl, butyl, isobutyl, s-butyl, t-butyl, pentyl, hexyl, etc.), a halogeno lower ($C_{1-6}$) alkyl group (for example, $CF_3$, $CF_2CF_3$, $CH_2F$, $CHF_2$, etc.), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the esterified carboxyl group in the carboxyl group optionally esterified or amidated as (12) include, for example, a lower ($C_{1-6}$) alkoxy-carbonyl group (for example, methoxycarbonyl, ethoxycarbonyl, propoxycarbonyl, isopropoxycarbonyl, butoxycarbonyl, s-butoxycarbonyl, t-butoxycarbonyl, pentyloxycarbonyl, isopentyloxycarbonyl, neopentyloxycarbonyl, hexyloxycarbonyl, etc.), a $C_{3-6}$ cycloalkoxy-carbonyl (for example, cyclopropoxycarbonyl, cyclobutyloxycarbonyl, cyclopentyloxycarbonyl, cyclohexyloxycarbonyl, etc.), a phenyl-$C_{1-6}$ alkoxy-carbonyl (for example, benzyloxycarbonyl, phenyloxycarbonyl, etc.), a nitroxy-$C_{1-6}$ alkoxy-carbonyl (for example, 2-nitroxyethoxycarbonyl, 3-nitroxypropoxycarbonyl, etc.), etc.

Examples of the amidated carboxyl group include a carbamoyl, a N-mono-lower ($C_{1-6}$) alkylcarbamoyl (for example, methylcarbamoyl, ethylcarbamoyl, propylcarbamoyl, isopropylcarbamoyl, butylcarbamoyl, isobutylcarbamoyl, s-butylcarbamoyl, t-butylcarbamoyl, pentylcarbamoyl, hexylcarbamoyl, etc.), a N,N-di-lower ($C_{1-6}$) alkylcarbamoyl (for example, N,N-dimethylcarbamoyl, N,N-diethylcarbamoyl, N,N- dipropylcarbamoyl, N,N-dibutylcarbamoyl, etc.), a $C_{3-6}$ cycloalkyl-carbamoyl (for example, cyclopropylcarbamoyl, cyclobutylcarbamoyl, cyclopentylcarbamoyl, cyclohexylcarbamoyl, etc.), a phenyl-$C_{1-6}$ alkyl-carbamoyl (for example, benzylcarbamoyl, phenethylcarbamoyl, etc.), a nitroxy-$C_{1-6}$ alkylamino-carbonyl (for example, 2-nitroxyethylcarbamoyl, 3-nitroxypropylcarbamoyl, etc.), a cyclic aminocarbonyl (for example, morpholinocarbonyl, piperidinocarbonyl, pyrrolidinocarbonyl, thiomorpholinocarbonyl, etc.), an anilinocarbonyl, etc.

Each of the "carboxyl group optionally esterified or amidated" as exemplified above may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkyl group (for example, methyl, ethyl, propyl, isopropyl, butyl, isobutyl, s-butyl, t-butyl, pentyl, hexyl, etc.), a halogeno lower ($C_{1-6}$) alkyl group (for example, $CF_3$, $CF_2CF_3$, $CH_2F$, $CHF_2$, etc.), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc. at any possible position.

Examples of the optionally substituted sulfonyl group as (13) include, for example, a lower ($C_{1-6}$) alkylsulfonyl (for example, methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl, etc.), a $C_{3-6}$ cycloalkylsulfonyl (for example, cyclopropylsulfonyl, cyclobutylsulfonyl, cyclopentylsulfonyl, cyclohexylsulfonyl, etc.), a phenyl-$C_{1-6}$ alkylsulfonyl (for example, benzylsulfonyl, phenethylsulfonyl, etc.), a lower ($C_{1-6}$) alkoxysulfonyl (for example, methoxysulfonyl, ethoxysulfonyl, propoxysulfonyl, isopropoxysulfonyl, butoxysulfonyl, isobutoxysulfonyl, s-butoxysulfonyl, t-butoxysulfonyl, pentyloxysulfonyl, hexyloxysulfonyl, etc.), a $C_{3-6}$ cycloalkyloxysulfonyl (for example, cyclopropoxysulfonyl, cyclobutyloxysulfonyl, cyclopentyloxysulfonyl, cyclohexyloxysulfonyl, etc.), a phenyl-$C_{1-6}$alkoxysulfonyl (for example, benzyloxysulfonyl, phenethyloxysulfonyl, etc.), a sulfamoyl, a lower ($C_{1-6}$) alkylaminosulfonyl (for example, methylaminosulfonyl, ethylaminosulfonyl, propylaminosulfonyl, isopropylaminosulfonyl, butylaminosulfonyl, isobutylaminosulfonyl, s-butylaminosulfonyl, t-butylaminosulfonyl, pentylaminosulfonyl, hexylaminosulfonyl, etc.), a $C_{3-6}$ cycloalkylaminosulfonyl (for example, cyclopropylaminosulfonyl, cyclobutylaminosulfonyl, cyclopentylaminosulfonyl, cyclohexylaminosulfonyl, etc.), a phenyl-$C_{1-6}$ alkylaminosulfonyl (for example, benzylaminosulfonyl, phenethylaminosulfonyl, etc.), a cyclic aminosulfonyl (for example, morpholinosulfonyl, piperidinosulfonyl, pyrrolidinosulfonyl, thiomorpholinosulfonyl, etc.), a nitroxy-$C_{1-6}$ alkylaminosulfonyl (for example, 2-nitroxyethylaminosulfonyl, 3-nitroxypropylaminosulfonyl, etc.), an anilinosulfonyl, etc.

Each of the "optionally substituted sulfonyl group" as exemplified above may be substituted with 1 to 3 identical or different substituents selected from, for example, a halogen atom (for example, chlorine, bromine, fluorine, iodine, etc.), a hydroxy group, a nitro group, a cyano group, a lower ($C_{1-6}$) alkyl group (for example, methyl, ethyl, propyl, isopropyl, butyl, isobutyl, s-butyl, t-butyl, pentyl, hexyl, etc.), a halogeno lower ($C_{1-6}$) alkyl group (for example, $CF_3$, $CF_2CF_3$, $CH_2F$, $CHF_2$, etc.), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

Examples of the lower acyl group as (14) include, for example, a lower acyl group derived from a carboxylic acid, a sulfinic acid, a sulfonic acid, etc.

Here, examples of the lower acyl group derived from a carboxylic acid include, for example, a lower ($C_{1-6}$) alkyl-carbonyl (alkanoyl) (for example, formyl, acetyl, propionyl, butyryl, isobutyryl, valeryl, pivaloyl, etc.), a $C_{3-6}$ cycloalkyl-carbonyl (for example, cyclopropylcarbonyl, cyclobutylcarbonyl, cyclopentylcarbonyl, cyclohexylcarbonyl, etc.), benzoyl, etc.

Examples of the lower acyl group derived from a sulfinic acid include, for example, a lower ($C_{1-6}$) alkylsulfinyl (for example, methylsulfinyl, ethylsulfinyl, propylsulfinyl, isopropylsulfinyl, butylsulfinyl, isobutylsulfinyl, s-butylsulfinyl, t-butylsulfinyl, pentylsulfinyl, hexylsulfinyl, etc.), a $C_{3-6}$ cycloalkylsulfinyl (for example, cyclopropylsulfinyl, cyclobutylsulfinyl, cyclopentylsulfinyl, cyclohexylsulfonyl, etc.), phenylsulfinyl, etc.

Examples of the lower acyl group derived from a sulfonic acid include, for example, a lower ($C_{1-6}$) alkylsulfonyl (for example, methylsulfonyl, ethylsulfonyl, propylsulfonyl, isopropylsulfonyl, butylsulfonyl, isobutylsulfonyl, s-butylsulfonyl, t-butylsulfonyl, pentylsulfonyl, hexylsulfonyl, etc.), a $C_{3-6}$ cycloalkylsulfonyl (for example, cyclopropylsulfonyl, cyclobutylsulfonyl, cyclopentylsulfonyl, cyclohexylsulfonyl, etc.), phenylsulfonyl, etc.

Each of the "lower acyl group" as exemplified above may be substituted with 1 to 3 identical or different substituents selected from, for example, a halogen atom (for example, chlorine, bromine, fluorine, iodine, etc.), a hydroxy group, nitro group, a cyano group, a lower ($C_{1-6}$) alkyl group (for example, methyl, ethyl, propyl, isopropyl, butyl, isobutyl, s-butyl, t-butyl, pentyl, hexyl, etc.), a halogeno lower ($C_{1-6}$) alkyl group (for example, $CF_3$, $CF_2CF_3$, $CH_2F$, $CHF_2$, etc.), a lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), a halogeno lower ($C_{1-6}$) alkoxy group (for example, $CF_3O$, $CHF_2O$, etc.), etc., at any possible position.

The optionally substituted phenyl group as (15) may be substituted with 1 to 3 identical or different substituents selected from, for example, a halogen atom (e.g. chlorine, bromine, fluorine, iodine, etc.), hydroxy group, nitro group, cyano group, lower ($C_{1-6}$) alkyl group (e.g. methyl, ethyl, propyl, isopropyl, butyl, isobutyl, s-butyl, t-butyl, pentyl, hexyl, etc.), halogeno-lower ($C_{1-6}$) alkyl group (e.g. $CF_3$, $CF_2CF_3$, $CH_2F$, $CHF_2$, etc.), lower ($C_{1-6}$) alkoxy group (e.g. methoxy, ethoxy, propoxy, isopropoxy, butoxy, s-butoxy, t-butoxy, pentyloxy, isopentyloxy, neopentyloxy, hexyloxy, etc.), halogeno-lower ($C_{1-6}$) aalkoxy group (e.g. $CF_3O$, $CHF_2O$, etc.), etc., at any possible position.

Examples of the divalent hydrocarbon group as (16) include, for example, a group of the formula:

—CH=CH—CH=CH—,

—CH=CH—CH$_2$—CH$_2$—,

—CH$_2$—CH=CH—CH$_2$—,

—CH=CH—CH$_2$,

—(CH$_2$)a-

(a is 3 or 4), etc.

Here, the above-mentioned divalent hydrocarbon group forms a 5- to 6-membered ring with two atoms constituting the ring A, and said 5- to 6-membered ring may be substituted with 1 to 3 identical or different substituents selected from, for example, lower ($C_{1-6}$) alkyl group (for example, methyl, ethyl, propyl, isopropyl, butyl, isobutyl, s-butyl, t-butyl, pentyl, hexyl, etc.), halogen atom (for example, chlorine, bromine, fluorine, iodine, etc.), lower ($C_{1-6}$) alkoxy group (for example, methoxy, ethoxy, propoxy, isopropoxy, butoxy, s-butoxy, t-butoxy, pentyloxy, isopentyloxy, neopentyloxy, hexyloxy, etc.), halogeno lower ($C_{1-6}$) alkyl group (for example, $CF_3$, $CF_2CF_3$, $CH_2F$, $CHF_2$, etc.), halogeno lower ($C_{1-6}$) alkoxy group (for example, $CF_3O$, $CF_2CF_3O$, $CH_2FO$, $CHF_2O$, etc.), lower ($C_{1-6}$) alkoxy-carbonyl group (for example, methoxycarbonyl, ethoxycarbonyl, propoxycarbonyl, isopropoxycarbonyl, butoxycarbonyl, s-butoxycarbonyl, t-butoxycarbonyl, pentyloxycarbonyl, isopentyloxycarbonyl, neopentyloxycarbonyl, hexyloxycarbonyl, etc.), cyano group, nitro group, hydroxy group, etc., at any possible position.

As the substituent for the ring A, a lower ($C_{1-6}$) alkyl group (preferably methyl) optionally halogenated, a lower ($C_{1-6}$) alkoxy group (preferably methoxy) optionally halogenated, etc. are preferable.

As the ring A, a group of the formula:

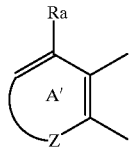

wherein the ring A' is an optionally substituted 5- to 6-membered aromatic heterocyclic ring (preferably, pyridine, pyrazole, pyrrole, furan, more preferably, pyridine, pyrazole) which may have an optional substituent in addition to the group Ra, Z is an oxygen atom, a sulfur atom or a nitrogen atom, and Ra is the above-mentioned substituent for the ring A (preferably, lower ($C_{1-6}$) alkyl group optionally halogenated, lower ($C_{1-6}$) alkoxy group optionally halogenated, etc.) is preferable.

As the substituent for the ring B, halogen atom (preferably chlorine), lower ($C_{1-6}$) alkyl group (preferably methyl) optionally halogenated, hydroxy group, lower ($C_{1-6}$) alkoxy group (preferably methoxy) optionally halogenated, etc. are preferable.

As the ring B, a group of the formula:

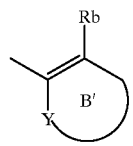

wherein the ring B' is an optionally substituted 5- to 6-membered aromatic homo- or hetero-cyclic ring (preferably, benzene, thiophene) in addition to the group Rb, Y is a carbon atom, an oxygen atom, a sulfur atom or a nitrogen atom and Rb is hydrogen atom or the above-mentioned substituent for the ring B (preferably halogen atom, lower ($C_{1-6}$) alkyl group optionally halogenated, hydroxy group, lower ($C_{1-6}$) alkoxy group optionally halogenated, etc.) is preferable.

In the above formula (I), $R^1$ is a hydrogen atom, a hydroxy group or a lower alkyl group (for example, lower ($C_{1-6}$) alkyl group (for example, methyl, ethyl, propyl, isopropyl, butyl, isobutyl, s-butyl, t-butyl, pentyl, hexyl, etc.), preferably methyl). As the group $R^1$, hydrogen atom, hydroxy group and methyl group are preferable, hydrogen atom and hydroxy group are more preferable, and in particular, hydrogen atom is preferable.

In the above formula (I), n is 0 or 1 (preferably, 1).

As the Compound (I), (S)-(−)-7-(2,5-dichlorothiophen-3-yl)-5-guanidinoimino-4-methyl-5,6,7,8-tetrahydroquinoline;

(±)-7-(2,5-dichlorothiophen-3-yl)-5-guanidinoimino-4-methyl-5,6,7,8-tetrahydroquinoline;

(S)-(−)-7-(2-chlorophenyl)-5-guanidinoimino-4-methyl-5,6,7,8-tetrahydroquinoline;

(±)-7-(2-chlorophenyl)-5-guanidinoimino-4-methyl-5,6,7,8-tetrahydroquinoline;

(±)-7-(2-bromophenyl)-5-guanidinoimino-4-methyl-5,6,7,8-tetrahydroquinoline;

7-(3,5-dichlorothiophen-2-yl)-5-guanidinoimino-4-methyl-5,6,7,8-tetrahydroquinoline;

7-(2,5-dichlorophenyl)-5-guanidinoimino-4-methyl-5,6,7,8-tetrahydroquinoline;

6-(2,5-dichlorothiophen-3-yl)-4-guanidinoimino-3-methyl-4,5,6,7-tetrahydroindazol;

(±)-7-(2,5-dichlorophenyl)-5-guanidinoimino-4-methyl-5,6,7,8-tetrahydrocinnoline;

(±)-7-(5-chloro-2-methylphenyl)-5-guanidinoimino-4-methyl-5,6,7,8-tetrahydroquinoline;

(±)-7-(5-fluoro-2-methylphenyl)-5-guanidinoimino-4-methyl-5,6,7,8-tetrahydroquinoline;

(±)-7-(2-chloro-5-fluorophenyl)-5-guanidinoimino-4-methyl-5,6,7,8-tetrahydroquinoline;

(±)-7-(5-chloro-2-fluorophenyl)-5-guanidinoimino-4-methyl-5,6,7,8-tetrahydroquinoline;

(±)-7-(5-fluoro-2-methylphenyl)-5-guanidinoimino-4-methyl-5,6,7,8-tetrahydrocinnoline (±) -7-(5-chloro-2-fluorophenyl)-5-guanidinoimino-4-methyl-5,6,7,8-tetrahydrocinnoline;

or a salt thereof are preferable.

Among others, (S)-(−)-7-(2,5-dichlorothiophen-3-yl)-5-guanidinoimino-4-methyl-5,6,7,8-tetrahydroquinoline;

(±)-7-(2,5-dichlorothiophen-3-yl)-5-guanidinoimino-4-methyl-5,6,7,8-tetrahydroquinoline;

(S)-(−)-7-(2-chlorophenyl)-5-guanidinoimino-4-methyl-5,6,7,8-tetrahydroquinoline;

(±)-7-(2-chlorophenyl)-5-guanidinoimino-4-methyl-5,6,7,8-tetrahydroquinoline;

(±)-7-(2,5-dichlorophenyl)-5-guanidinoimino-4-methyl-5,6,7,8-tetrahydrocinnoline;

(±)-7-(5-chloro-2-methylphenyl)-5-guanidinoimino-4-methyl-5,6,7,8-tetrahydroquinoline;

(±)-7-(5-fluoro-2-methylphenyl)-5-guanidinoimino-4-methyl-5,6,7,8-tetrahydroquinoline;

(±)-7-(2-chloro-5-fluorophenyl)-5-guanidinoimino-4-methyl-5,6,7,8-tetrahydroquinoline;

(±)-7-(5-chloro-2-fluorophenyl)-5-guanidinoimino-4-methyl-5,6,7,8-tetrahydroquinoline;

(±)-7-(5-fluoro-2-methylphenyl)-5-guanidinoimino-4-methyl-5,6,7,8-tetrahydrocinnoline;

(±)-7-(5-chloro-2-fluorophenyl)-5-guanidinoimino-4-methyl-5,6,7,8-tetrahydrocinnoline or a salt thereof are preferable.

The pro-drug of the compound of the formula (I) means a compound which is converted to the compound of the formula (I) under the physiological conditions or with a reaction due to an enzyme, an gastric acid, etc. in the living body, that is, a compound which is converted to the compound of the formula (I) with oxidation, reduction, hydrolysis, etc. according to an enzyme; a compound which is converted to the compound of the formula (I) with gastric acid, etc.; etc.

Examples of the pro-drug of the compound of the formula (I) include a compound wherein an amino group of the compound of the formula (I) is substituted with acyl, alkyl, phosphoric acid, etc. (e.g. a compound wherein an amino group of the compound of the formula (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc.); a compound wherein an hydroxy group of the compound of the formula (I) is substituted with acyl, alkyl, phosphoric acid, boric acid, etc. (e.g. a compound wherein an hydroxy group of the compound of the formula (I) is substituted with acetyl, palmitoyl, propanoyl, pivaloyl, succinyl, fumaryl, alanyl, dimethylaminomethylcarbonyl, etc.); a compound wherein a carboxyl group of the compound of the formula (I) is modified with ester, amide, etc. (e.g. a compound wherein a carboxyl group of the compound of the formula (I) is modified with ethylester, phenylester, carboxymethylester, dimethylaminomethylester, pivaloyloxymethylester, ethoxycarbonyloxyethylester, phthalidylester, (5-methyl-2-oxo1,3-dioxolen-4-yl)methylester, cyclohexyloxycarbonylethylester, methylamide, etc.); etc. These pro-drugs can be produced by per se known method from the compound of the formula (I).

The pro-drug of the compound of the formula (I) may be a compound which is converted into the compound of the formula (I) under the physiological conditions as described in "Pharmaceutical Research and Development", Vol. 7 (Drug Design) pages 163–198 published in 1990 by Hirokawa Publishing Co. (Tokyo, Japan).

Examples of the salt of Compound (I) or its synthetic intermediates include a pharmaceutically acceptable salt, for example, an inorganic acid salt such as hydrochloride, hydrobromide, sulfate, nitrate, phosphate, etc., an organic acid salt such as acetate, tartrate, citrate, fumarate, maleate, toluenesulfonate, methanesulfonate, etc., a salt with an amino acid such as an aspartic acid, a glutamic acid, a pyroglutamic acid, an arginine, a lysine, ornithine, etc., a metal salt such as sodium salt, potassium salt, calcium salt, aluminum salt, etc., a salt with a base such as triethylamine salt, guanidine salt, ammonium salt, hydrazine salt, quinine salt, cinchonine salt, etc., etc.

Compound (I) may be used as a hydrate.

When Compound (I) exists as configuration isomer, diastereomer, conformer, etc., it is possible to isolate individual isomers with per se known separation and purification method, if desired.

Compound (I) has geometrical isomerism at the position of a hydrazone structure based on configuration of a fused heterocyclic ring including the ring A, and exists as E-isomer, Z-isomer or a mixture thereof.

Further, when $R^1$ is a hydroxy group or a lower alkyl group, Compound (I) has geometrical isomerism based on double bond of a guanidino group, and exists as E-isomer, Z-isomer or a mixture thereof.

In Compound (I), the following individual isomers and a mixture thereof are included.

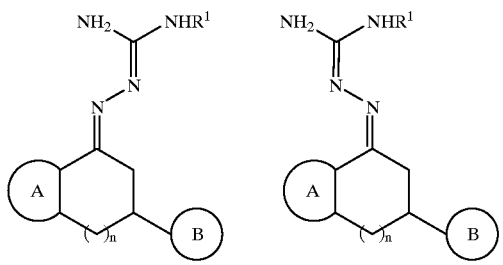

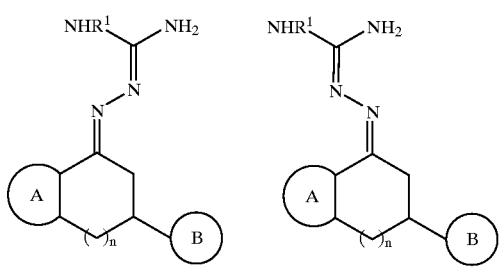

Also, Compound (I) has an optical isomer based on an asymmetric carbon existing at the position where the ring B is substituted, etc., and exists as R-isomer, S-isomer or a mixture thereof in connection with individual asymmetric carbon. It can be separated into individual R-isomer and S-isomer with usual optical resolution and individual optical isomers and a mixture thereof are included by Compound (I). For example, Compound (I) includes the following individual optical isomers and a mixture thereof.

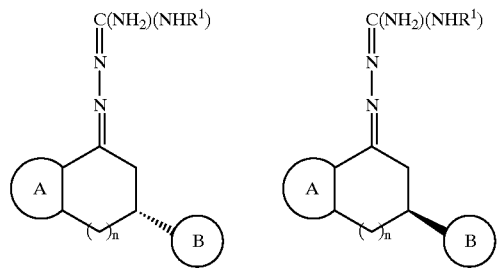

In the present specification the starting material or a, synthesis intermediate of Compound (I), or a salt, thereof, is also referred to as the starting material or synthesis intermediate of Compound (I), with "or a salt thereof" omitted.

In addition, Compound (I) is equivalent to Compound (Ia) and Compound (Ib) in view of its chemical structure.

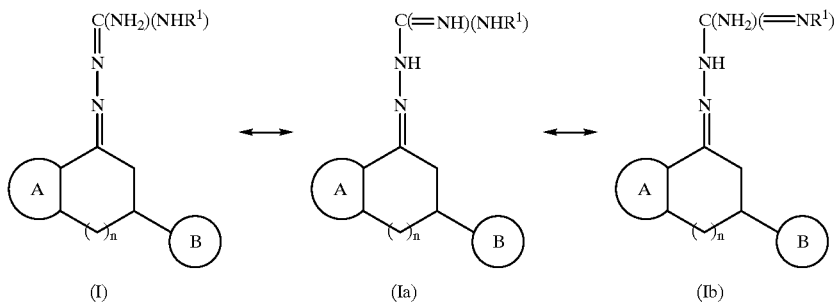

Compound (I) can be produced by a method described in e.g. Japanese Patent Unexamined Publication No. 309837/1995, Japanese Patent Application No. 224945/1997 (Japanese Patent Unexamined Publication No. 114753/1998), Japanese Patent Application No. 224946/1997 (Japanese Patent Unexamined Publication No. 114744/1998), etc. or a method similar thereto, and also by reacting a compound of the formula

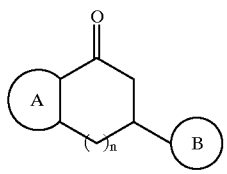

(II)

wherein each symbol is as defined above or a salt thereof with an aminoguanidine compound of the formula

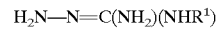

H$_2$N—N=C(NH$_2$)(NHR$^1$)  (III)

wherein each symbol is as defined above or a salt thereof, etc.

Compound (III) is usually used at about 1 to about 2 mol per mol of Compound (II). This reaction can be facilitated by the addition of triethylamine, pyrrolidine, sodium acetate, boron trifluoride diethylether, hydrochloric acid, sulfuric acid, p-toluenesulfonic acid, etc. as a catalyst, which is added at about 1/10 to about 10 mol, if necessary.

For example, this condensation reaction can be carried out in an inert solvent such as methanol, ethanol, propanol, isopropanol, n-butanol, tetrahydrofuran, diethylether, dimethoxyethane, 1,4-dioxane, toluene, benzene, xylene, dichloromethane, chloroform, 1,2-dichloroethane, dimethylformamide (DMF), dimethylsulfoxide (DMSO), acetic acid, pyridine, water, etc., or a mixed solvent thereof. The reaction is carried out in a temperature range from about 0° C. to about 180° C.

Compound (II) and Compound (III) used as the starting material can be produced by a known method or a method similar thereto. For example, they can be produced by the following Reaction Scheme I or Reference Example shown below.

Reaction Scheme I

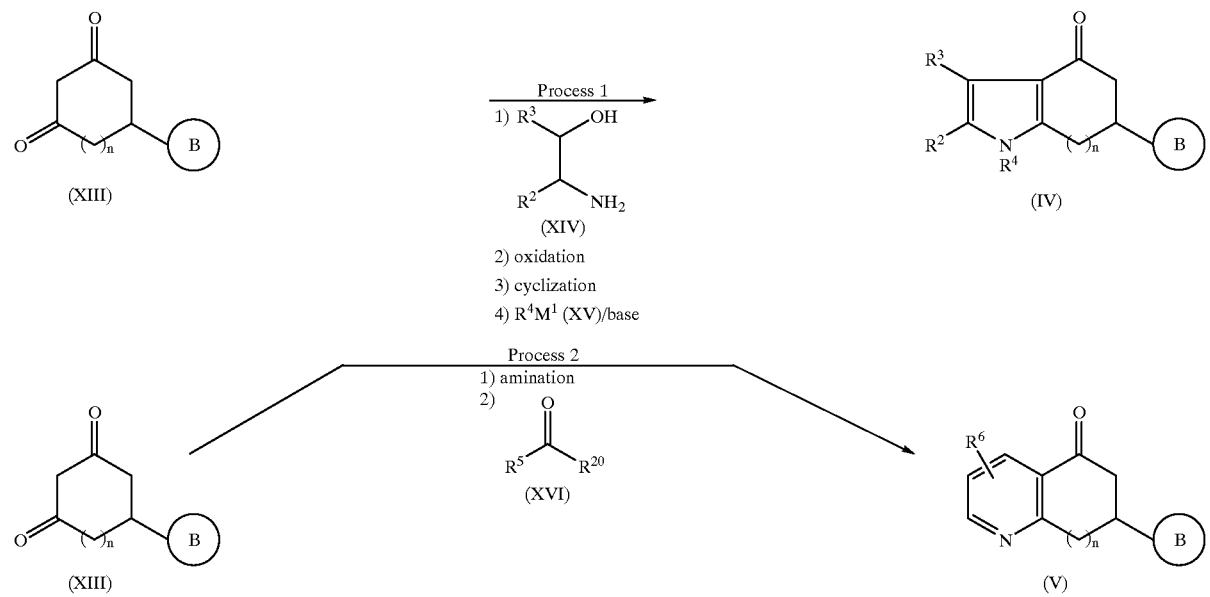

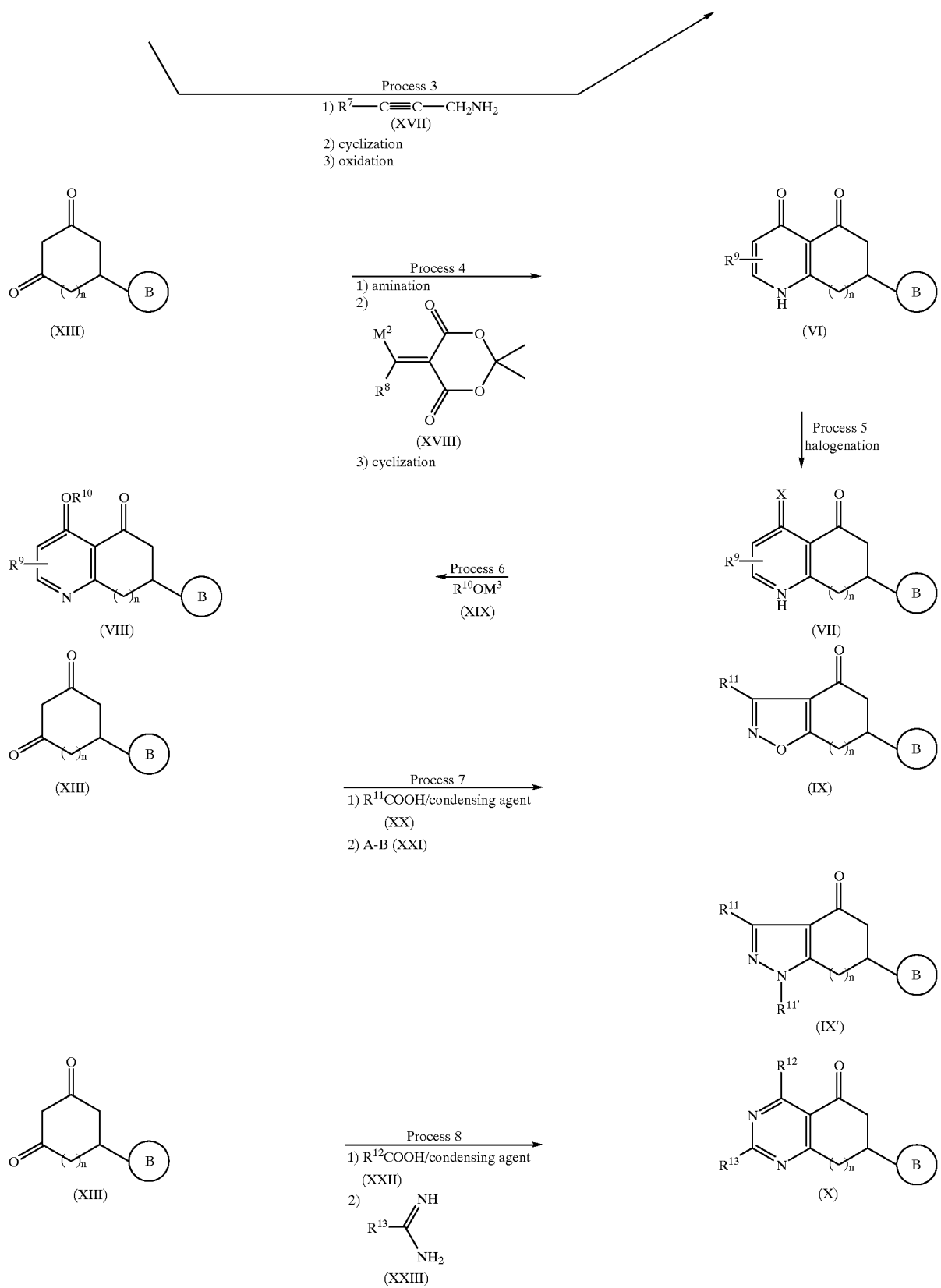

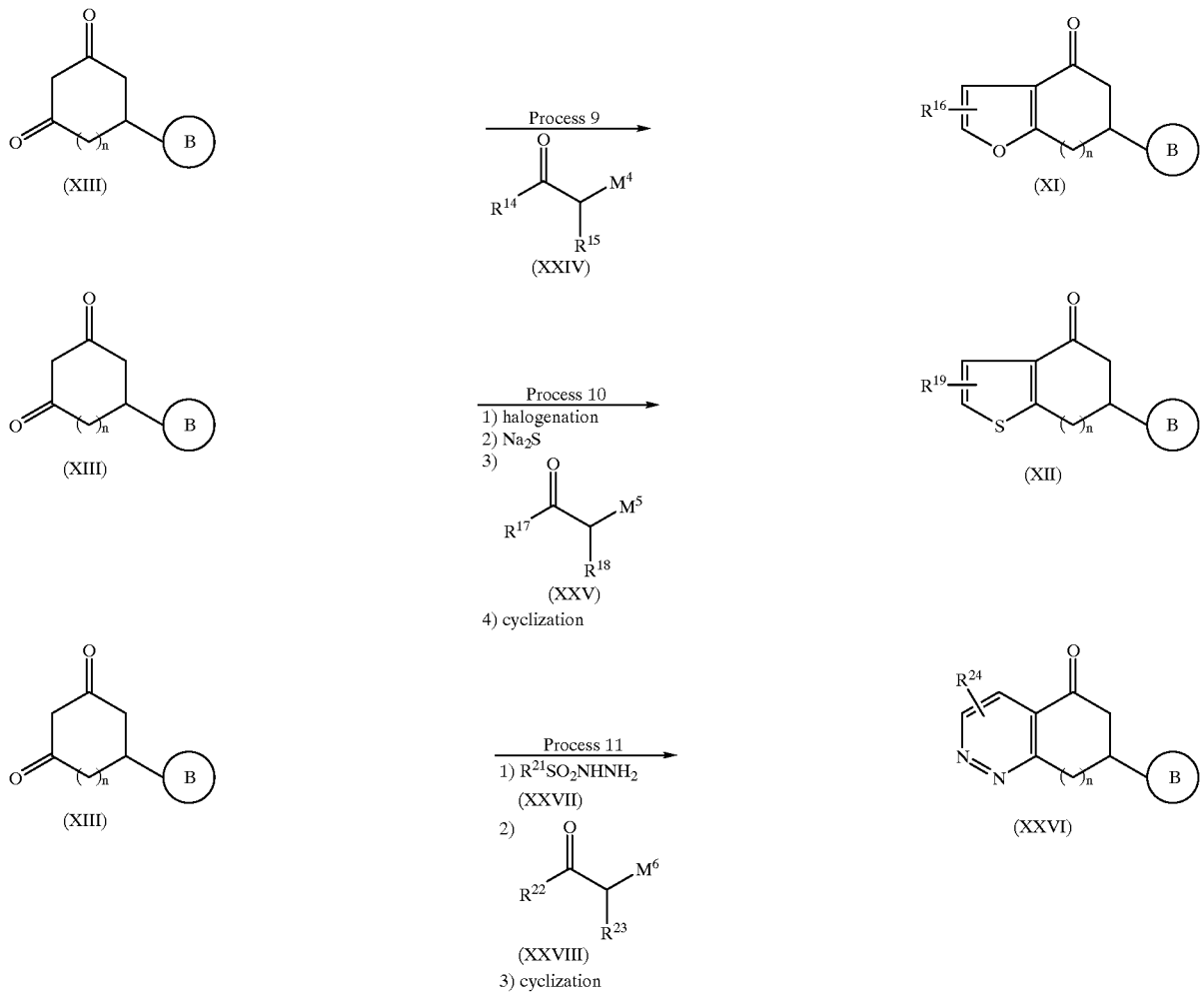

In the above-mentioned Reaction Scheme I, $R^2$ to $R^{19}$ and $R^{22}$ to $R^{24}$ are independently a substituent for the above-mentioned ring A, and $M^1$ to $M^6$ are independently a leaving group.

Each process of the Reaction Scheme I is hereinafter described in detail.

(Process 1)

Ketone Compound (IV) can be produced by reacting Compound (XIII) with Compound (XIV), followed by oxidation of a hydroxy group and cyclization. In addition, if necessary, the cyclized product is reacted with Compound (XV) in the presence of a base to produce Compound (IV) wherein the substituent $R^4$ is introduced into the ketone compound.

This condensation reaction can be carried out in an inert solvent such as tetrahydrofuran, diethylether, dimethoxyethane, methanol, ethanol, hexane, toluene, benzene, dichloromethane, acetic acid, etc., or a mixed solvent thereof, and in a temperature range from about 0° C. to about 130° C. The reaction time is about 1 hour to about 100 hours. Compound (XIV) is usually used at about 1 to about 2 mol per mol of Compound (XIII). This reaction can be facilitated by the addition of molecular sieves, etc.

Oxidation, ring-closure reaction (cyclization reaction) and dehydration reaction after the above reaction can be carried out by a known method. For example, when equivalent mol to about twice mol of aromatic halide is used as an oxidizing agent, the reaction is carried out in the presence of about 0.1 to about 20 mol % of transit metal catalyst and equivalent mol to about twice mol of base, in an inert solvent such as tetrahydrofuran, dimethoxyethane, dimethylformamide, N-methylpyrrolidone, hexane, toluene, benzene, dichloromethane, chloroform, etc., or a mixed solvent thereof, and in a temperature range from about 50° C. to about 200° C. The reaction time is about 1 hour to about 50 hours. Examples of the aromatic halide used as an oxidizing agent include bromobenzene, bromomesitylene, o-bromotoluene, etc. Examples of the transit metal catalyst include nickel, palladium, platinum, platinum, ruthenium, etc. This reaction can be facilitated by the addition of palladium catalyst such as tetrakis(triphenylphosphine) palladium, etc. As the base, potassium carbonate, sodium hydride, etc. can be employed. In addition, this reaction is preferably carried out in an inert gas (e.g., nitrogen, argon) atmosphere.

The reaction with Compound (XV) can be carried out in an inert solvent such as tetrahydrofuran, dimethoxyethane, dimethylformamide, N-methylpyrrolidone, hexane, toluene, benzene, dichloromethane, chloroform, etc., or a mixed solvent thereof, and in a temperature range from about 0° C. to about 150° C. The reaction time is about 1 hour to about 50 hours. As the base, triethylamine, lithium hydride, sodium hydride, sodium methoxide, sodium ethoxide, potassium t-butoxide, etc. can be employed. Compound (XV) is usually used at about 1 to about 2 mol per mol of Compound (XIII).

(Process 2)

Compound (XIII) is reacted with an aminating agent to produce an enamine derivative, which is reacted with Compound (XVI) (wherein $R^{20}$ is —$CH_2COCH_3$, —$C\equiv CH$, —$CH_2CH(OMe)_2$, etc.) to produce ketone Compound (V). Also, if necessary, in the presence of an aminating agent, Compound (XIII) is reacted with Compound (XVI) to produce ketone Compound (V), without isolating the enamine derivative.

Said amination is carried out in the presence of an aminating agent such as ammonium acetate, etc., in an inert solvent such as methanol, ethanol, benzene, toluene, chloroform, dichloromethane, 1,2-dichloroethane, tetrahydrofuran, diethylether, hexane, ethyl acetate, dimethylformamide, etc., or a mixed solvent thereof, and in a temperature range from about 0° C. to about 150° C. The reaction time is about 1 hour to about 100 hours. The aminating agent is usually used at about 1 to about 10 mol per mol of Compound (XIII).

Condensation. and cyclization reaction can be carried out in an inert solvent such as methanol, ethanol, benzene, toluene, chloroform, dichloromethane, 1,2-dichloroethane, tetrahydrofuran, diethylether, hexane, ethyl acetate, dimethylformamide, dimethylsulfoxide, etc., or a mixed solvent thereof, and in a temperature range from about 0° C. to about 150° C. The reaction time is about 1 hour to about 50 hours. Compound (XVI) is usually used at about 1 to about 5 mol per mol of Compound (XIII).

In addition, when the enamine derivative is not isolated, said amination is carried out in the presence of an aminating agent such as ammonium acetate, etc., according to a method similar to that described above.

(Process 3)

Compound (XIII) is reacted with Compound (XVII), followed by cyclization and oxidation to produce ketone Compound (V).

This condensation reaction can be carried out in an inert solvent such as tetrahydrofuran, diethylether, dimethoxyethane, methanol, ethanol, hexane, toluene, benzene, dichloromethane, etc., or a mixed solvent thereof, and in a temperature range from about 0° C. to about 130° C. The reaction time is about 1 hour to about 100 hours. Compound (XVII) is usually used at about 1 to about 2 mol per mol of Compound (XIII).

The ring-closure reaction and oxidation after the above reaction can be carried out in the absence of a solvent or in an inert solvent such as diphenylether, tetrahydrofuran, dimethylformamide, dimethylsulfoxide, xylene, toluene, etc., or a mixed solvent thereof, in the air (or under oxygen atmosphere) and in a temperature range from room temperature to about 300° C. The reaction time is about 1 hour to about 10 hours.

(Process 4)

Compound (XIII) is reacted with an aminating agent and then with Compound (XVIII), followed by cyclization to produce ketone Compound (VI).

Said amination is carried out according to a method described in Process 2.

Condensation reaction after the reaction can be carried out in an inert solvent such as methanol, ethanol, benzene, toluene, chloroform, dichloromethane, 1,2-dichloroethane, tetrahydrofuran, diethylether, hexane, ethyl acetate, dimethylformamide, dimethylsulfoxide, etc., or a mixed solvent thereof, and in a temperature range from about 0° C. to about 100° C. The reaction time is about 1 hour to about 50 hours. Compound (XVIII) is usually used at about 1 to about 2 mol per mol of Compound (XIII).

Ring-closure reaction after the reaction can be carried out in the absence of a solvent or in an inert solvent such as tetrahydrofuran, diphenylether, dimethoxyethane, methanol, ethanol, dichloromethane, chloroform, hexane, benzene, toluene, etc., or a mixed solvent thereof, and in a temperature range from about 50° C. to about 300° C. The reaction time is about 10 minutes to about 5 hours.

(Process 5)

Compound (VI) produced in Process 4 is halogenated to produce ketone Compound (VII) (wherein X is a halogen atom).

Said halogenation can be carried out by a known method. For example, when phosphorus oxychloride is used as a halogenating agent, about 1 to about 20 times of a halogenating agent is used and the reaction is carried out in the absence of a solvent or in an inert solvent such as tetrahydrofuran, dimethoxyethane, hexane, toluene, benzene, dichloromethane, chloroform, etc., or a mixed solvent thereof, and in a temperature range from about 0° C. to about 150° C. The reaction time is about 30 minutes to about 10 hours. This reaction can be facilitated by the addition of dimethylformamide, etc.

(Process 6)

Compound (VII) produced in Process 5 is reacted with Compound (XIX) to produce ketone Compound (VIII).

This reaction can be carried out in an inert solvent such as tetrahydrofuran, diethylether, dimethoxyethane, methanol, ethanol, hexane, toluene, benzene, dichloromethane, chloroform, dimethylformamide, dimethylsulfoxide, etc., or a mixed solvent thereof, and in a temperature range from about 0° C. to about 150° C. The reaction time is about 30 minutes to about 50 hours. Compound (XIX) is usually used at about 1 to about 2 mol per mol of Compound (VII). If necessary, abase such as lithium hydride, sodium hydride, sodium methoxide, sodium ethoxide, potassium t-butoxide, etc. can be used for the reaction.

(Process 7)

Compound (XIII) is reacted with Compound (XX) and then with Compound (XXI) (wherein A-B is an optionally substituted hydrazine, hydroxylamine, etc.), followed by cyclization to produce ketone Compound (IX) or (IX').

The condensation reaction can be carried out by a known method, for example, in the presence of a condensing agent such as DCC, WSC, etc., in an inert solvent such as tetrahydrofuran, diethylether, dimethoxyethane, dimethylformamide, dimethylsulfoxide, hexane, toluene, benzene, dichloromethane, chloroform, ethyl acetate, etc., or a mixed solvent thereof, and in a temperature range from about 0° C. to about 150° C. The reaction time is about 1 hour to about 50 hours. Compound (XX) is usually used at about 1 to about 3 mol per mol of Compound (XIII) and also used as a solvent.

Ring-closure reaction after the reaction can be carried out in an inert solvent such as tetrahydrofuran, diphenylether, dimethoxyethane, methanol, ethanol, hexane, toluene, benzene, dichloromethane, chloroform, dimethylformamide, dimethylsulfoxide, etc., or a mixed solvent thereof, and in a temperature range from about 0° C. to about 150° C. The reaction time is about 1 hour to about 50 hours. Compound (XXI) is usually used at about 1 to about 2 mol per mol of Compound (XIII).

(Process 8)

Compound (XIII) is reacted with Compound (XXII) and then with Compound (XXIII), followed by cyclization to produce ketone Compound (X).

The condensation reaction is carried out according to similar condensation reaction described in Process 7.

Cyclization reaction after the reaction can be carried out in an inert solvent such as tetrahydrofuran, diphenylether, dimethoxyethane, methanol, ethanol, hexane, benzene, toluene, dichloromethane, chloroform, dimethylformamide, dimethylsulfoxide, etc., or a mixed solvent thereof, and in a temperature range from about 0° C. to about 150° C. The reaction time is about 1 hour to about 100 hours. This reaction can be facilitated by reacting the first product obtained in the condensation reaction with an amine to produce an enamine derivative and reacting the enamine derivative with Compound (XXIII).

(Process 9)

Compound (XIII) is reacted with Compound (XXIV), followed by cyclization to produce ketone Compound (XI).

This condensation reaction can be carried out in an inert solvent such as tetrahydrofuran, diethylether, dimethoxyethane, methanol, ethanol, hexane, toluene, benzene, dichloromethane, chloroform, dimethylformamide, dimethylsulfoxide, etc., or a mixed solvent thereof, in the presence of a base, and in a temperature range from about 0° C. to about 100° C. The reaction time is about 30 minutes to about 20 hours. As the base, lithium hydride, sodium hydride, sodium methoxide, sodium ethoxide, potassium t-butoxide, etc. can be employed. Compound (XXIV) is usually used at about 1 to about 2 mol per mol of Compound (XIII).

Cyclization reaction after the reaction can be carried out in the absence of a solvent or in an inert solvent such as tetrahydrofuran, diphenylether, dimethoxyethane, methanol, ethanol, dimethylformamide, dimethylsulfoxide, xylene, toluene, dichloromethane, chloroform, etc., or a mixed solvent thereof, and in a temperature range from room temperature to about 300° C. The reaction time is about 1 hour to about 50 hours.

(Process 10)

Compound (XIII) is halogenated and reacted with Na$_2$S, etc., and then the obtained product is reacted with Compound (XXV), followed by cyclization to produce ketone Compound (XII).

The halogenation is carried out by a known method. For example, when phosphorus trichloride is used as a halogenating agent, about ⅓ to about 5 times mol of the halogenating agent is used and the reaction is carried out in the absence of a solvent or in an inert solvent such as tetrahydrofuran, dimethoxyethane, hexane, toluene, benzene, dichloromethane, chloroform, etc., or a mixed solvent thereof, and in a temperature range from about 0° C. to about 150° C. The reaction time is about 30 minutes to about 10 hours.

The reaction with Na$_2$S, etc. is carried out in an inert solvent such as water, tetrahydrofuran, diethylether, dimethoxyethane, methanol, ethanol, hexane, toluene, benzene, dichloromethane, chloroform, etc., or a mixed solvent thereof, and in a temperature range from about 0° C. to about 100° C. The reaction time is about 30 minutes to about 10 hours.

This condensation reaction can be carried out in an inert solvent such as tetrahydrofuran, diethylether, dimethoxyethane, methanol, ethanol, hexane, toluene, benzene, dichloromethane, chloroform, dimethylformamide, dimethylsulfoxide, etc., or a mixed solvent thereof, in the presence of a base, and in a temperature range from about 0° C. to about 100° C. The reaction time is about 30 minutes to about 20 hours. As the base, lithium hydride, sodium hydride, sodium methoxide, sodium ethoxide, potassium t-butoxide, etc. can be employed. Compound (XXV) is usually used at about 1 to about 2 mol per mol of Compound (XIII).

Cyclization reaction after the reaction can be carried out in the absence of a solvent or in an inert solvent such as tetrahydrofuran, diphenylether, dimethoxyethane, methanol, ethanol, dimethylformamide, dimethylsulfoxide, xylene, toluene, dichloromethane, chloroform, etc., or a mixed solvent thereof, and in a temperature range from room temperature to about 300° C. The reaction time is about 1 hour to about 100 hours.

(Process 11)

Compound (XIII) is reacted with Compound (XXVII) [wherein R$^{21}$ is an optionally substituted phenyl such as phenyl, 4-methylphenyl, 4-methoxyphenyl, etc.] to produce a hydrazide derivative, which is reacted with Compound (XXVIII) in the presence of a base to produce ketone Compound (XXVI).

The reaction with Compound (XXVII) can be carried out in an inert solvent such as methanol, ethanol, toluene, benzene, dichloromethane, chloroform, 1,2-dichloroethane, tetrahydrofuran, diethylether, hexane, ethyl acetate, dimethylformamide, etc.,., or a mixed solvent thereof, and in a temperature range from about 0° C. to about 150° C. The reaction time is about 1 hour to about 100 hours. Aminating agent is usually used at about 1 to about 10mol per mol of Compound (XIII).

The reaction with Compound (XXVIII) and cyclization reaction can be carried out in an inert solvent such as methanol, ethanol, toluene, benzene, dichloromethane, chloroform, 1,2-dichloroethane, tetrahydrofuran, diethylether, hexane, ethyl acetate, dimethylformamide, dimethylsulfoxide, etc., or a mixed solvent thereof, and in a temperature range from about 0° C. to about 150° C. The reaction time is about 1 hour to about 50 hours. As the base, potassium carbonate, lithium hydride, sodium hydride, sodium methoxide, sodium ethoxide, potassium t-butoxide, etc. can be employed. Compound (XVIII) is usually used at about 1 to about 5 mol per mol of Compound (XIII).

The ketone compounds obtained in these Processes 1 to 11 can be used for the subsequent reaction without isolating or purifying.

In all of the above-mentioned processes, when the compounds have a carbonyl group, an amino group, a hydroxy group or a carboxyl group, these groups may be protected by ordinary protective groups introduced according to a conventional method. After the reaction, if necessary, the protective groups may be removed to obtain the desired compound.

Examples of the carbonyl-protective group include an optionally substituted cyclic or non-cyclic acetal or ketal, an optionally substituted cyclic or non-cyclic dithioacetal or dithioketal, etc.

Examples of the amino-protective group include a lower ($C_{1-6}$) alkyl-carbonyl (e.g. formyl, acetyl, propionyl, butyryl, isobutyryl, valeryl, pivaloyl, etc.), benzoyl, etc.

Examples of the hydroxy-protective group include methoxydimethylmethyl, trimethylsilyl, t-butyldimethylsilyl, trimethylsilylethoxymethyl (SEM), methoxymethyl, benzyloxymethyl, tetrahydropyranyl (THP), etc.

Examples of the carboxyl-protective group include lower ($C_{1-6}$)alkyl (e.g. methyl, ethyl, propyl, isopropyl, butyl, isobutyl, s-butyl, t-butyl, pentyl, hexyl, etc.), $C_{7-12}$ aralkyl (e.g. benzyl, phenethyl, 4-phenylpropyl, 4-phenylbutyl, 1-naphthylmethyl, etc.). In addition, the carboxyl group can be protected by transformation to 2-oxazoline ring.

These protective groups may be introduced or removed by per se known methods (e.g. a method described in Protective Groups in Organic Chemistry (J. F. W. McOmie et al.; Plenum Press Inc.) or the methods analogous thereto. For example, employable methods for removing the protective groups are methods using an acid, a base, reduction, ultraviolet ray, hydrazine, phenylhydrazine, sodium N-methyldithiocarbamate, tetrabutylammonium fluoride, palladium acetate, etc.

In the above Compound (I) or the starting material compound or synthesis intermediate thereof, basic compounds can be converted to salts using acid by a conventional method. The appropriate acid for this reaction is preferably an acid capable of providing a pharmacologically acceptable salt. Examples of such acids include inorganic acids such as hydrochloric acid, hydrobromic acid, phosphoric acid, sulfuric acid, nitric acid or sulfamic acid, etc., and organic acids such as acetic acid, tartaric acid, citric acid, fumaric acid, maleic acid, p-toluenesulfonic acid, methanesulfonic acid, glutamic acid or pyroglutamic acid, etc. When the compound obtained is a salt, it may be converted to a free base by a conventional method.

In the above Compound (I) or the starting material compound or synthesis intermediate thereof, acidic compounds having an acidic group such as —COOH, etc. can be converted to salts by a conventional method. Preferable examples of the salts include salts with alkali metal, alkaline earth metal, ammonium, substituted ammonium, etc., more specifically exemplified by salts with sodium, potassium, lithium, calcium, magnesium, aluminum, zinc, ammonium, tri-$C_{1-6}$ alkylammonium (e.g. trimethylammonium, triethylammonium, etc.), triethanolammonium, etc.

Unless otherwise stated, the above reactions are each carried out using the starting material normally in an equimolar amount, reaction time being normally 1 to 24 hours.

The thus-obtained Compound (I) or starting material compound thereof may be isolated from the reaction mixture by ordinary means of separation and purification such as extraction, concentration, neutralization, filtration, crystallization, recrystallization, column (or thin layer) chromatography, etc.

Na—H exchange inhibitor of the present invention which comprises Compound (I) exhibits excellent cell disorder ameliorating activity or cell-protecting activity (especially on the myocardium) in animals, especially mammals (for example, human, monkey, swine, dog, cat, rabbit, guinea pig, rat, mouse, etc.) and is useful as an agent for the prevention or treatment of ischemic disease (for example, ischemic cardiac disease, etc. such as myocardial infarction and dysfunctions accompanying thereto, unstable angina, etc.), restenosis after PTCA, arrhythmia, cardiac insufficiency, hypercardia, hypertension and tissue disorders accompanying thereto, ischemic encephalic disease (for example, cerebral infarction, cerebral hemorrhage, cerebral disorders accompanying to subarachnoid hemorrhage, etc.) (preferably, an agent for the prevention or treatment of ischemic cardiac disease such as myocardial infarction and dysfunctions accompanying thereto, unstable angina, etc., restenosis after PTCA, arrhythmia, cardiac insufficiency, hypercardia, etc.; more preferably an agent for the prevention or treatment of ischemic cardiac disease such as myocardial infarction, etc., cardiac insufficiency, etc.). Here, conception of the prevention of cardiac insufficiency includes the treatment of prognosis of myocardial infarction. Also, conception of the treatment of cardiac insufficiency includes inhibition of evolution or grade of cardiac insufficiency, etc.

The Compound (I) used as an active ingredient in the present invention is of low toxicity, shows good absorbability when orally administered and is superior in stability, and therefore, it can be orally or non-orally safely administered as such, or as pharmaceutical compositions such as powders, granules, tablets, capsules (including soft capsules, microcapsule), liquid preparations, injections, suppositories, etc. in combination with an appropriate pharmaceutically acceptable carrier, excipient, diluent, etc., when used as an agent as described above.

Na—H exchange inhibitor and pharmaceutical composition of the present invention can be prepared as pharmaceutical preparations by ordinary methods. The content ratio of Compound (I) in the pharmaceutical composition of the present invention is about 0.01 to about 20% (W/W).

In the present specification, "non-oral" includes subcutaneous injection, intravenous injection, intramuscular injection, intraperitoneal injection, drip infusion, etc.

Injectable preparations, for example, aqueous or oily suspensions for aseptic injection, can be prepared by methods known in relevant fields, using an appropriate dispersing agent or wetting agent and a suspending agent. The aseptic injectable preparation may be an aseptically injectable solution or suspension in a diluent or solvent which permits non-toxic non-oral administration, such as an aqueous solution, etc. Acceptable vehicles or solvents include water, Ringer's solution, isotonic saline, etc. It is also possible to use aseptic non-volatile oils in common use as solvents or suspending media. For this purpose, any non-volatile oil or fatty acid can be used, including natural, synthetic or semi-synthetic fatty oils or fatty acids, and natural, synthetic or semi-synthetic mono-, di- or tri-glycerides.

Suppositories for rectal administration may be produced as a mixture of the drug and an appropriate non-irritative shaping agent, such as cacao butter or polyethylene glycol, which is solid at normal temperatures and which is liquid at intestinal temperatures and melts and releases the drug in the rectum.

Solid dosage form for oral administration include the above-mentioned forms such as powders, granules, tablets, pills, capsules, etc. In these dosage form, the active ingredient compound may be mixed with at least one additive such as sucrose, lactose, cellulose sugar, mannitol, maltitol, dextran, starch, agar, alginate, chitin, chitosan, pectin, gum traganth, gum arabic, gelatin, collagen, casein, albumin, synthetic or semi-synthetic polymer or glyceride. Such dosage forms may contain the usual additional additives, including inert diluents, lubricants such as magnesium stearate, etc., preservatives such as paraben, sorbic acid, etc., antioxidants such as ascorbic acid, α-tocopherol, cysteine, etc., disintegrating agents, binders, thickening agents, buffers, sweeteners, flavoring agents, perfumes, etc. Tablets and pills may be produced with enteric coating.

Liquid dosage forms for oral administration include pharmaceutically acceptable emulsions, syrups, elixirs, suspensions, solutions, etc., which may contain inert diluents, such as water, in common use in relevant fields.

Although varying depending on the subject of administration, route of administration and symptoms, the dose is normally about 0.005 to 10 mg/kg, preferably 0.01 to 5 mg/kg, and more preferably about 0.02 to 1 mg/kg (about 0.3 to 600 mg/man, preferably 0.6 to 300 mg/man, and more preferably 1.2 to 60 mg/man), based on Compound (I), per administration in the case of oral administration in a patient (adult weighing about 60 kg) with myocardial infarction. It is desirable that such dosage be given about 1 to 3 times per day, depending on symptoms. In acute onset of disease, e.g., just after onset of myocardial infarction, higher doses and especially higher dosing frequencies, e.g., 4 administrations per day, may be necessary. In the case of a patient with myocardial infarction under intensive care treatment, in particular, about 100 mg/man per day may be necessary for intravenous administration.

By using Compound (I) of the present invention in combination with a compound having endothelin antagonistic activity or a salt thereof, Compound (I) can perform remarkable effects in the prevention or treatment of ischemic diseases, especially ischemic cardiac disease, and in particular, myocardial infarction, cardiac insufficiency, arrhythmia, etc., and cover up defects observed in administration of a medicine consisting of a single component. For example, Compound (I) combined with a compound having endothelin antagonistic activity or a salt thereof performs especially remarkable effects (e.g. treatment effect, safety, stability, dose, administration route, method of use, etc.) which were not observed in the administration of the respective compounds singly.

Examples of the compound having endothelin antagonistic activity or a salt thereof include, for example, compounds described in EP-A-552489, EP-A-528312, EP-A-499266, W091/13089, EP-A-436189, EP-A-457195, EP-A-510526, W092/12991, Japanese Patent Unexamined Publication No. 288099/1992, Japanese Patent Unexamined Publication No. 244097/1992, Japanese Patent Unexamined Publication No. 261198/1992, EP-A-496452, EP-A-526708, EP-A-526642, EP-A-510526, EP-A-460679, W092/20706, EP-A-626174, EP-A-655463, EP-A-714909, Japanese Patent Unexamined Publication No. 1995 (H7)-173161, etc. Among others, the following compounds are preferably employed:

disodium salt of Cyclo[-D-Asp-Asp (R1)-Asp-D-Thg(2)-Leu-D-Trp-], in which Asp (R1) is aspartic acid β-4-phenylpiperazineamide residue and Thg(2) is 2-thienylglycine residue (hereinbelow, referred to as Compound A);

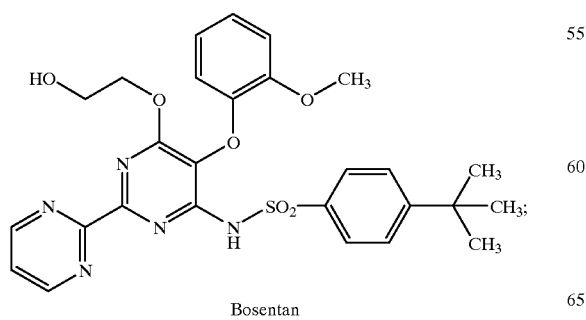

Bosentan

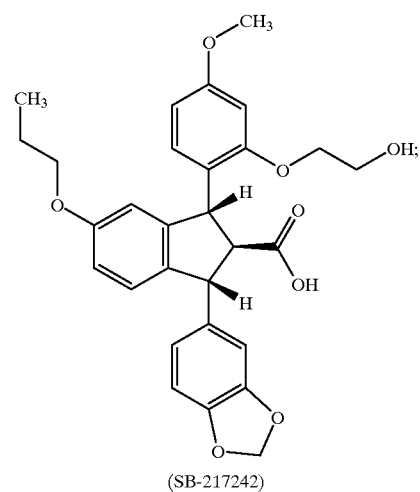

(SB-217242)

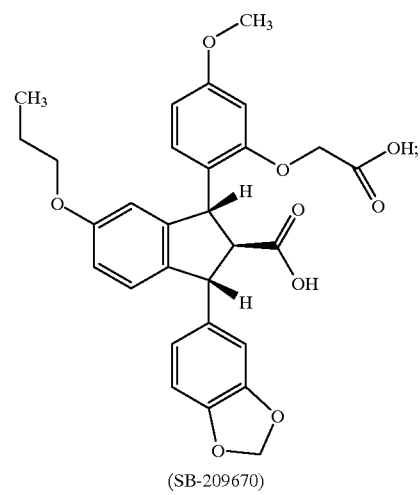

(SB-209670)

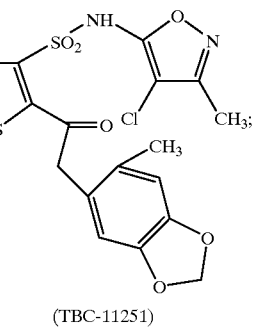

(TBC-11251)

-continued
Cyclo[-Asp-Pro-Val-leu-Trp-];
(BQ-123)

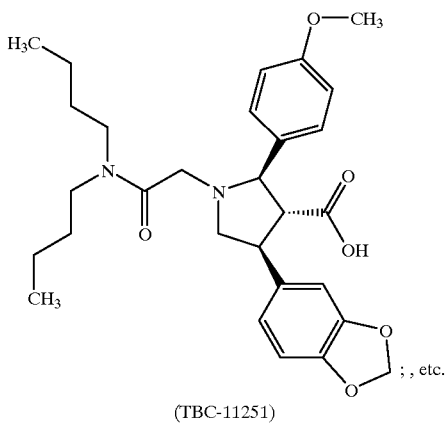

(TBC-11251)

; , etc.

Among others, Cyclo[-D-Asp-Asp (R1)-Asp-D-Thg(2)-Leu-D-Trp] in which Asp (R1) is aspartic acid β-4-phenylpiperazineamide residue and Thg(2) is 2-thienylglycine residue, or a salt thereof is preferable, and in particular, 2Na salt of Cyclo[-D-Asp-Asp (R1)-Asp-D-Thg(2)-Leu-D-Trp-], in which Asp (R1) is aspartic acid β-4-phenylpiperazineamide residue and Thg(2) is 2-thienylglycine residue, is preferable.

To state further, in the case of using the compound having endothelin antagonistic activity or a salt thereof in combination with the Compound (I) having activity for inhibiting Na—H exchange, these drugs can be formulated by mixing individually or simultaneously with pharmaceutically acceptable carriers, excipients, binders, diluents, etc., which can be administered orally or non-orally as a pharmaceutical composition. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g. a diluent when administered (e.g. a kit for injection which comprises two or more ampoules each comprising a powdery component and a diluent for mixing and dissolving two or more components when administered, etc.), a kit for administering the individually formulated agents simultaneously or with time intervals to the one and the same subject (e.g. a kit for tablets to be administered simultaneously or with time intervals, characterized by having two or more tablets each comprising an agent and said tablets being put in one or separate bags and, if necessary, a column to describe the time each agent is to be administered, etc.), etc. are also included by the pharmaceutical composition of the present invention.

When the compound having endothelin antagonistic activity or a salt thereof is used in combination with the Compound (I) having activity for inhibiting Na—H exchange, the dose of individual drugs is determined in accordance with the minimal recommendable clinical dose of individual drugs, and can be selected dependent on the subject, age, body weight, symptom, dose interval, administration route, type of formulation, combination of drugs, etc.

The dose to be administered to a specific patient is dependent on the age, body weight, general health conditions, sex, diet, dose interval, administration route, excretion rate, combination of drugs, conditions of the disease then treated, other factors, etc.

Typical daily dose of combination of the compound having endothelin antagonistic activity or a salt thereof with the compound (I) having activity for inhibiting Na—H exchange is within the range of from about ⅕₀ of the minimal recommendable clinical dose to the maximum recommendable clinical dose (preferably from minimal recommendable clinical dose or less, more preferably ½ of minimal recommendable clinical dose or less) in the case of practical administration of these compounds individually.

For example, in case of the treatment of myocardial infarction in human adult (body weight: about 60 kg) by oral administration, a single dose of the compound having activity for inhibiting Na—H exchange usually ranges from about 0. 002 to about 5 mg/kg, preferably from 0.005 to 2 mg/kg, more preferably from 0.02 to 1 mg/kg, and it is desirable that such dosage is given about once to about 3 times a day, depending on symptoms. In acute onset of disease, for example, just after myocardial infarction, higher dose and especially higher dosing frequencies, for, example, 4 times a day, may be necessary. In particular, in the case of a patient with myocardial infarction under intensive care treatment, about 50 mg/patient per day may be necessary for intravenous administration.

On the other hand, the dose ranging from about 10–300 mg/human/day (preferably, about 20–200 mg/human/day, more preferably, about 50–100 mg/human/day) of the endothelin antagonist (preferably by intravenous administration) is effectively combined with the Na—H exchange inhibitor. Needless to state, while these dosage ranges can be adjusted by a necessary unit base for dividing a daily dose, such doses are decided by taking into consideration the diseases to be treated, conditions of such disease, the age, body weight, general health conditions, sex, diet, dose intervals, administration route, excretion rate, combination of drugs, and other factors.

BEST MODE FOR CARRYING OUT THE INVENTION

The present invention is hereinafter described in more detail by means of the following Reference Examples of starting material production and Working Examples of Compound (I) production, which are not to be construed as limitative. In the present specification, room temperature means 0 to 25° C. and the abbreviations used are defined as follows:

| | |
|---|---|
| mp | melting point |
| s | singlet |
| d | doublet |
| t | triplet |
| dd | double doublet |
| ddd | double double doublet |
| q | quartet |
| m | multiplet |
| br | broad |
| $CDCl_3$ | heavy chloroform |
| $CD_3OD$ | heavy methanol |
| DMSO | dimethylsulfoxide |
| DCC | dicyclohexylcarbodiimide |
| WSC | water-soluble carbodiimide |

WORKING EXAMPLE

Reference Example 1

A mixture of 5-phenylcyclohexane-1,3-dione (15.0 g), 2-aminoethanol (6.3 g), molecular sieves 4A (100 g) and tetrahydrofuran (200 ml) was refluxed for 12 hours and cooled, and insoluble materials were filtered off. Under reduced pressure, the solvent was evaporated to give oil, which was dissolved in dimethylformamide (5 ml). To the solution were added 2-bromomesitylene (0.20 g), tetrakistriphenylphosphine palladium (30 mg) and potassium carbonate (0.28 g), and the mixture was stirred at 150° C. for 2 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was purified with silica gel column chromatography (EtOAc/hexane) to give colorless crystals of 6-phenyl-4,5,6,7-tetrahydroindol-4-one (0.11 g).

mp. 187–189° C.

$^1$H-NMR(CDCl$_3$) δ: 2.72 (1H, s), 2.76 (1H, dd, J=16, 20 Hz), 3.02 (1H, dd, J=16, 26 Hz), 3.06 (1H, dd, J=16, 20 Hz), 3.43–3.61 (1H, m), 6.56 (1H, t, J=3 Hz), 6.72 (1H, t, J=3 Hz), 7.10–7.48 (5H, m) 9.31 (1H, br).

Reference Example 2

A mixture of 5-phenylcyclohexane-1,3-dione (5.0 g), 3-aminopropan-2-ol (2.6 g), molecular sieves 4A (30 g) and tetrahydrofuran (70 ml) was refluxed for 12 hours and cooled, and insoluble materials were filtered off. Under reduced pressure, the solvent was evaporated, and the residue was dissolved in dimethylformamide (130 ml). To the solution were added 2-bromomesitylene (5.3 g), tetrakistriphenylphosphine palladium (0.77 g) and potassium carbonate (7.3 g), and the mixture was stirred at 150° C. for 4 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was purified with silica gel column chromatography (EtOAc/hexane), and the resulting crystals were recrystallized from ethyl acetate-hexane to give colorless crystals of 3-methyl-6-phenyl-4,5,6,7-tetrahydroindol-4-one (2.3 g).

mp. 169° C. (decomp.)

$^1$H-NMR(CDCl$_3$) δ: 2.32 (3H, s), 2.70 (1H, s), 2.74 (1H, dd, J=16, 21 Hz), 2.98 (1H, dd, J=13, 16 Hz), 3.02 (1H, s), 3.42–3.62 (1H, m), 6.45 (1H, s), 7.15–7.42 (5H, m) 8.14 (1H, br).

Reference Example 3

A mixture of 5-phenylcyclohexane-1,3-dione (4.0 g), 4-aminobutan-2-ol (2.5 g), molecular sieves 4A (24 g) and tetrahydrofuran (60 ml) was refluxed for 13 hours and cooled, and insoluble materials were filtered off. Under reduced pressure, the solvent was evaporated, and the residue was dissolved in dimethylformamide (100 ml). To the solution were 2-bromomesitylene(4.2 g), tetrakistriphenylphosphine palladium (0.6 g) and potassium carbonate (5.9 g), and the mixture was stirred at 150° C. for 5 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was purified with silica gel column chromatography (EtOAc/hexane) to give colorless crystals of 3-ethyl-6-phenyl-4,5,6,7-tetrahydroindol-4-one (2.6 g).

mp. 177–179° C.

$^1$H-NMR(CDCl$_3$) δ: 1.22 (3H, t, J=7 Hz), 2.64–2.86 (4H, m), 2.89–3.09 (2H, m), 3.42–3.63 (1H, m), 6.48 (1H, s), 7.22–7.42 (5H, m) 8.25 (1H, br).

Reference Example 4

A mixture of 5-phenylcyclohexane-1,3-dione (4.0 g), 2-aminopropanol (2.1 g), molecular sieves 4A (24 g) and tetrahydrofuran (60 ml) was refluxed for 14 hours and cooled, and insoluble materials were filtered off. Under reduced pressure, the solvent was evaporated, and the residue was dissolved in dimethylformamide (100 ml). To the solution were added 2-bromomesitylene (4.2. g), tetrakistriphenylphosphine palladium (0.6 g) and potassium carbonate (5.9 g), and the mixture was stirred at 150° C. for 3.5 hours and concentrated under reduced pressure. The residue was dissolved in ethyl acetate, and the solution was washed with water and saturated brine, dried with magnesium sulfate and concentrated under reduced pressure. The residue was purified with silica gel column chromatography (EtOAc), and the resulting crystals were recrystallized from ethyl acetate-hexane to give colorless crystals of 2-methyl-6-phenyl-4,5,6,7-tetrahydroindol-4-one (3.2 g).

mp. 203–205° C.

$^1$H-NMR(CDCl$_1$) δ: 2.24 (3H, s), 2.63–2.84 (2H, m), 2.85–3.14 (2H, m), 3.41–3.59 (1H, m), 6.21 (1H, s), 7.21–7.41 (5H, m) 8.85 (1H, br).

Reference Example 5

A mixture of 5-phenylcyclohexane-1,3-dione (4.0 g), 2-aminocyclohexanol (3.2 g), molecular sieves 4A (24 g) and tetrahydrofuran (60 ml) was refluxed for 12 hours and cooled, and insoluble materials were filtered off. Under reduced pressure, the solvent was evaporated, and the residue was dissolved in dimethylformamide (100 ml). To the solution were added 2-bromomesitylene (4.2 g), tetrakistriphenylphosphine palladium (0.6 g) and potassium carbonate (5.9 g), and the mixture was stirred at 150° C. for 4 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was purified with silica gel column chromatography (EtOAc), and the resulting crystals were recrystallized from ethyl acetate-hexane to give colorless crystals of 2-phenyl-1,2,3,4,5,6,7,8-octahydrocarbazol-4-one (3.4 g).

mp. 257–259° C.

$^1$H-NMR(CDCl$_3$) δ: 1.60–1.90 (4H, m), 2.26–2.82 (6H, m), 2.84–3.06 (2H, m), 3.40–3.60 (1H, m), 7.16–7.48 (5H, m), 8.07 (1H, br).

Reference Example 6

A mixture of 5-phenylcyclohexane-1,3-dione (2.0 g), 3-aminopropan-2-ol (0.97 g), molecular sieves 4A (12 g) and tetrahydrofuran (30 ml) was refluxed for 12 hours and cooled, and insoluble materials were filtered off. Under reduced pressure, the solvent was evaporated, and the residue was dissolved in dimethylformamide (40 ml). To the mixture were added 2-bromomesitylene (2.0 g), tetrakistriphenylphosphine palladium (0.29 g) and potassium carbonate (2.7 g), and the mixture was stirred at 150° C. for 5 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was recrystallized from ethyl acetate-hexane to give colorless crystals of 3-methyl-6-(2-methylphenyl)-4,5,6,7-tetrahydroindol-4-one (1.1 g).

mp. 190–191° C.

$^1$H-NMR(CDCl$_3$) δ: 2.33 (3H, s), 2.34 (3H, s), 2.53–3.08 (4H, m), 3.67–3.85 (1H, m), 6.46 (1H, s), 7.05–7.34 (4H, m), 8.30 (1H, br).

Reference Example 7

To a suspension of 60% sodium hydride (0.14 g, washed with hexane thrice) in dimethylformamide (10 ml) was added 6-phenyl-4,5,6,7-tetrahydroindol-4-one (0.6 g), and the mixture was stirred at room temperature for 30 minutes. To the mixture was added a solution of methyl iodide (0.44 g) in dimethylformamide (1 ml) at 0° C., and the mixture was stirred at room temperature for 3.5 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane). The resulting crystals were recrystallized from ethyl acetate-hexane to give colorless crystals of 1-methyl-6-phenyl-4,5,6,7-tetrahydroindol-4-one (0.57 g).

mp. 166–167° C.

$^1$H-NMR(CDCl$_3$) δ: 2.71 (1H, s), 2.75 (1H, dd, J=16, 21 Hz), 2.87 (1H, dd, J=11, 16 Hz), 3.05 (1H, dd, J=5, 16 Hz), 3.43–3.66 (1H, m), 3.56 (3H, s), 6.46–6.67 (2H, m), 7.22–7.44 (5H, m).

Reference Example 8

To a suspension of 60% sodium hydride (0.085 g, washed with hexane thrice) in dimethylformamide (10 ml) was added 3-methyl-6-phenyl-4,5,6,7-tetrahydroindol-4-one (0.4 g), and the mixture was stirred at room temperature for 30 minutes. To the mixture was added a solution of methyl iodide (0.28 g) in dimethylformamide (1 ml) at 0° C., and the mixture was stirred at room temperature for 1 hour. Under reduced pressure, the solvent was evaporated, and the residue was dissolved in ethyl acetate. The solution was washed with water and saturated brine, dried with magnesium sulfate and concentrated under reduced pressure, and the residue was recrystallized from ethyl acetate-hexane to give colorless crystals of 1,3-dimethyl-6-phenyl-4,5,6,7-tetrahydroindol-4-one (0.37 g).

mp. 155–156° C.

$^1$H-NMR(CDCl$_3$) δ: 2.31 (3H, s), 2.57–3.08 (4H, m), 3.36–3.62 (1H, m), 3.48 (3H, s), 6.32 (1H, s), 7.20–7.45 (5H, m).

Reference Example 9

To a suspension of 60% sodium hydride (0.18 g, washed with hexane thrice) in dimethylformamide (10 ml) was added 6-phenyl-4,5,6,7-tetrahydroindol-4-one (0.8 g), and the mixture was stirred at room temperature for 30 minutes. To the mixture was added a solution of 1-bromopropane (0.51 g) in dimethylformamide (3 ml), and the mixture was stirred at the same temperature for 1 hour. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give 6-phenyl-1-propyl-4,5,6,7-tetrahydroindol-4-one (0.92 g) as oil.

$^1$H-NMR(CDCl$_3$) δ: 0.92 (3H, t, J=7 Hz), 1.63–1.85 (2H, m), 2.6–2.77 (2H, m), 2.87 (1H, dd, J=11, 16 Hz), 3.04 (1H, dd, J=5, 16 Hz), 3.42–3.61 (1H, m), 3.77 (1H, t, J=7 Hz), 6.59 (1H, d, J=3 Hz), 6.76 (1H, d, J=3 Hz), 7.22–7.44 (5H, m).

Reference Example 10

To a suspension of 60% sodium hydride (0.18 g, washed with hexane thrice) in dimethylformamide (10 ml) was added 6-phenyl-4,5,6,7-tetrahydroindol-4-one (0.8 g), and the mixture was stirred at room temperature for 30 minutes. To the mixture was added a solution of benzyl bromide (0.71 g) in dimethylformamide (3 ml), and the mixture was stirred at the same temperature for 2.5 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) and recrystallized from ethyl acetate-isopropylether to give colorless crystals of 1-benzyl-6-phenyl-4,5,6,7-tetrahydroindol-4-one (0.86 g).

mp. 122–123° C.

$^1$H-NMR(CDCl$_3$) δ: 2.61–3.06 (4H, m), 3.41–3.61 (1H, m), 5.05 (2H, s), 6.66 (1H, dd, J=3, 6 Hz), 7.03 (1H, dd, J=3, 7 Hz), 7.20–7.40 (8H, m).

Reference Example 11

To a suspension of 60% sodium hydride (0.17 g, washed with hexane thrice) in dimethylformamide (10 ml) was added 6-phenyl-4,5,6,7-tetrahydroindol-4-one (0.8 g), and the mixture was stirred at room temperature for 30 minutes. To the mixture was added a solution of benzoyl chloride (0.59 g) in dimethylformamide (3 ml), and the mixture was stirred at the same temperature for 3 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give colorless crystals of 1-benzoyl-6-phenyl-4,5,6,7-tetrahydroindol-4-one (0.78 g).

mp. 140–142° C.

$^1$H-NMR(CDCl$_3$) δ: 2.72–2.99 (2H, m), 3.22–3.43 (1H, m), 3.45–3.80 (2H, m), 6.64 (1H, d, J=4 Hz), 6.91 (1H, d, J=4 Hz), 7.22 (5H, m), 7.45–7.60 (3H, m) 7.63–7.83 (2H, m).

Reference Example 12

To a suspension of 60% sodium hydride (0.18 g, washed with hexane thrice) in dimethylformamide (10 ml was added 6-phenyl-4,5,6,7-tetrahydroindol-4-one (0.8 g), and the mixture was stirred at room temperature for 30 minutes. To the mixture was added a solution of methanesulfonylchloride (0.48 g) in dimethylformamide (3 ml), and the mixture was stirred at the same temperature for 3 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) and recrystallized from ethyl acetate-hexane to give colorless crystals of 1-methanesulfonyl-6-phenyl-4,5,6,7-tetrahydroindol-4-one (0.51 g).

mp. 172–173° C.

¹H-NMR(CDCl₃) δ: 2.65–2.92 (2H, m), 3.03–3.32 (1H, m), 3.21 (3H, s), 3.44–3.66 (2H, m), 6.71 (1H, d, J=3 Hz), 7.14 (1H, d, J=3 Hz), 7.21–7.43 (5H, m).

Reference Example 13

To a suspension of 60% sodium hydride (0.085 g, washed with hexane thrice) in dimethylformamide (10 ml) was added 3-methyl-6-phenyl-4,5,6,7-tetrahydroindol-4-one (0.4 g), and the mixture was stirred at room temperature for 30 minutes. To the mixture was added a solution of methanesulfonylchloride (0.22 g) in dimethylformamide (2 ml), and the mixture was stirred at the same temperature for 18 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give colorless crystals of 1-methanesulfonyl-3-methyl-6-phenyl-4,5,6,7-tetrahydroindol-4-one (0.50 g).

mp. 80–83° C.

¹H-NMR(CDCl₃) δ: 2.29 (3H, s), 2.62–2.88 (2H, m), 2.95–3.28 (1H, m), 3.17 (3H, s), 3.41–3.63 (2H, m), 6.87 (1H, s), 7.15–7.43 (5H, m).

Reference Example 14

To a suspension of 60% sodium hydride (0.13 g, washed with hexane thrice) in dimethylformamide (10 ml) was added 3-ethyl-6-phenyl-4,5,6,7-tetrahydroindol-4-one (0.64 g), and the mixture was stirred at room temperature for 30 minutes. To the mixture was added a solution of methanesulfonylchloride (0.34 g) in dimethylformamide (1 ml), and the mixture was stirred at the same temperature for 24 hours and then at 40° C. for 5 hours. Under reduced pressure, the solvent was evaporated, and the residue was dissolved in ethyl acetate. The solution was washed with water and saturated brine, dried with magnesium sulfate and concentrated under reduced pressure. The residue was recrystallized from diisopropylether and hexane to give colorless crystals of 3-ethyl-1-methanesulfonyl-6-phenyl-4,5,6,7-tetrahydroindol-4-one (0.26 g).

mp. 153–154° C.

¹H-NMR(CDCl₃) δ: 1.18 (3H, t, J=7 Hz), 2.57–3.28 (5H, m), 3.16 (3H, s), 3.38–3.57 (2H, m), 6.87 (1H, s), 7.17–7.43 (5H, m).

Reference Example 15

To a suspension of 60% sodium hydride (0.12 g, washed with hexane thrice) in dimethylformamide (10 ml) was added 3-methyl-6-(2-methylphenyl)-4,5,6,7-tetrahydroindol-4-one (0.60 g), and the mixture was stirred at room temperature for 30 minutes. To the mixture was added a solution of methanesulfonylchloride (0.43 g) in dimethylformamide (3 ml), and the mixture was stirred at the same temperature for 12 hours. To the mixture was added methanesulfonylchloride (0.74 g), and the mixture was stirred for 3 hours. To the mixture was added sodium hydrogen carbonate solution, and the mixture was extracted with ethyl acetate. The organic layer was washed with water and saturated brine, dried with magnesium sulfate and concentrated under reduced pressure, and the residue was purified with silica gel column chromatography (EtOAc/hexane) to give crystals, which were recrystallized from ethyl acetate-hexane to give colorless crystals of 1-methanesulfonyl-3-methyl-6-(2-methylphenyl)-4,5,6,7-tetrahydroindol-4-one (0.35 g).

mp. 163–165° C.

¹H-NMR(CDCl₃) δ: 2.31 (3H, s), 2.37 (3H, s), 2.57–2.89 (5H, m), 3.04 (1H, dd, J=11, 17 Hz), 3.43 (1H, dd, J=4, 17 Hz), 3.63–3.87 (2H, m), 6.89 (1H, s), 7.15–7.34 (4H, m).

Reference Example 16

A mixture of 5-(2-fluorophenyl)-1,3-cyclohexanedione (2.0 g), 3-aminopropan-2-ol (0.95 g), molecular sieves 4A (12 g) and tetrahydrofuran (30 ml) was refluxed for 12 hours and cooled, and insoluble materials were filtered off. Under reduced pressure, the solvent was evaporated, and the residue was dissolved in dimethylformamide (40 ml). To the solution were added 2-bromomesitylene (1.9 g), tetrakistriphenylphosphine palladium (0.28 g) and potassium carbonate (2.7 g), and the mixture was stirred at 150° C. for 5 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was recrystallized from ethyl acetate-hexane to give 6-(2-fluorophenyl)-3-methyl-4,5,6,7-tetrahydroindol-4-one (0.96 g).

mp. 198–200° C.

¹H-NMR(CDCl₃) δ: 2.31 (3H, s), 2.63 (1H, dd, J=4, 16 Hz), 2.80 (1H, dd, J=12, 16 Hz), 2.83–3.16 (2H, m), 3.68–3.86 (1H, m), 6.42 (1H, s), 6.97–7.34 (4H, m), 9.71 (1H, br).

Reference Example 17

To a suspension of 60% sodium hydride (0.16 g, washed with hexane thrice) in dimethylformamide (10 ml) was added 3-methyl-6-(2-fluorophenyl)-4,5,6,7-tetrahydroindol-4-one (0.80 g), and the mixture was stirred at room temperature for 30 minutes. To the mixture was added methanesulfonylchloride (0.41 g) in dimethylformamide (3 ml), and the mixture was stirred at the same temperature for 14 hours. Under reduced pressure, the solvent was evaporated, and the residue was dissolved in ethyl acetate. The mixture was washed with sodium hydrogen carbonate solution, water and saturated brine, dried with magnesium sulfate and concentrated under reduced pressure. The residue was purified with silica gel column chromatography (EtOAc/hexane), and the resulting crystals were recrystallized from ethyl acetate-hexane to give colorless crystals of 1-methanesulfonyl-3-methyl-6-(2-fluorophenyl)-4,5,6,7-tetrahydroindol-4-one (0.47 g).

mp. 130–134° C.

¹H-NMR(CDCl₃) δ: 3.00 (3H, s), 2.71 (1H, dd, J=4, 16 Hz), 2.87 (1H, dd, J=13, 16 Hz), 2.83–3.26 (1H, m), 3.46 (1H, dd, J=4, 18 Hz), 3.68–3.94 (1H, m), 6.88 (1H, s), 7.02–7.35 (4H, m).

Reference Example 18

A mixture of 5-(2-chlorophenyl)cyclohexane-1,3-dione (2.0 g), 3-aminopropan-2-ol (0.88 g), molecular sieves 4A (12 g) and tetrahydrofuran (30 ml) was refluxed for 12 hours and cooled, and insoluble materials were filtered off. Under reduced pressure, the solvent was evaporated, and the residue was dissolved in dimethylformamide (40 ml). To the solution were added 2-bromomesitylene(1.8 g), tetrakistriphenylphosphine palladium (0.26 g) and potassium carbonate (2.5 g), and the mixture was stirred at 150° C. for 5 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was recrystallized from ethyl acetate-hexane to give 6-(2-chlorophenyl)-3-methyl-4,5,6,7-tetrahydroindol-4-one (1.3 g).

mp. 201–209° C.

$^1$H-NMR(CDCl$_3$) δ: 2.33 (3H, s), 2.54–2.86 (1H, m), 2.90 (1H, dd, J=11, 16 Hz), 3.1 (1H, dd, J=5, 16 Hz), 3.94–4.15 (1H, m), 6.46 (1H, s), 7.14–7.43 (4H, m), 8.27 (1H, br).

Reference Example 19

To a suspension of 60% sodium hydride (0.18 g, washed with hexane thrice) in dimethylformamide (10 ml) was added 6-(2-chlorophenyl)-3-methyl-4,5,6,7-tetrahydroindol-4-one (1.0 g), and the mixture was stirred at room temperature for 30 minutes. To the mixture was added methanesulfonylchloride (0.53 g) in dimethylformamide (3 ml), and the mixture was stirred at the same temperature for 9 hours. Under reduced pressure, the solvent was evaporated, and the residue was dissolved in ethyl acetate. The mixture was washed with sodium hydrogen carbonate solution, water and saturated brine, dried with magnesium sulfate and concentrated under reduced pressure. The residue was purified with silica gel column chromatography (EtOAc/hexane), and the resulting crystals were recrystallized from ethyl acetate-hexane to give colorless crystals of 6-(2-chlorophenyl)-1-methanesulfonyl-3-methyl-4,5,6,7-tetrahydroindol-4-one (0.3 g).

mp. 167–168° C.

$^1$H-NMR(CDCl$_3$) δ: 2.3 (3H, s), 2.64–2.79 (1H, m), 2.82 (1H, dd, J=11, 16 Hz), 3.03 (1H, dd, J=11, 18 Hz), 3.19 (3H, s), 3.49 (1H, dd, J=4, 18 Hz), 3.93–4.11 (1H, m), 6.88 (1H, s), 7.12–7.46 (4H, m).

Reference Example 20

A mixture of 5-thienylcyclohexane-1,3-dione (2.0 g), 3-aminopropan-2-ol (1.0 g), molecular sieves 4A (12 g) and tetrahydrofuran (30 ml) was refluxed for 12 hours and cooled, and insoluble materials were filtered off. Under reduced pressure, the solvent was evaporated, and the residue was dissolved in dimethylformamide (40 ml). To the mixture were added 2-bromomesitylene (2.1 g), tetrakistriphenylphosphine palladium (0.30 g) and potassium carbonate (2.8 g), and the mixture was stirred at 150° C. for 7 hours and concentrated under reduced pressure. The residue was dissolved in ethyl acetate, and the solution was washed with sodium hydrogen carbonate solution, water and saturated brine, dried with magnesium sulfate and concentrated under reduced pressure. The residue was recrystallized from ethyl acetate-hexane to give 3-methyl-6-(2-thienyl)-4,5,6,7-tetrahydroindol-4-one (0.72 g).

mp. 195–196° C.

$^1$H-NMR(CDCl$_3$) δ: 2.31 (3H, s), 2.72 (1H, dd, J=11, 16 Hz), 2.88 (1H, dd, J=5, 16 Hz), 3.00 (1H, dd, J=11, 16 Hz), 3.20 (1H, dd, J=5, 16 Hz), 3.70–3.93 (1H, m), 6.46 (1H, s), 6.86–7.02 (2H, m), 7.18 (1H, dd, J=1 Hz), 8.18 (1H, br).

Reference Example 21

To a suspension of 60% sodium hydride (0.11 g, washed with hexane thrice) in dimethylformamide (10 ml) was added 3-methyl-6-(2-thienyl)-4,5,6,7-tetrahydroindol-4-one (0.60 g), and the mixture was stirred at room temperature for 30 minutes. To the mixture was added a solution of methanesulfonylchloride (0.36 g) in dimethylformamide (2 ml), and the mixture was stirred at the same temperature for 14 hours. Under reduced pressure, the solvent was evaporated, and the residue was dissolved in ethyl acetate. The solution was washed with sodium hydrogen carbonate solution, water and saturated brine, dried with magnesium sulfate and concentrated under reduced pressure, and the residue was purified with silica gel column chromatography (EtOAc/hexane). The resulting crystals were recrystallized from ethyl acetate-hexane to give colorless crystals of 1-methanesulfonyl-3-methyl-6-(2-thienyl)-4,5,6,7-tetrahydroindol-4-one (0.28 g).

mp. 135–136° C.

$^1$H-NMR(CDCl$_3$) δ: 2.28 (3H, s), 2.70–3.30 (3H, m), 3.19 (3H, s), 3.61 (1H, dd, J=5, 17 Hz), 3.76–3.93 (1H, m), 6.87 (1H, s), 6.84–6.98 (2H, m), 7.19 (1H, dd, J=1, 5 Hz).

Reference Example 22

To a suspension of 60% sodium hydride (0.16 g, washed with hexane thrice) in dimethylformamide (10 ml) was added 6-phenyl-4,5,6,7-tetrahydroindol-4-one (0.8 g), and the mixture was stirred at room temperature for 30 minutes. To the mixture was added p-toluene sulfonylchloride (0.76 g), and the mixture was stirred at the same temperature for 1 hour. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give colorless crystals of 1-(4-methylphenyl)sulfonyl-6-phenyl-4,5,6,7-tetrahydroindol-4-one (1.2 g).

mp. 118–120° C.

$^1$H-NMR(CDCl$_3$) δ: 2.44 (3H, s), 2.68 (1H, s), 2.86–3.07 (1H, m), 3.36–3.56 (2H, m), 6.66 (1H, d, J=3 Hz), 7.16–7.46 (8H, m), 7.73 (1H, d, J=9 Hz).

Reference Example 23

To a solution of 5-(2-methylphenyl)cyclohexane-1,3-dione (1.0 g), acetic acid (0.27 g) and dimethylaminopyridine (0.60 g) in dimethylformamide (45 ml) was added dicyclohexylcarbodiimide (1.0 g), and the mixture was stirred at room temperature for 12 hours. Under reduced pressure, the solvent was evaporated, and to the residue was added ethyl acetate. The organic layer was washed with potassium hydrogensulfate aqueous solution, and insoluble materials were filtered, to which was added 1N sodium hydroxide solution. The aqueous layer was neutralized with 1N hydrochloric acid and extracted with ethyl acetate. The organic layer was washed with water and saturated brine, dried with magnesium sulfate and concentrated under reduced pressure to give, the residue was recrystallized from ethyl acetate-hexane to give colorless crystals of 2-(1-hydroxyethylidene)-5-(2-methylphenyl)cyclohexane-1,3-dione (0.69 g).

mp 78–81° C.

$^1$H-NMR(CDCl$_3$) δ: 2.35 (3H, s), 2.55–2.99 (4H, m), 2.66 (3H, s), 3.46–3.67 (1H, m), 3.71–3.77 (1H, m), 7.10–7.32 (4H, m).

Reference Example 24

A solution of 2-(1-hydroxyethylidene)-5-(2-methylphenyl)cyclohexane-1,3-dione (0.45 g) and hydrazine hydrate (0.1 g) in ethanol (10 ml) was refluxed for 15 minutes. Under reduced pressure, the solvent was evaporated, and the residue was recrystallized from ethyl acetate-hexane to give colorless crystals of 3-methyl-6-(2-methylphenyl)-4,5,6,7-tetrahydroindazol-4-one (0.40 g).

mp. 205–207° C.

$^1$H-NMR(CDCl$_3$) δ: 2.34 (3H, s), 2.59 (3H, s), 2.5–2.83 (2H, m), 2.96 (1H, dd, J=11, 16 Hz), 3.1 (1H, dd, J=5, 16 Hz), 3.61–3.80 (1H, m), 7.17–7.34 (5H, m).

Reference Example 25

To a solution of 5-(2-chlorophenyl)cyclohexane-1,3-dione (1.5 g), acetic acid (0.73 g) and dimethylaminopyridine (0.12 g) in dimethylformamide (65 ml) was added dicyclohexylcarbodiimide (1.5 g), and the mixture was stirred at room temperature for 13 hours. Under reduced pressure, the solvent was evaporated, and to the residue was ethyl acetate. The solution was washed with sodium hydrogen carbonate solution, water and saturated brine, dried with magnesium sulfate and concentrated under reduced pressure, and the residue was recrystallized from ethyl acetate-hexane to give colorless crystals of 2-(1-hydroxyethylidene)-5-(2-chlorophenyl)cyclohexane-1,3-dione (1.4 g).

mp. 100–101° C.

$^1$H-NMR(CDCl$_3$) δ: 2.66 (3H, s), 2.53–3.04 (4H, m), 3.76–3.95 (1H, m), 7.17–7.45 (5H, m).

Reference Example 26

A solution of 2-(1-hydroxyethylidene)-5-(2-chlorophenyl)cyclohexane-1,3-dione (0.31 g) and hydrazine hydrate (0.065 g) in ethanol (10 ml) was refluxed for 30 minutes. Under reduced pressure, the solvent was evaporated, and the residue was recrystallized from ethyl acetate-hexane to give colorless crystals of 6-(2-chlorophenyl)-3-methyl-4,5,6,7-tetrahydroindazol-4-one (0.26 g).

mp. 168–170° C.

$^1$H-NMR(CDCl$_3$) δ: 2.59 (3H, s), 2.6–2.8 (2H, m), 2.94 (1H, dd, J=11, 16 Hz), 3.22 (1H, dd, J=4, 16 Hz), 3.90–4.06 (1H, m), 7.07–7.43 (4H, m).

Reference Example 27

To a solution of 5-(2-methoxyphenyl)-1,3-cyclohexanedione (2.0 g), acetic acid (0.99 g) and dimethylaminopyridine (1.7 g) in dimethylformamide (100 ml) was added dicyclohexylcarbodiimide (2.5 g), and the mixture was stirred at room temperature for 15 hours. Under reduced pressure, the solvent was evaporated, and to the residue was added ethyl acetate. The solution was washed with potassium hydrogen sulfate solution and water, and to the solution was added 1N sodium hydroxide solution. The aqueous layer was neutralized with 1N hydrochloric acid and extracted with ethyl acetate. The organic layer was washed with water and saturated brine, dried with magnesium sulfate and concentrated under reduced pressure, and the residue was recrystallized from diisopropylether/hexane to give colorless crystals of 2-acetyl-5-(2-methoxyphenyl) cyclohexane-1,3-dione (2.0 g).

mp 65–66° C.

$^1$H-NMR(CDCl$_3$) δ: 2.53–3.06 (4H, m), 2.65 (3H, s), 3.61–3.80 (1H, m), 3.84 (3H, m), 6.84–7.03 (2H, m), 7.06–7.18 (2H, m), 7.20–7.40 (2H, m).

Reference Example 28

A solution of 2-acetyl-5-(2-methoxyphenyl)cyclohexane-1,3-dione (0.10 g) and hydrazine hydrate (0.21 g) in ethanol (20 ml) was refluxed for 30 minutes. Under reduced pressure, the solvent was evaporated, and the residue was recrystallized from ethyl acetate-hexane to give colorless crystals of 6-(2-methoxyphenyl)-3-methyl-4,5,6,7-tetrahydroindazol-4-one (0.77 g).

mp. 183–185° C.

$^1$H-NMR(CDCl$_3$) δ: 2.57 (3H, s), 2.69 (1H, dd, J=5, 17 Hz), 2.82 (1H, dd, J=11, 13 Hz), 3.01 (1H, dd, J=11, 16 Hz), 3.14 (1H, dd, J=5, 16 Hz), 3.74–3.94 (1H, m), 3.82 (3H, s), 6.86–7.0 (2H, m), 7.17–7.31 (2H, m).

Reference Example 29

A mixture of 6-(2-methoxyphenyl)-3-methyl-4,5,6,7-tetrahydroindazol-4-one (0.28 g), lithium iodide (0.44 g) and collidine (0.79 g) was refluxed for 5 hours. Under reduced pressure, collidine was evaporated, and the residue was extracted with ethyl acetate. The organic layer was washed with water and saturated brine, dried with magnesium sulfate and concentrated under reduced pressure to give, the residue was purified with silica gel column chromatography (EtOAc/hexane). The resulting crystals were recrystallized from acetone-hexane to give colorless crystals of 6-(2-hydroxyphenyl)-3-methyl-4,5,6,7-tetrahydroindazol-4-one (0.05 g).

mp. 252–255° C.

$^1$H-NMR(CDCl$_3$) δ: 2.52 (3H, s), 2.69 (1H, dd, J=4, 17 Hz), 2.89 (1H, dd, J=12, 17 Hz), 3.02–3.07 (4H, m), 3.33–3.56 (2H, br), 3.70–3.88 (1H, m), 6.77–6.88 (2H, m), 7.05–7.19 (2H, m).

Reference Example 30

To a solution of 5-(2-chlorophenyl)cyclohexane-1,3-dione (1.0 g), propionic acid (0.60 g) and dimethylaminopyridine (0.82 g) in dimethylformamide (30 ml) was added dicyclohexylcarbodiimide (1.2 g), and the mixture was stirred at room temperature for 13 hours. Under reduced pressure, the solvent was evaporated, and to the residue was ethyl acetate. The mixture was washed with 1N hydrochloric acid and water, and to the mixture was added 1N sodium hydroxide solution. The aqueous layer was washed with diethylether, neutralized with 1N hydrochloric acid and extracted with ethyl acetate. The organic layer was washed with water and saturated brine, dried with magnesium sulfate and concentrated under reduced pressure, and the residue was recrystallized from diisopropylether and hexane to give colorless crystals of 5-(2-chlorophenyl)-2-propionylcyclohexane-1,3-dione (0.67 g).

mp 63–64° C.

$^1$H-NMR(CDCl$_3$) δ: 1.07 (3H, t, J=7 Hz), 1.50 (1H, br), 2.57 (1H, dd, J=12, 16 Hz), 2.67 (1H, dd, J=2, 5 Hz), 2.68–2.96 (2H, m), 3.02 (2H, q, J=7 Hz), 3.66 (1H, m), 6.97–7.48 (4H, m).

Reference Example 31

A solution of 5-(2-chlorophenyl)-2-propionylcyclohexane-1,3-dione (0.6 g) and hydrazine hydrate hydrazine hydrate (0.12 g) in ethanol (20 ml) was refluxed for 2 hours. Under reduced pressure, the solvent was evaporated, and the residue was recrystallized from ethyl acetate-hexane to give colorless crystals of 6-(2-chlorophenyl)-3-ethyl-4,5,6,7-tetrahydroindazol-4-one (0.47 g).

mp. 180–181° C.

$^1$H-NMR(CDCl$_3$) δ: 1.33 (3H, t, J=7 Hz), 2.74 (1H, s), 2.78 (1H, s), 2.94 (1H, dd, J=11, 16 Hz), 3.01 (2H, q, J=7 Hz), 3.22 (1H, dd, J=5, 16 Hz), 3.86–4.06 (1H, m), 7.16–7.37 (3H, m), 7.41 (1H, dd, J=2, 7 Hz).

Reference Example 32

To 60% sodium hydride (0.22 g, washed with hexane thrice) was added ethanol (30 ml). To the mixture was added 5-phenylcyclohexane-1,3-dione (1.0 g) and then was added chloroacetone (0.49 g) at 0° C., and the mixture was stirred at room temperature for 20 minutes and refluxed for 13 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give colorless crystals of 3-methyl-6-phenyl-4,5,6,7-tetrahydrobenzofuran-4-one (0.18 g).

mp. 104–106° C.

$^1$H-NMR(CDCl$_3$) δ: 2.23 (3H, s), 2.60–2.86 (2H, m), 2.92–3.23 (2H, m), 3.42–3.64 (1H, m), 7.11 (1H, s), 7.16–7.48 (5H, m).

Reference Example 33

To a solution of 5-(3-bromophenyl)cyclohexane-1,3-dione (mp182–183° C.; 1.34 g) in DMF (20 ml) was added sodium methoxide (0.30 g), and the mixture was stirred, under argon atmosphere, at room temperature for 15 minutes. To the mixture was added chloroacetone (0.45 ml), and the mixture was stirred at 90° C. for 2 hours. To the mixture was added potassium carbonate (0.69 g), and the mixture was stirred at 150° C. overnight (13 hours). The reaction solution was cooled, to which was added ice-water. The mixture was extracted with ethyl acetate, and the upper layer was washed with saturated brine, dried (anhydrous magnesium sulfate), and concentrated under reduced pressure. The residue was subjected to silica gel chromatography and eluted with ethyl acetate/hexane to give 6-(3-bromophenyl)-3-methyl-4,5,6,7-tetrahydrobenzofuran-4-one (0.14 g).

$^1$H-NMR(CDCl$_3$) δ: 2.22 (3H,d,J=1.4 Hz), 2.72 (2H,d,J= 8.4 Hz), 2.98 (1H,dd,J=11.0&17.0 Hz), 3.13(1H,dd,J= 5.4&17.0 Hz), 3.49 (1H,m), 7.12 (1H,s), 7.20–7.44 (4H,m).

Reference Example 34

In dimethylformamide (10 ml) was suspended 60% sodium hydride (0.44 g, washed with hexane thrice), and to the suspension were added 5-(4-methylphenyl)cyclohexane-1,3-dione (2.0 g) and chloroacetone (0.92 g). The mixture was stirred at room temperature for 1 hour and then at 150° C. for 13 hours. Under reduced pressure, the solvent was evaporated, and the residue was dissolved in ethyl acetate, water and saturated brine, dried with magnesium sulfate and concentrated under reduced pressure. The residue was purified with silica gel column chromatography (EtOAc/hexane), and the resulting crystals were recrystallized from hexane to give colorless crystals of 3-methyl-6-(4-methylphenyl)-4,5,6,7-tetrahydrobenzofuran-4-one (0.51 g).

mp. 113–114° C.

$^1$H-NMR(CDCl$_3$) δ: 2.22 (3H, s), 2.35 (3H, s), 2.60–2.76 (2H, m), 2.99 (1H, dd, J=11, 17 Hz), 3.13 (1H, dd, J=6, 17 Hz), 3.40–3.60 (1H, m), 7.04–7.30 (4H, m), 7.11 (1H, s).

Reference Example 35

To a solution of 5-(4-fluorophenyl)cyclohexane-1,3-dione (mp175–176° C.; 1.03 g) in ethanol (10 ml) was added sodium ethoxide (0.37 g), and the mixture was stirred, under argon atmosphere, at room temperature for 15 minutes. To the mixture was added a solution of chloroacetone (0.45 ml) in DMF (10 ml), and the mixture was stirred at 100° C. overnight (13 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(4-fluorophenyl)-3-methyl-4,5,6,7-tetrahydrobenzofuran-4-one (0.12 g).

mp81–82° C. (isopropylether).

$^1$H-NMR(CDCl$_3$) δ: 2.22 (3H,d,J=1.2 Hz), 2.71 (2H,d,J= 8.6 Hz), 2.97 (1H,dd,J=10.6&16.8 Hz), 3.13(1H,dd,J= 5.4&17.0 Hz), 3.52 (1H,m), 7.04 (2H,t,J=8.6 Hz), 7.12 (1H,s), 7.26 (2H,dd,J=5.2&8.6 Hz).

Reference Example 36

In dimethylformamide (10 ml) was suspended 60% sodium hydride (0.44 g, washed with hexane thrice), and to the suspension was added 5-(4-bromophenyl)cyclohexane-1,3-dione (2.6 g) and then was added chloroacetone (0.92 g), and the mixture was stirred at room temperature for 1 hour and then at 150° C. for 13 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane). The resulting crystals were recrystallized from hexane to give colorless crystals of 3-methyl-6-(4-bromophenyl)-4,5,6,7-tetrahydrobenzofuran-4-one (0.35 g).

mp. 102–103° C.

$^1$H-NMR(CDCl$_3$) δ: 2.21 (3H, s), 2.66–2.77 (2H, m), 2.97 (1H, dd, J=11, 17 Hz), 3.18 (1H, dd, J=12, 17 Hz), 3.40–3.62 (1H, m), 7.08–7.24 (2H, m), 7.12 (1H, s), 7.43–7.55 (2H, m).

Reference Example 37

A mixture of 5-(4-methoxyphenyl)cyclohexane-1,3-dione (0.95 g), dimethyl-1,2-propadien-1-yl sulfonium bromide (1.5 g), sodium ethoxide (0.31 g) and ethanol (10 ml) was refluxed for 5 hours. Under reduced pressure, the solvent was evaporated, and the residue was dissolved in ethyl acetate. The solution was washed with water and saturated brine, dried with magnesium sulfate and concentrated under reduced pressure. The residue was dissolved in toluene (20 ml), and to the solution was added p-toluenesulfonic acid (0.85 g). The mixture was stirred at room temperature for 1 hour. To the mixture was added ethyl acetate, and the mixture was washed with sodium hydrogen carbonate solution, water and saturated brine, dried with magnesium sulfate and concentrated under reduced pressure. The residue was purified with silica gel column chromatography (EtOAc/hexane) to give colorless crystals of 6-(4-methoxyphenyl)-3-methyl-4,5,6,7-tetrahydrobenzofuran-4-one (0.14 g).

mp. 82–83° C.

$^1$H-NMR(CDCl$_3$) δ: 2.21 (3H, d, J=1 Hz), 2.60–2.80 (2H, m), 2.93 (1H, dd, J=11, 17 Hz), 3.09 (1H, dd, J=5, 17 Hz), 3.36–3.55 (1H, m), 3.79 (3H, s), 6.83–6.94 (2H, m), 7.10 (1H, d, J=1 Hz), 7.13–7.24 (2H, m).

Reference Example 38

To 60% sodium hydride (0.21 g, washed with hexane thrice) was added ethanol (30 ml), and to the mixture was added 5-(2-methylphenyl)cyclohexane-1,3-dione (1.0 g) and then was added chloroacetone (0.45 g) at 0° C. The mixture was stirred at room temperature for 20 minutes and was refluxed for 24 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give oil of 3-methyl-6-(2-methylphenyl)-4,5,6,7-tetrahydrobenzofuran-4-one (0.18 g).

$^1$H-NMR(CDCl$_3$) δ: 2.24 (3H, s), 2.36 (3H, s), 2.54–2.83 (2H, m), 2.88–3.15 (2H, m), 3.66–3.86 (1H, m), 7.12 (1H, s), 7.16–7.33 (5H, m).

Reference Example 39

To a solution of 5-(2,5-dimethylphenyl)cyclohexane-1,3-dione (mp194–195° C.; 1.08 g) in DMF (20 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (16 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2,5-dimethylphenyl)-3-methyl-4,5,6,7-tetrahydrobenzofuran-4-one (0.36 g).

$^1$H-NMR(CDCl$_3$) δ: 2.23 (3H,d,J=1.4 Hz), 2.30 (3H,s), 2.32 (3H,s), 2.60 (1H,dd,J=4.4&16.4 Hz), 2.75 (1H,dd,J=12.2&16.4 Hz), 2.99 (1H,d,J=2.0 Hz), 3.03 (1H,s), 3.73 (1H,m), 6.99 (2H,d,J=7.6 Hz), 7.09 (1H,d,J=7.6 Hz), 7.10 (1H,s), 7.11 (1H,s).

Reference Example 40

To a solution of 5-(2-trifluoromethylphenyl)cyclohexane-1,3-dione (mp198–199° C.; 1.28 g) in DMF (20 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (14 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 3-methyl-6-(2-trifluoromethylphenyl)-4,5,6,7-tetrahydrobenzofuran-4-one (0.28 g).

$^1$H-NMR(CDCl$_3$) δ: 2.24 (3H,d,J=1.2 Hz), 2.65 (1H,dd, J=4.8&16.6 Hz), 2.80 (1H,dd,J=12.2&16.4 Hz), 2.96–3.18 (2H,m), 3.98 (1H,m), 7.13 (1H,s), 7.40 (1H,m), 7.59 (2H, d,J=3.6 Hz), 7.69 (1H,d,J=8.0 Hz).

Reference Example 41

To a solution of 5-(2-fluorophenyl)cyclohexane-1,3-dione (mp180–181° C.; 1.03 g) in DMF (20 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (14 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-fluorophenyl)-3-methyl-4,5,6,7-tetrahydrobenzofuran-4-one (0.22 g).

mp71–72° C. (isopropylether).

$^1$H-NMR(CDCl$_3$) δ: 2.23 (3H,d,J=1.0 Hz), 2.69 (1H,dd, J=4.4&16.2 Hz), 2.85 (1H,dd,J=11.8&16.2 Hz), 2.98–3.22 (2H,m), 3.82 (1H,m), 7.03–7.17 (2H,m), 7.12 (1H,s), 7.22–7.31 (2H,m).

Reference Example 42

In dimethylformamide (10 ml) was suspended 60% sodium hydride (0.39 g, washed with hexane thrice), and to the suspension was added 5-(2,4-difluorophenyl)cyclohexane-1,3-dione (2.0 g) and then was added chloroacetone (0.83 g). The mixture was stirred at room temperature for 1 hour and then at 150° C. for 12 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane). The resulting crystals were recrystallized from hexane to give colorless crystals of 6-(2,4-difluorophenyl)-3-methyl-4,5,6,7-tetrahydrobenzofuran-4-one (0.13 g).

mp. 101–102° C.

$^1$H-NMR(CDCl$_3$) δ: 2.22 (3H, d, J=1 Hz), 2.67 (1H, dd, J=5, 16 Hz), 2.81 (1H, dd, J=11, 16 Hz), 2.92–3.23 (2H, m), 3.66–3.88 (1H, m), 6.76–6.92 (2H, m), 7.11 (1H, d, J=1 Hz), 7.14–7.30 (2H, m).

Reference Example 43

To a solution of 5-(2-chlorophenyl)cyclohexane-1,3-dione (mp157–158° C.; 1.11 g) in DMF (20 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (15 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-chlorophenyl)-3-methyl-4,5,6,7-tetrahydrobenzofuran-4-one (0.35 g).

$^1$H-NMR(CDCl$_3$) δ: 2.23 (3H,s), 2.73 (1H,s), 2.77 (1H, d,J=5.2 Hz), 2.97 (1H,dd,J=10.6&17.0 Hz), 3.20 (1H,dd,J= 5.2&16.8 Hz), 4.05 (1H,m), 7.12 (1H,s), 7.20–7.34 (3H,m), 7.41 (1H,dd,J=1.2& 7.0 Hz).

Reference Example 44

To a solution of 5-(2,3-dichlorophenyl)cyclohexane-1,3-dione(mp205–206° C.; 1.29 g) in ethanol (10 ml) was added sodium ethoxide (0.37 g), and the mixture was stirred, under argon atmosphere, at room temperature for 15 minutes. To the mixture was added a solution of chloroacetone (0.45 ml) in DMF (10 ml), and the mixture was stirred at 100° C. overnight (13 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2,3-dichlorophenyl)-3-methyl-4,5,6,7-tetrahydrobenzofuran-4-one (0.18 g).

mp116–117° C. (isopropylether).

$^1$H-NMR(CDCl$_3$) δ: 2.23 (3H,d,J=1.4 Hz), 2.72 (1H,s), 2.76 (1H,d,J=2.4 Hz), 2.95 (1H,dd,J=10.6&16.8 Hz), 3.21 (1H,dd,J=5.0&17.0 Hz), 4.10 (1H,m), 7.13 (1H,s), 7.22–7.28 (2H,m), 7.39–7.43 (1H,m).

Reference Example 45

To a solution of 5-(2,6-dichlorophenyl)cyclohexane-1,3-dione (mp203–204° C.; 1.29 g) in DMF (20 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (15 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2,6-dichlorophenyl)-3-methyl-4,5,6,7-tetrahydrobenzofuran-4-one (0.42 g).

$^1$H-NMR(CDCl$_3$) δ: 2.24 (3H,s), 2.47 (1H,dd,J=4.4&16.8 Hz), 2.89 (1H,dd,J=5.8&17.2 Hz), 3.61 (1H,dd,J=14.0&16.8 Hz), 3.87 (1H,dd,J=12.4&17.2 Hz), 4.54 (1H,m), 7.13 (1H,s), 7.15 (1H,dt,J=1.0&8.0 Hz), 7.28–7.39 (2H,m).

Reference Example 46

To a solution of 5-(2-bromophenyl)cyclohexane-1,3-dione (mp174–175° C.; 1.07 g) in DMF (15 ml) was added 60% sodium hydride (0.18 g), and the mixture was stirred, under argon atmosphere, at room temperature for 15 minutes. To the mixture was added chloroacetone (0.36 ml), and the mixture was stirred at 150° C. overnight (13 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-bromophenyl)-3-methyl-4,5,6,7-tetrahydrobenzofuran-4-one (0.28 g).

$^1$H-NMR(CDCl$_3$) δ: 2.23 (3H,s), 2.72 (1H,s), 2.76 (1H, d,J=2.4 Hz), 2.94 (1H,dd,J=10.8&17.2 Hz), 3.20 (1H,dd,J=5.2&17.0 Hz), 4.02 (1H,m), 7.09–7.17 (1H,m), 7.13 (1H,s), 7.29–7.35 (2H,m), 7.59 (1H,d,J=8.4 Hz ).

Reference Example 47

To a solution of 5-(2-methoxyphenyl)cyclohexane-1,3-dione (mp144–145° C.; 1.09 g) in DMF (15 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (14 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-methoxyphenyl)-3-methyl-4,5,6,7-tetrahydrobenzofuran-4-one (0.20 g).

mp79–80° C. (isopropylether).

$^1$H-NMR(CDCl$_3$) δ: 2.23 (3H,d,J=1.2 Hz), 2.66 (1H,dd, J=4.2&16.4 Hz), 2.84 (1H,dd,J=12.0&16.4 Hz), 3.05 (1H, d,J=3.4 Hz), 3.09 (1H,s), 3.83 (3H,s), 3.88 (1H,m), 6.90 (1H,d,J=8.2 Hz), 6.95 (1H,dt,J=1.2&7.6 Hz), 7.10 (1H,d,J=1.4 Hz), 7.18–7.29 (2H,m).

Reference Example 48

To a solution of 5-(2-furyl)cyclohexane-1,3-dione (mp155–156° C.; 0.89 g) in DMF (18 ml) was added 60% sodium hydride (0.22 g), and the mixture was stirred, under argon atmosphere, at room temperature for 15 minutes. To the mixture was added chloroacetone (0.45 ml), and the mixture was stirred at 150° C. overnight (15 hours). The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-furyl)-3-methyl-4,5,6,7-tetrahydrobenzofuran-4-one (0.23 g).

mp60–61° C. (isopropylether).

$^1$H-NMR(CDCl$_3$) δ: 2.21 (3H,d,J=1.4 Hz), 2.70 (1H,dd, J=10.2& 16.4 Hz), 2.84 (1H,dd,J=5.0&16.8 Hz), 3.05 (1H, dd,J=9.6&17.2 Hz), 3.24 (1H,dd,J=5.4&17.2 Hz), 3.63 (1H, m), 6.09 (1H,d,J=3.2 Hz), 6.31 (1H,dd,J=1.8&3.4 Hz), 7.11 (1H,s), 7.35 (1H,d,J=1.8 Hz).

Reference Example 49

In dimethylformamide (10 ml) was suspended 60% sodium hydride (0.44 g, washed with hexane thrice), and to the suspension was added 5-(2-thienyl)cyclohexane-1,3-dione (1.9 g) and then was added chloroacetone (0.92 g). The mixture was stirred at room temperature for 1 hour and then at 150° C. for 13 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane). The resulting crystals were recrystallized from hexane to give colorless crystals of 3-methyl-6-(2-thienyl)-4,5,6,7-tetrahydrobenzofuran-4-one (0.34 g).

mp. 81–82° C.

$^1$H-NMR(CDCl$_3$) δ: 2.22 (3H, s), 2.75 (1H, dd, J=11, 17 Hz), 2.90 (1H, dd, J=4, 17 Hz), 3.05 (1H, dd, J=10, 17 Hz), 3.30 (1H, dd, J=5, 17 Hz), 3.76–3.93 (1H, m), 6.87–7.03 (2H, m), 7.12 (1H, s), 7.21 (1H, dd, J=1, 5 Hz)

Reference Example 50

To a solution of 5-(5-methyl-2-thienyl)cyclohexane-1,3-dione (mp178–179° C.; 1.04 g) in ethanol (15 ml) was added sodium ethoxide (0.37 g), and the mixture was stirred, under argon atmosphere, at room temperature for 15 minutes. To the mixture was added chloroacetone (0.45 ml), and the mixture was stirred at 100° C. for 1 hour. The reaction solution was cooled concentrated under reduced pressure. To the residue was added mesitylene(15 ml), and the mixture was stirred at 150° C. for 4 hours. The reaction solution was cooled and concentrated under reduced pressure. To the residue was added ice-water, and the mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(5-methyl-2-thienyl)-3-methyl-4,5,6,7-tetrahydrobenzofuran-4-one (0.18 g).

$^1$H-NMR(CDCl$_3$) δ: 2.21 (3H,s), 2.45 (3H,s), 2.69 (1H, dd,J=11.0&16.4 Hz), 2.85 (1H,dd,J=4.4&16.4 Hz), 3.00 (1H,dd,J=10.4&17.2 Hz), 3.24 (1H,dd,J=5.0&17.0 Hz), 3.73 (1H,m), 6.59 (1H,d,J=3.2 Hz), 6.67 (1H,d,J=3.4 Hz), 7.11 (1H,s).

Reference Example 51

To a solution of 5-phenylcyclohexane-1,3-dione (0.94 g) in DMF (20 ml) were added potassium carbonate (0.76 g), bromomethyltrifluoromethylketone (1.05 g), and the mixture was stirred, under argon atmosphere, at room temperature for 2 hours. To the mixture was added potassium carbonate (0.69 g), and the mixture was stirred at 150° C. overnight (13 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-phenyl-3-trifluoromethyl-4,5,6,7-tetrahydrobenzofuran-4-one (0.14 g).

mp107–108° C. (isopropylether).

$^1$H-NMR(CDCl$_3$) δ: 2.80 (1H,d,J=2.4 Hz), 2.85 (1H,s), 3.09 (1H,dd,J=10.8&17.2 Hz), 3.23 (1H,dd, J=5.4&17.2 Hz), 3.59 (1H,m), 7.26–7.44 (5H,m), 7.72 (1H,d,J=1.4 Hz).

Reference Example 52

To a solution of 5-(4-fluorophenyl)cyclohexane-1,3-dione (1.03 g) in ethanol (20 ml) was added sodium ethoxide (0.37 g), and the mixture was stirred, under argon atmosphere, at room temperature for 15 minutes. To the mixture was added bromomethyltrifluoromethylketone (1.05 g), and the mixture was stirred, under argon atmosphere, at room temperature for 2 hours. The reaction solution was concentrated under reduced pressure, and to the residue were added DMF (20 ml) and potassium carbonate (0.69 g). The mixture was stirred, under argon atmosphere, at 150° C. overnight (15 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(4-fluorophenyl)-3-trifluoromethyl-4,5,6,7-tetrahydrobenzofuran-4-one (0.27 g).

mp105–106° C. (isopropylether).

$^1$H-NMR(CDCl$_3$) δ: 2.76 (1H,d,J=2.2 Hz), 2.80 (1H,s), 3.04 (1H,dd,J=11.0&17.2 Hz), 3.21 (1H,dd,J=5.6&17.2 Hz), 3.57 (1H,m), 7.05 (2H,t,J=8.8 Hz), 7.25 (2H,dd,J=5.8&8.8 Hz), 7.73 (1H,s).

Reference Example 53

A mixture of 5-(2-methylphenyl)cyclohexane-1,3-dione (2.0 g), 1-bromo-3,3,3-trifluoroacetone (1.9 g), potassium carbonate (2.7 g) and dimethylformamide (30 ml) was stirred at room temperature for 2 hours, and then at 150° C. for 12 hours. Under reduced pressure, the solvent was evaporated, and to the residue was added ethyl acetate. The mixture was washed with water and saturated brine, dried with magnesium sulfate and concentrated under reduced pressure, and the residue was purified with silica gel column chromatography (EtOAc/hexane). The resulting crystals were recrystallized from isopropylether and hexane to give colorless crystals of 3-trifluoromethyl-6-(2-methylphenyl)-4,5,6,7-tetrahydrobenzofuran-4-one (0.26 g).

mp. 105–107° C.

$^1$H-NMR(CDCl$_3$) δ: 2.37 (3H, s), 2.66–2.90 (2H, m), 2.97–3.19 (2H, m), 3.73–3.92 (1H, m), 7.18–7.33 (4H, m), 7.74 (1H, d, J=2 Hz).

Reference Example 54

To a solution of 5-(2-bromophenyl)cyclohexane-1,3-dione (1.34 g) in DMF (20 ml) was added sodium methoxide (0.30 g), and the mixture was stirred, under argon atmosphere, at room temperature for 15 minutes. To the mixture was added bromomethyltrifluoromethylketone (1.05 g), and the mixture was stirred, under argon atmosphere, at room temperature for 2 hours. To the mixture was added potassium carbonate (0.69 g), and the mixture was stirred, under argon atmosphere, at 150° C. overnight (15 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-bromophenyl)-3-trifluoromethyl-4,5,6,7-tetrahydrobenzofuran-4-one (0.29 g).

$^1$H-NMR(CDCl$_3$) δ: 2.82 (2H,d,J=8.4 Hz), 3.02 (1H,dd, J=10.8&17.4 Hz), 3.30 (1H,dd,J=5.0&17.2 Hz), 4.07 (1H, m), 7.12–7.21 (1H,m), 7.26–7.40 (2H,m), 7.62 (1H,d,J=8.2 Hz), 7.74 (1H,d,J=1.4 Hz).

Reference Example 55

To a solution of 5-(2-furyl)cyclohexane-1,3-dione (0.89 g) in ethanol (15 ml) was added sodium ethoxide (0.37 g), and the mixture was stirred, under argon atmosphere, at room temperature for 15 minutes. To the mixture was added bromomethyltrifluoromethylketone (1.05 g), and the mixture was stirred, under argon atmosphere, at room temperature for 2 hours. The reaction solution was concentrated under reduced pressure, and to the residue were added DMF (20 ml) and potassium carbonate (0.69 g). The mixture was stirred, under argon atmosphere, at 150° C. overnight (15 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-furyl)-3-trifluoromethyl-4,5,6,7-tetrahydrobenzofuran-4-one (0.23 g).

mp94–95° C. (isopropylether).

$^1$H-NMR(CDCl$_3$) δ: 2.79 (1H,dd,J=10.4&16.6 Hz), 2.93 (1H,dd,J=4.6 &17.2 Hz), 3.14 (1H,dd,J=9.0&17.2 Hz), 3.33 (1H,dd,J=5.0&17.6 Hz), 3.70 (1H,m), 6.12 (1H,d,J=3.2 Hz), 6.32 (1H,dd,J=1.8&3.2 Hz), 7.36 (1H,d,J=1.8 Hz), 7.72 (1H,d,J=1.4 Hz).

Reference Example 56

To a solution of 5-phenylcyclohexane-1,3-dione (0.94 g) in ethanol (15 ml) was added sodium ethoxide (0.37 g), and the mixture was stirred, under argon atmosphere, at room temperature for 15 minutes. To the mixture was added ethyl bromopyruvate (0.83 ml), and the mixture was stirred, under argon atmosphere, at room temperature for 2 hours. The reaction solution was concentrated under reduced pressure, and to the residue was added xylene (15 ml), and the mixture was stirred, under argon atmosphere, at 150° C. for 4 hours. The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 3-ethoxycarbonyl-6-phenyl-4,5,6,7-tetrahydrobenzofuran-4-one (1.04 g).

mp103–104° C. (isopropylether).

$^1$H-NMR(CDCl$_3$) δ: 1.38 (3H,t,J=7.2 Hz), 2.81 (1H,d,J=1.6 Hz), 2.85 (1H,s), 3.08 (1H,dd,J=10.8&17.0 Hz), 3.23 (1H,dd,J=5.2&17.2 Hz), 3.57 (1H,m), 4.36 (2H,q,J=7.2 Hz), 7.27–7.41 (5H,m), 7.93 (1H,s).

Reference Example 57

To a solution of 5-(2-chlorophenyl)cyclohexane-1,3-dione (2.23 g) in ethanol (30 ml) was added sodium ethoxide (0.75 g), and the mixture was stirred, under argon atmosphere, at room temperature for 15 minutes. To the mixture was added ethyl bromopyruvate (1.66 ml), and the mixture was stirred, under argon atmosphere, at room temperature for 2 hours. The reaction solution was concentrated under reduced pressure, and to the residue were added DMF (30 ml) and potassium carbonate (1.38 g). The mixture was stirred, under argon atmosphere, at 150° C. overnight (14 hours). The reaction solution was cooled, and to the mixture was added ice-water. The mixture was extracted with ethyl acetate. The upper layer was washed with saturated brine, dried (anhydrous magnesium sulfate), and concentrated under reduced pressure, and the residue was subjected to silica gel chromatography and eluted with ethyl acetate/hexane to give 6-(2-chlorophenyl)-3-ethoxycarbonyl-4,5,6,7-tetrahydrobenzofuran-4-one (0.14 g).

$^1$H-NMR(CDCl$_3$) δ: 1.37 (3H,t,J=7.2 Hz), 2.82 (1H,s), 2.86 (1H,d,J=1.4 Hz), 3.03 (1H,dd,J=10.6&17.2 Hz), 3.29 (1H,dd,J=5.2&17.2 Hz), 4.07 (1H,m), 4.36 (2H,q,J=7.2 Hz), 7.20–7.33 (3H,m), 7.42 (1H,dd,J=2.2&6.4 Hz), 7.94 (1H,s).

Reference Example 58

To a solution of 2-butyn-1-ol (75.4 g) in tetrahydrofuran (800 ml) was added methanesulfonylchloride (129.4 g) and then was added dropwise triethylamine (130.6 g), and the mixture was stirred at room temperature for 19hours. Under reduced pressure, the solvent was evaporated, and to the residue was added sodium hydrogen carbonate solution. The mixture was extracted with ethyl acetate, and the organic layer was washed with water and saturated brine and dried with magnesium sulfate. Under reduced pressure, the solvent was evaporated, and the residue was dissolved in dimethylformamide (2000 ml). To the solution was added potassium phthalimide (166.6 g), and the mixture was stirred at 60° C. for 19 hours. Under reduced pressure, the solvent was evaporated, and to the residue was added water. Precipitated crystals were washed with water and ethyl acetate, and dried. To the resulting crystals were added ethanol (1500 ml) and hydrazine-hydrate (57.7 g), and the mixture was refluxed for 2.5 hours and cooled. To the mixture was added concentrated hydrochloric acid (140 ml) to make it acidic, insoluble materials were filtered off. Insoluble materials were washed with water, and the filtrate combined with washing solution was concentrated. To the residue was added ethanol, and insoluble materials were filtered off. The filtrate was concentrated, and the residue was recrystallized from ethyl acetate-ethanol to give 1-amino-2-butyne hydrochloride (75.0 g) as colorless crystals.

mp 205° C.

$^1$H-NMR(CDCl$_3$) δ: 1.85 (3H, t, J=3 Hz), 3.63 (2H, q, J=3 Hz), 8.46 (3H, br).

Reference Example 59

To a mixture of 5-(2-methylphenyl)cyclohexane-1,3-dione (1.5 g), 1-amino-2-butyne hydrochloride (0.86 g), molecular sieves 4A (2 g) and tetrahydrofuran (20 ml) was added triethylamine (0.74 g), and the mixture was stirred at room temperature for 1 hour and then refluxed for 17 hours and cooled. Insoluble materials were filtered off. Under reduced pressure, the solvent was evaporated, and the residue was stirred at 220° C. for 4 hours, to which were added ethyl acetate and sodium hydrogen carbonate solution. The organic layer was washed with water and saturated brine, dried with magnesium sulfate and concentrated under reduced pressure, and the residue was purified with silica gel column chromatography (EtOAc/hexane). The resulting crystals were recrystallized from ethyl acetate-hexane to give colorless crystals of 4-methyl-7-(2-methylphenyl)-5,6,7,8-tetrahydroquinolin-5-one (0.52 g).

mp. 104–106° C.

$^1$H-NMR(CDCl$_3$) δ: 2.36 (3H, s), 2.70 (3H, s), 2.75–3.03 (2H, m), 3.17–3.48 (2H, m), 3.54–3.77 (1H, m), 7.08 (1H, d, J=5 Hz), 7.10–7.34 (4H, m) 8.47 (1H, d, J=5 Hz).

Reference Example 60

In ethanol (20 ml) 5-(2,5-dimethylphenyl)cyclohexane-1,3-dione (1.73 g) and ammonium acetate (1.93 g) were refluxed for 14 hours. The reaction solution was concentrated under reduced pressure, and to the residue was added water (20 ml). The resulting crystals were filtered, washed with water and toluene, and dried to give 1-amino-5-(2,5-dimethylphenyl)cyclohexen-3-one (1.72 g) as pale yellow crystals.

mp. 169–170° C.

$^1$H-NMR(DMSO-d$_6$) δ: 2.11 (1H, d), 2.24 (3H, s), 2.25 (3H, s), 2.39 (2H, m), 2.51 (1H, m); 3.29 (1H, m), 5.01 (1H, s), 6.80 (2H, broad), 6.92 (1H,d), 7.04 (1H, d), 7.14 (1H, s).

Reference Example 61

In a mixture of ethanol (35 ml) and toluene (90 ml) was dissolved 1-amino-5-(2,5-dimethylphenyl)cyclohexen-3-one (1.7 g), and to the solution were added 3-oxobutylaldehydedimethylacetal (2.66 g) and granulated potassium hydroxide (440 mg). The mixture was stirred at 115° C. (bath temperature), and to the mixture was added granulated potassium hydroxide (90 mg), 30 minutes later; 1 hour later; and 1.5 hours, respectively. The reaction solution was stirred at the same temperature for 1 hour and cooled. Under reduced pressure, the solvent was evaporated, and to the residue were added ethyl acetate (40 ml) and water (20 ml). The mixture was shaken and separated ethyl acetate layer was washed with brine. Under reduced pressure, ethyl acetate was evaporated, and the residue was purified with silica gel column chromatography (EtOAc/hexane) and eluted with ethyl acetate/hexane to give 7-(2,5-dimethylphenyl)-4-methyl-5,6,7,8-tetrahydroquinolin-5-one (1.37 g) as colorless crystals.

mp. 95–96° C.

¹H-NMR(CDCl₃) δ: 2.33 (3H, s), 2.35 (3H, s), 2.72 (3H, s), 2.91 (2H, m), 3.35 (2H, m), 3.66 (1H, m), 7.09 (4H, m), 8.50 (1H, d).

Reference Example 62

To a mixture of 5-(2-fluorophenyl)cyclohexane-1,3-dione (0.98 g), 1-amino-2-butyne hydrochloride (0.5 g), molecular sieves 4A (2 g) and tetrahydrofuran (20 ml) was added triethylamine (0.48 g), and the mixture was stirred at room temperature for 1 hour, refluxed for 12 hours and cooled. Insoluble materials were filtered off. Under reduced pressure, the solvent was evaporated, and the residue was stirred for 6 hours at 220° C. and cooled, to which were added ethyl acetate and sodium hydrogen carbonate solution. The organic layer was washed with water and saturated brine, dried with magnesium sulfate and concentrated under reduced pressure, and the residue was purified with silica gel column chromatography (EtOAc/hexane) to give oil of 7-(2-fluorophenyl)-4-methyl-5,6,7,8-tetrahydroquinolin-5-one (0.35 g).

¹H-NMR(CDCl₃) δ: 2.70 (3H, s), 2.83–3.08 (2H, m), 3.29–3.46 (2H, m), 3.71–3.77 (1H, m), 7.02–7.36 (5H, m), 8.49 (1H, d, J=4 Hz).

Reference Example 63

To a mixture of 5-(2,4-difluorophenyl)cyclohexane-1,3-dione (2.0 g), 1-amino-2-butyne hydrochloride (0.94 g), molecular sieves 4A (4 g) and tetrahydrofuran (40 ml) was added triethylamine (0.90 g), and the mixture was stirred at room temperature for 1 hour, refluxed for 12 hours and cooled. Insoluble materials were filtered off. Under reduced pressure, the solvent was evaporated, and the residue was stirred for 5 hours at 220° C., to which were added ethyl acetate and sodium hydrogen carbonate solution. The organic layer was washed with water and saturated brine, dried with magnesium sulfate and concentrated under reduced pressure to give, the residue was purified with silica gel column chromatography (EtOAc/hexane). The resulting crystals were recrystallized from isopropylether and hexane to give colorless crystals of 7-(2,4-difluorophenyl)-4-methyl-5,6,7,8-tetrahydroquinolin-5-one (0.47 g).

mp. 106–107° C.

¹H-NMR(CDCl₃) δ: 2.70 (3H, s), 2.78–3.04 (2H, m), 3.46–3.52 (1H, m), 3.63–3.83 (1H, m), 6.75–6.93 (2H, m), 7.10 (1H, d, J=5 Hz), 7.12–7.32 (1H, m), 8.49 (1H, d, J=5 Hz).

Reference Example 64

To a mixture of 5-(2-chlorophenyl)-1,3-cyclohexanedione (1.1 g), 1-amino-2-butyne hydrochloride (0.5 g), molecular sieves 4A (2 g) and tetrahydrofuran (20 ml) was added triethylamine (0.48 g), and the mixture was stirred at room temperature for 1 hour and then refluxed for 12 hours and cooled. Insoluble materials were filtered, and under reduced pressure, the solvent was evaporated. The residue was stirred for 4 hours at 220° C., to which were added ethyl acetate and sodium hydrogen carbonate solution. The organic layer was washed with water and saturated brine, and dried with magnesium sulfate. Under reduced pressure, the mixture was concentrated, and the residue was subjected to silica gel column chromatography (EtOAc/hexane) to give crystals, which were recrystallized from ethyl acetate-hexane to give colorless crystals of 7-(2-chlorophenyl)-4-methyl-5,6,7,8-tetrahydroquinolin-5-one (0.20 g)

mp. 97–98° C.

¹H-NMR(CDCl₃) δ: 2.71 (3H, s), 2.84 (1H, dd, J=13, 16 Hz), 3.02 (1H, ddd, J=2, 4, 16, Hz), 3.30 (1H, dd, J=12, 17 Hz), 3.48 (1H,ddd, J=2, 4, 17 Hz), 3.88–4.07 (1H, m), 7.11 (1H, d, J=5 Hz), 7.16–7.34 (4H, m), 8.50 (1H, d, J=5 Hz).

Reference Example 65

To a solution of 1-amino-5-(2-chlorophenyl)cyclohexen-3-one (2.7 g) in ethanol (50 ml) and toluene (150 ml) were added acetylacetoaldehyde-dimethylacetal (4.0 g) and 85% potassium hydroxide (0.67 g), and the mixture was refluxed. With intervals of 30 minutes, 85% potassium hydroxide (0.14 g) was added 3 times to the mixture. Then, the mixture was refluxed for 1 hour. Under reduced pressure, the solvent was evaporated, and to the residue was added ethyl acetate. The mixture was washed with water and saturated brine, and dried with magnesium sulfate. Under reduced pressure, the mixture was concentrated, and the residue was subjected to silica gel column chromatography (EtOAc/hexane) to give crystals of 7-(2-chlorophenyl)-4-methyl-5,6,7,8-tetrahydroquinolin-5-one (2.5 g).

Melting Point and NMR data agreed with those of the compound obtained in Reference Example 64.

Reference Example 66

A mixture of 5-(2,3-dichlorophenyl)cyclohexane-1,3-dione (1.8 g) and ammonium acetate (1.7 g) in ethanol (20 ml) was refluxed for 14 hours, and the reaction solution was concentrated under reduced pressure. To the residue was added water (20 ml), and the resulting crystals were filtered. The crystals were washed with water and toluene, and dried to give 1-amino-5-(2,3-dichlorophenyl)cyclohexen-3-one (1.6 g) as pale yellow crystals.

mp. 209–210° C.

¹H-NMR(DMSO-d₆) δ: 2.24 (1H, dd), 2.61 (3H, m), 3.67 (1H, m), 5.03 (1H, s), 6.90 (2H, broad), 7.37 (1H, t), 7.48 (1H, dd), 7.55 (1H, dd).

Reference Example 67

In a mixture of ethanol (30 ml) and toluene (90 ml) was dissolved 1-amino-5-(2, 3-dichlorophenyl)cyclohexen-3-one (1.5 g), and to the solution were added 3-oxobutylaldehydedimethylacetal (2 g) and granulated potassium hydroxide (330 mg). The mixture was stirred at 115° C. (bath temperature), and to the mixture was added granulated potassium hydroxide (70 mg), 30 minutes later; 1 hour later; and 1.5 hours, respectively. The reaction solution was stirred at the same temperature for 1 hour, cooled and concentrated under reduced pressure, and to the residue were added ethyl acetate (50 ml) and water (20 ml). The mixture was shaken and separated ethyl acetate layer was washed with brine. Under reduced pressure, ethyl acetate was evaporated, and the residue was purified with silica gel column chromatography (EtOAc/hexane) and eluted with ethyl acetate/hexane to give 7-(2,3-dichlorophenyl)-4-methyl-5,6,7,8-tetrahydroquinolin-5-one (1.05 g) as colorless crystals.

mp. 123–124° C.

¹H-NMR(CDCl₃) δ: 2.72 (3H, s), 2.81 (1H, dd), 3.03 (1H, dd), 3.29 (1H, dd), 3.49 (1H, ddd), 4.03 (1H, m), 7.13 (1H, d), 7.24 (2H, m), 7.43 (1H, m), 8.51 (1H, d).

Reference Example 68

A mixture of 5-(2,6-dichlorophenyl)cyclohexane-1,3-dione (1.8 g) and ammonium acetate (1.7 g) in ethanol (20 ml) was refluxed for 60 hours, and the reaction solution was concentrated under reduced pressure. To the residue were added ethyl acetate (80 ml) and water (20 ml), and the mixture was shaken and separated. The ethyl acetate layer was washed with water (10 ml, thrice) and concentrated under reduced pressure. To the residue was added ethyl acetate (8 ml) to precipitate crystals, which were filtered and dried to give 1-amino-5-(2,6-dichlorophenyl)cyclohexen-3-one (1.43 g) as pale yellow crystals.

mp. 216–217° C.

$^1$H-NMR(DMSO-d$_6$) δ: 2.00 (1H, dd), 2.24 (1H, dd), 3.05 (1H, dd), 3.28 (1H, dd), 4.14 (1H, m), 5.04 (1H, s), 6.87 (2H, broad), 7.32 (1H, t), 7.47 (2H, m).

Reference Example 69

In a mixture of ethanol (23 ml) and toluene (70 ml) was dissolved 1-amino-5-(2,6-dichlorophenyl)cyclohexen-3-one (1.25 g), and to the solution were added 3-oxobutylaldehydedimethylacetal (1.84 g) and granulated potassium hydroxide (303 mg). The mixture was stirred at 115° C. (bath temperature), and to the mixture was added granulated potassium hydroxide (62 mg), 30 minutes later; 1 hour later; and 1.5 hours, respectively. The reaction solution was stirred at the same temperature for 1 hour, cooled and concentrated under reduced pressure, and to the residue were added ethyl acetate (50 ml) and water (15 ml). The mixture was separated and the separated upper layer was washed with saturated brine and concentrated under reduced pressure. The residue was purified with silica gel column chromatography (EtOAc/hexane) and eluted with ethyl acetate/hexane, which was concentrated under reduced pressure. The residue was dissolved in a mixture of ether (4 ml) and ethanol (2 ml), and to the solution was added concentrated hydrochloric acid (0.25 ml). Precipitated crystals were filtered, washed with the same mixed solvent and dried to give 7-(2,6-dichlorophenyl)-4-methyl-5,6,7,8-tetrahydroquinolin-5-one hydrochloride (0.75 g) as colorless crystals.

mp. 184–185° C.

$^1$H-NMR(DMSO-d$_6$) δ: 2.60 (1H, ddd), 2.79 (3H, s), 3.35 (1H, ddd), 3.74 (1H, dd), 4.19 (1H, dd), 4.53 (1H, m), 7.38 (1H, t), 7.54 (2H, d), 7.75 (1H, d), 8.77 (1H, d).

Reference Example 70

To a mixture of 5-(2-bromophenyl)cyclohexane-1,3-dione (1.5 g), 1-amino-2-butyne hydrochloride (0.59 g) and tetrahydrofuran (30 ml) was added triethylamine (0.57 g). The mixture was stirred at room temperature for 1 hour, refluxed for 13 hours and cooled, and insoluble materials were filtered off. Under reduced pressure, the solvent was evaporated, and to the residue was added diphenylether. The mixture was stirred at 250° C. for 12 hours and cooled, and to the mixture was added diethylether. The mixture was extracted with 1N hydrochloric acid, and the aqueous layer was washed with diethylether, neutralized with 1N sodium hydroxide and extracted with ethyl acetate. The organic layer was washed with water and saturated brine, dried with magnesium sulfate and concentrated under reduced pressure to give crystals of 7-(2-bromophenyl)-4-methyl-5,6,7,8-tetrahydroquinolin-5-one (0.52 g).

mp. 106–107° C.

$^1$H-NMR(CDCl$_3$) δ: 2.71 (3H, s), 2.82 (1H, dd, J=13, 16 Hz), 3.03 (1H, ddd, J=2, 4, 10 Hz), 3.28 (1H, dd, J=12, 17 Hz), 3.49 (1H, dq, J=2, 4, 11 Hz), 3.86–4.06 (1H, m), 7.08–7.47 (4H, m), 7.57–7.66 (1H, m), 8.50 (1H, d, J=5 Hz).

Reference Example 71

To a mixture of 5-(2-methoxyphenyl)-1,3-cyclohexanedione (1.0 g), 1-amino-2-butyne hydrochloride (0.5 g), molecular sieves 4A (2 g) and tetrahydrofuran (20 ml) was added triethylamine (0.48 g). The mixture was stirred at room temperature for 1 hour, refluxed for 12 hours and cooled, and insoluble materials were filtered off. Under reduced pressure, the solvent was evaporated, and the residue was stirred for 4 hours at 220° C. and cooled, to which was added ethyl acetate and sodium hydrogen carbonate solution. The organic layer was washed with water and saturated brine, dried with magnesium sulfate and concentrated under reduced pressure, and the residue was purified with silica gel column chromatography (EtOAc/hexane) to give oil of 7-(2-methoxyphenyl)-4-methyl-5,6,7,8-tetrahydroquinolin-5-one (0.4 g).

$^1$H-NMR(CDCl$_3$) δ: 2.70 (3H, s), 2.75–3.05 (2H, m), 3.23–3.48 (2H, m), 3.71–3.93 (1H, m), 3.83 (3H, s), 6.86 (2H, m), 7.07 (1H, d, J=5 Hz), 7.18–7.32 (2H, m) 8.47 (1H, d, J=5 Hz).

Reference Example 72

To a solution of boron tribromide (0.96 g) in dichloromethane (30 ml) was added dropwise at −78° C. a solution of 7-(2-methoxyphenyl)-4-methyl-5,6,7,8-tetrahydroquinolin-5-one (0.33 g) in dichloromethane (1 ml), and the mixture was gradually warmed to room temperature and stirred at room temperature for 1.5 hours. To the mixture were added carefully ice and sodium hydrogen carbonate solution, and the mixture was extracted with ethyl acetate. The organic layer was washed with water and saturated brine, dried with magnesium sulfate and concentrated under reduced pressure, and the residue was purified with silica gel column chromatography (EtOAc/hexane) to give colorless crystals of 7-(2-hydroxyphenyl)-4-methyl-5,6,7,8-tetrahydroquinolin-5-one (0.23 g).

mp. 198–199° C.

$^1$H-NMR(CDCl$_3$) δ: 2.75 (3H, s), 2.86–3.27 (3H, m), 3.65–3.96 (2H, m), 6.73–6.96 (2H, m), 7.01–7.30 (5H, m) 7.18 (1H, d, J=5 Hz), 8.51 (1H, d, J=5 Hz).

Reference Example 73

A mixture of 5-(2-furyl)cyclohexane-1,3-dione (1.78 g) and ammonium acetate (2.3 g) in ethanol (35 ml) was refluxed for 15 hours, and the reaction solution was concentrated under reduced pressure. To the residue was added water (30 ml), and the resulting crystals were filtered. The crystals were washed with water and ethyl acetate, and dried to give 1-amino-5-(2-furyl)cyclohexen-3-one (1.35 g) as pale yellow crystals.

mp. 144–145° C.

$^1$H-NMR(DMSO-d$_6$) δ: 2.31 (3H, m), 2.62 (1H, dd), 3.29 (1H, m), 4.96 (1H, s), 6.12 (1H, d), 6.37 (1H, m), 6.84 (2H, broad), 7.54 (1H,d).

Reference Example 74

In a mixture of ethanol (30 ml) and toluene (90 ml) was dissolved 1-amino-5-(2-furyl)cyclohexen-3-one (1.25 g), and to the solution were added 3-oxobutylaldehydedimethylacetal (2.36 g) and granulated potassium hydroxide (390 mg). The mixture was stirred at 115° C. (bath temperature), and to the mixture was added granulated potassium hydroxide (80 mg), 30 minutes later; 1 hour later; and 1.5 hours later; respectively. The reaction solution was stirred at the same temperature for 1 hour. The reaction solution was cooled, and concentrated under reduced pressure, and to the residue was added ethyl acetate (50 ml) and water (15 ml). The mixture was shaken and the separated upper layer was washed with saturated brine. Under reduced pressure, ethyl acetate was evaporated, and the residue was purified with silica gel column chromatography (EtOAc/hexane) and eluted with ethyl acetate/hexane to give 7-(2-furyl)-4-methyl-5,6,7,8-tetrahydroquinolin-5-one (1.0 g) as colorless crystals.

mp. 70–71° C.

$^1$H-NMR(CDCl$_3$) δ: 2.68 (3H, s), 2.92 (1H, dd), 3.08 (1H, dd), 3.40 (1H, dd), 3.59 (2H, m), 6.08 (1H, d), 6.31 (1H, dd), 7.08 (1H, d), 7.36 (1H, d), 8.49 (1H, d).

Reference Example 75

To a mixture of 5-(2-thienyl)cyclohexane-1,3-dione (1.5 g), 1-amino-2-butyne hydrochloride (0.82 g), molecular sieves 4A (3 g) and tetrahydrofuran (30 ml) was added triethylamine (0.78 g). The mixture was stirred at room temperature for 1 hour, refluxed for refluxed for 12 hours and cooled, and insoluble materials were filtered off. Under reduced pressure, the solvent was evaporated, and to the residue was added diphenylether (80 ml), and the mixture was stirred at 250° C. for 6 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give colorless crystals of 4-methyl-7-(2-thienyl)-5,6,7,8-tetrahydroquinolin-5-one (0.67 g).

mp. 105–107° C.

$^1$H-NMR(CDCl$_3$) δ: 2.69 (3H, s), 2.90 (1H, dd, J=11, 16 Hz), 3.14 (1H, ddd, J=2, 4, 11 Hz), 3.37 (1H, dd, J=11, 16 Hz), 3.61 (1H, ddd, J=2, 4, 11 Hz), 3.69–3.88 (1H, m), 6.86–7.04 (2H, m), 7.09 (1H, d, J=5 Hz), 7.21 (1H, dd, J=1, 5 Hz), 8.49 (1H, d, J=5 Hz).

Reference Example 76

A mixture of 5-(5-methyl-2-thienyl)cyclohexane-1,3-dione (4.16 g) and ammonium acetate (4.6 g) in ethanol (50 ml) was refluxed for 15 hours, and the reaction solution was concentrated under reduced pressure. To the residue was added water (60 ml), and the resulting crystals were filtered. The crystals were washed with water and toluene, and dried to give 1-amino-5-(5-methyl-2-thienyl)cyclohexen-3-one (3.37 g) as pale yellow crystals.

mp. 172–173° C.

$^1$H-NMR(DMSO-d$_6$) δ: 2.38 (6H, m), 2.61 (1H, dd), 3.42 (1H, m), 4.98 (1H, s), 6.62 (1H, dd), 6.68 (1H, d), 6.83 (2H, broad).

Reference Example 77

In a mixture of ethanol (30 ml) and toluene (90 ml) was dissolved 1-amino-5-(5-methyl-2-thienyl)cyclohexen-3-one (1.66 g). To the solution were added 3-oxobutylaldehydedimethylacetal (2.6 g) and granulated potassium hydroxide (430 mg), and the mixture was stirred at 115° C. (bath temperature). To the mixture were added granulated potassium hydroxide (80 mg), 30 minutes later; 1 hour later; 1.5 hours later; respectively. The reaction solution was stirred at the same temperature for 1 hour and cooled. Under reduced pressure, the solvent was evaporated, and to the residue were added ethyl acetate (50 ml) and water (10 ml). The mixture was shaken, and the separated upper layer was washed with saturated brine and concentrated under reduced pressure. The residue was purified with silica gel column chromatography (EtOAc/hexane) and eluted with ethyl acetate/hexane to give 4-methyl-7-(5-methyl-2-thienyl)-5,6,7,8-tetrahydroquinolin-5-one (1.78 g) as pale yellow oil.

$^1$H-NMR(CDCl$_3$) δ: 2.45 (3H, s), 2.68 (3H, s), 2.86 (1H, dd), 3.10 (1H, ddd), 3.33 (1H, dd), 3.53 (1H, dd), 3.70 (1H, m), 6.60 (1H, dd), 6.67 (1H, d), 7.08 (1H, d), 8.48 (1H, d).

Reference Example 78

To a mixture of 5-(5-chloro-2-thienyl)cyclohexane-1,3-dione (2.2 g), 1-amino-2-butyne hydrochloride (1.0 g) and tetrahydrofuran (40 ml) was added triethylamine (0.96 g), and the mixture was stirred at room temperature for 1 hour, refluxed for 12 hours and cooled. Insoluble materials were filtered off, and under reduced pressure, the solvent was evaporated. The residue was stirred at 250° C. for 3.5 hours, cooled and purified with silica gel column chromatography (EtOAc/hexane) to give oil of 7-(5-chloro-2-thienyl)-4-methyl-5,6,7,8-tetrahydroquinolin-5-one (0.79 g).

$^1$H-NMR(CDCl$_3$) δ: 2.68 (3H, s), 2.84 (1H, dd, J=11, 17 Hz), 3.08 (1H, dq, J=2, 4, 10 Hz), 3.31 (1H, dd, J=11, 17 Hz), 3.47–3.77 (3H, m), 6.63–6.8 (2H, m), 7.11 (1H, d, J=5 Hz), 8.49 (1H, d, J=5 Hz).

Reference Example 79

A solution of 5-(3-methyl-2-thienyl)-1,3-cyclohexanedione (3.0 g) and ammonium acetate (3.3 g) in ethanol (60 ml) was refluxed for 13 hours. Under reduced pressure, the solvent was evaporated, and to the residue were added ethyl acetate and water to precipitate crystals, which were filtered, washed with water and dried to give pale yellow crystals of 1-amino-5-(3-methyl-2-thienyl)cyclohexen-3-one (2.7 g).

$^1$H-NMR(CDCl$_3$) δ: 2.19 (3H, s), 2.39 (1H, dd, J=12, 17 Hz), 2.46–2.75 (4H, m), 3.52–3.76 (1H, m), 5.31 (1H, s), 5.71 (1H, br), 6.81 (1H, d, J=5 Hz), 7.08 (1H, d, J=5 Hz).

Reference Example 80

To a solution of 1-amino-5-(3-methyl-2-thienyl)cyclohexen-3-one (2.7 g) in ethanol (50 ml) and toluene (150 ml) were added acetylacetoaldehydedimethylacetal (4.3 g) and 85% potassium hydroxide (0.71 g), and the mixture was refluxed. With 30 minutes interval, 85% potassium hydroxide (0.15 g) was added thrice to the mixture, and the mixture was refluxed for 1 hour. Under reduced pressure, the solvent was evaporated, and to the residue was added ethyl acetate. The mixture was washed with water and saturated brine, dried with magnesium sulfate and concentrated under reduced pressure, and the residue was purified with silica gel column chromatography (EtOAc/hexane) to give crystals of 4-methyl-7-(3-methyl-2-thienyl)-5,6,7,8-tetrahydroquinolin-5-one (2.3 g).

mp. 104–105° C.

$^1$H-NMR(CDCl$_3$) δ: 2.23 (3H, s), 2.71 (3H, s), 2.83 (1H, dd, J=12, 16 Hz), 3.03 (1H, dq, J=2, 4, 17 Hz), 3.31 (1H, dd, J=12, 17 Hz), 3.49 (1H, dq, J=2, 14, 17 Hz), 3.68–3.89 (1H, m), 6.84 (1H, d, J=5 Hz), 7.07–7.16 (2H, m), 8.50 (1H, d, J=5 Hz).

Reference Example 81

A solution of 5-(3-chloro-2-thienyl)-1,3-cyclohexanedione (0.6 g) and ammonium acetate (0.61 g) in ethanol (20 ml) was refluxed for 13 hours. Under reduced pressure, the solvent was evaporated, and to the residue were added ethyl acetate and water. The organic layer was washed with water and saturated brine, dried with magnesium sulfate and concentrated under reduced pressure. The residue was dissolved in ethanol (6 ml) and toluene (18 ml). To the solution were added acetylacetoaldehydedimethylacetal (0.86 g) and powdery 85% potassium hydroxide (0.14 g), and the mixture was refluxed. With 30 minutes interval, powdery 85% potassium hydroxide (0.029 g) was added thrice to the mixture, and the mixture was refluxed for 1 hour. Under reduced pressure, the solvent was evaporated, and to the residue was added ethyl acetate. The mixture was washed with water and saturated brine, dried with magnesium sulfate and concentrated under reduced pressure, and the residue was purified with silica gel column chromatography (EtOAc/hexane) to give oil of crude 7-(3-chloro-2-thienyl)-4-methyl-5,6,7,8-tetrahydroquinolin-5-one (0.3 g).

$^1$H-NMR(CDCl$_3$) δ: 2.70 (3H, s), 2.82 (1H, dd, J 12, 17 Hz), 3.08 (1H, ddd, J=2, 4, 16 Hz), 3.32 (1H, dd, J=11, 17 Hz), 3.54 (1H, ddd, J=2, 4, 17 Hz), 3.86–4.06 (1H, m), 6.93 (1H, d, J=5 Hz), 7.12 (1H, d, J=5 Hz), 7.2 (1H, d, J=5 Hz), 8.50 (1H, d, J=5 Hz).

Reference Example 82

To a mixture of 5-(2-pyridyl)cyclohexane-1,3-dione (2.0 g), 1-amino-2-butyne hydrochloride (0.1.1 g), molecular sieves 4A (2 g), tetrahydrofuran (30 ml) and ethanol (10 ml) was added triethylamine (2.1 g), and the mixture was stirred at room temperature for 1 hour, refluxed for 4 hours and cooled. Insoluble materials were filtered off. Under reduced pressure, the solvent was evaporated, and the residue was purified with silica gel column chromatography (EtOAc/MeOH) to give solid. The solid was stirred for 10 hours at 220° C., to which were added ethyl acetate and sodium hydrogen carbonate solution. The organic layer was washed with water and saturated brine, dried with magnesium sulfate and concentrated under reduced pressure, and the residue was purified with silica gel column chromatography (EtOAc/hexane) to give oil of 4-methyl-7-(2-pyridyl)-5,6,7,8-tetrahydroquinolin-5-one (0.28 g).

$^1$H-NMR(CDCl$_3$) δ: 2.69 (3H, s), 2.98 (1H, ddd, J=1, 4, 16 Hz), 3.15 (1H, dd, J=11, 16 Hz), 3.37–3.76 (3H, m), 7.08 (1H, d, J=5 Hz), 7.18 (1H, ddd, J=1, 5, 8 Hz), 7.24 (1H, d, J=8 Hz), 7.66 (1H, dt, J=2, 8 Hz), 8.47 (1H, d, J=5 Hz), 8.58 (1H, ddd, J=1, 2, 5 Hz).

Reference Example 83

To a mixture of 5-(4-pyridyl)cyclohexane-1,3-dione (0.90 g), 1-amino-2-butyne hydrochloride (0.5 g), molecular sieves 4A (2 g) and tetrahydrofuran (20 ml) was added triethylamine (0.48 g), and the mixture was stirred at room temperature for 1 hour, refluxed for 15 hours and cooled, insoluble materials were filtered off. Under reduced pressure, the solvent was evaporated, and the residue was stirred for 3.5 hours at 220° C. and cooled, to which were added ethyl acetate and sodium hydrogen carbonate solution. The organic layer was washed with water and saturated brine, dried with magnesium sulfate and concentrated under reduced pressure, and the residue was purified with silica gel column chromatography (EtOAc/MeOH) to give oil of 4-methyl-7-(4-pyridyl)-5,6,7,8-tetrahydroquinolin-5-one (0.1 g).

$^1$H-NMR(CDCl$_3$) δ: 2.69 (3H, s), 2.87 (1H, dd, J=12, 16 Hz), 2.92–3.08 (1H, m), 3.25–3.62 (3H, m), 7.12 (1H, d, J=5 Hz), 7.22–7.35 (1H, m), 8.50 (1H, d, J=5 Hz), 8.57–8.65 (1H, m).

Reference Example 84

To a mixture of 5-(4-fluorophenyl)cyclohexane-1,3-dione (0.98 g), 1-amino-2-butyne hydrochloride (0.5 g), molecular sieves 4A (2 g) and tetrahydrofuran (20 ml) was added triethylamine (0.48 g), and the mixture was refluxed for 14 hours and cooled. Insoluble materials were filtered off. Under reduced pressure, the solvent was evaporated, and the residue was stirred for 6 hours at 220° C. and cooled, to which were added ethyl acetate and sodium hydrogen carbonate solution. The organic layer was washed with water and saturated brine, dried with magnesium sulfate and concentrated under reduced pressure, and the residue was purified with silica gel column chromatography (EtOAc/hexane) to give oil of 7-(4-fluorophenyl)-4methyl-5,6,7,8-tetrahydroquinolin-5-one (0.35 g).

$^1$H-NMR(CDCl$_3$) δ: 2.70 (3H, s), 2.80–3.08 (2H, m), 3.29–3.55 (2H, m), 3.71–3.88 (1H, m), 7.02–7.36 (5H, m), 8.50 (1H, d, J=5 Hz).

Reference Example 85

A solution of 5-phenylcyclohexane-1,3-dione (5.0 g), ammonium acetate (6.1 g) in ethanol (100 ml) was refluxed for 13 hours. Under reduced pressure, the solvent was evaporated, and to the residue were added ethyl acetate and water. Precipitated crystals were filtered, washed with water and dried to give pale yellow crystals of 1-amino-5-phenylcyclohexen-3-one (5.2 g).

mp. 190–191° C.

$^1$H-NMR(CDCl$_3$) δ: 2.40–2.86 (4H, m), 3.26–3.45 (1H, m), 4.95 (2H, br), 5.35 (1H, d, J=1 Hz), 7.16–7.43 (2H, m).

Reference Example 86

To a solution of 5-methoxymethylene-2,2-dimethyl-[1,3]dioxane-4,6-dione (1.8 g) in acetonitrile (15 ml) was added 1-amino-5-phenylcyclohexen-3-one (2.0 g), and the mixture was stirred at room temperature for 24 hours. The resulting crystals were filtered and washed with acetonitrile to give crystals of 2,2-dimethyl-5-[(3-oxo-5-phenyl-1-cyclohexenylamino)methylene]-[1,3]dioxane-4,6-dione (1.2 g).

mp 201° C. (decomp.)

$^1$H-NMR(CDCl$_3$) δ: 1.74 (6H, s), 2.59–2.97 (4H, m), 3.36–3.58 (1H, m), 5.99 (1H, s), 7.22–7.50 (5H, m), 8.39 (1H, d, J=14 Hz), 11.03 (1H, d, J=12 Hz).

Reference Example 87

A solution of 2,2-dimethyl-5-[(3-oxo-5-phenyl-1-cyclohexenylamino)methylene]-[1,3]dioxane-4,6-dione (1.0 g) in diphenylether (15 ml) was stirred at 260–280° C. for 30 minutes. Under reduced pressure, the solvent was evaporated, and the resulting crystals were washed with petroleum ether. The crystals were recrystallized from ethanol to give crystals of 7-phenyl-1,4,5,6,7,8-hexahydroquinoline-4,5-dione (0.51 g).

mp 207–209° C.

$^1$H-NMR(CDCl$_3$) δ: 2.84–3.17 (2H, m), 3.34 (1H, dd, J=11, 13 Hz), 3.32–3.64 (2H, m), 6.80 (1H, d, J=6 Hz), 7.24–7.48 (5H, m), 8.42 (1H, d, J=6 Hz).

Reference Example 88

Under ice-cooling, to phosphorus oxychloride (3.6 g) was added 7-phenyl-1,4,5,6,7,8-hexahydroquinoline-4,5-dione (0.35 g), and the mixture was stirred at 100° C. for 2 hours and cooled. Under reduced pressure, phosphorus oxychloride was evaporated, and to the residue was added 1N sodium hydroxide solution. The mixture was extracted with ethyl acetate, and the organic layer was washed with water and saturated brine, dried with magnesium sulfate and concentrated under reduced pressure to give colorless crystals of 4-chloro-7-phenyl-5,6,7,8-tetrahydroquinolin-5-one (0.35 g).

mp. 71–72° C.

$^1$H-NMR(CDCl$_3$) δ: 2.92 (1H, dd, J=12, 16 Hz), 3.06 (1H, ddd, J=3, 4, 17 Hz), 3.36 (1H, dd, J=12, 17 Hz), 3.40–3.61 (1H, m), 7.21–7.45 (5H, m), 7.37 (1H, d, J=5 Hz), 8.51 (1H, d, J=5 Hz).

Reference Example 89

To a solution of 4-chloro-7-phenyl-5,6,7,8-tetrahydroquinolin-5-one (0.23 g) in methanol (20 ml) was added sodium methoxide (0.096 g), and the mixture was refluxed for 1 hour and cooled. The solvent was evaporated, and to the residue was added ethyl acetate. The organic layer was washed with water and saturated brine, dried with magnesium sulfate and concentrated under reduced pressure, and the residue was recrystallized from ethyl acetate-hexane to give crystals of 4-methoxy-7-phenyl-5,6,7,8-tetrahydroquinolin-5-one (0.21 g).

mp. 130–131° C.

$^1$H-NMR(CDCl$_3$) δ: 2.86 (1H, dd, J=13, 16 Hz), 2.99 (1H, ddd, J=2, 5, 18 Hz), 3.28 (1H, dd, J=12, 16 Hz), 3.34–3.57 (2H, m), 3.99 (3H, s), 6.83 (1H, d, J=6 Hz), 7.20–7.43 (5H, m), 8.52 (1H, d, J=6 Hz).

Reference Example 90

A solution of 5-(2-chlorophenyl)cyclohexane-1,3-dione (2.5 g) and ammonium acetate (2.6 g) in ethanol (50 ml) was refluxed for 12 hours. Under reduced pressure, the solvent was evaporated, and to the residue was added sodium hydrogen carbonate solution. The mixture was extracted with ethyl acetate, and the organic layer was washed with water and saturated brine, and dried with magnesium sulfate. Under reduced pressure, the solvent was evaporated to give crystals, which were recrystallized from ethyl acetate-hexane to give pale yellow crystals of 1-amino-5-(2-chlorophenyl)cyclohexen-3-one (2.2 g).

mp. 199° C. (decomp.)

$^1$H-NMR(CDCl$_3$) δ: 2.44–2.72 (4H, m), 3.77–3.97 (1H, m), 4.68 (2H, br), 5.35 (1H, s), 7.15–7.43 (4H, m).

Reference Example 91

To a solution of 5-methoxymethylene-2,2-dimethyl-[1,3]dioxane-4,6-dione (1.7 g) in acetonitrile (15 ml) was added 1-amino-5-(2-chlorophenyl)cyclohexen-3-one (2.2 g), and the mixture was stirred at room temperature for 13 hours. Precipitated crystals were filtered and washed with acetonitrile to give colorless crystals of 2,2-dimethyl-5-[(3-oxo-5-(2-chlorophenyl)-1-cyclohexenylamino)methylene]-[1,3]dioxane-4,6-dione (1.7 g).

mp. 112° C. (decomp.)

$^1$H-NMR(CDCl$_3$) δ: 1.75 (6H, s), 2.62–2.84 (3H, m), 2.95 (1H, dd, J=5, 17 Hz), 3.89–4.09 (1H, m), 6.0 (1H, d, J=2 Hz), 7.14–7.52 (4H, m), 8.38 (1H, d, J=14 Hz), 11.03 (1H, d, J=14 Hz).

Reference Example 92

A mixture of 2,2-dimethyl-5-[(3-oxo-5-(2-chlorophenyl)-1-cyclohexenylamino)methylene]-[1,3]dioxane-4,6-dione (1.6 g) in diphenylether (20 ml) was stirred at 260° C. for 30 minutes. Under reduced pressure, the solvent was evaporated, and the resulting crystals were washed with petroleum ether and recrystallized from ethanol to give 7-(2-chlorophenyl)-1,4,5,6,7,8-hexahydroquinoline-4,5-dione (1.1 g).

mp. 243° C. (decomp.)

$^1$H-NMR(DMSO-d$_6$) δ: 2.59–2.77 (1H, m), 2.92–3.6 (3H, m), 3.77–4.0 (1H, m), 6.53 (1H, bs), 7.23–7.58 (4H, m), 8.03 (1H, bs).

Reference Example 93

Under ice-cooling, to phosphorus oxychloride (5.4 g) was added 7-(2-chlorophenyl)-1,4,5,6,7,8-hexahydroquinoline-4,5-dione (0.60 g), and the mixture was stirred at 100° C. for 2 hours and cooled. Under reduced pressure, phosphorus oxychloride was evaporated, and to the residue was added 1N sodium hydroxide solution. The mixture was extracted with ethyl acetate, and the organic layer was washed with water and saturated brine, dried with magnesium sulfate and concentrated under reduced pressure to give colorless crystals of 4-chloro-7-(2-chlorophenyl)-5,6,7,8-tetrahydroquinolin-5-one (0.55 g).

mp. 130–131° C.

$^1$H-NMR(CDCl$_3$) δ: 2.89 (1H, dd, J=12, 16 Hz), 3.08 (1H, dq, J=2, 4, 17 Hz), 3.32 (1H, dd, J=12, 17 Hz), 3.53 (1H, dq, J=2, 4, 17 Hz), 3.92–4.08 (1H, m), 7.16–7.58 (5H, m), 8.52 (1H, d, J=5 Hz).

Reference Example 94

To a solution of 4-chloro-7-(2-chlorophenyl-5,6,7,8-tetrahydroquinolin-5-one (0.2 g) in methanol (20 ml) was added sodium methoxide (0.074 g), and the mixture was refluxed for 2 hours and cooled. The solvent was evaporated, and to the residue was added ethyl acetate. The organic layer was washed with water and saturated brine, dried with magnesium sulfate and concentrated under reduced pressure, and the residue was purified with silica gel column chromatography (EtOAc/hexane) to give colorless crystals of 7-(2-chlorophenyl)-4-methoxy-5,6,7,8-tetrahydroquinolin-5-one (0.1 g).

mp. 116–117° C.

$^1$H-NMR(CDCl$_3$) δ: 2.81 (1H, dd, J=12, 16 Hz), 3.0 (1H, dq, J=2, 4, 17 Hz), 3.25 (1H, dd, J=12, 17 Hz), 3.45 (1H, dq, J=2, 4, 17 Hz), 3.80–4.16 (1H, m), 4.00 (3H, s), 6.85 (1H, d, J=6 Hz), 7.16–7.45 (5H, m), 8.53 (1H, d, J=6 Hz).

Reference Example 95

To a mixture of 5-phenylcyclohexane-1,3-dione (1.2 g) and ammonium acetate (0.49 g) in ethanol (30 ml) was added 3-butyn-2-one (0.44 g), and the mixture was stirred at room temperature for 1.5 hours and refluxed for 18 hours. Under reduced pressure, the solvent was evaporated, and the residue was dissolved in ethyl acetate. The solution was washed with sodium hydrogen carbonate solution, water and saturated brine, dried with magnesium sulfate and concentrated under reduced pressure, and the residue was purified with silica gel column chromatography (EtOAc/hexane) to give colorless crystals of 2-methyl-7-phenyl-5,6,7,8-tetrahydroquinolin-5-one (0.88 g).

mp. 79–81° C.

$^1$H-NMR(CDCl$_3$) δ: 2.61 (3H, s), 2.85 (1H, dd, J=12, 17 Hz), 3.00 (1H, ddd, J=1, 4, 17 Hz), 3.23–3.63 (3H, m), 7.18 (1H, d, J=8 Hz), 7.22–7.43 (5H, m) 8.21 (1H, d, J=8 Hz).

Reference Example 96

To a mixture of 5-phenylcyclohexane-1,3-dione (2.0 g) and ammonium acetate (0.90 g) in ethanol (30 ml) was added acetylacetone (1.1 g), and the mixture was stirred at room temperature for 1 hour and refluxed for 21 hours. Under reduced pressure, the solvent was evaporated, and the residue was dissolved in ethyl acetate. The solution was washed with sodium hydrogen carbonate solution, water and saturated brine, dried with magnesium sulfate and concentrated under reduced pressure, and insoluble materials were filtered off. The filtrate was concentrated, and the residue was purified with silica gel column chromatography (EtOAc/hexane). The resulting crystals were recrystallized from diisopropylether and hexane to give colorless crystals of 2,4-dimethyl-7-phenyl-5,6,7,8-tetrahydroquinolin-5-one (0.6 g).

mp. 97–99° C.

$^1$H-NMR(CDCl$_3$) δ: 2.51 (3H, s), 2.64 (3H, s), 2.70–3.01 (2H, m), 3.17–3.53 (3H, m), 6.92 (1H, s), 7.15–7.42 (5H, m).

Reference Example 97

A mixture of 5-(2-methylphenyl)cyclohexane-1,3-dione (1.0 g) and ammonium acetate (0.42 g) in ethanol (20 ml) was stirred at room temperature for 15 minutes. To the mixture was added 3-butyn-2-one (0.54 g), and the mixture was refluxed for 16 hours. Under reduced pressure, the solvent was evaporated, and the residue was dissolved in ethyl acetate. The solution was washed with sodium hydrogen carbonate solution, water and saturated brine, dried with magnesium sulfate and concentrated under reduced pressure, and the residue was purified with silica gel column chromatography (EtOAc/hexane) to give colorless crystals of 2,4-dimethyl-7-(2-methylphenyl)-5,6,7,8-tetrahydroquinolin-5-one (0.50 g).

mp. 106–107° C.

$^1$H-NMR(CDCl$_3$) δ: 2.36 (3H, s), 2.53 (3H, s), 2.66 (3H, s), 2.73–3.00 (2H, m), 3.15–3.37 (2H, m), 3.54–3.77 (1H, m), 6.95 (1H, s), 7.00–7.33 (4H, m).

Reference Example 98

A mixture of 5-(2-fluorophenyl)cyclohexane-1,3-dione (1.0 g) and ammonium acetate (0.97 g) in 1-pentanol (30 ml) was refluxed for 30 minutes. To the mixture was added 3-butyn-2-one (0.97 g), and the mixture was refluxed for 14.5 hours. To the mixture was added 3-butyn-2-one (0.49 g), and the mixture was refluxed for 5 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give oil of 7-(2-fluorophenyl)-2,4-dimethyl-5,6,7,8-tetrahydroquinolin-5-one (0.12 g).

$^1$H-NMR(CDCl$_3$) δ: 2.54 (3H, s), 2.66 (3H, s), 2.77–3.04 (2H, m), 3.24–3.44 (2H, m), 3.51–3.94 (1H, m), 6.96 (1H, s), 7.00–7.33 (4H, m).

Reference Example 99

A mixture of 5-(2-chlorophenyl)cyclohexane-1,3-dione (1.1 g) and ammonium acetate (1.1 g) in 1-pentanol (30 ml) was refluxed for 30 minutes. To the mixture was added 3-butyn-2-one (0.97 g), and the mixture was refluxed for 14.5 hours. To the mixture was added 3-butyn-2-one (0.49 g), and the mixture was refluxed for 5 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (EtOAc/hexane) to give oil of 7-(2-chlorophenyl)-2,4-dimethyl-5,6,7,8-tetrahydroquinolin-5-one (0.2 g).

$^1$H-NMR(CDCl$_3$) δ: 2.54 (3H, s), 2.67 (3H, s), 2.8 (1H, dd, J=12, 16 Hz), 2.9–3.07 (1H, m), 3.27 (1H, dd, J=11, 17 Hz), 3.35–3.52 (1H, m), 3.76–4.08 (1H, m), 6.97 (1H, s), 7.17–7.54 (4H, m).

Reference Example 100

To a mixture of 5-(2-methylphenyl) cyclohexane-1,3-dione (1.0 g) and ammonium acetate (0.8 g) in 1-pentanol (30 ml) was added 3-butyn-2-one (1.1 g), and the mixture was refluxed for 7 hours. Under reduced pressure, the solvent was evaporated, and to the residue was added ethyl acetate. The mixture was washed with sodium hydrogen carbonate solution, water and saturated brine, dried with magnesium sulfate and concentrated under reduced pressure, and the residue was purified with silica gel column chromatography (EtOAc/hexane) to give oil of 2,4-dimethyl-7-(2-pyridyl)-5,6,7,8-tetrahydroquinolin-5-one (0.08 g).

$^1$H-NMR(CDCl$_3$) δ: 2.53 (3H, s), 2.66 (3H, s), 2.89–3.33 (1H, m), 3.12 (1H, dd, J=11, 16 Hz), 3.31–3.53 (2H, m), 3.56–3.72 (1H, m), 6.94 (1H, s), 7.13–7.30 (2H, m), 7.60–7.72 (1H, m), 8.58 (1H, d, J=5 Hz).

Reference Example 101

A mixture of 5-(2-methylphenyl)cyclohexane-1,3-dione (1.3 g) and ammonium acetate (0.49 g) in ethanol (30 ml) was stirred at room temperature for 30 minutes, and to the mixture was added 3-butyn-2-one (0.44 g). The reaction solution was stirred at room temperature for 1.5 hours and refluxed for 27 hours. Under reduced pressure, the solvent was evaporated, and the residue was dissolved in ethyl acetate. The solution was washed with sodium hydrogen carbonate solution, water and saturated brine, dried with magnesium sulfate and concentrated under reduced pressure, and the residue was purified with silica gel column chromatography (EtOAc/hexane) to give colorless crystals of 2-methyl-7-(2-methylphenyl)-5,6,7,8-tetrahydroquinolin-5-one (0.88 g).

mp. 76–77° C.

$^1$H-NMR(CDCl$_3$) δ: 2.37 (3H, s), 2.62 (3H, s), 2.65–3.0 (2H, m), 3.16–3.43 (2H, m), 3.56–3.82 (1H, m), 7.03–7.33 (5H, m) 8.23 (1H, d, J=8 Hz).

Reference Example 102

To a mixture of 2-acetyl-5-(2-chlorophenyl)cyclohexane-1,3-dione (0.48 g), pyrrolidine (0.16 ml) and anhydrous sodium sulfate (1.02 g) was added benzene (15 ml), and the mixture was stirred, under argon atmosphere, at 90° C. for 2 hours and cooled. The reaction solution was concentrated under reduced pressure, and to the residue were added formamidine acetate (0.19 g), potassium carbonate (0.25 g) and methanol (10 ml). The mixture was stirred, under argon atmosphere, at 90° C. for 2 hours and cooled, and the reaction solution was concentrated under reduced pressure. To the residue were added water and ethyl acetate, and the mixture was subjected to extraction. The upper layer was washed with saturated brine and dried (anhydrous magnesium sulfate), and the residue was purified with silica gel chromatography and eluted with ethyl acetate/hexane to give 7-(2-chlorophenyl)-4-methyl-5,6,7,8-tetrahydroquinazolin-5-one (41 mg).

$^1$H-NMR(CDCl$_3$) δ: 2.81–3.11 (2H,m), 2.90 (3H,s), 3.19–3.50 (2H,m), 4.00 (1H,m), 7.21–7.33 (3H,m), 7.44 (1H,dd,J=1.4&7.0 Hz), 9.06 (1H,s)

Reference Example 103

To a mixture of 2-acetyl-5-(2-chlorophenyl)cyclohexane-1,3-dione (0.79 g), pyrrolidine (0.27 ml) and anhydrous sodium sulfate (1.70 g) was added toluene (20 ml), and the mixture was stirred, under argon atmosphere, at 110° C. for 2 hours and cooled. The reaction solution was concentrated under reduced pressure. On the other hand, to acetamidine hydrochloride (0.28 g) were added sodium ethoxide (0.21 g) and ethanol (10 ml), and the mixture was stirred at room temperature for 2 hours. The reaction solution was added to the above described enamine residue, and the mixture was stirred, under argon atmosphere, at 90° C. for 5 hours and cooled. The reaction solution was concentrated under reduced pressure. To the residue were added water and ethyl acetate, and the mixture was subjected to extraction. The upper layer was washed with saturated brine and dried (anhydrous magnesium sulfate), and the residue was purified with silica gel chromatography and eluted with ethyl acetate/hexane to give 7-(2-chlorophenyl)-2,4-dimethyl-5,6,7,8-tetrahydroquinazolin-5-one (0.30 g).

mp108–109° C. (isopropylether).

$^1$H-NMR(CDCl$_3$) δ: 2.73 (3H,s), 2.78–3.08 (2H,m), 2.92 (3H,s), 3.14–3.44 (2H,m), 3.97 (1H,m), 7.2–7.4 (3H,m), 7.24 (1H,d,J=7.2 Hz).

Reference Example 104

In tetrahydrofuran (10 ml) was dissolved 4-methylpyridine-2,3-dicarboxylic acid anhydride (743 mg). While stirring the solution under ice-cooling, a solution of 2-methylphenylmagnesium bromide (1.1 M) in tetrahydrofuran (4.1 ml) was added dropwise to the solution. The mixture was stirred under ice-cooling for 30 minutes. To the reaction solution was added 2 N hydrochloric acid (3 ml), and the mixture was stirred at room temperature for 30 minutes. To the reaction solution was added 2 N hydrochloric acid to adjust the solution to pH 3, and to the mixture were added ethyl acetate (200 ml) and water (100 ml). The mixture was shaken, and the separated upper layer was washed with water (20 ml; thrice) and concentrated under reduced pressure. The residue was dissolved in benzene (10 ml). To the solution was added thionylchloride (2 ml), and the mixture was stirred at 90° C. (bath temperature) for 1.5 hours. The reaction solution was concentrated under reduced pressure to give the residue.

In tetrahydrofuran (15 ml) was dissolved 60% oily sodium hydride (640 mg), which had been washed with hexane to remove oil, and to the solution was added immediately dimethyl malonate (2.11 g) while stirring under ice-cooling. After hydrogen gas production had stopped, the bath was removed, and to the vigorously stirred solution was added a solution of the above-mentioned residue dissolved in tetrahydrofuran (12 ml). The mixture was stirred at room temperature for 30 minutes and concentrated under reduced pressure. To the residue were added 2 M sodium carbonate (20 ml) and water (12 ml), and the mixture was refluxed for 20 minutes and cooled. To the solution was added ethyl acetate (100 ml), and the mixture was shaken. The separated upper layer was washed with water (20 ml, twice) and concentrated under reduced pressure, and the residue was purified with silica gel chromatography and eluted with ethyl acetate/hexane to give 6-methoxycarbonyl-4-methyl-7-(2-methylphenyl)-5-oxo-cyclopenta-1,3-diene[2,1-b] pyridine (0.07 g) as yellow syrup.

$^1$H-NMR(CDCl$_3$) δ: 2.26 (3H, s), 2.62 (3H, s), 3.73 (3H, s), 7.05 (1H, d), 7.36 (4H, m), 8.40 (1H, d).

Reference Example 105

In a mixture of methanol (10 ml) and tetrahydrofuran (10 ml) was dissolved 6-methoxycarbonyl-4-methyl-7-(2-methylphenyl)-5-oxo-cyclopenta-1,3-diene[2,1-b]pyridine (110 mg). To the solution was added 5% Pd-C (35 mg), and the mixture was stirred under hydrogen atmosphere at normal temperature and normal pressure. After completion of reaction, the catalyst was filtered off, and the filtrate was concentrated under reduced pressure. The residue was dissolved in acetic acid (2 ml), and to the solution were added concentrated sulfuric acid (0.2 ml) and water (0.2 ml). The mixture was stirred at 130° C. (bath temperature) for 30 minutes. To the reaction solution was added water (30 ml), and the mixture was concentrated to about 5 ml. To the residue was added ethyl acetate (30 ml), and the mixture was washed with sodium hydrogen carbonate aqueous solution. The ethyl acetate layer was concentrated under reduced pressure, and the residue was purified with silica gel chromatography and eluted with ethyl acetate/hexane to give 4-methyl-7-(2-methylphenyl)-5-oxo-cyclopenta[2,1-b] pyridine (48 mg) as yellow syrup.

$^1$H-NMR(CDCl$_3$) δ: 2.45 (3H, s), 2.66 (1H, dd), 2.71 (3H, s), 3.29 (1H, dd), 4.86 (1H, dd), 6.68 (1H, dd), 7.10 (4H, m), 8.61 (1H, d).

Reference Example 106

In a solution of 40% methylamine in methanol (1 ml) was dissolved S-methylisothiosemicarbazide p-toluenesulfonate (831 mg), and the solution was allowed to stand for 10 days at room temperature. The reaction solution was concentrated under reduced pressure, and the residue was recrystallized from ethanol-ethyl acetate to give 1-amino-3-methylguanidine p-toluenesulfonate (650 mg) as colorless crystals.

mp 110–111° C.

$^1$H-NMR(DMSO-d$_6$) δ: 2.30 (3H, s), 2.73 (3H, m), 4.66 (2H, broad), 7.13 (2H, d), 7.28 (2H, broad), 7.50 (2H, d), 8.59 (1H, broad).

Reference Example 107

A mixture of 5-(3-thienyl)cyclohexane-1,3-dione (10.5 g) and ammonium acetate (13.1 g) in ethanol (200 ml) was refluxed for 16 hours. The reaction solution was concentrated under reduced pressure, and to the residue was added water (50 ml). The resulting crystals were filtered, washed with water and toluene, and dried to give 1-amino-5-(3-thienyl)cyclohexen-3-one (10 g) as pale yellow crystals.

mp 142–143° C.

$^1$H-NMR(DMSO-d$_6$) δ: 2.30 (2H, d), 2.52 (2H, d), 3.30 (1H, m), 4.99 (1H, s), 6.80 (2H, broad), 7.12 (1H, dd), 7.25 (1H, m), 7.47 (1H, dd).

Reference Example 108

In a mixture of ethanol (200 ml) and toluene (600 ml) was dissolved 1-amino-5-(3-thienyl)cyclohexen-3-one (10 g), and to the solution were added 3-oxobutylaldehydedimethylacetal (17.4 g) and granulated potassium hydroxide (2.87 g). The mixture was stirred at 115° C. (bath temperature), and to the reaction solution were added granulated potassium hydroxide (590 mg), 30 minutes later; 1 hour later; and 1.5 hours later; respectively. The reaction solution was stirred at the same temperature for 1 hour and cooled. Under reduced pressure, the solvent was evaporated, and to the residue were added ethyl acetate (250 ml) and water (70 ml). The mixture was shaken, and the separated ethyl acetate layer was washed with water (40 ml, thrice) and concentrated under reduced pressure. The residue was purified with silica gel column chromatography (EtOAc/hexane) and eluted with ethyl acetate/hexane to give 4-methyl-7-(3-thienyl)-5,6,7,8-tetrahydroquinolin-5-one (6.5 g) as pale yellow crystals.

mp. 92–93° C.

$^1$H-NMR(CDCl$_3$) δ: 2.69 (3H, s), 2.85 (1H, dd), 3.09 (1H, ddd), 3.28 (1H, dd), 3.61 (2H, m), 7.08 (3H, m), 7.38 (1H, m), 8.49 (1H, d).

Reference Example 109

In ethyl acetate (50 ml) was dissolved 4-methyl-7-(3-thienyl)-5,6,7,8-tetrahydroquinolin-5-one (1.22 g), and to the solution was added pyridine (474 mg). To the mixture was added, while stirring under ice-cooling, sulfuryl chloride (1.49 g), and the mixture was stirred for 30 minutes under the same condition. To the mixture was added excess sodium hydrogen carbonate solution, and the mixture was stirred at room temperature for 10 minutes. The separated ethyl acetate layer was concentrated under reduced pressure, and the residue was purified with silica gel column chromatography (EtOAc/hexane) and eluted with ethyl acetate/hexane to give 7-(2,5-dichlorothiophen-3-yl)-4-methyl-5,6,7,8-tetrahydroquinolin-5-one (720 mg) as colorless crystals.

mp. 130–131° C.

$^1$H-NMR(CDCl$_3$) δ: 2.67 (3H, s), 2.75 (1H, dd), 2.93 (1H, ddd), 3.22 (1H, dd), 3.39 (1H, ddd), 3.66 (1H, m), 6.72 (1H, s), 7.11 (1H, d), 8.50 (1H, d).

In addition, 7-(2-chlorothiophen-3-yl)-4-methyl-5,6,7,8-tetrahydroquinolin-5-one (310 mg) was obtained as pale yellow syrup.

$^1$H-NMR(CDCl$_3$) δ: 2.70 (3H, s), 2.77 (1H, dd), 2.97 (1H, ddd) , 3.29 (1H, dd), 3.32 (1H, ddd), 3.72 (1H, m), 6.89 (1H, d), 7.12 (2H, m), 8.50 (1H, d).

Reference Example 110

A mixture of 5-phenylcyclohexane-1,3-dione (1.0 g) and ammonium acetate (0.45 g) in ethanol (30 ml) was stirred at room temperature for 1 hour, refluxed for 6 hours and cooled. To the reaction solution was added ethyl propiolate (0.55 g), and the mixture was stirred at room temperature for 1 hour and refluxed 14.5 hours. Under reduced pressure, the solvent was evaporated, and the residue was dissolved in ethyl acetate. The solution was washed with sodium hydrogen carbonate solution, water and saturated brine, dried with magnesium sulfate and concentrated under reduced pressure, and the residue was recrystallized from ethanol to give colorless crystals of 7-phenyl-1,2,5,6,7,8-hexahydroquinoline-2,5-dione (0.19 g).

mp. 254° C. (decomp.)

$^1$H-NMR(DMSO-d$_6$) δ: 2.68–3.60 (5H, m), 6.28 (1H, d, J=9 Hz), 7.22–7.6 (5H, m), 7.82 (1H, dd, J=2, 9 Hz), 12.21 (1H, s).

Reference Example 111

In THF (10 ml) was dissolved 3-ethoxycarbonyl-6-phenyl-4,5,6,7-tetrahydrobenzofuran-4-one (0.71 g). To the solution was added 1N sodium hydroxide (5.0 ml), and the mixture was stirred at room temperature overnight (12 hours). The reaction solution was concentrated under reduced pressure, and to the residue was added potassium hydrogensulfate to make the mixture acidic. To the mixture was added ethyl acetate, and the mixture was subjected to extraction. The upper layer was washed with saturated brine, dried (anhydrous magnesium sulfate) and concentrated under reduced pressure, and the residue was washed with isopropylether to give 3-carboxy-6-phenyl-4,5,6,7-tetrahydrobenzofuran-4-one (0.59 g).

mp202–203° C.

$^1$H-NMR(CDCl$_3$) δ: 2.95 (1H,d,J=1.4 Hz), 2.99 (1H,s), 3.17 (1H,dd,J=10.6&17.6 Hz), 3.32(1H ,dd J=5.4&17.6 Hz), 3.68 (1H,m), 7.27–7.45 (6H,m), 8.14 (1H,s).

Reference Example 112

To a suspension of 3-carboxy-4-oxo-6-phenyl-4,5,6,7-tetrahydrobenzofuran (1.28 g) in dichloromethane (25 ml) were added, under ice-cooling, WSC (1.15 g) and N-hydroxybenzotriazole (0.92 g), and the mixture was stirred at room temperature for 30 minutes. To the mixture was added concentrated ammonia solution (4.1 g), and the mixture was stirred at room temperature overnight (12 hours). To the reaction solution was added water, and the mixture was subjected to extraction. The lower layer was washed with saturated brine, dried (anhydrous magnesium sulfate) and concentrated under reduced pressure, and the residue was washed with ethyl acetate and isopropylether to give 3-carbamoyl-6-phenyl-4,5,6,7-tetrahydrobenzofuran-4-one (0.36 g).

mp 252–253° C.

$^1$H-NMR(CDCl$_3$) δ: 2.89 (2H,d, J=8.6 Hz), 3.12 (1H,dd, J=10.617.2 Hz), 3.27 (1H,dd,J=5.417.2 Hz), 3.61 (1H,m), 5.64 (1H,broad), 7.27–7.43 (5H,m), 8.09 (1H,s), 9.49 (1H, broad).

Reference Example 113

To a mixed solution of acetone (294 ml) and an aqueous solution (1.4 l) of sodium hydroxide (22.0 g) was added 2-chlorobenzaldehyde (70.3 g), and the mixture was stirred at room temperature for 5 hours. Excess acetone was evaporated under reduced pressure, and to the residue was added ethyl acetate (1.4 l). The mixture was subjected to extraction, and the ethyl acetate layer was washed with brine and dried (anhydrous magnesium sulfate). Under pressure, ethyl acetate was evaporated to give crude 2-chlorobenzalacetone (94.6 g) as yellow oil, which was used for the following reaction without further purification.

To a solution of 20% sodium ethoxide in ethanol (170.1 g) was added diethyl malonate (80.1 g) at room temperature (immediately precipitated material was observed), and then a solution of crude 2-chlorobenzalacetone (94.6 g) in ethanol (40 ml). The mixture was stirred at 90° C. for 2 hours, cooled at room temperature and under-ice-cooling (for 1 hour). Precipitated materials were filtered and washed with ethyl acetate and isopropylether to give crude ethyl 6-(2-chlorophenyl)-2-hydroxy-4-oxo-2-cyclohexene-1-carboxylate monosodium salt (151.0 g) as pale yellow powder. To said powder was added 2 M sodium hydroxide (350 ml), and the mixture was stirred at 100° C. for 2 hours and cooled. To the mixture was added 2.5 M sulfuric acid (350 ml) for 15 minutes, and the mixture was stirred at 100° C. for 2 hours and cooled. To the mixture was added ethyl acetate (1.4 l), and the mixture was subjected to extraction.

The ethyl acetate layer was washed with brine, dried (anhydrous magnesium sulfate), and ethyl acetate was evaporated under reduced pressure. Precipitated crystals were washed with ethyl acetate-isopropylether (1:4) and isopropylether to give 5-(2-chlorophenyl)cyclohexane-1,3-dione (82.1 g) as colorless crystals.

mp 157–158° C.

Reference Example 114

To a mixture of acetone (125 ml), sodium hydroxide (8.7 g) and water (600 ml) was added 3-methyl-2-thiophenecarboxyaldehyde (25 g), and the mixture was stirred at room temperature for 13 hours. Excess acetone was evaporated under reduced pressure, and to the residue was added ethyl acetate. The mixture was subjected to extraction, and the ethyl acetate layer was washed with water and saturated brine, and dried. Under reduced pressure, ethyl acetate was evaporated to give oil.

To an ethanol solution of sodium ethoxide prepared from 60% sodium hydride (8 g, washed with hexane thrice) and ethanol (200 ml) was added at room temperature diethyl malonate (32.0 g) and then was added the above-mentioned oil. The reaction mixture was refluxed for 2 hours, cooled and subjected to ice-cooling. Precipitates were filtered and washed with cold ethanol, to which was added 2M sodium hydroxide (125 ml). The mixture was stirred at 100° C. for 2.5 hours and cooled, and to the mixture was added 5N sulfuric acid. The mixture was stirred at 100° C. for 1 hour and cooled, and precipitates were filtered, washed with water and toluene, and dried to give 5-(3-methyl-2-thienyl)cyclohexane-1,3-dione (20.9 g) as colorless crystals.

mp. 166–168° C.

$^1$H-NMR(CDCl$_3$) δ: 2.19 (3H, s), 2.43–2.69 (4H, m), 3.53–3.76 (1H, m), 4.4–6.4 (1H, br), 5.55 (1H, s), 6.81 (1H, d, J=5 Hz), 7.09 (1H, d, J=5 Hz).

Reference Example 115

To a mixture of acetone (25 ml), sodium hydroxide (1.3 g) and water (120 ml) was added 3-chloro-2-thiophenecarboxyaldehyde (4.2 g), and the mixture was stirred at room temperature for 13 hours. Excess acetone was evaporated under reduced pressure, and to the residue was added ethyl acetate. The mixture was subjected to extraction, and the ethyl acetate layer was washed with water and saturated brine, and dried. Under reduced pressure, ethyl acetate was evaporated to give oil. To a solution of sodium ethoxide (1.8 g) in ethanol (30 ml) was added at room temperature diethyl malonate (4.1 g) and then was added the above oil. The mixture was refluxed for 6 hours, cooled and subjected to ice-cooling, and precipitates were filtered and washed with cold ethanol. To the precipitates was added 2 M sodium hydroxide (16 ml), and the mixture was stirred at 100° C. for 2.5 hours and cooled. To the mixture was added 2.5 M sulfuric acid (16 ml), and the mixture was stirred at 100° C. for 30 minutes and cooled. Precipitates were filtered, washed with water and toluene, and dried to give crystals, which were recrystallized from ethyl acetate to give colorless crystals of 5-(3-chloro-2-thienyl)cyclohexane-1,3-dione (1.4 g).

mp. 145–146° C.

$^1$H-NMR(CDCl$_3$) δ: 2.47–3.07 (4H, m), 3.70–3.99 (1H, m), 5.11 (1H, br), 5.65 (1H, s), 6.90 (1H, d, J=5 Hz), 7.18 (1H, d, J=5 Hz).

Working Example 1
(Production of Compound 1)

A mixture of 6-phenyl-4,5,6,7-tetrahydroindol-4-one (0.11 g), aminoguanidine hydrochloride (0.06 g), concentrated hydrochloric acid (0.026 ml), water (0.026 ml) and ethanol (10 ml) was refluxed for 20 minutes. Under reduced pressure, the solvent was evaporated, and the residue was dissolved in water. The solution was washed with diethylether, and to the mixture was added 1N sodium hydroxide solution. The mixture was extracted with ethyl acetate, and the organic layer was dried with magnesium sulfate. Under reduced pressure, the solvent was evaporated, and the residue was dissolved in ethanol. To the solution was added 4N hydrochloric acid, and the solvent was evaporated. The residue was recrystallized from ethanol to give 4-guanidinoimino-6-phenyl-4,5,6,7-tetrahydroindole hydrochloride (Compound 1) (70 mg) as colorless crystals.

mp. 192–194° C.

Elemental Analysis for $C_{15}H_{17}N_5$.2HCl Calcd. C, 52.95; H, 5.63; N, 20.58. Found C, 52.83; H, 5.57; N, 20.42.

$^1$H-NMR(DMSO-d$_6$) δ: 2.68–3.16 (4H, m), 3.24–3.48 (1H, m), 6.84 (1H, s), 6.95 (1H, s), 7.21–7.50 (5H, m), 7.74 (4H, br), 10.15 (1H, br), 11.77 (1H, br).

Working Example 2
(Production of Compound 2)

A mixture of 3-methyl-6-phenyl-4,5,6,7-tetrahydroindol-4-one (0.8 g), aminoguanidine hydrochloride (0.41 g), concentrated hydrochloric acid (0.18 ml), water (0.18 ml) and ethanol (50 ml) was refluxed for 30 minutes. Under reduced pressure, the solvent was evaporated, and the residue was dissolved in water. The solution was washed with diethylether. To the mixture was added sodium hydroxide solution, and the mixture was extracted with ethyl acetate. The organic layer was washed with water and saturated brine, and dried with magnesium sulfate. Under reduced pressure, the solvent was evaporated, and to the residue was 1N hydrochloric acid (2 ml). The solvent was evaporated, and the residue was recrystallized from ethanol-ethyl acetate to give 4-guanidinoimino-3-methyl-6-phenyl-4,5,6,7-tetrahydroindole hydrochloride (Compound 2) (0.1 g) as colorless crystals.

mp. 176° C. (decomp.)

Elemental Analysis for $C_{16}H_{19}N_5$.2HCl.0.2H$_2$O Calcd. C, 53.70; H, 6.03; N, 19.57. Found C, 53.59; H, 6.05; N, 19.45.

$^1$H-NMR(DMSO-d$_6$) δ: 2.11 (3H, s), 2.63–3.16 (4H, m), 3.20–3.44 (1H, m), 6.4–8.1 (4H, br), (1H, s), 6.72, 7.20–7.50 (5H, m), 10.1 (1H, br), 11.48 (1H, s).

Working Example 3
(Production of Compound 3)

A mixture of 3-ethyl-6-phenyl-4,5,6,7-tetrahydroindol-4-one (0.5 g), aminoguanidine hydrochloride (0.25 g), concentrated hydrochloric acid (0.1 ml), water (0.1 ml) and ethanol (30 ml) was refluxed for 7 hours, and to the mixture was added 1N hydrochloric acid (0.1 ml). Under reduced pressure, the solvent was evaporated. The resulting crystals were washed with water and recrystallized from ethanol to give 3-ethyl-4-guanidinoimino-6-phenyl-4,5,6,7-tetrahydroindole hydrochloride (Compound 3) (0.22 g) as colorless crystals.

mp. 158–160° C.

$^1$H-NMR(DMSO-d$_6$) δ: 1.15 (3H, t, J=7 Hz), 2.48–2.76 (2H, m), 2.82–3.10 (2H, m), 3.14–3.35 (1H, m), 6.46 (1H, s), 6.6–8.4 (4H, br), 7.20–7.50 (5H, m), 10.7 (1H, s), 10.8 (1H, s).

Working Example 4
(Production of Compound 4)

A mixture of 2-methyl-6-phenyl-4,5,6,7-tetrahydroindol-4-one (0.8 g), aminoguanidine hydrochloride (0.41 g), concentrated hydrochloric acid (0.18 ml), water (0.18 ml) and ethanol (50 ml) was refluxed for 1 hour. Under reduced pressure, the solvent was evaporated. The residue was suspended in ethyl acetate, and the suspension was washed with water. Under reduced pressure, the solvent was evaporated. The residue was dissolved in ethanol, and to the solution was added 1N hydrochloric acid. The solvent was evaporated, and the residue was recrystallized from ethanol-ethyl acetate to give 4-guanidinoimino-2-methyl-6-phenyl-4,5,6,7-tetrahydroindole hydrochloride (Compound 4) (0.92 g) as colorless crystals.

mp. 215° C. (decomp.)

Elemental Analysis for $C_{16}H_{19}N_5 \cdot 2HCl$ Calcd. C, 54.24; H, 5.97; N, 19.77. Found C, 53.89; H, 5.99; N, 19.49.

$^1$H-NMR(DMSO-$d_6$) δ: 2.23 (3H, s), 2.80–3.21 (4H, m), 3.35–3.54 (1H, m), 6.44 (1H, s), 7.23–7.52 (5H, m), 8.02 (4H, br), 10.8 (1H, br), 12.29 (1H, br).

Working Example 5
(Production of Compound 5)

A mixture of 2-phenyl-1,2,3,4,5,6,7,8-octahydrocarbazol-4-one (0.8 g), aminoguanidine hydrochloride (0.35 g), concentrated hydrochloric acid (0.15 ml), water (0.15 ml) and ethanol (50 ml) was refluxed for 1 hour. Under reduced pressure, the solvent was evaporated, and to the residue was added sodium hydrogen carbonate solution. The solution was extracted with ethyl acetate. The organic layer was washed with water and saturated brine, and dried with magnesium sulfate. Under reduced pressure, the solvent was evaporated, and the residue was purified with silica gel column chromatography (EtOAc/MeOH) and dissolved in ethanol. To the solution was added 1N hydrochloric acid (4 ml), and the solvent was evaporated. The residue was recrystallized from ethanol to give 4-guanidinoimino-2-phenyl-1,2,3,4,5,6,7,8-octahydrocarbazole hydrochloride (Compound 5) (0.53 g) as amorphous.

$^1$H-NMR(DMSO-$d_6$) δ: 1.56–1.83 (4H, m), 2.40–2.70 (5H, m), 2.75–3.38 (4H, m), 6.4–8.4 (5H, br), 7.20–7.52 (5H, m), 10.72 (1H, s).

Working Example 6
(Production of Compound 6)

A mixture of 3-methyl-6-(2-methylphenyl)-4,5,6,7-tetrahydroindol-4-one (0.70 g), aminoguanidine hydrochloride (0.34 g), concentrated hydrochloric acid (0.44 ml), water (0.44 ml) and ethanol (50 ml) was refluxed for 12 hours. Under reduced pressure, the solvent was evaporated. To the residue was added sodium hydrogen carbonate solution, and the mixture was extracted with ethyl acetate. The organic layer was washed with water and saturated brine, dried with magnesium sulfate and concentrated under reduced pressure, and the residue was purified with silica gel column chromatography (EtOAc/MeOH/Et$_3$N). The resulting oil was dissolved in ethanol, and to the solution was added 1N hydrochloric acid. The solvent was evaporated, and the residue was recrystallized from ethanol-ethyl acetate to give 4-guanidinoimino-3-methyl-6-(2-methylphenyl)-4,5,6,7-tetrahydroindole hydrochloride (Compound 6) (0.04 g) as colorless crystals.

mp. 187° C. (decomp.)

Elemental Analysis for $C_{17}H_{21}N_5 \cdot 2HCl \cdot 0.5H_2O$ Calcd. C, 54.14; H, 6.56; N, 17.54. Found C, 54.36; H, 6.53; N, 17.59.

$^1$H-NMR(DMSO-$d_6$) δ: 2.22 (3H, s), 2.34 (3H, s), 2.4–2.65 (1H, m), 2.7–3.02 (3H, m), 3.34–3.53 (1H, m), 6.48 (1H, s), 6.85–7.8 (4H, br), 7.1–7.48 (4H, m), 10.36 (1H, s), 10.77 (1H, s).

Working Example 7
(Production of Compound 7)

A mixture of 1-methyl-6-phenyl-4,5,6,7-tetrahydroindol-4-one (0.50 g), aminoguanidine hydrochloride (0.26 g), concentrated hydrochloric acid (0.11 ml), water (0.11 ml) and ethanol (50 ml) was refluxed for 30 minutes. Under reduced pressure, the solvent was evaporated, and the residue was dissolved in water. The solution was washed with diethylether, and to the mixture was added 1N sodium hydroxide solution. The mixture was extracted with ethyl acetate, and the organic layer was dried with magnesium sulfate. Under reduced pressure, the solvent was evaporated, and the residue was dissolved in ethanol. To the solution was added 1N hydrochloric acid, and the solvent was evaporated. The residue was recrystallized from ethanol to give 4-guanidinoimino-1-methyl-6-phenyl-4,5,6,7-tetrahydroindole hydrochloride (Compound 7) (0.37 g) as colorless crystals.

mp. 205° C. (decomp.)

Elemental Analysis for $C_{16}H_{19}N_5 \cdot 2HCl$ Calcd. C, 54.24; H, 5.97; N, 19.77. Found C, 53.97; H, 5.91; N, 19.55.

$^1$H-NMR(DMSO-$d_6$) δ: 2.78–3.24 (4H, m), 3.30–3.50 (1H, m), 6.62 (3H, s), 6.88 (1H, d, J=3 Hz), 7.16 (1H, d, J=3 Hz), 7.22–7.57 (5H, m), 7.97 (4H, br), 10.5 (1H, br).

Working Example 8
(Production of Compound 8)

A mixture of 1,3-dimethyl-6-phenyl-4,5,6,7-tetrahydroindol-4-one (0.31 g), aminoguanidine hydrochloride (0.15 g), concentrated hydrochloric acid (0.065 ml), water (0.065 ml) and ethanol (50 ml) was refluxed for 5 hours. Under reduced pressure, the solvent was evaporated, and the residue was dissolved in water. The solution was washed with diethylether, and to the mixture was added sodium hydrogen carbonate solution. The mixture was extracted with ethyl acetate, and the organic layer was dried with magnesium sulfate. Under reduced pressure, the solvent was evaporated, and the residue was dissolved in ethanol. To the solution was added 1N hydrochloric acid. The solvent was evaporated, and the residue was recrystallized from ethanol-ethyl acetate to give 4-guanidinoimino-1,3-dimethyl-6-phenyl-4,5,6,7-tetrahydroindole hydrochloride (Compound 8) (0.1 g) as colorless crystals.

mp. 230° C. (decomp.)

Elemental Analysis for $C_{17}H_{21}N_5 \cdot HCl \cdot 0.5H_2O$ Calcd. C, 59.90; H, 6.80; N, 20.55. Found C, 60.14; H, 6.63; N, 20.49.

$^1$H-NMR(DMSO-$d_6$) δ: 2.19 (3H, s), 2.35–3.56 (5H, m), 3.45 (3H, s), 6.49 (1H, s), 6.8–8.4 (4H, br), 7.22–7.48 (5H, m), 10.68 (1H, br).

Working Example 9
(Production of Compound 9)

A mixture of 6-phenyl-1-propyl-4,5,6,7-tetrahydroindol-4-one (0.80 g), aminoguanidine hydrochloride (0.46 g), concentrated hydrochloric acid (0.19 ml), water (0.19 ml) and ethanol (50 ml) was refluxed for 30 minutes. Under reduced pressure, the solvent was evaporated, and the residue was dissolved in water and washed with diethylether. To the mixture was added 1N sodium hydroxide solution, and the mixture was extracted with ethyl acetate. The organic layer was washed with water and saturated brine and dried with magnesium sulfate. Under reduced pressure, the solvent was evaporated, and the residue was dissolved in ethanol. To the solution was added a solution of 4N hydrochloric acid in ethyl acetate (2 ml). The solvent was evaporated, and the residue was recrystallized from ethanol to give 4-guanidinoimino-6-phenyl-1-propyl-4,5,6,7-tetrahydroindole hydrochloride (Compound 9) (1.0 g) as colorless crystals of E/Z compounds.

mp. 155° C. (decomp.)

Elemental Analysis for $C_{18}H_{23}N_5.2HCl$ Calcd. C, 56.54; H, 6.59; N, 18.32. Found C, 56.23; H, 6.59; N, 18.22.

$^1$H-NMR(DMSO-d$_6$) δ: 0.86 (3H, t, J=7 Hz), 1.58–1.83 (2H, m), 2.73–3.53 (5H, m), 3.72–4.08 (2H, m), 6.89 (1H, d, J=3 Hz), 7.07 (1H, d, J=3 Hz), 7.21–7.60 (5H, m), 7.8–8.2 (4H, br), 10.2–11.0 (1H, br). and δ: 0.83 (3H, t, J=7 Hz), 1.58–1.83 (2H, m), 2.73–3.53 (5H, m), 3.72–4.08 (2H, m), 6.56 (1H, d, J=3 Hz), 6.75 (1H, d, J=3 Hz), 7.21–7.60 (5H, m), 7.2–7.75 (4H, br), 10.76 (1H, br).

Working Example 10
(Production of Compound 10)

A mixture of 1-benzyl-6-phenyl-4,5,6,7-tetrahydroindol-4-one (0.8 g), aminoguanidine hydrochloride (0.32 g), concentrated hydrochloric acid (0.13 ml), water (0.13 ml) and ethanol (50 ml) was refluxed for 30 minutes. Under reduced pressure, the solvent was evaporated, and the residue was washed with water and dissolved in ethanol. To the solution was added a solution of 4N hydrochloric acid-ethyl acetate (1 ml), and the mixture was concentrated. The residue was recrystallized from ethanol to give 1-benzyl-4-guanidinoimino-6-phenyl-4,5,6,7-tetrahydroindole hydrochloride (Compound 10) (0.67 g) as colorless crystals.

mp. 142° C. (decomp.)

$^1$H-NMR(DMSO-d$_6$) δ: 2.45–2.79 (2H, m), 2.90–3.10 (2H, m), 3.13–3.37 (1H, m), 5.13 (2H, s), 6.63 (1H, d, J=3 Hz), 6.83–8.12 (4H, br), 6.87 (1H, d, J=3 Hz), 7.06–7.42 (10H, m), 10.82 (1H, br).

Working Example 11
(Production of Compound 11)

A mixture of 1-benzoyl-6-phenyl-4,5,6,7-tetrahydroindol-4-one (0.68 g), aminoguanidine hydrochloride (0.26 g), concentrated hydrochloric acid (0.11 ml), water (0.11 ml) and ethanol (50 ml) was refluxed for 30 minutes. Under reduced pressure, the solvent was evaporated, and the residue was washed with water to give crystals, which were recrystallized from ethanol to give 1-benzoyl-4-guanidinoimino-6-phenyl-4,5,6,7-tetrahydroindole hydrochloride (Compound 11) (0.83 g) as colorless crystals.

mp. 168° C. (decomp.)

Elemental Analysis for $C_{22}H_{21}N_5O.HCl.H_2O$ Calcd. C, 62.04; H, 5.68; N, 16.44. Found C, 61.89; H, 5.98; N, 16.45.

$^1$H-NMR(DMSO-d$_6$) δ: 2.67 (1H, dd, J=13, 16 Hz), 3.01–3.53 (4H, m), 6.91 (1H, d, J=3 Hz), 6.96 (1H, d, J=3 Hz), 7.22–7.78 (10H, m) 7.0–8.2 (4H, br). 10.92 (1H, s).

Working Example 12
(Production of Compound 12)

A mixture of 1-methanesulfonyl-6-phenyl-4,5,6,7-tetrahydroindol-4-one (0.40 g), aminoguanidine hydrochloride (0.17 g), concentrated hydrochloric acid (0.069 ml), water (0.069 ml) and ethanol (40 ml) was refluxed for 20 minutes. Under reduced pressure, the solvent was evaporated, and the residue was washed with water, dried and recrystallized from ethanol to give 4-guanidinoimino-1-methanesulfonyl-6-phenyl-4,5,6,7-tetrahydroindole hydrochloride (Compound 12) (0.41 g) as colorless crystals.

mp. 270° C. (decomp.)

Elemental Analysis for $C_{16}H_{19}N_5O_2S.HCl$ Calcd. C, 50.32; H, 5.28; N, 18.34. Found C, 50.05; H, 5.22; N, 18.19.

$^1$H-NMR(DMSO-d$_6$) δ: 2.48–2.69 (1H, m), 2.95–3.66 (4H, m), 3.50 (3H, s), 6.95 (1H, d, J=4 Hz), 7.18 (1H, d, J=3 Hz), 7.24–7.51 (5H, m), 7.13–8.0 (4H, br), 10.8 (1H, br).

Working Example 13
(Production of Compound 13)

A mixture of 1-methanesulfonyl-3-methyl-6-phenyl-4,5,6,7-tetrahydroindol-4-one (0.41 g), aminoguanidine hydrochloride (0.16 g), concentrated hydrochloric acid (0.068 ml), water (0.068 ml) and ethanol (30 ml) was refluxed for 20 minutes. The reaction solution was allowed to stand in a refrigerator for 12 hours, and precipitated crystals were filtered, which were washed with ethanol and recrystallized from water to give 4-guanidinoimino-1-methanesulfonyl-3-methyl-6-phenyl-4,5,6,7-tetrahydroindole hydrochloride (Compound 13) (0.25 g) as colorless crystals.

mp. 260° C. (decomp.)

Elemental Analysis for $C_{17}H_{21}N_5O_2S.HCl.0.5H_2O$ Calcd. C, 50.42; H, 5.73; N, 17.30. Found C, 50.56; H, 5.45; N, 17.33.

$^1$H-NMR(DMSO-d$_6$) δ: 2.26 (3H, s), 2.48–2.71 (1H, m), 2.95–3.66 (4H, m), 3.45 (3H, s), 6.9–8.3 (4H, br), 6.96 (1H, s), 7.20–7.53 (5H, m), 10.84 (1H, br).

Working Example 14
(Production of Compound 14)

A mixture of 3-ethyl-1-methanesulfonyl-6-phenyl-4,5,6,7-tetrahydroindol-4-one (0.25 g), aminoguanidine hydrochloride (0.091 g), concentrated hydrochloric acid (0.039 ml), water (0.039 ml) and ethanol (30 ml) was refluxed for 1 hour. Under reduced pressure, the solvent was evaporated, and the residue was washed with ethyl acetate and water to give 3-ethyl-4-guanidinoimino-1-methanesulfonyl-6-phenyl-4,5,6,7-tetrahydroindole hydrochloride (Compound 14) (0.92 g) as colorless crystals.

mp. 260° C. (decomp.)

Elemental Analysis for $C_{18}H_{23}N_5O_2S.HCl$ Calcd. C, 52.74; H, 5.90; N, 17.08. Found C, 52.37; H, 5.89; N, 16.93.

$^1$H-NMR(DMSO-d$_6$) δ: 1.18 (3H, t, J=7 Hz), 2.40–2.83 (1H, m), 2.73 (2H, d, J=7 Hz), 2.96–3.59 (4H, m), 3.46 (3H, s), 6.8–8.0 (4H, br), 6.92 (1H, s), 7.22–7.53 (5H, m), 10.8 (1H, br).

Working Example 15
(Production of Compound 15)

A mixture of 1-methanesulfonyl-3-methyl-6-(2-methylphenyl)-4,5,6,7-tetrahydroindol-4-one (0.20 g), aminoguanidine hydrochloride (0.073 g), concentrated hydrochloric acid (0.032 ml), water (0.032 ml) and ethanol (20 ml) was refluxed for 30 minutes. Under reduced pressure, the solvent was evaporated, and to the residue was added sodium hydrogen carbonate solution. The mixture was extracted with ethyl acetate, and the organic layer was purified with silica gel column chromatography (EtOAc/MeOH). To the resulting crystals was added 1N hydrochloric acid, and the mixture was concentrated. The residue was recrystallized from ethanol-ethyl acetate to give 4-guanidinoimino-1-methanesulfonyl-3-methyl-6-(2-methylphenyl)-4,5,6,7-tetrahydroindole hydrochloride (Compound 15) (0.16 g) as colorless crystals.

mp. 228–230° C.

Elemental Analysis for $C_{18}H_{23}N_5O_2S.HCl.0.6H_2O$ Calcd. C, 51.38; H, 6.04; N, 16.65. Found C, 51.54; H, 6.03; N, 16.40.

$^1$H-NMR(DMSO-d$_6$) δ: 2.26 (3H, s), 2.36 (3H, s), 2.89–3.58 (5H, m), 3.45 (3H, s), 6.8–8.1 (4H, br), 7.15–7.28 (3H, m), 7.48 (1H, d, J=7H), 10.76 (1H, s).

Working Example 16
(Production of Compound 16)

A mixture of 1-methanesulfonyl-3-methyl-6-(2-fluorophenyl)-4,5,6,7-tetrahydroindol-4-one (0.30 g), aminoguanidine hydrochloride (0.11 g), concentrated hydrochloric acid (0.047 ml), water (0.047 ml) and ethanol (30 ml)

was refluxed for 4 hours. Under reduced pressure, the solvent was evaporated, and the residue was recrystallized from ethanol to give 6-(2-fluorophenyl)-4-guanidinoimino-1-methanesulfonyl-3-methyl-4,5,6,7-tetrahydroindole hydrochloride (Compound 16) (0.2 g) as colorless crystals.

mp. 286° C. (decomp.)

Elemental Analysis for $C_{17}H_{20}FN_5O_2S \cdot HCl \cdot 0.5H_2O$ Calcd. C, 48.28; H, 5.24; N, 16.56. Found C, 48.26; H, 5.07; N, 16.82.

$^1$H-NMR(DMSO-$d_6$) δ: 2.26 (3H, s), 2.44–2.74 (1H, m), 2.98–3.64 (3H, m), 3.46 (3H, s), 6.8–8.0 (4H, br), 6.99 (1H, s), 7.17–7.63 (4H, m), 10.81 (1H, s).

Working Example 17
(Production of Compound 17)

A mixture of 6-(2-chlorophenyl)-1-methanesulfonyl-3-methyl-4,5,6,7-tetrahydroindol-4-one (0.25 g), aminoguanidine hydrochloride (0.086 g), concentrated hydrochloric acid (0.11 ml), water (0.11 ml) and ethanol (30 ml) was refluxed for 5hours. Under reduced pressure, the solvent was evaporated, and the residue was recrystallized form water-ethanol to give 6-(2-chlorophenyl)-4-guanidinoimino-1-methanesulfonyl-3-methyl-4,5,6,7-tetrahydroindole hydrochloride (Compound 17) (0.22 g) as colorless crystals.

mp. 258° C. (decomp.)

Elemental Analysis for $C_{17}H_{20}ClN_5O_2S \cdot HCl \cdot 0.5H_2O$ Calcd. C, 46.47; H, 5.05; N, 15.94. Found C, 46.39; H, 4.92; N, 15.98.

$^1$H-NMR(DMSO-$d_6$) δ: 2.26 (3H, d, J=1 Hz), 2.53–2.74 (1H, m), 2.96–3.56 (3H, m), 3.45 (3H, s), 3.58–3.81 (1H, m), 6.99 (1H, d, J=1 Hz), 7.1–7.85 (4H, br), 7.27–7.66 (4H, m), 10.92 (1H, s).

Working Example 18
(Production of Compound 18)

A mixture of 1-methanesulfonyl-3-methyl-6-(2-thienyl)-4,5,6,7-tetrahydroindol-4-one (0.20 g), aminoguanidine hydrochloride (0.075 g), concentrated hydrochloric acid (0.032 ml), water (0.032 ml) and ethanol (30 ml) was refluxed for 1 hour. Under reduced pressure, the solvent was evaporated, and the residue was recrystallized from ethanol to give 4-guanidinoimino-1-methanesulfonyl-3-methyl-6-(2-thienyl)-4,5,6,7-tetrahydroindole hydrochloride (Compound 18) (0.26 g) as colorless crystals.

mp. 297° C. (decomp.)

Elemental Analysis for $C_{15}H_{19}N_5O_2S_2 \cdot HCl$ Calcd. C, 44.82; H, 5.02; N, 17.42. Found C, 44.76; H, 4.97; N, 17.43.

$^1$H-NMR(DMSO-$d_6$) δ: 2.24 (3H, d, J=1 Hz), 2.67 (1H, dd, J=11, 16 Hz), 2.96–3.52 (3H, m), 3.33 (3H, s), 3.58–3.76 (1H, m), 6.7–7.8 (4H, br), 6.95–7.03 (2H, m), 7.09 (1H, d, J=3 Hz), 7.40 (1H, dd, J=1, 5 Hz), 10.99 (1H, s).

Working Example 19
(Production of Compound 19)

A mixture of 1-(4-methylphenyl)sulfonyl-6-phenyl-4,5,6,7-tetrahydroindol-4-one (1.0 g), aminoguanidine hydrochloride (0.32 g), concentrated hydrochloric acid (0.14 ml), water (0.14 ml) and ethanol (50 ml) was refluxed for 20 minutes. Under reduced pressure, the solvent was evaporated, and the residue was washed with water, dried and recrystallized from ethanol to give 4-guanidinoimino-1-(4-methylphenyl)sulfonyl-6-phenyl-4,5,6,7-tetrahydroindole hydrochloride (Compound 19) (1.1 g) as colorless crystals.

mp. 252–256° C.

Elemental Analysis for $C_{22}H_{23}N_5O_2S \cdot HCl$ Calcd. C, 57.70; H, 5.28; N, 15.29. Found C, 57.33; H, 5.26; N, 15.23.

$^1$H-NMR(DMSO-$d_6$) δ: 2.41 (3H, s), 2.48–2.74 (1H, m), 2.85–3.06 (2H, m), 3.16–3.40 (2H, m), 6.97 (1H, d, J=4 Hz), 7.21–7.52 (8H, m), 7.81 (1H, d, J=8 Hz), 6.8–8.1 (4H, br), 10.84 (1H, d, J=9 Hz).

Working Example 20
(Production of Compound 20)

A mixture of 3-methyl-6-(2-methylphenyl)-4,5,6,7-tetrahydroindazol-4-one (0.15 g), aminoguanidine hydrochloride (0.072 g), concentrated hydrochloric acid (0.062 ml), water (0.062 ml) and ethanol (30 ml) was stirred at 50° C. for 3 hours and at 80° C. for 1.5 hours. Under reduced pressure, the solvent was evaporated. To the residue was added water, and the mixture was washed with diethylether. To the aqueous layer was added sodium hydrogen carbonate solution, and the mixture was extracted with ethyl acetate. The organic layer was washed with water and saturated brine, dried with magnesium sulfate and concentrated under reduced pressure, and to the residue was added 1N hydrochloric acid (1.5 ml). Under reduced pressure, the solvent was evaporated, and the resulting crystals were recrystallized from ethanol to give 4-guanidinoimino-3-methyl-6-(2-methylphenyl)-4,5,6,7-tetrahydroindazole hydrochloride (Compound 20) (0.18 g) as colorless crystals.

mp. 211° C. (decomp.)

Elemental Analysis for $C_{16}H_{20}N_6 \cdot 2HCl \cdot 0.3H_2O$ Calcd. C, 51.29; H, 6.08; N, 22.43. Found C, 51.64; H, 6.07; N, 22.33.

$^1$H-NMR(DMSO-$d_6$) δ: 2.33 (3H, s), 2.47 (3H, s), 2.4–2.66 (4H, m), 2.77–3.04 (2H, m), 3.36–3.48 (1H, m), 6.9–7.9 (4H, br), 7.14–7.25 (3H, m), 7.38–7.47 (1H, m), 10.71 (1H, s).

Working Example 21
(Production of Compound 21)

A mixture of 3-methyl-6-(2-chlorophenyl)-4,5,6,7-tetrahydroindazol-4-one (0.22 g), aminoguanidine hydrochloride (0.098 g), concentrated hydrochloric acid (0.084 ml), water (0.084 ml) and ethanol (40 ml) was refluxed for 4 hours. Under reduced pressure, the solvent was evaporated, and to the residue was added water. The mixture was washed with diethylether and concentrated under reduced pressure, and the resulting crystals were recrystallized from water-ethanol to give 4-guanidinoimino-6-(2-chlorophenyl)-3-methyl-4,5,6,7-tetrahydroindazole hydrochloride (Compound 21) (0.26 g) as colorless crystals.

mp. 220° C. (decomp.)

Elemental Analysis for $C_{15}H_{17}ClN_6 \cdot 2HCl \cdot 0.5H_2O$ Calcd. C, 45.19; H, 5.06; N, 21.08. Found C, 45.41; H, 4.76; N, 21.08.

$^1$H-NMR(DMSO-$d_6$) δ: 2.48 (3H, s), 2.68 (1H, dd, J=12, 17 Hz), 2.94 (2H, d, J=8 Hz), 3.05 (1H, dd, J=2, 16 Hz), 3.53–3.72 (1H, m), 6.9–7.9 (4H, br), 7.24–7.53 (3H, m), 7.56–7.63 (1H, m), 10.86 (1H, s).

Working Example 22
(Production of Compound 22)

A mixture of 6-(2-chlorophenyl)-3-methyl-4,5,6,7-tetrahydroindazol-4-one (1.05 g), aminoguanidine hydrochloride (0.47 g), concentrated hydrochloric acid (0.44 ml), water (0.44 ml) and ethanol (70 ml) was refluxed for 6 hours. Under reduced pressure, the solvent was evaporated, and to the residue was added sodium hydrogen carbonate solution. The mixture was extracted with ethyl acetate. The organic layer was washed with water and saturated brine, and dried with magnesium sulfate. Under reduced pressure, the solvent was evaporated to give 4-guanidinoimino-6-(2-chlorophenyl)-3-methyl-4,5,6,7-tetrahydroindazole (0.6 g) as amorphous. To a solution of 4-guanidinoimino-6-(2-chlorophenyl)-3-methyl-4,5,6,7-tetrahydroindazole (0.3 g) in ethanol (10 ml) was added methanesulfonic acid (0.18 g), and the mixture was concentrated. The resulting crystals were recrystallized from water-ethanol to give 4-guanidinoimino-6-(2-chlorophenyl)-3-methyl-4,5,6,7-tetrahydroindazole methanesulfonate (Compound 22) (0.28 g).

mp. 235° C. (decomp.)

$^1$H-NMR(DMSO-d$_6$) δ: 2.41 (6H, s), 2.47 (3H, s), 2.64 (1H, dd, J=12, 16 Hz), 2.84–3.07 (3H, m), 3.53–3.72 (1H, m), 6.9–7.9 (4H, br), 7.24–7.53 (3H, m), 7.58–7.67 (1H, m), 10.39 (1H, s).

Working Example 23
(Production of Compound 23)

To a solution of 4-guanidinoimino-6-(2-chlorophenyl)-3-methyl-4,5,6,7-tetrahydroindazole (0.3 g) in ethanol (10 ml) was added benzenesulfonic acid (0.18 g), and the mixture was concentrated. The resulting crystals were recrystallized from water-ethanol to give 4-guanidinoimino-6-(2-chlorophenyl)-3-methyl-4,5,6,7-tetrahydroindazole benzenesulfonate (Compound 23) (0.39 g).

mp. 160–162° C.

Elemental Analysis for $C_{15}H_{17}ClN_6 \cdot 2PhSO_3H$ Calcd. C, 51.22; H, 4.62; N, 13.27. Found C, 51.11; H, 4.67; N, 13.27.

$^1$H-NMR(DMSO-d$_6$) δ: 2.45 (3H, s), 2.63 (1H, dd, J=13, 16 Hz), 2.82–3.07 (3H, m), 3.51–3.74 (1H, m), 6.9–7.9 (4H, br), 7.24–7.69 (14H, m), 10.30 (1H, s).

Working Example 24
(Production of Compound 24)

To a solution of 4-guanidinoimino-6-(2-chlorophenyl)-3-methyl-4,5,6,7-tetrahydroindazole (0.3 g) in ethanol (10 ml) was added sulfuric acid (0.053 ml), and the mixture was concentrated. The resulting crystals were recrystallized from water-ethanol to give 4-guanidinoimino-6-(2-chlorophenyl)-3-methyl-4,5,6,7-tetrahydroindazole sulfate (Compound 24) (0.29 g).

mp. 196° C. (decomp.)

Elemental Analysis for $C_{15}H_{17}ClN_6 \cdot H_2SO_4 \cdot EtOH$ Calcd. C, 44.30; H, 5.47; N, 18.23. Found C, 44.16; H, 5.35; N, 18.05.

$^1$H-NMR(DMSO-d$_6$) δ: 2.46 (3H, s), 2.64 (1H, dd, J=12, 16 Hz), 2.82–3.09 (3H, m), 3.4–3.8 (1H, m), 6.9–8.0 (4H, br), 7.34–7.53 (3H, m), 7.60–7.66 (1H, m), 10.31 (1H, s).

Working Example 25
(Production of Compound 25)

A mixture of 6-(2-methoxyphenyl)-3-methyl-4,5,6,7-tetrahydroindazol-4-one (0.2 g), aminoguanidine hydrochloride (0.095 g), concentrated hydrochloric acid (0.12 ml), water (0.12 ml) and ethanol (30 ml) was refluxed for 1 hour. Under reduced pressure, the solvent was evaporated, and to the residue was added water. The mixture was washed with ethyl acetate and concentrated under reduced pressure, and the resulting crystals were recrystallized from water-ethanol to give 4-guanidinoimino-6-(2-methoxyphenyl)-3-methyl-4,5,6,7-tetrahydroindazole hydrochloride (Compound 25) (0.3 g) as colorless crystals.

mp. 202° C. (decomp.)

$^1$H-NMR(DMSO-d$_6$) δ: 2.46 (3H, s), 2.6 (1H, dd, J=8, 20 Hz), 2.76–3.04 (3H,m), 3.43–3.63 (1H, m), 3.81 (3H, s), 6.8–8.1 (4H, br), 6.89–7.07 (2H, m), 7.22–7.40 (1H, m), 10.77 (1H, s).

Working Example 26
(Production of Compound 26)

A mixture of 6-(2-hydroxyphenyl)-3-methyl-4,5,6,7-tetrahydroindazol-4-one (0.04 g), aminoguanidine hydrochloride (0.02 g), concentrated hydrochloric acid (0.041 ml), water (0.041 ml) and ethanol (10 ml) was refluxed for 3 hours. Under reduced pressure, the solvent was evaporated. To the residue was added water, and the mixture was washed with ethyl acetate. Under reduced pressure, the solvent was evaporated, and the resulting crystals were recrystallized from ethanol to give 4-guanidinoimino-6-(2-hydroxyphenyl)-3-methyl-4,5,6,7-tetrahydroindazole hydrochloride (Compound 26) (0.06 g) as colorless crystals.

mp. 168° C. (decomp.)

Elemental Analysis for $C_{15}H_{18}N_6O \cdot 2HCl \cdot 2H_2O$ Calcd. C, 44.23; H, 5.94; N, 20.63. Found C, 44.13; H, 5.85; N, 20.77.

$^1$H-NMR(DMSO-d$_6$) δ: 2.45 (3H, s), 2.4–2.72 (1H, m), 2.74–3.03 (3H, m), 3.34–3.60 (1H, m), 6.7–8.0 (4H, br), 6.72–6.93 (2H, m), 7.02–7.16 (1H, m), 7.21–7.30 (1H, m), 10.59 (1H, s).

Working Example 27
(Production of Compound 27)

A mixture of 6-(2-chlorophenyl)-3-ethyl-4,5,6,7-tetrahydroindazol-4-one (0.44 g), aminoguanidine hydrochloride (0.19 g), concentrated hydrochloric acid (0.24 ml), water (0.24 ml) and ethanol (40 ml) was refluxed for 4 hours. Under reduced pressure, the solvent was evaporated. The resulting crystals were recrystallized from ethanol-water to give 6-(2-chlorophenyl)-3-ethyl-4-guanidinoimino-4,5,6,7-tetrahydroindazole hydrochloride (Compound 27) (0.6 g) as colorless crystals.

mp. 196–200° C.

$^1$H-NMR(DMSO-d$_6$) δ: 1.23 (3H, t, J=7 Hz), 2.69 (1H, dd, J=12, 16 Hz), 2.81–3.15 (3H, m), 2.95 (2H, q, J=7 Hz), 3.51–3.71 (1H, m), 6.7–8.2 (4H, br), 7.24–7.51 (3H, m), 7.6 (1H, dd, J=2, 7 Hz), 10.89 (1H, s).

Working Example 28
(Production of Compounds 28–29)

A solution of 2-acetyl-5-(2-chlorophenyl)cyclohexane-1,3-dione (0.5 g), methylhydrazine sulfate (0.30 g) and triethylamine (0.21 g) in ethanol (20 ml) was refluxed for 30 minutes. Under reduced pressure, the solvent was evaporated, and the residue was dissolved in ethyl acetate. The solution was washed with sodium hydrogen carbonate solution, water and saturated brine and dried with magnesium sulfate. Under reduced pressure, the solvent was evaporated, and the residue was dissolved in ethanol (20 ml). To the solution were added aminoguanidine hydrochloride (0.23 g), concentrated hydrochloric acid (0.48 ml) and water (0.48 ml), and the mixture was refluxed for 4 hours. Under reduced pressure, the solvent was evaporated, and to the residue was added sodium hydrogen carbonate solution. The mixture was extracted with ethyl acetate, and the organic layer was washed with water and saturated brine, and dried with sodium sulfate. Under reduced pressure, the solvent was evaporated, and the resulting crystals were recrystallized from ethyl acetate-methanol to give crystals (0.34 g). The mother liquor was concentrated, and to the residue was added ethyl acetate. Insoluble materials were filtered off, and the filtrate was concentrated to give amorphous (0.14 g). To the amorphous was added 1N hydrochloric acid (1 ml), and the mixture was concentrated under reduced pressure. The resulting crystals were recrystallized from water-ethanol to give 6-(2-chlorophenyl)-4-guanidinoimino-1,3-dimethyl-4,5,6,7-tetrahydroindazole hydrochloride (Compound 28) (0.12 g) as colorless crystals.

mp. 193° C. (decomp.)

Elemental Analysis for $C_{16}H_{19}N_6 \cdot 2HCl \cdot 0.1H_2O$ Calcd. C, 47.39; H, 5.27; N, 20.72. Found C, 47.18; H, 5.29; N, 20.54.

$^1$H-NMR(DMSO-d$_6$) δ: 2.39 (3H, s), 2.64 (1H, dd, J=12, 16 Hz), 2.84–3.14 (3H, m), 3.56–3.77 (1H, m), 3.69 (3H, s), 7.1–8.0 (4H, br), 7.27–7.55 (3H, m), 7.62 (1H, dd, J=2, 7 Hz), 11.02 (1H, s).

To the crystals obtained by recrystallization from ethyl acetate-methanol was added 1N hydrochloric acid (2.5 ml), and the mixture was concentrated under reduced pressure. The resulting crystals were recrystallized from water-ethanol to give 6-(2-chlorophenyl)-4-guanidinoimino-2,3-dimethyl-4,5,6,7-tetrahydroindazole hydrochloride (Compound 29) (0.27 g) as colorless crystals.

mp. 182–183° C.

Elemental Analysis for $C_{16}H_{19}N_6 \cdot 2HCl \cdot 0.5H_2O$ Calcd. C, 46.56; H, 5.37; N, 20.36. Found C, 46.59; H, 5.40; N, 20.37.

$^1$H-NMR(DMSO-$d_6$) δ: 2.54 (3H, s), 2.65 (1H, dd, J=12, 17 Hz), 2.8–2.95 (2H, m), 3.03 (1H, dd, J=3, 16 Hz), 3.4–3.8 (1H, m), 3.75 (3H, s), 7.0–8.3 (4H, br), 7.26–7.56 (3H, m), 7.6 (1H, dd, J=1, 7 Hz), 10.76 (1H, s).

Working Example 29
(Production of Compounds 30a and 30b)

A solution of 2-acetyl-5-(2-chlorophenyl)cyclohexane-1,3-dione (0.5 g), hydroxylamine hydrochloride (0.13 g) and triethylamine (0.19 g) in ethanol (15 ml) was refluxed for 24 hours. To the solution was added triethylamine (0.19 g), and the mixture was refluxed for 24 hours. Under reduced pressure, the solvent was evaporated, and the residue was dissolved in ethyl acetate. The solution was washed with water and saturated brine, and dried with magnesium sulfate. Under reduced pressure, the solvent was evaporated, and the residue was purified with silica gel column chromatography (EtOAc/hexane) to give oil (0.2 g). The oil was dissolved in ethanol (20 ml), and to the solution were added aminoguanidine hydrochloride (0.089 g), concentrated hydrochloric acid (0.038 ml) and water (0.038 ml). The mixture was refluxed for 3 hours. Under reduced pressure, the solvent was evaporated. To the residue was added sodium hydrogen carbonate solution, and the mixture was extracted with ethyl acetate. The organic layer was washed with water and saturated brine, and dried with sodium sulfate. Under reduced pressure, the solvent was evaporated, and the residue was purified with silica gel column chromatography (EtOAc-EtOAc/MeOH) to give oil. To the oil was added 1N hydrochloric acid (1 ml), and the mixture was concentrated. The resulting crystals were recrystallized from ethanol to give crystals of 6-(2-chlorophenyl)-4-guanidinoimino-3-methyl-4,5,6,7-tetrahydrobenz[d]isoxazole hydrochloride (Compound 30a) and 6-(2-chlorophenyl)-4-guanidinoimino-3-methyl-4,5,6,7-tetrahydrobenz[c]isoxazole hydrochloride (Compound 30b), as a mixture of about 1:2 (0.25 g).

$^1$H-NMR(DMSO-$d_6$) δ: 2.50 (3H, s), 2.37–2.83 (1H, m), 2.96–3.23 (3H, m), 3.28–3.9 (1H, m), 7.2–7.8 (4H, br), 7.27–7.63 (4H, m), 10.97 (1H, s). and 2.72 (3H, s), 2.37–2.83 (1H, m), 2.96–3.23 (3H, m), 3.28–3.9 (1H, m), 7.2–7.8 (4H, br), 7.27–7.63 (4H, m), 10.97 (1H, s).

Working Example 30
(Production of Compound 31)

A mixture of 3-methyl-6-phenyl-4,5,6,7-tetrahydrobenzofuran-4-one (0.18 g), aminoguanidine hydrochloride (0.092 g), concentrated hydrochloric acid (0.04 ml), water (0.040 ml) and ethanol (20 ml) was refluxed for 30 minutes. Under reduced pressure, the solvent was evaporated, and the residue was recrystallized from ethanol to give 4-guanidinoimino-3-methyl-6-phenyl-4,5,6,7-tetrahydrobenzofuran hydrochloride (Compound 31) (0.10 g) as colorless crystals.

mp. 250° C. (decomp.)

Elemental Analysis for $C_{16}H_{18}N_4O \cdot HCl$ Calcd. C, 60.28; H, 6.01; N, 17.57. Found C, 59.92; H, 5.95; N, 17.66.

$^1$H-NMR(DMSO-$d_6$) δ: 2.20 (3H, s), 2.36–2.72 (1H, m), 2.89–3.12 (3H, m), 3.20–3.50 (1H, m), 6.80–8.0 (4H, br), 7.25–7.48 (6H, m), 10.80 (1H, s).

Working Example 31
(Production of Compound 32)

To a mixture of 6-(3-bromophenyl)-3-methyl-4,5,6,7-tetrahydrobenzofuran-4-one (0.14 g) and aminoguanidine hydrochloride (51 mg) were added ethanol (10 ml) and 6N hydrochloric acid (0.04 ml), and the mixture was stirred at 90° C. for 2 hours and cooled. The reaction solution was concentrated under reduced pressure, and the residue was washed with ethanol, ethyl acetate and isopropylether, and dried to give (E)-6-(3-bromophenyl)-4-guanidinoimino-3-methyl-4,5,6,7-tetrahydrobenzofuran hydrochloride (Compound 32) (76 mg).

mp285° C. (decomp.).

Elemental Analysis for $C_{16}H_{17}N_4OBr \cdot HCl$ Calcd. C,48.32; H,4.56; N,14.09. Found C,48.14; H,4.44; N,13.91.

$^1$H-NMR(DMSO-$d_6$) δ: 2.20 (3H,d,J=1.2 Hz), 2.63 (1H, dd,J=12.4&16.2 Hz), 2.98–3.10 (3H,m), 3.24–3.44 (1H,m), 7.0–7.8 (4H,broad), 7.32 (1H,t,J=7.6 Hz), 7.40 (1H,s), 7.45 (1H,t,J=1.8 Hz), 7.49 (1H,t,J=1.8 Hz), 7.67 (1H,s).

Working Example 32
(Production of Compound 33)

A mixture of 3-methyl-6-(4-methylphenyl)-4,5,6,7-tetrahydrobenzofuran-4-one (0.30 g), aminoguanidine hydrochloride (0.14 g), concentrated hydrochloric acid (0.062 ml), water (0.062 ml) and ethanol (30 ml) was refluxed for 30 minutes. Under reduced pressure, the solvent was evaporated, and the residue was recrystallized from ethanol to give 4-guanidinoimino-3-methyl-6-(4-methylphenyl)-4,5,6,7-tetrahydrobenzofuran hydrochloride (Compound 33) (0.30 g) as colorless crystals.

mp. 260° C. (decomp.)

Elemental Analysis for $C_{17}H_{20}N_4O \cdot HCl$ Calcd. C, 61.35; H, 6.36; N, 16.83. Found C, 60.97; H, 6.07; N, 16.76.

$^1$H-NMR(DMSO-$d_6$) δ: 2.19 (3H, s), 2.29 (3H, s), 2.52–2.64 (1H, m), 2.86–3.08 (3H, m), 3.18–3.52 (2H, m), 6.7–7.9 (4H, br), 7.09–7.36 (4H, m), 7.39 (1H, s), 10.86 (1H, s).

Working Example 33
(Production of Compound 34)

To a mixture of 6-(4-fluorophenyl)-3-methyl-4,5,6,7-tetrahydrobenzofuran-4-one (0.12 g) and aminoguanidine hydrochloride (59 mg) were added ethanol (10 ml) and 6N hydrochloric acid (0.046 ml), and the mixture was stirred at 90° C. for 1 hour and cooled. The reaction solution was concentrated under reduced pressure, and the residue was washed with ethanol and isopropylether, and dried to give (E)-6-(4-fluorophenyl)-4-guanidinoimino-3-methyl-4,5,6,7-tetrahydrobenzofuran hydrochloride (Compound 34) (0.12 g).

mp277° C. (decomp.).

Elemental Analysis for $C_{16}H_{17}N_4OF \cdot HCl \cdot 0.2H_2O$ Calcd. C,56.46; H,5.45; N,16.46. Found C,56.27; H,5.38; N,16.64.

$^1$H-NMR(DMSO-$d_6$) δ: 2.19 (3H,s), 2.70 (1H,dd,J= 12.2&16.6 Hz), 2.96–3.09 (3H,m), 3.2–3.5 (1H,m), 6.9–7.7 (4H,broad), 7.18 (2H,t,J=5.8&8.6 Hz), 7.41 (1H,s), 7.48 (2H,dd,J=5.8&8.6 Hz).

Working Example 34
(Production of Compound 35)

A mixture of 3-methyl-6-(4-bromophenyl)-4,5,6,7-tetrahydrobenzofuran-4-one (0.30 g), aminoguanidine hydrochloride (0.11 g), concentrated hydrochloric acid (0.049 ml), water (0.049 ml) and ethanol (30 ml) was refluxed for 2 hours. Under reduced pressure, the solvent was evaporated, and the residue was recrystallized from ethanol to give 4-guanidinoimino-3-methyl-6-(4-bromophenyl)-4,5,6,7-tetrahydrobenzofuran hydrochloride (Compound 35) (0.25 g) as colorless crystals.

mp. 235° C. (decomp.)

Elemental Analysis for $C_{16}H_{17}N_4OBr.HCl$ Calcd. C, 48.32; H, 4.56; N, 14.09. Found C, 48.25; H, 4.71; N, 14.34.

$^1$H-NMR(DMSO-$d_6$) δ: 2.20 (3H, s), 2.5–2.77 (1H, m), 2.86–3.13 (2H, m), 3.20–3.50 (1H, m), 7.0–7.8 (4H, br), 7.37–7.63 (4H, m), 7.40 (1H, s), 10.86 (1H, s).

Working Example 35
(Production of Compound 36)

A mixture of 3-methyl-6-(4-methoxyphenyl)-4,5,6,7-tetrahydrobenzofuran-4-one (0.10 g), aminoguanidine hydrochloride (0.045 g), concentrated hydrochloric acid (0.02 ml), water (0.02 ml) and ethanol (30 ml) was refluxed for 2 hours. Under reduced pressure, the solvent was evaporated, and the residue was recrystallized from ethanol to give 4-guanidinoimino-6-(4-methoxyphenyl)-3-methyl-4,5,6,7-tetrahydrobenzofuran hydrochloride (Compound 36) (0.08 g) as colorless crystals.

mp. 182° C. (decomp.)

$^1$H-NMR(DMSO-$d_6$) δ: 2.20 (3H, s), 2.48–2.68 (1H, m), 2.90–3.08 (3H, m), 3.20–3.50 (1H, m), 3.75 (3H, s), 6.8–8.0 (4H, br), 6.86–6.97 (2H, m), 7.28–7.42 (2H, m), 7.37 (1H, s), 10.78 (1H, s).

Working Example 36
(Production of Compound 37)

A mixture of 3-methyl-6-(2-methylphenyl)-4,5,6,7-tetrahydrobenzofuran-4-one (0.18 g), aminoguanidine hydrochloride (0.087 g), concentrated hydrochloric acid (0.037 ml), water (0.037 ml) and ethanol (20 ml) was refluxed for 1 hour. Under reduced pressure, the solvent was evaporated, and the residue was recrystallized from ethanol to give 4-guanidinoimino-3-methyl-6-(2-methylphenyl)-4,5,6,7-tetrahydrobenzofuran hydrochloride (Compound 37) (0.17 g) as colorless crystals.

mp. 266° C. (decomp.)

Elemental Analysis for $C_{17}H_{20}N_4O.HCl$ Calcd. C, 61.35; H, 6.36; N, 16.83. Found C, 61.02; H, 6.04; N, 16.81.

$^1$H-NMR(CD$_3$OD) δ: 2.24 (3H, s), 2.38 (3H, s), 2.59 (1H, dd, J=41, 44 Hz), 2.84–3.12 (1H, m), 3.52–3.70 (1H, m), 7.08–7.60 (5H, m).

Working Example 37
(Production of Compound 38)

To a mixture of 6-(2,5-dimethylphenyl)-3-methyl-4,5,6,7-tetrahydrobenzofuran-4-one (0.36 g) and aminoguanidine hydrochloride (157 mg) were added ethanol (28 ml) and 6N hydrochloric acid (0.12 ml), and the mixture was stirred at 90° C. for 2 hours and cooled. The reaction solution was concentrated under reduced pressure, and the residue was washed with ethanol, ethyl acetate and isopropylether, and dried to give (E)-4-guanidinoimino-6-(2,5-dimethylphenyl)-3-methyl-4,5,6,7-tetrahydrobenzofuran hydrochloride (Compound 38) (0.21 g).

mp235–236° C.

$^1$H-NMR(DMSO-$d_6$) δ: 2.21 (3H,s), 2.27 (3H,s), 2.29 (3H,s), 2.5–2.64 (1H,m), 2.90–3.01 (3H,m), 3.3–3.6 (1H,m), 6.97 (1H,d,J=7.6 Hz), 7.08 (1H,d,J=7.6 Hz), 7.10 (4H, broad), 7.26 (1H,s), 7.40 (1H,s).

Working Example 38
(Production of Compound 39)

To a mixture of 3-methyl-6-(2-trifluoromethylphenyl)-4,5,6,7-tetrahydrobenzofuran-4-one (0.28 g) and aminoguanidine hydrochloride (105 mg) were added ethanol (20 ml) and 6N hydrochloric acid (0.082 ml), and the mixture was stirred at 90° C. for 2 hours and cooled. The reaction solution was concentrated under reduced pressure, and the residue was washed with ethanol, ethyl acetate and isopropylether, and dried to give (E)-4-guanidinoimino-3-methyl-6-(2-trifluoromethylphenyl)-4,5,6,7-tetrahydrobenzofuran hydrochloride (Compound 39) (0.21 g).

mp275° C. (decomp.).

Elemental Analysis for $C_{17}H_{17}N_4OF_3.HCl.0.3H_2O$ Calcd. C,52.06; H,4.78; N,14.29. Found C,52.82; H,4.63; N,14.39.

$^1$H-NMR(DMSO-$d_6$) δ: 2.21 (3H,d,J=1.2 Hz), 2.71–3.24 (4H,m), 3.53 (1H,m), 7.36 (4H,broad), 7.46 (1H,s), 7.53 (1H,t,J=8.2 Hz), 7.74 (1H,d,J=8.0 Hz), 7.75 (1H,d,J=8.0 Hz), 7.97 (1H,d,J=7.8 Hz).

Working Example 39
(Production of Compound 40)

To a mixture of 6-(2-fluorophenyl)-3-methyl-4,5,6,7-tetrahydrobenzofuran-4-one (0.21 g) and aminoguanidine hydrochloride (95 mg) were added ethanol (17 ml) and 6N hydrochloric acid (0.074 ml), and the mixture was stirred at 90° C. for 2 hours and cooled. The reaction solution was concentrated under reduced pressure, and the residue was washed with ethanol, ethyl acetate and isopropylether, and dried to give (E)-6-(2-fluorophenyl)-4-guanidinoimino-3-methyl-4,5,6,7-tetrahydrobenzofuran hydrochloride (Compound 40) (0.19 g).

mp288° C. (decomp.).

Elemental Analysis for $C_{16}H_{17}N_4OF.HCl.0.2H_2O$ Calcd. C,56.46; H,5.45; N,16.46. Found C,56.46; H,5.35; N,16.74.

$^1$H-NMR(DMSO-$d_6$) δ: 2.20 (3H,s), 2.69 (1H,dd,J=12.0&16.4 Hz), 2.98–3.11 (3H,m), 3.58 (1H,m), 7.0–7.7 (4H,broad), 7.16–7.55 (4H,m), 7.41 (1H,s).

Working Example 40
(Production of Compound 41)

A mixture of 6-(2,4-difluorophenyl)-3-methyl-4,5,6,7-tetrahydrobenzofuran-4-one (0.13 g), aminoguanidine hydrochloride (0.058 g), concentrated hydrochloric acid (0.074 ml), water (0.074 ml) and ethanol (30 ml) was refluxed for 3 hours. Under reduced pressure, the solvent was evaporated, and the residue was recrystallized form water-ethanol to give 6-(2,4-difluorophenyl)-4-guanidinoimino-3-methyl-4,5,6,7-tetrahydrobenzofuran hydrochloride (Compound 41) (0.17 g) as colorless crystals.

mp. 278° C. (decomp.)

Elemental Analysis for $C_{16}H_{16}F_2N_4O.HCl.0.1H_2O$ Calcd. C, 53.89; H, 4.86; N, 15.71. Found C, 53.80; H, 4.90; N, 15.97.

$^1$H-NMR(DMSO-$d_6$) δ: 2.20 (3H, d, J=1 Hz), 2.68 (1H, dd, J=1, 5 Hz), 2.80–3.66 (4H, m), 6.9–7.85 (4H, br), 7.05–7.62 (3H, m), 7.42 (1H, d, J=1 Hz), 10.92 (1H, s).

Working Example 41
(Production of Compound 42)

To a mixture of 6-(2-chlorophenyl)-3-methyl-4,5,6,7-tetrahydrobenzofuran-4-one (0.35 g) and aminoguanidine hydrochloride (148 mg) were added ethanol (27 ml) and 6N hydrochloric acid (0.12 ml), and the mixture was stirred at 90° C. for 2 hours and cooled. The reaction solution was concentrated under reduced pressure, and the residue was washed with ethanol, ethyl acetate and isopropylether, and dried to give (E)-6-(2-chlorophenyl)-4-guanidinoimino-3- methyl-4,5,6,7-tetrahydrobenzofuran hydrochloride (Compound 42) (0.38 g).

mp300° C. (decomp.).

Elemental Analysis for $C_{16}H_{17}N_4OCl·HCl$ Calcd. C,54.40; H,5.14; N,15.86. Found C,54.19; H,5.13; N,15.81.

$^1$H-NMR(DMSO-$d_6$) δ: 2.21 (3H,s), 2.69 (1H,dd,J=12.0&16.2 Hz), 2.99–3.09 (3H,m), 3.71 (1H,m), 7.0–7.8 (4H,broad), 7.27–7.51 (3H,m), 7.42 (1H,s), 7.61 (1H,dd,J=2.0&7.4 Hz).

Working Example 42
(Production of Compound 43)

To a mixture of 6-(2,3-dichlorophenyl)-3-methyl-4,5,6,7-tetrahydrobenzofuran-4-one (0.15 g) and aminoguanidine hydrochloride (56 mg) were added ethanol (10 ml) and 6N hydrochloric acid (0.044 ml), and the mixture was stirred at 90° C. for 2 hours and cooled. The reaction solution was concentrated under reduced pressure, and the residue was washed with ethanol, ethyl acetate and isopropylether, and dried to give (E)-6-(2,3-dichlorophenyl)-4-guanidinoimino-3-methyl-4,5,6,7-tetrahydrobenzofuran hydrochloride (Compound 43) (0.16 g).

mp286° C. (decomp.).

Elemental Analysis for $C_{16}H_{16}N_4OCl_2·HCl$ Calcd. C,49.57; H,4.42; N,14.45. Found C,49.31; H,4.55; N,14.14.

$^1$H-NMR(DMSO-$d_6$) δ: 2.21 (3H,d,J=1.0 Hz), 2.68 (1H, dd,J=12.2&16.2 Hz), 2.98–3.09 (3H,m), 3.77 (1H,m), 7.39 (4H,broad), 7.39–7.49 (1H,m), 7.44 (1H,s), 7.61 (2H,d,J=8.4 Hz).

Working Example 43
(Production of Compound 44)

To a mixture of 6-(2,6-dichlorophenyl)-3-methyl-4,5,6,7-tetrahydrobenzofuran-4-one (0.42 g) and aminoguanidine hydrochloride (157 mg) were added ethanol (30 ml) and 6N hydrochloric acid (0.12 ml), and the mixture was stirred at 90° C. for 2 hours and cooled. The reaction solution was concentrated under reduced pressure, and the residue was washed with ethanol, ethyl acetate and isopropylether, and dried to give (E)-6-(2,6-dichlorophenyl)-4-guanidinoimino-3-methyl-4,5,6,7-tetrahydrobenzofuran hydrochloride (Compound 44) (0.33 g).

mp280° C. (decomp.).

Elemental Analysis for $C_{16}H_{17}N_4OCl·HCl·H_2O$ Calcd. C,47.37; H,4.72; N,13.81. Found C,47.73; H,4.77; N,13.84.

$^1$H-NMR(DMSO-$d_6$) δ: 2.21 (3H,s), 2.87 (1H,t,J=5.4 Hz), 2.95 (1H,t,J=5.2 Hz), 3.24 (1H,dd,J=13.4&16.8 Hz), 3.59 (1H,dd,J=11.8&16.6 Hz), 4.22 (1H,m), 7.2–7.8 (4H, broad), 7.38 (1H,t,J=8.0 Hz), 7.46 (1H,s), 7.55 (1H,t,J=8.4 Hz).

Working Example 44
(Production of Compound 45)

To a mixture of 6-(2-bromophenyl)-3-methyl-4,5,6,7-tetrahydrobenzofuran-4-one (0.28 g) and aminoguanidine hydrochloride (102 mg) were added ethanol (20 ml) and 6N hydrochloric acid (0.080 ml), and the mixture was stirred at 90° C. for 2 hours and cooled. The reaction solution was concentrated under reduced pressure, and the residue was washed with ethanol, ethyl acetate and isopropylether, and dried to give (E)-6-(2-bromophenyl)-4-guanidinoimino-3-methyl-4,5,6,7-tetrahydrobenzofuran hydrochloride (Compound 45) (0.31 g).

mp296° C. (decomp.).

Elemental Analysis for $C_{16}H_{17}N_4OBr·HCl$ Calcd. C,48.32; H,4.56; N,14.09. Found C,48.16; H,4.48; N,13.90.

$^1$H-NMR(DMSO-$d_6$) δ: 2.21 (3H,d,J=1.2 Hz), 2.67 (1H, dd,J=11.8&15.8 Hz), 2.96–3.09 (3H,m), 3.68 (1H,m), 7.1–7.8 (4H,broad), 7.21–7.48 (4H,m), 7.44 (1H,s), 7.65 (2H,dt,J=1.2&8.2 Hz).

Working Example 45
(Production of Compound 46)

To a mixture of 6-(2-methoxyphenyl)-3-methyl-4,5,6,7-tetrahydrobenzofuran-4-one (0.19 g) and aminoguanidine hydrochloride (82 mg) were added ethanol (15 ml) and 6N hydrochloric acid (0.064 ml), and the mixture was stirred at 90° C. for 2 hours and cooled. The reaction solution was concentrated under reduced pressure, and the residue was washed with ethanol, ethyl acetate and isopropylether, and dried to give (E)-4-guanidinoimino-6-(2-methoxyphenyl)-3-methyl-4,5,6,7-tetrahydrobenzofuran hydrochloride (Compound 46) (0.19 g).

mp279° C. (decomp.).

Elemental Analysis for $C_{17}H_{20}N_4O_2·HCl·0.3H_2O$ Calcd. C,57.64; H,6.15; N,15.82. Found C,57.45; H,6.07; N,15.82.

$^1$H-NMR(DMSO-$d_6$) δ: 2.20 (3H,d,J=1.2 Hz), 2.66 (1H, dd,J=12.0&16.4 Hz), 2.83–3.10 (3H,m), 3.62 (1H,m), 3.82 (3H,s), 6.96 (1H,t,J=7.4 Hz), 7.03 (1H,d,J=7.4 Hz), 7.1–7.7 (4H,broad), 7.23–7.37 (2H,m), 7.40 (1H,d,J=1.2 Hz).

Working Example 46
(Production of Compound 47)

To a mixture of 6-(2-furyl)-3-methyl-4,5,6,7-tetrahydrobenzofuran-4-one (0.22 g) and aminoguanidine hydrochloride (113 mg) were ethanol (20 ml) and 6N hydrochloric acid (0.088 ml), and the mixture was stirred at 90° C. for 2 hours and cooled. The reaction solution was concentrated under reduced pressure, and the residue was washed with ethanol, ethyl acetate and isopropylether, and dried to give (E)-6-(2-furyl)-4-guanidinoimino-3-methyl-4,5,6,7-tetrahydrobenzofuran hydrochloride (Compound 47) (0.22 g).

mp 300° C. or more

Elemental Analysis for $C_{14}H_{16}N_4O_2·HCl$ Calcd. C,54.46; H,5.55; N,18.15. Found C,54.23; H,5.51; N,18.19.

$^1$H-NMR(DMSO-$d_6$) δ: 2.18 (3H,d,J=1.0 Hz), 2.67 (1H, dd,J=9.0&16.0 Hz), 2.94 (1H,dd,J=9.4&16.4 Hz), 3.08–3.19 (2H,m), 3.50 (1H,m), 6.27 (1H,d,J=3.2 Hz), 6.41 (1H,dd,J=1.8&3.2 Hz), 7.37 (4H,broad), 7.40 (1H,s), 7.59 (1H,d,J=1.2 Hz).

Working Example 47
(Production of Compound 48)

A mixture of 3-methyl-6-(2-thienyl)-4,5,6,7-tetrahydrobenzofuran-4-one (0.30 g), aminoguanidine hydrochloride (0.15 g), concentrated hydrochloric acid (0.065 ml), water (0.065 ml) and ethanol (30 ml) was refluxed for 2.5 hours. Under reduced pressure, the solvent was evaporated, and the residue was recrystallized from ethanol to give 4-guanidinoimino-3-methyl-6-(2-thienyl)-4,5,6,7-tetrahydrobenzofuran hydrochloride (Compound 48) (0.36 g) as colorless crystals.

mp. 285° C. (decomp.)

Elemental Analysis for $C_{14}H_{16}N_4OS·HCl$ Calcd. C, 51.77; H, 5.27; N, 17.25. Found C, 51.69; H, 5.31; N, 17.38.

$^1$H-NMR(DMSO-$d_6$) δ: 2.19 (3H, s), 2.71 (1H, dd, J=11, 17 Hz), 2.96 (1H, dd, J=10, 17 Hz), 3.12–3.3 (2H, m), 3.62.–3.79 (1H, m), 6.8–7.9 (4H, br), 6.99 (1H, dd, J=4, 5 Hz), 7.08 (1H, d, J=3 Hz), 7.3–7.42 (2H, m), 11.05 (1H, s).

Working Example 48
(Production of Compound 49)

To a mixture of 6-(5-methyl-2-thienyl)-3-methyl-4,5,6,7-tetrahydrobenzofuran-4-one (0.18 g) and aminoguanidine hydrochloride (81 mg) were added ethanol (15 ml) and 6N hydrochloric acid (0.063 ml), and the mixture was stirred at 90° C. for 2 hours and cooled. The reaction solution was concentrated under reduced pressure, and the residue was washed with ethanol, ethyl acetate and isopropylether, and dried to give (E)-4-guanidinoimino-6-(5-methyl-2-thienyl)-5-methyl-4,5,6,7-tetrahydrobenzofuran hydrochloride (Compound 49) (0.18 g).

mp287° C. (decomp.).

Elemental Analysis for $C_{15}H_{18}N_4OS \cdot HCl \cdot 0.2H_2O$ Calcd. C,52.60; H,5.71; N,16.45. Found C,52.70; H,5.61; N,16.56.

$^1$H-NMR(DMSO-$d_6$) δ: 2.18 (3H,d,J=1.4 Hz), 2.40 (3H, s), 2.61–2.97 (2H,m), 3.06–3.19 (2H,m), 3.63 (1H,m), 6.65 (1H,dd,J=1.2&3.4 Hz), 6.82 (1H,d,J=3.2 Hz), 7.40 (1H,s), 7.41 (4H,broad).

Working Example 49
(Production of Compound 50)

To 6-phenyl-3-trifluoromethyl-4,5,6,7-tetrahydrobenzofuran-4-one (0.13 g) and aminoguanidine hydrochloride (51 mg) were added ethanol (10 ml) and 6N hydrochloric acid (0.04 ml), and the mixture was stirred at 900° C. for 4 hours and cooled. The reaction solution was concentrated under reduced pressure, and the residue was washed with ethanol, ethyl acetate and isopropylether and dried to give (E)-4-guanidinoimino-6-phenyl-3-trifluoromethyl-4,5,6,7-tetrahydrobenzofuran hydrochloride (Compound 50) (0.12 g).

mp291° C. (decomp.).

$^1$H-NMR(DMSO-$d_6$) δ: 2.69 (1H,dd,J=12.2&16.4 Hz), 3.04–3.17 (3H,m), 3.2–3.5 (1H,m), 7.2–7.9 (4H,broad), 7.28–7.46 (5H,m), 8.45 (1H,s).

Working Example 50
(Production of Compound 51)

To a mixture of 6-(4-fluorophenyl)-3-trifluoromethyl-4,5,6,7-tetrahydrobenzofuran-4-one (0.25 g) and aminoguanidine hydrochloride (93 mg) were ethanol (20 ml) and 6N hydrochloric acid (0.072 ml), and the mixture was stirred at 90° C. for 4 hours and cooled. The reaction solution was concentrated under reduced pressure, and the residue was washed with ethanol, ethyl acetate and isopropylether, and dried to give (E)-6-(4-fluorophenyl)-4-guanidinoimino-3-trifluoromethyl-4,5,6,7-tetrahydrobenzofuran hydrochloride (Compound 51) (0.20 g).

mp283° C. (decomp.).

$^1$H-NMR(DMSO-$d_6$) δ: 2.68 (1H,dd,J=12.4&16.0 Hz), 3.04–3.15 (3H,m), 3.2–3.5 (1H,m), 7.0–7.8 (4H,broad), 7.20 (2H,t,J=9.0 Hz), 7.49 (2H,dd,J=5.4&8.8 Hz), 8.45 (1H,d,J=1.4 Hz).

Working Example 51
(Production of Compound 52)

A mixture of 3-trifluoromethyl-6-(2-methylphenyl)-4,5,6,7-tetrahydrobenzofuran-4-one (0.15 g), aminoguanidine hydrochloride (0.06 g), concentrated hydrochloric acid (0.025 ml), water (0.025 ml) and ethanol (30 ml) was refluxed for 6 hours. Under reduced pressure, the solvent was evaporated, and the residue was recrystallized from ethanol-ethyl acetate to give 3-trifluoromethyl-4-guanidinoimino-6-(2-methylphenyl)-4,5,6,7-tetrahydrobenzofuran hydrochloride (Compound 52) (0.08 g) as colorless crystals.

mp. 247° C. (decomp.)

Elemental Analysis for $C_{17}H_{17}F_3N_4O \cdot HCl$ Calcd. C, 52.79; H, 4.69; N, 14.48. Found C, 52.79; H, 4.44; N, 14.46.

$^1$H-NMR(DMSO-$d_6$) δ: 2.37 (3H, s), 2.66 (1H, dd, J=13, 16 Hz), 2.96–3.72 (4H, m), 6.2–8.2 (4H, br), 7.12–7.33 (3H, m), 7.46 (1H, d, J=7 Hz), 8.43 (1H, s), 11.21 (1H, s).

Working Example 52
(Production of Compound 53)

To a mixture of 6-(2-bromophenyl)-3-trifluoromethyl-4,5,6,7-tetrahydrobenzofuran-4-one (0.29 g) and aminoguanidine hydrochloride (90 mg) were ethanol (16 ml) and 6N hydrochloric acid (0.070 ml), and the mixture was stirred at 90° C. for 4 hours and cooled. The reaction solution was concentrated under reduced pressure, and the residue was washed with ethanol, ethyl acetate and isopropylether, and dried to give (E)-6-(2-bromophenyl)-4-guanidinoimino-3-trifluoromethyl-4,5,6,7-tetrahydrobenzofuran hydrochloride (Compound 53) (0.13 g).

mp289° C. (decomp.).

Elemental Analysis for $C_{16}H_{14}N_4OBrF_3 \cdot HCl$ Calcd. C,42.55; H,3.35; N,12.40. Found C,42.67; H,3.35; N,12.26.

$^1$H-NMR(DMSO-$d_6$) δ: 2.76 (1H,dd,J=12.8&16.2 Hz), 3.05–3.15 (3H,m), 3.73 (1H,m), 7.0–8.0 (4H,broad), 7.26 (1H,t,J=7.0 Hz), 7.46 (1H,t,J=7.2 Hz), 7.63 (1H,d,J=7.2 Hz), 7.68 (1H,d,J=8.0 Hz), 8.45 (1H,s).

Working Example 53
(Production of Compound 54)

To a mixture of 6-(2-furyl)-3-trifluoromethyl-4,5,6,7-tetrahydrobenzofuran-4-one (0.22 g) and aminoguanidine hydrochloride (90 mg) were ethanol (16 ml) and 6N hydrochloric acid (0.070 ml), and the mixture was stirred at 90° C. for 4 hours and cooled. The reaction solution was concentrated under reduced pressure, and the residue was washed with ethanol, ethyl acetate and isopropylether, and dried to give (E)-6-(2-furyl)-4-guanidinoimino-3-trifluoromethyl-4,5,6,7-tetrahydrobenzofuran hydrochloride (Compound 54) (0.12 g).

mp282° C. (decomp.).

$^1$H-NMR(DMSO-$d_6$) δ: 2.75 (1H,dd,J=10.8&16.6 Hz), 3.04 (1H,dd,J=9.4&17.2 Hz), 3.20–3.31 (2H,m), 3.59 (1H, m), 6.28 (1H,d,J=3.4 Hz), 6.40 (1H,dd,J=2.0&3.2 Hz), 7.10 (4H,broad), 7.57 (1H,d,J=1.8 Hz), 8.36 (1H,d,J=1.4 Hz).

Working Example 54
(Production of Compound 55)

To a mixture of 3-ethoxycarbonyl-6-phenyl-4,5,6,7-tetrahydrobenzofuran-4-one (0.28 g) and aminoguanidine hydrochloride (111 mg) were ethanol (20 ml) and 6N hydrochloric acid (0.086 ml), and the mixture was stirred at 90° C. for 2 hours and cooled. The reaction solution was concentrated under reduced pressure, and the residue was washed with ethanol, ethyl acetate and isopropylether, and dried to give (E)-3-ethoxycarbonyl-4-guanidinoimino-6-phenyl-4,5,6,7-tetrahydrobenzofuran hydrochloride (Compound 55) (0.25 g).

mp260° C. (decomp.).

$^1$H-NMR(DMSO-$d_6$) δ: 1.29 (3H,t,J=7.0 Hz), 2.69 (1H, dd,J=12.8&16.4 Hz), 2.98–3.11 (3H,m), 3.2–3.5 (1H,m), 4.25 (2H,q,J=7.0 Hz), 7.2–7.9 (4H,broad), 7.28–7.46 (5H, m), 8.38 (1H,s).

Working Example 55
(Production of Compound 56)

To a mixture of 6-(2-chlorophenyl)-3-ethoxycarbonyl-4,5,6,7-tetrahydrobenzofuran-4-one (0.14 g) and aminoguanidine hydrochloride (49 mg) were ethanol (9 ml) and 6N hydrochloric acid (0.038 ml), and the mixture was stirred at 90° C. for 2 hours and cooled. The reaction solution was concentrated under reduced pressure, and the residue was washed with ethanol, ethyl acetate and isopropylether, and dried to give (E)-6-(2-chlorophenyl)-3-ethoxycarbonyl-4-guanidinoimino-4,5,6,7-tetrahydrobenzofuran hydrochloride (Compound 56) (90 mg).

mp277° C. (decomp.).

Elemental Analysis for $C_{18}H_{19}N_4O_3Cl.HCl$ Calcd. C,52.57; H,4.90; N,13.62. Found C,52.37; H,4.90; N,13.69.

$^1$H-NMR(DMSO-$d_6$) δ: 1.29 (3H,t,J=7.0 Hz), 2.71 (1H, dd,J=12.4& 16.0 Hz), 2.99–3.13 (3H,m), 3.75 (1H,m), 4.26 (2H,q,J=7.0 Hz), 7.1–8.2 (4H,m), 7.29–7.62 (4H,m), 8.39 (1H,s).

Working Example 56
(Production of Compound 57)

A mixture of 4-methyl-7-(2-methylphenyl)-5,6,7,8-tetrahydroquinolin-5-one (0.30 g), aminoguanidine hydrochloride (0.14 g), concentrated hydrochloric acid (0.018 ml), water (0.018 ml) and ethanol (30 ml) was refluxed for 7 hours. Under reduced pressure, the solvent was evaporated, and the residue was dissolved in water. The solution was washed with ethyl acetate and concentrated under reduced pressure, and the residue was recrystallized from ethyl acetate-ethanol to give 5-guanidinoimino-4-methyl-7-(2-methylphenyl)-5,6,7,8-tetrahydroquinoline hydrochloride (Compound 57) (0.4 g) as colorless crystals.

mp. 218° C. (decomp.)

Elemental Analysis for $C_{18}H_{21}N_5.2HCl.0.5H_2O$ Calcd. C, 55.53; H, 6.21; N, 17.99. Found C, 55.54; H, 6.19; N, 18.11.

$^1$H-NMR(DMSO-$d_6$) δ: 2.35 (3H, s), 2.64–2.96 (1H, m), 2.91 (3H, s), 3.07–3.61 (4H, m), 6.9–8.4 (4H, br), 7.03–7.30 (3H, m), 7.37–7.48 (1H, m), 7.86 (1H, d, J=6 Hz), 8.65 (1H, d, J=6 Hz), 11.36 (1H, s).

Working Example 57
(Production of Compound 58)

A mixture of 7-(2,5-dimethylphenyl)-4-methyl-5,6,7,8-tetrahydroquinolin-5-one (100 mg), aminoguanidine hydrochloride (46 mg) and concentrated hydrochloric acid (0.1 ml) in ethanol (2 ml) was refluxed for 1 hour and 30 minutes. The reaction solution was cooled, and precipitated crystals were filtered, washed with ethanol and dried to give 7-(2, 5-dimethylphenyl)-5-guanidinoimino-4-methyl-5,6,7,8-tetrahydroquinoline hydrochloride (Compound 58) (131 mg) as pale yellow crystals.

mp. 260–262° C.

$^1$H-NMR(DMSO-$d_6$) δ: 2.28 (3H, s), 2.30 (3H, s), 2.77 (1H, m), 2.88 (3H, s), 3.13 (1H, m), 3.40 (3H, m), 6.99 (1H, d), 7.10 (1H, d), 7.28 (1H, s), 7.85 (2H, d), 7.90 (4H, broad), 8.64 (1H, d.)

Working Example 58
(Production of Compound 59)

A mixture of 7-(2-fluorophenyl)-4-methyl-5,6,7,8-tetrahydroquinolin-5-one (0.35 g), aminoguanidine hydrochloride (0.16 g), concentrated hydrochloric acid (0.21 ml), water (0.21 ml) and ethanol (40 ml) was refluxed for 7 hours. Under reduced pressure, the solvent was evaporated, and the residue was dissolved in water. The solution was washed with ethyl acetate, and to the mixture was added sodium hydrogen carbonate solution, and the mixture was extracted with ethyl acetate. The organic layer was washed with water and saturated brine, and dried with magnesium sulfate. Under reduced pressure, the solvent was evaporated, and the residue was dissolved in ethanol. To the solution was added 1N hydrochloric acid (3 ml), and the mixture was concentrated under reduced pressure. The residue was recrystallized from ethanol to give 7-(2-fluorophenyl)-5-guanidinoimino-4-methyl-5,6,7,8-tetrahydroquinoline hydrochloride (Compound 59) (0.33 g) as colorless crystals.

mp. 240 0° C. (decomp.)

Elemental Analysis for $C_{17}H_{18}FN_5.2HCl.0.2H_2O$ Calcd. C, 52.64; H, 5.30; N, 18.06. Found C, 52.63; H, 5.17; N, 17.92.

$^1$H-NMR(DMSO-$d_6$) δ: 2.80–4.0 (5H, m), 2.83 (3H, s), 7.19–7.44 (3H, m), 7.50–8.02 (4H, br), 7.51–7.63 (1H, m), 7.77 (1H, d, J=6 Hz), 8.60 (1H, d, J=6 Hz), 11.28 (1H, s).

Working Example 59
(Production of Compound 60)

A mixture of 7-(2,4-difluorophenyl)-4-methyl-5,6,7,8-tetrahydroquinolin-5-one (0.43 g), aminoguanidine hydrochloride (0.18 g), concentrated hydrochloric acid (0.39 ml), water (0.39 ml) and ethanol (50 ml) was refluxed for 7 hours. Under reduced pressure, the solvent was evaporated, and the residue was dissolved in water. The solution was washed with ethyl acetate, and the mixture was concentrated under reduced pressure. The residue was recrystallized from water-ethanol to give 7-(2,4-difluorophenyl)-5-guanidinoimino-4-methyl-5,6,7,8-tetrahydroquinoline hydrochloride (Compound 60) (0.45 g) as colorless crystals.

mp. 286° C. (decomp.)

Elemental Analysis for $C_{17}H_{17}N_5F_2.2HCl.0.2H_2O$ Calcd. C, 50.31; H, 4.82; N, 17.25. Found C, 50.20; H, 4.77; N, 17.31.

$^1$H-NMR(DMSO-$d_6$) δ: 2.70–3.03 (1H, m), 2.88 (3H, s), 3.14–3.32 (1H, m), 3.32–3.64 (3H, m), 7.08–7.34 (2H, m), 7.50–8.40 (4H, br), 7.83 (1H, d, J=6 Hz), 8.63 (1H, d, J=6 Hz), 11.59 (1H, s).

Working Example 60
(Production of Compound 61)

A mixture of 7-(2-chlorophenyl)-4-methyl-5,6,7,8-tetrahydroquinolin-5-one (0.20 g), aminoguanidine hydrochloride (0.085 g), concentrated hydrochloric acid (0.11 ml), water (0.11 ml) and ethanol (20 ml) was refluxed for 6 hours. Under reduced pressure, the solvent was evaporated, and the residue was dissolved in water. The mixture was washed with ethyl acetate and concentrated under reduced pressure. The residue was recrystallized from ethyl acetate-ethanol to give 7-(2-chlorophenyl)-5-guanidinoimino-4-methyl-5,6,7, 8-tetrahydroquinoline hydrochloride (Compound 61) (0.21 g) as colorless crystals.

mp. 204° C. (decomp.)

Elemental Analysis for $C_{17}H_{18}N_5Cl.2HCl.0.8H_2O$ Calcd. C, 49.18; H, 5.24; N, 16.87. Found C, 49.46; H, 5.10; N, 16.88.

$^1$H-NMR(DMSO-$d_6$) δ: 2.65–3.00 (1H, m), 2.88 (3H, s), 3.15–3.78 (4H, m), 7.2–8.2 (4H, br), 7.28–7.53 (3H, m), 7.58–7.66 (1H, m), 7.83 (1H, d, J=6 Hz), 8.63 (1H, d, J=6 Hz), 11.45 (1H, s).

Working Example 61
(Production of Compound 62)

A mixture of 7-(2,3-dichlorophenyl)-4-methyl-5,6,7,8-tetrahydroquinolin-5-one (306 mg), aminoguanidine hydrochloride (122 mg) and concentrated hydrochloric acid (0.2 ml) in ethanol (4 ml) was refluxed for 1 hour. The reaction solution was cooled, and precipitated crystals were filtered, washed with ethanol and dried to give 7-(2,3-dichlorophenyl)-5-guanidinoimino-4-methyl-5,6,7,8-tetrahydroquinoline hydrochloride (Compound 62) (425 mg) as colorless crystals.

mp. 270–272° C.

Elemental Analysis for $C_{17}H_{17}N_5Cl_2.2HCl$ Calcd. C, 46.92; H, 4.40; N, 16.09. Found C, 46.99; H, 4.42; N, 15.90.

$^1$H-NMR(DMSO-$d_6$) δ: 2.88 (4H, m), 3.27 (1H, dd), 3.45 (2H, m), 3.74 (1H, m), 7.46 (1H, t), 7.63 (2H, d), 7.82 (1H, d), 7.94 (4H, broad), 8.63 (1H, d), 11.50 (1H, broad).

Working Example 62
(Production of Compound 63)

A mixture of 7-(2,6-dichlorophenyl)-4-methyl-5,6,7,8-tetrahydroquinolin-5-one (171 mg), aminoguanidine hydrochloride (67 mg) and concentrated hydrochloric acid (0.1 ml) in ethanol (3 ml) was refluxed for 2 hours. The reaction solution was concentrated under reduced pressure, and precipitated crystals were recrystallized form ethanol to give 7-(2,6-dichlorophenyl)-5-guanidinoimino-4-methyl-5,6,7,8-tetrahydroquinoline hydrochloride (Compound 63) (195 mg) as colorless crystals.

mp. 300° C. or more

Elemental Analysis for $C_{17}H_{17}N_5Cl_2.2HCl.1/4H_2O$ Calcd. C, 56.44; H, 4.47; N, 15.93. Found C, 56.24; H, 4.35; N, 16.19.

$^1$H-NMR(DMSO-$d_6$) δ: 2.85 (3H, s), 3.07 (1H, dd), 3.28 (1H, d), 3.38 (1H, dd), 4.10 (2H, m), 7.41 (1H, t), 7.57 (2H, d), 7.80 (1H, d), 7.89 (4H, broad), 8.62 (1H, d), 11.46 (1H, broad).

Working Example 63
(Production of Compound 64)

In methanol (1200 ml) was suspended (±)-7-(2-chlorophenyl)-5-guanidinoimino-4-methyl-5,6,7,8-tetrahydroquinoline hydrochloride (123.9 g), and to the suspension was added dropwise 28% sodium methoxide in methanol (119.2 ml). The mixture was stirred at 50° C. for 30 minutes. Under reduced pressure, the solvent was evaporated, and to the residue was added water. The crystals were filtered, washed with water and dried to give colorless crystals of (±)-7-(2-chlorophenyl)-5-guanidinoimino-4-methyl-5,6,7,8-tetrahydroquinoline (109.3 g).

To a solution of (±)-7-(2-chlorophenyl)-5-guanidinoimino-4-methyl-5,6,7,8-tetrahydroquinoline (109.3 g) in isopropylalcohol (700 ml) was added dropwise a solution of L-pyroglutamic acid (10 g) in isopropylalcohol (700 ml) at 50° C. for 1.5 hours, and the mixture was stirred at 50° C. for 1 hour and then at room temperature for 2 days. The crystals were filtered and washed with isopropylalcohol to give (−)-7-(2-chlorophenyl)-5-guanidinoimino-4-methyl-5,6,7,8-tetrahydroquinoline L-pyroglutamate (55.5 g, 88%ee), which was recrystallized from ethanol to give crystals of L-pyroglutamate (44.3 g, 97%ee). The thus obtained crystals of salt was suspended in methanol (500 ml), and to the suspension was added a solution of 28% sodium methoxide in methanol (10.9 ml). The mixture was stirred at 50° C. for 30 minutes, and under reduced pressure, the solvent was evaporated to give crystals, which were washed with water and dried to give (−)-7-(2-chlorophenyl)-5-guanidinoimino-4-methyl-5,6,7,8-tetrahydroquinoline (38.9 g). (This compound was confirmed to be S-isomer (absolute configuration), according to X-ray crystal structure analysis.)

In ethanol (400 ml) was dissolved said (−)-isomer, and to the mixture was added methanesulfonic acid (14.3 g). Under reduced pressure, the solvent was evaporated to give crystals, which were recrystallized from ethanol to give (−)-7-(2-chlorophenyl)-5-guanidinoimino-4-methyl-5,6,7,8-tetrahydroquinoline methanesulfonate (Compound 64) (46.8 g, 99.2%ee).

mp. 194–195° C.

Elemental Analysis for $C_{17}H_{18}N_5Cl.2MeSO_3H$ Calcd. C, 43.88; H, 5.04; N, 13.47; Cl, 6.82. Found C, 43.67; H, 4.90; N, 13.18; Cl, 6.76.

$^1$H-NMR(DMSO-$d_6$) δ: 2.40 (6H, s), 2.78 (1H, dd, J=12, 18 Hz), 2.89 (3H, s), 3.08–3.32 (2H, m), 3.44–3.80 (2H, m), 7.2–8.1 (4H, br), 7.31–7.56 (3H, m), 7.58–7.66 (1H, m), 7.86 (1H, d, J=6 Hz), 8.66 (1H, d, J=6 Hz), 10.77 (1H, s).

Working Example 64
(Production of Compound 65)

With using CHIRALCEL OD (eluted with isopropylalcohol-hexane), (±)-7-(2-chlorophenyl)-4-methyl-5,6,7,8-tetrahydroquinolin-5-one (1.0 g) was subjected to optical resolution to give (−)-7-(2-chlorophenyl)-4-methyl-5,6,7,8-tetrahydroquinolin-5-one (0.33 g), which was dissolved in ethanol (25 ml). To the solution were added aminoguanidine hydrochloride (0.16 g), concentrated hydrochloric acid (0.3 ml) and water (0.3 ml), and the mixture was refluxed for 6 hours. Under reduced pressure, the solvent was evaporated, and the residue was. dissolved in water. The solution was washed with diethylether. To the solution was added sodium hydrogen carbonate solution, and the mixture was extracted with ethyl acetate. The organic layer was washed with water and saturated brine, and dried with magnesium sulfate. Under reduced pressure, the solvent was evaporated, and the resulting crystals were dissolved in ethanol. To the solution was added methanesulfonic acid (2.4 mmol), and the mixture was concentrated. The resulting crystals were recrystallized from ethanol-acetone to give (+)-7-(2-chlorophenyl)-5-guanidinoimino-4-methyl-5,6,7,8-tetrahydroquinoline methanesulfonate (Compound 65) (0.52 g) as colorless crystals.

mp. 194–196° C.

Elemental Analysis for $C_{17}H_{18}ClN_5.2MeSO_3H$ Calcd. C, 43.88; H, 5.04; N, 13.47; Cl, 6.82. Found C, 43.59; H, 4.59; N, 13.38; Cl, 6.82.

$^1$H-NMR(DMSO-$d_6$) was agreed with that of Compound 64.

Working Example 65
(Production of Compound 66)

A mixture of 7-(2-bromophenyl)-4-methyl-5,6,7,8-tetrahydroquinolin-5-one (0.49 g), aminoguanidine hydrochloride (0.19 g), concentrated hydrochloric acid (0.39 ml), water (0.39 ml) and ethanol (50 ml) was refluxed for 6.5 hours. Under reduced pressure, the solvent was evaporated, and the residue was dissolved in water. The solution was washed with ethyl acetate. Under reduced pressure, the solvent was evaporated, and the residue was recrystallized from ethanol-water to give 7-(2-bromophenyl)-5-guanidinoimino-4-methyl-5,6,7,8-tetrahydroquinoline hydrochloride (Compound 66) (0.47 g) as colorless crystals.

mp. 233° C. (decomp.)

Elemental Analysis for $C_{17}H_{18}BrCl_2N_5.2HCl.0.5H_2O$ Calcd. C, 44.96; H, 4.66; N, 15.42. Found C, 45.23; H, 4.67; N, 15.61.

$^1$H-NMR(DMSO-$d_6$) δ: 2.75–3.03 (1H, m), 2.88 (3H, s), 3.16–3.60 (4H, m), 7.22–7.35 (1H, m), 7.41–7.56 (1H, m), 7.69–7.75 (2H, m), 7.4–8.6 (4H, br), 7.82 (1H, d, J=6 Hz), 8.63 (1H, d, J=6 Hz), 11.39 (1H, s).

Working Example 66
(Production of Compound 67)

A mixture of 7-(2-methoxyphenyl)-4-methyl-5,6,7,8-tetrahydroquinolin-5-one (0.40 g), aminoguanidine hydrochloride (0.17 g), concentrated hydrochloric acid (0.22 ml), water (0.22 ml) and ethanol (40 ml) was refluxed for 6 hours. Under reduced pressure, the solvent was evaporated, and the residue was dissolved in water. The solution was washed with ethyl acetate and concentrated under reduced pressure. The residue was recrystallized from ethyl acetate-ethanol to give 5-guanidinoimino-7-(2-methoxyphenyl)-4-methyl-5,6,7,8-tetrahydroquinoline hydrochloride (Compound 67) (0.3 g) as colorless crystals.

mp. 192° C. (decomp.)

Elemental Analysis for $C_{18}H_{21}N_5O.2HCl.0.2H_2O$ Calcd. C, 54.06; H, 5.90; N, 17.51. Found C, 54.15; H, 5.93; N, 17.71.

¹H-NMR(DMSO-d₆) δ: 2.70–3.90 (5H, m), 2.87 (3H, s), 3.83 (3H, s), 6.93–7.06 (2H, m), 7.23–7.40 (2H, m), 7.50–8.02 (4H, br), 7.78 (1H, d, J=6 Hz), 8.61 (1H, d, J=6 Hz), 11.20 (1H, s).

Working Example 67
(Production of Compound 68)

A mixture of 7-(2-hydroxyphenyl)-4-methyl-5,6,7,8-tetrahydroquinolin-5-one (0.08 g), aminoguanidine hydrochloride (0.037 g), concentrated hydrochloric acid (0.048 ml), water (0.048 ml) and ethanol (10 ml) was refluxed for 4 hours and cooled. Under reduced pressure, the solvent was evaporated, and the residue was dissolved in water. The solution was washed with ethyl acetate and concentrated under reduced pressure. The resulting crystals were washed with ethanol, while heating, to give 5-guanidinoimino-7-(2-hydroxyphenyl)-4-methyl-5,6,7,8-tetrahydroquinoline hydrochloride (Compound 68) (0.09 g) as colorless crystals.

mp. 161° C. (decomp.)

¹H-NMR(DMSO-d₆) δ: 2.78–3.03 (1H, m), 2.90 (3H, s), 3.08–3.97 (1H, m), 3.36–3.62 (3H, m), 6.76–7.32 (6H, m), 7.4–8.2 (4H, br), 7.89 (1H, d, J=6 Hz), 8.65 (1H, d, J=6 Hz), 9.8 (1H, br), 11.38 (1H, s).

Working Example 68
(Production of Compound 69)

A mixture of 7-(2-furyl)-4-methyl-5,6,7,8-tetrahydroquinolin-5-one (227 mg), aminoguanidine hydrochloride (122 mg) and concentrated hydrochloric acid (0.1 ml) in ethanol (3 ml) was refluxed for 2 hours. The reaction solution was cooled, and precipitated crystals were filtered and washed with ethanol to give 7-(2-furyl)-5-guanidinoimino-4-methyl-5,6,7,8-tetrahydroquinoline hydrochloride (Compound 69) (305 mg) as colorless crystals.

mp. 300° C. or more

Elemental Analysis for $C_{15}H_{17}N_5O.2HCl$ Calcd. C, 50.57; H, 5.38; N, 19.66. Found C, 50.62; H, 5.25; N, 19.67.

¹H-NMR(DMSO-d₆) δ: 2.85 (3H, s), 2.98 (1H, dd), 3.30 (2H, m), 3.56 (2H, m), 6.42 (2H, d), 7.63 (1H, d), 7.82 (1H, d), 7.98 (4H, broad), 8.64 (1H, d), 11.79 (1H, s).

Working Example 69
(Production of Compound 70)

A mixture of 4-methyl-7-(2-thienyl)-5,6,7,8-tetrahydroquinolin-5-one (0.52 g), aminoguanidine hydrochloride (0.25 g), concentrated hydrochloric acid (0.53 ml), water (0.53 ml) and ethanol (50 ml) was refluxed for 7 hours. Under reduced pressure, the solvent was evaporated, and the residue was dissolved in water. The solution was washed with diethylether and concentrated under reduced pressure, and the residue was recrystallized from water-ethanol to give 5-guanidinoimino-4-methyl-7-(2-thienyl)-5,6,7,8-tetrahydroquinoline hydrochloride (Compound 70) (0.57 g) as colorless crystals.

mp. 225° C. (decomp.)

Elemental Analysis for $C_{15}H_{17}N_5S.2HCl.H_2O$ Calcd. C, 46.16; H, 5.42; N, 17.94. Found C, 46.44; H, 5.51; N, 18.13.

¹H-NMR(DMSO-d₆) δ: 2.60–3.08 (1H, m), 2.86 (3H, s), 3.28–3.80 (4H, m), 6.96–7.08 (1H, m), 7.14 (1H, s), 7.43 (1H, d, J=5 Hz), 7.6–8.2 (4H, br), 7.81 (1H, d, J=6 Hz), 8.63 (1H, d, J=6 Hz), 11.69 (1H, s).

Working Example 70
(Production of Compound 71)

A mixture of 4-methyl-7-(5-methyl-2-thienyl)-5,6,7,8-tetrahydroquinolin-5-one (257 mg), aminoguanidine hydrochloride (117 mg) and concentrated hydrochloric acid (0.2 ml) in ethanol (5 ml) was refluxed for 30 minutes. The reaction solution was cooled, and precipitated crystals were filtered, washed with ethanol and dried to give 5-guanidinoimino-4-methyl-7-(5-methyl-2-thienyl)-5,6,7,8-tetrahydroquinoline hydrochloride (Compound 71) (273 mg) as pale yellow crystals.

mp. 271–273° C.

Elemental Analysis for $C_{16}H_{19}N_5S.2HCl$ Calcd. C, 49.74; H, 5.48; N, 18.13. Found C, 49.66; H, 5.31; N, 18.06.

¹H-NMR(DMSO-d₆) δ: 2.41 (3H, s), 2.86 (3H, s), 2.94 (1H, dd), 3.31 (2H, m), 3.52 (2H, m), 6.66 (1H, dd), 6.90 (1H, d), 7.82 (1H, d), 7.96 (4H, broad), 8.63 (1H, d), 11.73 (1H, s).

Working Example 71
(Production of Compound 72)

A mixture of 7-(5-chloro-2-thienyl)-4-methyl-5,6,7,8-tetrahydroquinolin-5-one (0.79 g), aminoguanidine hydrochloride (0.33 g), concentrated hydrochloric acid (0.7 ml), water (0.7 ml) and ethanol (40 ml) was refluxed for 8.5 hours. Under reduced pressure, the solvent was evaporated, and the residue was washed with ethanol and recrystallized from ethanol-water. The resulting crystals were washed with ethanol to give 7-(5-chloro-2-thienyl)-4-methyl-5,6,7,8-tetrahydroquinoline hydrochloride (Compound 72) (0.26 g) as crystals.

mp. 215° C. (decomp.)

Elemental Analysis for $C_{15}H_{16}ClN_5S.2HCl.0.2H_2O$ Calcd. C, 43.90; H, 4.52; N, 17.07. Found C, 43.88; H, 4.44; N, 16.91.

¹H-NMR(DMSO-d₆) δ: 2.7–3.12 (1H, m), 2.86 (3H, s), 3.22–3.75 (4H, m), 6.9–7.2 (2H, m), 7.6–8.8 (4H, br), 7.81 (1H, d, J=5 Hz), 8.63 (1H, d, J=5 Hz), 11.79 (1H, s).

Working Example 72
(Production of Compound 73)

A mixture of 4-methyl-6-(3-methyl-2-thienyl)-4,5,6,7-tetrahydroquinolin-5-one (0.8 g), aminoguanidine hydrochloride (0.36 g), concentrated hydrochloric acid (0.78 ml), water (0.78 ml) and ethanol (50 ml) was refluxed for 5 hours. Under reduced pressure, the solvent was evaporated, and to the residue was added water. The mixture was washed with ethyl acetate. Under reduced pressure, the solvent was evaporated, and the resulting crystals were recrystallized from ethanol to give 5-guanidinoimino-4-methyl-7-(3-methyl-2-thienyl)-5,6,7,8-tetrahydroquinoline hydrochloride (Compound 73) (0.94 g) as colorless crystals.

mp. 184–187° C.

Elemental Analysis for $C_{16}H_{19}ClN_5S.2HCl.1H_2O$ Calcd. C, 47.53; H, 5.73; N, 17.32. Found C, 47.58; H, 5.76; N, 17.32.

¹H-NMR(DMSO-d₆) δ: 2.21 (3H, s), 2.76 (1H, dd, J=12, 19 Hz), 2.88 (3H, s), 3.2–3.57 (3H, m), 3.62–3.83 (1H, m), 6.87 (1H, d, J=5 Hz), 7.33 (1H, d, J=5 Hz), 7.4–8.4 (4H, br), 7.84 (1H, d, J=6 Hz), 8.64 (1H, d, J=6 Hz), 11.46 (1H, s).

Working Example 73
(Production of Compound 74)

A mixture of 7-(3-chloro-2-thienyl)-4-methyl-5,6,7,8-tetrahydroquinolin-5-one (0.3 g), aminoguanidine hydrochloride (0.14 g), concentrated hydrochloric acid (0.27 ml), water (0.27 ml) and ethanol (30 ml) was refluxed for 6 hours. Under reduced pressure, the solvent was evaporated, and to the residue was added water. The mixture was washed with ethyl acetate, and to the mixture was added sodium hydrogen carbonate solution. The mixture was extracted with ethyl acetate, and the organic layer was washed with water and saturated brine. Under reduced pressure, the solvent was evaporated, and the residue was dissolved in ethanol. To the solution was added a solution of 4N hydrochloric acid-ethyl acetate (0.4 ml), and the mixture was concentrated under reduced pressure. The resulting crystals were recrystallized from ethanol-water to give 7-(3-chloro-2-thienyl)-5-guanidinoimino-4-methyl-5,6,7,8-tetrahydroquinoline hydrochloride (Compound 74) (0.23 g) as colorless crystals.

mp. 203° C. (decomp.)

Elemental Analysis for $C_{15}H_{16}ClN_5S.2HCl$ Calcd. C, 44.29; H, 4.46; N, 17.22. Found C, 44.27; H, 4.46; N, 17.01.

$^1$H-NMR(DMSO-$d_6$) δ: 2.7–2.97 (1H, m), 2.86 (3H, s), 3.22–4.4 (4H, m), 7.08 (1H, d, J=5 Hz), 7.4–8.4 (4H, br), 7.63 (1H, d, J=5 Hz), 7.8 (1H, d, J=5 Hz), 8.62 (1H, d, J=6 Hz), 11.43 (1H, s).

Working Example 74
(Production of Compound 75)

A mixture of 4-methyl-7-(2-pyridyl)-5,6,7,8-tetrahydroquinolin-5-one (0.28 g), aminoguanidine hydrochloride (0.14 g), concentrated hydrochloric acid (0.41 ml), water (0.41 ml) and ethanol (30 ml) was refluxed for 6 hours. Under reduced pressure, the solvent was evaporated, and the residue was dissolved in water. The solution was washed with ethyl acetate and concentrated under reduced pressure, and the residue was recrystallized from water-ethanol to give 5-guanidinoimino-4-methyl-7-(2-pyridyl)-5,6,7,8-tetrahydroquinoline hydrochloride (Compound 75) (0.37 g) as colorless crystals.

mp. 260° C. (decomp.)

Elemental Analysis for $C_{16}H_{18}N_6.3HCl.0.2H_2O$ Calcd. C, 47.18; H, 5.30; N, 20.63. Found C, 47.16; H, 5.45; N, 20.86.

$^1$H-NMR(DMSO-$d_6$) δ: 2.82 (3H, s), 3.03–3.78 (5H, m), 7.4–8.3 (4H, br), 7.53–7.63 (1H, m), 7.78 (1H, d, J=8 Hz), 7.84 (1H, d, J=6 Hz), 8.06–8.17 (1H, m), 8.65 (1H, d, J=6 Hz), 8.70 (1H, d, J=5 Hz), 11.57 (1H, s).

Working Example 75
(Production of Compound 76)

A mixture of 4-methyl-7-(4-pyridyl)-5,6,7,8-tetrahydroquinolin-5-one (0.1 g), aminoguanidine hydrochloride (0.049 g), concentrated hydrochloric acid (0.15 ml), water (0.15 ml) and ethanol (10 ml) was refluxed for 6 hours. Under reduced pressure, the solvent was evaporated, and the residue was dissolved in water. The solution was washed with ethyl acetate. Under reduced pressure, the solvent was evaporated, and the residue was recrystallized from ethanol-water to give 5-guanidinoimino-4-methyl-7-(4-pyridyl)-5,6,7,8-tetrahydroquinoline hydrochloride (Compound 76) (0.13 g) as colorless crystals.

mp. 267° C. (decomp.)

Elemental Analysis for $C_{16}H_{18}N_6.3HCl.0.5H_2O$ Calcd. C, 46.56; H, 5.37; N, 20.36. Found C, 46.66; H, 5.41; N, 20.51.

$^1$H-NMR(DMSO-$d_6$) δ: 2.70–4.2 (5H, m), 2.85 (3H, s), 7.60–8.4 (4H, br), 7.76 (1H, d, J=6 Hz), 8.17 (2H, d, J=5 Hz), 8.61 (1H, d, J=6 Hz), 8.97 (2H, d, J=5 Hz), 11.82 (1H, s).

Working Example 76
(Production of Compound 77)

A mixture of 7-(4-fluorophenyl)-4-methyl-5,6,7,8-tetrahydroquinolin-5-one (0.2 g), aminoguanidine hydrochloride (0.091 g), concentrated hydrochloric acid (0.2 ml), water (0.2 ml) and ethanol (30 ml) was refluxed for 5 hours. Under reduced pressure, the solvent was evaporated, and the residue was dissolved in water. The solution was washed with ethyl acetate. Under reduced pressure, the solvent was evaporated, and the residue was recrystallized from ethanol-ethyl acetate and then recrystallized from ethanol-water to give 7-(4-fluorophenyl)-5-guanidinoimino-4-methyl-5,6,7,8-tetrahydroquinoline hydrochloride (Compound 77) (0.17 g) as colorless crystals.

mp. 259° C. (decomp.)

Elemental Analysis for $C_{17}H_{18}FN_5.2HCl.H_2O$ Calcd. C, 50.75; H, 5.51; N, 17.41. Found C, 51.02; H, 5.58; N, 17.38.

$^1$H-NMR(DMSO-$d_6$) δ: 2.73–2.87 ($_1$H, m), 2.86 (3H, s), 3.00–4.1 (4H, m), 7.13–7.32 (2H, m), 7.43–7.60 (2H, m), 7.60–8.08 (4H, br), 7.78 (1H, d, J=6 Hz), 8.61 (1H, d, J=6 Hz), 11.41 (1H, s).

Working Example 77
(Production of Compound 78)

To a solution of aminoguanidine hydrochloride (0.023 g) in ethanol (10 ml) was added methanesulfonic acid (0.02 g), and the mixture was refluxed for 30 minutes. To the solution was added 4-methoxy-7-phenyl-5,6,7,8-tetrahydroquinolin-5-one (0.05 g), and the mixture was stirred at room temperature for 2 hours and 20 minutes and at 50° C. for 25 minutes. To the mixture was added methanesulfonic acid (0.02 g), and the mixture was stirred at 50° C. for 5 hours. Under reduced pressure, the solvent was evaporated, and the residue was dissolved in water. The solution was washed with ethyl acetate. Under reduced pressure, the solvent was evaporated, and the residue was recrystallized from ethanol-water to give 5-guanidinoimino-4-methoxy-7-phenyl-5,6,7,8-tetrahydroquinoline methanesulfonate (Compound 78) (0.09 g) as colorless crystals.

mp. 203° C. (decomp.)

Elemental Analysis for $C_{16}H_{18}N_6.2MeSO_3H.H_2O$ Calcd. C, 41.19; H, 5.09; N, 12.64. Found C, 41.17; H, 5.25; N, 12.75.

$^1$H-NMR(DMSO-$d_6$) δ: 2.38 (6H, s), 2.66–2.88 (1H, m), 3.03–3.90 (4H, m), 4.19 (3H, s), 6.8–8.4 (4H, br), 7.22–7.48 (5H, m), 7.64 (1H, d, J=7 Hz), 8.73 (1H, d, J=7 Hz), 10.87 (1H, s).

Working Example 78
(Production of Compound 79)

To a solution of aminoguanidine hydrochloride (0.048 g) in methanol (20 ml) was added methanesulfonic acid (0.042 g), and the mixture was refluxed for 1 hour. To the mixture were added 7-(2-chlorophenyl)-4-methoxy-5,6,7,8-tetrahydroquinolin-5-one (0.12 g) and methanesulfonic acid (0.042 g), and the mixture was stirred at 50° C. for 9 hours and at 60° C. for 16 hours. Under reduced pressure, the solvent was evaporated. To the residue was added water, and the mixture was washed with ethyl acetate. Under reduced pressure, the solvent was evaporated, and the residue was recrystallized from water-ethanol to give 7-(2-chlorophenyl)-5-guanidinoimino-4-methoxy-5,6,7,8-tetrahydroquinoline methanesulfonate (Compound 79) (0.19 g) as colorless crystals.

mp. 158–159° C.

Elemental Analysis for $C_{17}H_{18}ClN_5O.2MeSO_3H.H_2O$ Calcd. C, 41.19; H, 5.09; N, 12.64. Found C, 41.17; H, 5.25; N, 12.75.

$^1$H-NMR(DMSO-$d_6$) δ: 2.54 (6H, s), 2.72–2.84 (1H, m), 3.06–3.57 (3H, m), 3.63–4.3 (1H, m), 4.21 (3H, s), 7.2–8.0 (4H, br), 7.36–7.63 (5H, m), 8.61 (1H, d, J=7 Hz).

Working Example 79
(Production of Compounds 80–81)

A mixture of 4-chloro-7-(2-chlorophenyl)-5,6,7,8-tetrahydroquinolin-5-one (0.1 g), aminoguanidine hydrochloride (0.040 g), concentrated hydrochloric acid (0.034 ml), water (0.034 ml) and ethanol (20 ml) was stirred at room temperature for 30 minutes and at 50° C. for 5 hours.

Under reduced pressure, the solvent was evaporated, and the residue was dissolved in water. The solution was washed with ethyl acetate, and to the solution was added sodium hydrogen carbonate solution. The mixture was extracted with ethyl acetate, and the organic layer was washed with water and saturated brine, and dried with magnesium sulfate. Under reduced pressure, the solvent was evaporated, and the residue was purified with silica gel column chromatography (EtOAc/MeOH/Et$_3$N). To the resulting two kinds of amorphous was added 1N hydrochloric acid and concentrated to give 7-(2-chlorophenyl)-4-ethoxy-5-guanidinoimino-5,6,7,8-tetrahydroquinoline hydrochloride (Compound 80) (0.05 g) as colorless crystals and 7-(2-chlorophenyl)-5-guanidinoimino-1,4,5,6,7,8-hexahydroquinoline-4-one hydrochloride (Compound 81) (0.04 g) as amorphous, respectively.

7-(2-chlorophenyl)-4-ethoxy-5-guanidinoimino-5,6,7,8-tetrahydroquinoline hydrochloride (Compound 80)

mp.214° C. (decomp.)

Elemental Analysis for $C_{16}H_{16}F_2N_4O \cdot HCl \cdot 0.1H_2O$ Calcd. C, 53.89; H, 4.86; N, 15.71. Found C, 53.80; H, 4.90; N, 15.97.

$^1$H-NMR(DMSO-d$_6$) δ: 1.47 (3H, t, J=7 Hz), 2.81 (1H, dd, J=12, 16 Hz), 3.06–3.88 (4H, m), 4.29–4.66 (2H, m), 6.4–8.4 (4H, br), 7.28–7.62 (4H, m), 8.69 (1H, d, J=7 Hz), 11.48 (1H, s).

7-(2-chlorophenyl)-5-guanidinoimino-1,4,5,6,7,8-hexahydroquinoline-4-one hydrochloride (Compound 81)

$^1$H-NMR(DMSO-d$_6$) δ: 2.87 (1H, dd, J=3, 16 Hz), 3.16 (1H, dd, J=13, 17 Hz), 3.25–3.65 (2H, m), 3.86–4.08 (1H, m), 7.14 (1H, d, J=7 Hz), 7.31–7.63 (5H, m), 7.8–8.25 (4H, br), 8.45 (1H, d, J=7 Hz), 10.43 (1H, br), 11.21 (1H, s).

Working Example 80
(Production of Compound 82)

A mixture of 2-methyl-7-phenyl-5,6,7,8-tetrahydroquinolin-5-one (0.3 g), aminoguanidine hydrochloride (0.15 g), concentrated hydrochloric acid (0.063 ml), water (0.063 ml) and ethanol (30 ml) was refluxed for 7 hours. Under reduced pressure, the solvent was evaporated, and the residue was dissolved in water. The solution was washed with diethylether, and to the solution was added sodium hydrogen carbonate solution. The mixture was extracted with ethyl acetate, and the organic layer was washed with water and saturated brine, and dried with magnesium sulfate. Under reduced pressure, the solvent was evaporated, and the residue was dissolved in ethanol. To the solution was added 1N hydrochloric acid, and the solvent was evaporated. The residue was recrystallized from ethanol to give 5-guanidinoimino-2-methyl-7-phenyl-5,6,7,8-tetrahydroquinoline hydrochloride (Compound 82) (0.34 g) as colorless crystals.

mp. 300° C. or more

Elemental Analysis for $C_{17}H_{19}N_5 \cdot 2HCl$ Calcd. C, 55.74; H, 5.78; N, 19.12. Found C, 55.41; H, 5.60; N, 18.94.

$^1$H-NMR(DMSO-d$_6$) δ: 2.65–2.96 (1H, m), 2.78 (3H, s), 3.15–3.61 (4H, m), 7.25–7.55 (5H, m), 7.6–8.7 (4H, br), 7.78 (1H, d, J=8 Hz), 9.72 (1H, d, J=8 Hz), 11.51 (1H, s).

Working Example 81
(Production of Compound 83)

A mixture of 2,4-dimethyl-7-phenyl-5,6,7,8-tetrahydroquinolin-5-one (0.30 g), aminoguanidine hydrochloride (0.14 g), concentrated hydrochloric acid (0.06 ml), water (0.06 ml) and ethanol (30 ml) was refluxed for 4 hours. Under reduced pressure, the solvent was evaporated, and the residue was dissolved in water. The solution was washed with diethylether, and to the solution was added sodium hydrogen carbonate solution. The mixture was extracted with ethyl acetate, and the organic layer was washed with water and saturated brine, and dried with magnesium sulfate. Under reduced pressure, the solvent was evaporated, and the residue was dissolved in ethanol. To the solution was added 1N hydrochloric acid, and the solvent was evaporated. The residue was recrystallized from ethanol to give 5-guanidinoimino-2,4-dimethyl-7-phenyl-5,6,7,8-tetrahydroquinoline hydrochloride (Compound 83) (0.25 g) as colorless crystals.

mp. 270° C. (decomp.)

Elemental Analysis for $C_{18}H_{21}N_5 \cdot 2HCl$ Calcd. C, 56.85; H, 6.10; N, 18.41. Found C, 56.49; H, 6.00; N, 18.04.

$^1$H-NMR(DMSO-d$_6$) δ: 2.5–3.8 (5H, m), 2.72 (3H, s), 2.82 (3H, s), 7.23–7.60 (6H, m), 7.6–8.2 (4H, br), 7.71 (1H, s), 11.33 (1H, s).

Working Example 82
(Production of Compound 84)

A mixture of 2,4-dimethyl-7-(2-methylphenyl)-5,6,7,8-tetrahydroquinolin-5-one (0.48 g), aminoguanidine hydrochloride (0.21 g), concentrated hydrochloric acid (0.19 ml), water (0.19 ml) and ethanol (50 ml) was refluxed for 4 hours. Under reduced pressure, the solvent was evaporated, and the residue was dissolved in water. The solution was washed with diethylether, and to the solution was added sodium hydrogen carbonate solution. The mixture was extracted with ethyl acetate, and the organic layer was washed with water and saturated brine, and dried with magnesium sulfate. Under reduced pressure, the solvent was evaporated. The residue was dissolved in ethanol, and to the solution was added 1N hydrochloric acid. Under reduced pressure, the solvent was evaporated to give 5-guanidinoimino-2,4-dimethyl-7-(2-methylphenyl)-5,6,7,8-tetrahydroquinoline hydrochloride (Compound 84) (0.58 g) as amorphous.

$^1$H-NMR(DMSO-d$_6$) δ: 2.34 (3H, s), 2.62–2.92 (1H, m), 2.74 (3H, s), 2.85 (3H, s), 3.10–3.58 (4H, m), 7.10–7.50 (4H, m), 7.63–8.40 (4H, br), 7.74 (1H, s), 11.33 (1H, s).

Working Example 83
(Production of Compound 85)

A mixture of 7-(2-fluorophenyl)-2,4-dimethyl-5,6,7,8-tetrahydroquinolin-5-one (0.12 g), aminoguanidine hydrochloride (0.052 g), concentrated hydrochloric acid (0.067 ml), water (0.067 ml) and ethanol (10 ml) was refluxed for 7 hours. Under reduced pressure, the solvent was evaporated, and the residue was dissolved in water. The solution was washed with ethyl acetate. Under reduced pressure, the solvent was evaporated, and the residue was recrystallized from ethanol to give 7-(2-fluorophenyl)-5-guanidinoimino-2,4-dimethyl-5,6,7,8-tetrahydroquinoline hydrochloride (Compound 85) (0.12 g).

mp. 232° C. (decomp.)

Elemental Analysis for $C_{18}H_{20}FN_5 \cdot 2HCl \cdot 1.2H_2O$ Calcd. C, 51.48; H, 5.86; N, 16.68. Found C, 51.37; H, 5.97; N, 16.68.

$^1$H-NMR(DMSO-d$_6$) δ: 2.70 (3H, s), 2.82 (3H, s), 2.60–2.96 (1H, m), 3.11–3.28 (1H, m), 3.34–3.63 (3H, m), 7.17–7.43 (3H, m), 7.51–7.62 (3H, m), 7.69 (1H, s), 7.83 (4H, br), 11.35 (1H, s).

Working Example 84
(Production of Compound 86)

A mixture of 7-(2-chlorophenyl)-2,4-dimethyl-5,6,7,8-tetrahydroquinolin-5-one (0.20 g), aminoguanidine hydrochloride (0.081 g), concentrated hydrochloric acid (0.1 ml), water (0.1 ml) and ethanol (20 ml) was refluxed for 13.5 hours. Under reduced pressure, the solvent was evaporated, and the residue was dissolved in water. The solution was washed with ethyl acetate. Under reduced pressure, the solvent was evaporated, and the residue was recrystallized from ethanol to give 7-(2-chlorophenyl)-5-guanidinoimino-2,4-dimethyl-5,6,7,8-tetrahydroquinoline hydrochloride (Compound 86) (0.11 g) as colorless crystals.

mp. 227° C. (decomp.)

Elemental Analysis for $C_{18}H_{21}ClN_5 \cdot 2HCl \cdot 0.5H_2O$ Calcd. C, 51.02; H, 5.47; N, 16.53. Found C, 50.96; H, 5.34; N, 16.64.

$^1$H-NMR(DMSO-$d_6$) δ: 2.73 (3H, s), 2.85 (3H, s), 2.6–3.0 (1H, m), 3.24 (1H, dd, J=5, 19 Hz), 3.33–3.76 (3H, m), 7.30–7.56 (3H, m), 7.6–8.3 (4H, br), 7.64 (1H, dd, J=2, 7 Hz), 7.74 (1H, s), 11.47 (1H, s).

Working Example 85
(Production of Compound 87)

A mixture of 2,4-dimethyl-7-(2-pyridyl)-5,6,7,8-tetrahydroquinolin-5-one (0.08 g), aminoguanidine hydrochloride (0.037 g), concentrated hydrochloric acid (0.079 ml), water (0.079 ml) and ethanol (10 ml) was refluxed for 7 hours. Under reduced pressure, the solvent was evaporated, and the residue was dissolved in water. The solution was washed with ethyl acetate. Under reduced pressure, the solvent was evaporated, and the residue was recrystallized from water-ethanol to give 5-guanidinoimino-2,4-dimethyl-7-(2-pyridyl)-5,6,7,8-tetrahydroquinoline hydrochloride (Compound 87) (0.1 g) as colorless crystals.

mp. 201° C. (decomp.)

Elemental Analysis for $C_{17}H_{20}N_6 \cdot 3HCl \cdot 3H_2O$ Calcd. C, 43.28; H, 6.20; N, 17.81. Found C, 43.36; H, 5.98; N, 18.04.

$^1$H-NMR(DMSO-$d_6$) δ: 2.73 (3H, s), 2.83 (3H, s), 3.12 (1H, dd, J=10, 18 Hz), 3.24–3.80 (5H, m), 7.2–8.40 (4H, br), 7.57–7.66 (1H, m), 7.76 (1H, s), 7.82 (1H, d, J=8 Hz), 8.12–8.23 (1H, m), 8.73 (1H, d, J=4 Hz), 11.62 (1H, s).

Working Example 86
(Production of Compound 88)

A mixture of 2-methyl-7-(2-methylphenyl)-5,6,7,8-tetrahydroquinolin-5-one (0.3 g), aminoguanidine hydrochloride (0.26 g), concentrated hydrochloric acid (0.12 ml), water (0.12 ml) and ethanol (30 ml) was refluxed for 2.5 hours. Under reduced pressure, the solvent was evaporated, and the residue was dissolved in water. The solution was washed with diethylether, and to the solution was added sodium hydrogen carbonate solution. The mixture was extracted with ethyl acetate, and the organic layer was washed with water and saturated brine, and dried with magnesium sulfate. Under reduced pressure, the solvent was evaporated, and the residue was dissolved in ethanol. To the solution was added 1N hydrochloric acid (2.5 ml), and the solvent was evaporated. The residue was washed with ethanol to give 5-guanidinoimino-2-methyl-7-(2-methylphenyl)-5,6,7,8-tetrahydroquinoline hydrochloride (Compound 88) (0.32 g) as colorless crystals.

mp. 206° C. (decomp.)

Elemental Analysis for $C_{18}H_{21}N_5 \cdot 2HCl \cdot 0.3H_2O$ Calcd. C, 56.05; H, 6.17; N, 18.16. Found C, 56.12; H, 6.36; N, 18.23.

$^1$H-NMR(DMSO-$d_6$) δ: 2.36 (3H, s), 2.65–2.90 (1H, m), 2.79 (3H, s), 3.10–3.65 (4H, m), 7.10–7.32 (4H, m), 7.42 (1H, d, J=7 Hz), 7.80 (1H, d, J=8 Hz), 7.6–8.7 (4H, br), 9.34 (1H, d, J=8 Hz), 11.51 (1H, s).

Working Example 87
(Production of Compound 89)

To a mixture of 7-(2-chlorophenyl)-4-methyl-5,6,7,8-tetrahydroquinazolin-5-one (40 mg) and aminoguanidine hydrochloride (16 mg) were added ethanol (3 ml) and 6N hydrochloric acid (0.025 ml), and the mixture was stirred at 90° C. for 3 hours and cooled. The reaction solution was concentrated under reduced pressure, and the residue was washed with ethanol, ethyl acetate and isopropylether, and dried to give (E)-7-(2-chlorophenyl)-5-guanidinoimino-4-methyl-5,6,7,8-tetrahydroquinazoline hydrochloride (Compound 89) (38 mg).

mp 284° C. (decomp.).

Elemental Analysis for $C_{16}H_{17}N_6Cl \cdot 2HCl \cdot 0.5H_2O$ Calcd. C, 46.79; H, 4.91; N, 20.46. Found C, 46.73; H, 4.62; N, 20.55.

$^1$H-NMR(DMSO-$d_6$) δ: 2.7–3.0 (2H,m), 2.83 (3H,s), 3.1–3.4 (2H,m), 3.59 (1H,m), 7.32–7.64 (4H,m), 7.76 (4H, broad), 8.89 (1H,s).

Working Example 88
(Production of Compound 90)

To a mixture of 7-(2-chlorophenyl)-2,4-dimethyl-5,6,7,8-tetrahydroquinazolin-5-one (0.20 g) and aminoguanidine hydrochloride (77 mg) were added ethanol (14 ml) and 6N hydrochloric acid (0.12 ml), and the mixture was stirred at 90° C. for 3 hours and cooled. The reaction solution was concentrated under reduced pressure, and the residue was washed with ethanol, ethyl acetate and isopropylether, and dried to give (E)-7-(2-chlorophenyl)-5-guanidinoimino-2,4-dimethyl-5,6,7,8-tetrahydroquinazoline hydrochloride (Compound 90) (0.14 g).

mp 242–244° C.

Elemental Analysis for $C_{17}H_{19}N_6Cl \cdot 2HCl \cdot 0.2H_2O$ Calcd. C, 48.69; H, 5.14; N, 20.04. Found C, 48.65; H, 5.09; N, 19.84.

$^1$H-NMR(DMSO-$d_6$) δ: 2.65 (3H,s), 2.7–3.0 (2H,m), 2.86 (3H,s), 3.1–3.4(2H,m), 3.59 (1H,m), 7.30–7.52 (3H,m), 7.61 (1H,dd,J=1.4& 7.4 Hz), 7.80 (4H,broad).

Working Example 89
(Production of Compound 91)

A mixture of 4-methyl-7-(2-methylphenyl)-5-oxo-cyclopenta[2,1-b]pyridine (48 mg), aminoguanidine hydrochloride (25 mg) and concentrated hydrochloric acid (40 mg) in ethanol (1 ml) was refluxed for 2 hours. The reaction solution was cooled, and precipitated crystals were filtered, washed with ethanol and dried to give 5-guanidinoimino-4-methyl-7-(2-methylphenyl)cyclopenta[2,1-b]pyridine hydrochloride (Compound 91) (48 mg) as yellow crystals.

mp. 203–204° C. decomp.

Elemental Analysis for $C_{17}H_{19}N_5 \cdot 2HCl \cdot 2H_2O$ Calcd. C, 50.75; H, 6.26; N, 17.41. Found C, 50.89; H, 6.36; N, 17.45.

$^1$H-NMR(DMSO-$d_6$) δ: 2.40 (3H, s), 2.75 (3H, s), 2.80 (1H, dd), 3.62 (1H, dd), 4.99 (1H, dd), 6.66 (1H, dd), 7.19 (3H, m), 7.45 (1H, d), 7.74 (4H, broad), 8.51 (2H, d), 11.45 (1H, s).

Working Example 90
(Production of Compound 92)

A mixture of 6-(2-chlorophenyl)-3-methyl-4-oxo-4,5,6,7-tetrahydroindazole (78 mg), 1-amino-3-methylguanidine p-toluenesulfonate (86 mg) and concentrated hydrochloric acid (0.1 ml) in ethanol (1 ml) was stirred at room temperature for 60 hours, and crystals precipitated during the reaction were filtered and washed with ethanol. To the crystals were added ethyl acetate (60 ml) and 2 N sodium hydroxide (5 ml) to dissolve the crystals. The separated ethyl acetate layer was washed with water (10 ml, thrice), to which was added 2 N hydrochloric acid (0.3 ml). The mixture was concentrated under reduced pressure, and the residue was washed with a mixture of ether/ethanol=4/1 and dried to give 6-(2-chlorophenyl)-3-methyl-4-(1-methylguanidin-3-yl)imino-4,5,6,7-tetrahydroindazole hydrochloride (Compound 92) (80 mg) as colorless solid.

mp. 240° C. decomp.

$^1$H-NMR(DMSO-$d_6$) δ: 2.50 (3H, s), 2.69 (1H, dd), 2.92 (5H, m), 3.08 (1H, dd), 3.58 (1H, m), 7.27–7.43 (2H, m), 7.49 (1H, dd), 7.59 (1H, dd), 7.69 (1H, broad), 7.80 (2H, broad).

Working Example 91
(Production of Compound 93)

A mixture of 6-(2-chlorophenyl)-3-methyl-4-oxo-4,5,6,7-tetrahydroindazole (1.14 g), 1-amino-3-hydroxyguanidine p-toluenesulfonate (1.26 g) and concentrated hydrochloric acid (0.44 ml) in ethanol (12 ml) was stirred at 85° C. (bath temperature) for 1 hour. The reaction solution was concentrated under reduced pressure, and to the residue were added ethyl acetate (50 ml), tetrahydrofuran (20 ml) and an aqueous solution (20 ml) of anhydrous potassium carbonate (1.4 g). The mixture was shaken, and the separated upper layer was washed with an aqueous solution (10 ml) of anhydrous potassium carbonate (0.7 g) and water (10 ml, thrice). To the upper layer was added 2 N hydrochloric acid (2.3 ml), and the mixture was concentrated under reduced pressure. To the residue was added a mixture of ether (30 ml) and ethanol (15 ml), and the mixture was stirred at room temperature for 15 hours to give solidified powder. The powder was stirred in ethanol (4 ml) at 90° C. (bath temperature) for 1 hours, and precipitated crystals were filtered off. The filtrate was concentrated under reduced pressure, and the residue was dissolved in ethanol (12 ml). The solution was stirred at 90° C. (bath temperature) for 14 hours. The reaction solution cooled, and crystals precipitated while stirring were filtered, washed with ethanol and dried to give 6-(2-chlorophenyl)-4-(1-hydroxyguanidin-3-yl)imino-3-methyl-4,5,6,7-tetrahydroindazole hydrochloride (Compound 93) (604 mg) as pale yellow crystals.

mp. 234–235° C. decomp.

$^1$H-NMR(DMSO-$d_6$) δ: 2.50 (3H, s), 2.69 (1H, dd), 2.94 (2H, d), 3.08 (1H, dd), 3.57 (1H, m), 7.27–7.52 (3H, m), 7.60 (1H, dd), 7.98 (2H, broad), 10.66 (1H, s), 10.95 (1H, s).

Working Example 92
(Production of Compound 94)

A mixture of 7-(2,5-dimethylphenyl)-4-methyl-5,6,7,8-tetrahydroquinolin-5-one (100 mg), 1-amino-3-hydroxyguanidine p-toluenesulfonate (131 mg) and concentrated hydrochloric acid (0.1 ml) in ethanol (2 ml) was stirred at 85° C. (bath temperature) for 1 hour. The reaction solution was concentrated under reduced pressure, and to the residue were added ethyl acetate (20 ml), tetrahydrofuran (12 ml) and 0.2 N sodium hydroxide (10 ml). The mixture was shaken, and the separated upper layer was washed with 0.2 N sodium hydroxide (5 ml) and water (5 ml, thrice). To the upper layer was added 2 N hydrochloric acid (0.5 ml), and the mixture was concentrated under reduced pressure. The residue was washed with a mixture of ether (4 ml) and ethanol (2 ml), and dried to give 7-(2,5-dimethylphenyl)-5-(1-hydroxyguanidin-3-yl)imino-4-methyl-5,6,7,8-tetrahydroquinoline hydrochloride (Compound 94) (121 mg) as yellow crystals.

mp. 190–192° C. decomp.

$^1$H-NMR(DMSO-$d_6$) δ: 2.27 (3H, s), 2.30 (3H, s), 2.79 (1H, m), 2.89 (3H, s), 3.19 (1H, d), 3.39 (3H, m), 7.00. (1H, d), 7.10 (1H, d), 7.26 (1H, s), 7.83 (1H, d), 8.33 (2H, broad), 8.63 (1H, d), 10.40 (1H, broad), 11.15 (1H, broad), 11.34 (1H, broad).

Working Example 93
(Production of Compound 95)

A mixture of 7-(2,3-dichlorophenyl)-4-methyl-5,6,7,8-tetrahydroquinolin-5-one (306 mg), 1-amino-3-hydroxyguanidine p-toluenesulfonate (320 mg) and concentrated hydrochloric acid (0.2 ml) in ethanol (6 ml) was stirred at 85° C. (bath temperature) for 2 hours and 30 minutes. The reaction solution was concentrated under reduced pressure, and to the residue were added ethyl acetate (30 ml), tetrahydrofuran (20 ml) and 0.2 N sodium hydroxide (25 ml). The mixture was shaken, and the separated upper layer was washed with 0.2 N sodium hydroxide (10 ml) and water (10 ml, thrice). To the upper layer was added 2 N hydrochloric acid (1 ml), and the mixture was concentrated under reduced pressure. The residue was recrystallized form ethanol and dried to give 7-(2,3-dichlorophenyl)-5-(1-hydroxyguanidin-3-yl)imino-4-methyl-5,6,7,8-tetrahydroquinoline hydrochloride (Compound 95) (390 mg) as yellow crystals.

mp. 196–198° C. decomp.

$^1$H-NMR(DMSO-$d_6$) δ: 2.89 (4H, m), 3.27 (1H, dd), 3.47 (2H, m), 3.73 (1H, m), 7.46 (1H, t), 7.62 (2H, dd), 7.81 (1H, d), 8.34 (2H, broad), 8.63 (1H, d), 10.40 (1H, broad), 11.15 (1H, broad), 11.45 (1H, broad).

Working Example 94
(Production of Compound 96)

A mixture of 7-(2,6-dichlorophenyl)-4-methyl-5,6,7,8-tetrahydroquinolin-5-one (153 mg), 1-amino-3-hydroxyguanidine p-toluenesulfonate (262 mg) and concentrated hydrochloric acid (0.1 ml) in ethanol (3 ml) was stirred at 90° C. (bath temperature) for 1.5 hours. The reaction solution was concentrated under reduced pressure, and to the residue were added ethyl acetate (30 ml), tetrahydrofuran (20 ml) and 0.2 N sodium hydroxide (15 ml). The mixture was shaken, and the separated upper layer was washed with 0.2 N sodium hydroxide (10 ml) and water (10 ml, thrice). To the upper layer was added 2 N hydrochloric acid (0.5 ml), and the mixture was concentrated under reduced pressure. The residue was washed with a mixture of ether (3 ml) and ethanol (1.5 ml) and dried to give 7-(2,6-dichlorophenyl)-5-(1-hydroxyguanidin-3-yl)imino-4-methyl-5,6,7,8-tetrahydroquinoline hydrochloride (Compound 96) as pale yellow crystals.

mp. 193–195° C. decomp.

Elemental Analysis for $C_{17}H_{17}N_5Cl_2O \cdot 2HCl \cdot 3/4H_2O$ Calcd. C, 43.94; H, 4.45; N, 15.07. Found C, 43.94; H, 4.63; N, 14.87.

$^1$H-NMR(DMSO-$d_6$) δ: 2.85 (3H, s), 3.07 (1H, dd), 3.26 (1H, d), 3.38 (1H, dd), 4.08 (2H, m), 7.41 (1H, t), 7.57 (2H, d), 7.78 (1H, d), 8.35 (2H, broad), 8.62 (1H, d), 10.38 (1H, broad), 11.13 (1H, broad), 11.40 (1H, broad).

Working Example 95
(Production of Compound 97)

A mixture of 7-(2-furyl)-4-methyl-5,6,7,8-tetrahydroquinolin-5-one (227 mg), 1-amino-3-hydroxyguanidine p-toluenesulfonate (314 mg) and concentrated hydrochloric acid (0.1 ml) in ethanol (3 ml) was stirred at 90° C. (bath temperature) for 2 hours. The reaction solution was concentrated under reduced pressure, and to the residue were added ethyl acetate (30 ml), tetrahydrofuran (20 ml) and 0.2 N sodium hydroxide (20 ml). The mixture was shaken, and the separated upper layer was washed with 0.2 N sodium hydroxide (10 ml) and water (10 ml, thrice). To the upper layer was added 2 N hydrochloric acid (1 ml), and the mixture was concentrated under reduced pressure. The residue in ethanol (3 ml) was stirred at 90° C. (bath temperature) for 3 hours and cooled, and crystals precipitated while stirring was filtered, washed with ethanol and dried to give 7-(2-furyl)-5-(1-hydroxyguanidin-3-yl)imino-4-methyl-5,6,7,8-tetrahydroquinoline hydrochloride (Compound 97) (154 mg) as pale yellow crystals.

mp. 196–198° C. decomp.

$^1$H-NMR(DMSO-d$_6$) δ: 2.86 (3H, s), 2.96 (1H, dd), 3.23 (2H, m), 3.54 (2H, m), 6.40 (2H, m), 7.61 (1H, s), 7.79 (1H, d), 8.45 (2H, broad), 8.62 (1H, d), 10.40 (1H, broad), 11.17 (1H, broad), 11.69 (1H, broad).

Working Example 96
(Production of Compound 98)

A mixture of 4-methyl-7-(5-methyl-2-thienyl)-5,6,7,8-tetrahydroquinolin-5-one (257 mg), 1-amino-3-hydroxyguanidine p-toluenesulfonate (285 mg) and concentrated hydrochloric acid (0.2 ml) in ethanol (3 ml) was stirred at 90° C. (bath temperature) for 1 hour. The reaction solution was concentrated under reduced pressure, and to the residue were added ethyl acetate (30 ml), tetrahydrofuran (20 ml) and 0.2 N sodium hydroxide (20 ml). The mixture was shaken, and the separated upper layer was washed with 0.2 N sodium hydroxide (10 ml) and water (10 ml, thrice). To the upper layer was added 2 N hydrochloric acid (1 ml), and the mixture was concentrated under reduced pressure. The residue in ethanol (1 ml) was stirred at room temperature for 15 hours to give crystals, which were filtered and dried to give 5-(1-hydroxyguanidin-3-yl)imino-4-methyl-7-(5-methyl-2-thienyl)-5,6,7,8-tetrahydroquinoline hydrochloride (Compound 98) (163 mg) as pale yellow crystals.

mp. 210–212° C. decomp.

$^1$H-NMR(DMSO-d$_6$) δ: 2.41 (3H, s), 2.85 (3H, s), 2.92 (1H, dd), 3.37 (2H, m), 3.54 (2H, m), 6.67 (1H, m), 6.88 (1H, d), 7.79 (1H, d), 8.43 (2H, broad), 8.63 (1H, d), 10.38 (1H, broad), 11.16 (1H, broad), 11.62 (1H, broad).

Working Example 97
(Production of Compound 99)

A mixture of 7-phenyl-1,2,5,6,7,8-hexahydroquinoline-2,5-dione (0.19 g), aminoguanidine hydrochloride (0.092 g), concentrated hydrochloric acid (0.04 ml), water (0.04 ml) and ethanol (20 ml) was refluxed for 1 hour. Under reduced pressure, the solvent was evaporated, and the residue was recrystallized from ethanol to give 5-guanidinoimino-7-phenyl-1,2,5,6,7,8-hexahydroquinolin-2-one hydrochloride (Compound 99) (0.21 g) as colorless crystals.

mp. 300° C. or more $^1$H-NMR(DMSO-d$_6$) δ: 2.45–3.6 (5H, m), 6.26 (1H, d, J=9 Hz), 7.0–8.2 (4H, br), 7.20–7.50 (5H, m), 8.41 (1H, d, J=9 Hz), 10.94 (1H, s), 11.90 (1H, s).

Working Example 98
(Production of Compound 100)

A mixture of 4-methyl-7-(3-thienyl)-5,6,7,8-tetrahydroquinolin-5-one (243 mg), aminoguanidine hydrochloride (122 mg) and concentrated hydrochloric acid (0.2 ml) in ethanol (3 ml) was refluxed for 2 hours. The reaction solution was cooled, and precipitated crystals were filtered, washed with ethanol and dried to give 5-guanidinoimino-4-methyl-7-(3-thienyl)-5,6,7,8-tetrahydroquinoline hydrochloride (Compound 100) (362 mg) as colorless crystals.

mp. 300° C. or more $^1$H-NMR(DMSO-d$_6$) δ: 2.86 (3H, s), 2.90 (1H, dd), 3.36 (4H, m), 7.24 (1H, dd), 7.49 (1H, d), 7.56 (1H, m), 7.82 (1H, d), 7.90 (4H, broad), 8.64 (1H, d), 11.65 (1H, broad).

Working Example 99
(Production of Compound 101)

A mixture of 7-(2-chlorothiophen-3-yl)-4-methyl-5,6,7,8-tetrahydroquinolin-5-one (147 mg), aminoguanidine hydrochloride (63 mg) and concentrated hydrochloric acid (0.1 ml) in ethanol (3 ml) was stirred at 90° C. (bath temperature) for 14 hours. The reaction solution was cooled, and precipitated crystals were filtered, washed with ethanol and dried to give 7-(2-chlorothiophen-3-yl)-5-guanidinoimino-4-methyl-5,6,7,8-tetrahydroquinoline hydrochloride (Compound 101) (148 mg) as colorless crystals.

mp. 281–283° C. (decomp.)

Elemental Analysis for $C_{15}H_{18}N_5ClS.2HCl$ Calcd. C, 44.29; H, 4.46; N, 17.22. Found C, 44.29; H, 4.54; N, 17.21.

$^1$H-NMR(DMSO-d$_6$) δ: 2.86 (4H, m), 3.15 (1H, dd), 3.39 (3H, m), 7.25 (1H, d), 7.55 (1H, d), 7.82 (1H, d), 7.92 (4H, broad), 8.62 (1H, d), 11.43 (1H, broad).

Working Example 100
(Production of Compound 102)

A mixture of 7-(2,5-dichlorothiophene-3-yl)-4-methyl-5,6,7,8-tetrahydroquinolin-5-one (218 mg), aminoguanidine hydrochloride (83 mg) and concentrated hydrochloric acid (0.1 ml) in ethanol (4 ml) was stirred at 100° C. (bath temperature) for 14 hours. The reaction solution was cooled, and precipitated crystals were filtered, washed with ethanol and dried to give 7-(2,5-dichlorothiophene-3-yl)-5-guanidinoimino-4-methyl-5,6,7,8-tetrahydroquinoline hydrochloride (Compound 102) (250 mg) as pale yellow crystals.

mp. 300° C. or more

Elemental Analysis for $C_{15}H_{15}N_5Cl_2S.2HCl$ Calcd. C, 40.83; H, 3.88; N, 15.87. Found C, 40.75; H, 3.64; N, 15.69.

$^1$H-NMR(DMSO-d$_6$) δ: 2.85 (4H, m), 3.12 (1H, dd), 3.36 (3H, m), 7.42 (1H, s), 7.79 (1H, d), 7.90 (4H, broad), 8.62 (1H, d), 11.44 (1H, broad).

Working Example 101
(Production of Compound 103)

A mixture of 4-methyl-7-(3-thienyl)-5,6,7,8-tetrahydroquinolin-5-one (243 mg), 1-amino-3-hydroxyguanidine p-toluenesulfonate (393 mg) and concentrated hydrochloric acid (0.2 ml) in ethanol (3 ml) was stirred at 90° C. (bath temperature) for 2 hours. The reaction solution was concentrated under reduced pressure, and to the residue were added ethyl acetate (30 ml), tetrahydrofuran (20 ml) and 0.2 N sodium hydroxide (20 ml). The mixture was shaken, and the separated upper layer was washed with 0.2 N sodium hydroxide (10 ml) and water (10 ml, thrice). To the upper layer was added 2 N hydrochloric acid (1 ml), and the mixture was concentrated under reduced pressure. To the residue was added ether (3 ml), and the mixture was stirred at 90° C. (bath temperature) for 2 hours and cooled to give crystals, which were filtered, washed with ethanol and dried to give 5-(1-hydroxyguanidin-3-yl)imino-4-methyl-7-(3-thienyl)-5,6,7,8-tetrahydroquinoline hydrochloride (Compound 103) (233 mg) as pale yellow crystals.

mp. 201–202° C. decomp.

$^1$H-NMR(DMSO-d$_6$) δ: 2.86 (4H, m), 3.35 (4H, m), 7.23 (1H, dd), 7.47 (1H, dd), 7.58 (1H, dd), 7.78 (1H, d), 8.42 (2H, broad), 8.63 (1H, d), 10.40 (1H, broad), 11.15 (1H, broad), 11.58 (1H, broad).

Working Example 102
(Production of Compound 104)

A mixture of 7-(2-chlorothiophen-3-yl)-4-methyl-5,6,7,8-tetrahydroquinolin-5-one (222 mg), 1-amino-3-hydroxyguanidine p-toluenesulfonate (314 mg) and concentrated hydrochloric acid (0.1 ml) in ethanol (4 ml) was stirred at 90° C. (bath temperature) for 2 hours. The reaction solution was concentrated under reduced pressure, and to the residue were added ethyl acetate (30 ml), tetrahydrofuran (20 ml) and 0.2 N sodium hydroxide (20 ml). The mixture was shaken, and the separated upper layer was washed with 0.2 N sodium hydroxide (15 ml) and water (10 ml, thrice). To the upper layer was added 2 N hydrochloric acid (0.8 ml), and the mixture was concentrated under reduced pressure. To the residue was added ether (3 ml), and the mixture was stirred at 90° C. (bath temperature) for 3 hours and cooled to give crystals, which were filtered, washed with ethanol and dried to give 7-(2-chlorothiophen-3-yl)-5-(1-hydroxyguanidin-3-yl)imino-4-methyl-5,6,7,8-tetrahydroquinoline hydrochloride (Compound 104) (183 mg) as pale yellow crystals.

mp. 199–200° C. decomp.

Elemental Analysis for $C_{18}H_{16}N_5ClOS.2HCl.1/2H_2O$ Calcd. C, 41.73; H, 4.44; N, 16.22. Found C, 41.64; H, 4.42; N, 16.24.

$^1$H-NMR(DMSO-$d_6$) δ: 2.87 (4H, m), 3.15 (1H, dd), 3.39 (3H, m), 7.25 (1H, d), 7.54 (1H, d), 7.81 (1H, d), 8.36 (2H, broad), 8.62 (1H, d), 10.40 (1H, broad), 11.15 (1H, broad), 11.43 (1H, broad).

Working Example 103
(Production of Compound 105)

A mixture of 7-(2,5-dichlorothiophen-3-yl)-4-methyl-5,6,7,8-tetrahydroquinolin-5-one (250 mg), 1-amino-3-hydroxyguanidine p-toluenesulfonate (314 mg) and concentrated hydrochloric acid (0.1 ml) in ethanol (4 ml) was stirred at 105° C. (bath temperature) for 2 hours. The reaction solution was concentrated under reduced pressure, and to the residue were added ethyl acetate (40 ml), tetrahydrofuran (25 ml) and 0.2 N sodium hydroxide (25 ml). The mixture was shaken, and the separated upper layer was washed with 0.2 N sodium hydroxide (15 ml) and water (10 ml, thrice). To the upper layer was added 2 N hydrochloric acid (0.8 ml), and the mixture was concentrated under reduced pressure. To the residue was added ethanol (4 ml), and the mixture was stirred at 90° C. (bath temperature) for 3 hours and cooled to give crystals, which were filtered, washed with ethanol and dried to give 7-(2,5-dichlorothiophen-3-yl)-5-(1-hydroxyguanidin-3-yl)imino-4-methyl-5,6,7,8-tetrahydroquinoline hydrochloride (Compound 105) (205 mg) as colorless crystals.

mp. 196–197° C. decomp.

$^1$H-NMR(DMSO-$d_6$) δ: 2.85 (4H, m), 3.14 (1H, dd), 3.35 (3H, m), 7.41 (1H, s), 7.77 (1H, d), 8.40 (2H, broad), 8.61 (1H, d), 10.40 (1H, broad), 11.16 (1H, broad), 11.41 (1H, broad).

Working Example 104
(Production of Compound 106)

A mixture of 7-(2-chlorophenyl)-4-methyl-5,6,7,8-tetrahydroquinolin-5-one (679 mg), 1-amino-3-hydroxyguanidine p-toluenesulfonate (917 mg) and concentrated hydrochloric acid (0.3 ml) in ethanol (10 ml) was stirred at 90° C. (bath temperature) for 3 hours. The reaction solution was concentrated under reduced pressure, and to the residue were added ethyl acetate (40 ml), tetrahydrofuran (30 ml) and 0.2 N sodium hydroxide (50 ml). The mixture was shaken, and the separated upper layer was washed with 0.2 N sodium hydroxide (20 ml) and water (15 ml, thrice). To the upper layer was added 2 N hydrochloric acid (2.5 ml), and the mixture was concentrated under reduced pressure. To the residue was added ethanol (10 ml), and the mixture was stirred at 900° C. (bath temperature) for 3 hours and cooled to give crystals, which were filtered to give 7-(2-chlorophenyl)-5-(1-hydroxyguanidin-3-yl)imino-4-methyl-5,6,7,8-tetrahydroquinoline hydrochloride (Compound 106) (790 mg) as pale yellow crystals.

mp. 185–187° C.

Elemental Analysis for $C_{17}H_{18}N_5ClO.2HCl.4/5H_2O$ Calcd. C, 47.36; H, 5.05; N, 16.24 Found C, 47.56; H, 4.83; N, 15.95.

$^1$H-NMR(DMSO-$d_6$) δ: 2.89 (4H, m), 3.24 (1H, dd), 3.43 (2H, m), 3.67 (1H, m), 7.48 (3H, m), 7.61 (1H, dd), 7.81 (1H, d), 8.35 (2H, broad), 10.39 (1H, broad), 11.14 (1H, broad), 11.44 (1H, broad).

Working Example 105
(Production of Compound 107)

To a mixture of 3-carbamoyl-6-phenyl-4,5,6,7-tetrahydrobenzofuran-4-one (0.24 g) and aminoguanidine hydrochloride (104 mg) were added ethanol (20 ml) and 6N hydrochloric acid (0.081 ml), and the mixture was stirred at 90° C. for 2 hours and cooled. Precipitated crystals were washed with ethanol and isopropylether, and dried to give (E)-3-carbamoyl-4-guanidinoimino-6-phenyl-4,5,6,7-tetrahydrobenzofuran hydrochloride (Compound 107) (0.28 g).

mp 294° C. (decomp.).

Elemental Analysis for $C_{16}H_{17}N_5O_2.HCl$ Calcd. C,55.25; H,5.22; N,20.14. Found C,55.12; H,5.09; N,20.04.

$^1$H-NMR(DMSO-$d_6$) δ: 2.68 (1H,dd,J=12.8&16.2 Hz), 3.05–3.15 (3H,m), 3.3–3.5 (1H,m), 7.28–7.46 (5H,m), 7.59 (5H,broad), 8.09 (1H,s), 8.22 (1H,broad).

Reference Example 116

To a solution of 5-(2-chlorophenyl)cyclohexane-1,3-dione (3.0 g) in chloroform(10 ml) was added phosphorus trichloride (0.62 g), and the mixture was stirred at 100° C. for 2.5 hours. To the mixture was added phosphorus trichloride (0.62 g), and the mixture was stirred at 100° C. for 2 hours. The reaction solution was concentrated under reduced pressure, and to the residue was added ice-water. The mixture was extracted with ethyl acetate, and the organic layer was washed with water and saturated brine, dried with magnesium sulfate and concentrated under reduced pressure to give 3-chloro-5-(2-chlorophenyl)-2-cyclohexen-1-one, which was dissolved in ethanol (3 ml). To the solution were added sodium sulfide 9 hydrate (2.0 g) and water (3 ml), and the mixture was stirred at room temperature for 2 hours and concentrated under reduced pressure. The residue was dissolved in water, and the solution was washed with diethylether. To the aqueous layer was added 4N hydrochloric acid to make the solution acidic, and the solution was extracted with ethyl acetate. The organic layer was washed with water and saturated brine, dried with magnesium sulfate and concentrated under reduced pressure to give oil of 5-(2-chlorophenyl)-3-mercapto-2-cyclohexen-1-one (1.8 g).

$^1$H-NMR(CDCl$_3$) δ: 2.50–2.80 (4H,m), 3.52 (1H,s), 3.83–4.01 (1H,m), 6.20 (1H,s), 7.14–7.43 (4H,m).

Reference Example 117

To a solution of 5-(2-chlorophenyl)-3-mercapto-2-cyclohexen-1-one (1.8 g) and chloroacetone (0.7 g) in ethanol (20 ml) was added a solution of 20% sodium ethoxide in ethanol (0.48 g), and the mixture was stirred at room temperature for 5 hours. The reaction solution was concentrated under reduced pressure, and to the residue was ethyl acetate. The mixture was subjected to extraction, and the organic layer was washed with water and saturated brine, dried with magnesium sulfate and concentrated under reduced pressure to give 5-(2-chlorophenyl)-3-(2-oxopropylthio)-2-cyclohexen-1-one (2.3 g).

mp. 81–82° C.

$^1$H-NMR(CDCl$_3$) δ: 2.33 (3H,s), 2.52–2.80 (4H,m), 3.76 (2H,s), 3.79–3.99 (1H,m), 5.85 (1H,s), 7.16–7.43 (4H,m).

Reference Example 118

A solution of 5-(2-chlorophenyl)-3-(2-oxopropylthio)-2-cyclohexen-1-one (1.0 g) in xylene (10 ml) was refluxed for 7.5 days and cooled, and the reaction solution was purified with silica gel column chromatography (EtOAc/hexane) to give oil of 6-(2-chlorophenyl)-3-methyl-4,5,6,7-tetrahydrobenzothiophene-4-one (0.07 g).

$^1$H-NMR(CDCl$_3$) δ: 2.48 (3H,s), 2.64–2.92 (2H,m), 3.09 (1H,dd,J=11,17 Hz), 3.35 (1H,dd,J=4,17 Hz), 3.96–4.13 (1H,m), 6.70 (1H,s), 7.14–7.50 (4H,m).

Reference Example 119

A solution of 5-(2-thiazolyl)-cyclohexane-1,3-dione (0.93 g) and ammonium acetate (1.1 g) in ethanol (20 ml) was refluxed for 13 hours. Under reduced pressure, the solvent was evaporated, and to the residue was added sodium hydrogen carbonate solution. The aqueous layer was washed with ethyl acetate and concentrated, and to the residue was ethanol-ethyl acetate (1:1). Insoluble materials were filtered and concentrated under reduced pressure. To the residue was added ethanol, and insoluble materials were filtered and concentrated under reduced pressure to give solid, which was dissolved in ethanol (10 ml) and toluene (30 ml). To the solution were added 3-oxobutylaldehydedimethylacetal (1.6 g) and powdery 85% potassium hydroxide (0.26 g), and the mixture was refluxed. To the mixture was added powdery 85% potassium hydroxide (0.054 g), 30 minutes later; were added powdery 85% potassium hydroxide (0.054 g) and 3-oxobutylaldehydedimethylacetal(0.063 g), 1 hour later; and powdery 85% potassium hydroxide (0.054 g), 1.5 hours later; and then the mixture was refluxed for 1 hours. Under reduced pressure, the solvent was evaporated, and to the residue was added ethyl acetate. The mixture was washed with water and saturated brine, dried with magnesium sulfate and concentrated under reduced pressure, and the residue was purified with silica gel column chromatography (EtOAc/hexane) to give crystals of 7-(2-thiazolyl)-4-methyl-5,6,7,8-tetrahydroquinolin-5-one (0.76 g).

mp. 88–89° C.

$^1$H-NMR(CDCl$_3$) δ: 2.70 (3H,s), 3.09 (1H,dd,J=10,17 Hz), 3.16–3.28 (1H,m), 3.53 (1H,dd,J=10,17 Hz), 3.68 (1H,dd,J=5,17 Hz), 3.86–4.06 (1H,m), 7.11 (1H,d,J=5 Hz), 7.28 (1H,d,J=4 Hz), 7.75 (1H,d,J=4 Hz), 8.50 (1H,d,J=5 Hz).

Reference Example 120

To a solution of 5-(3-chlorothiophen-2-yl)cyclohexane-1,3-dione (2.0 g), acetic acid (0.90 g) and dimethylaminopyridine (1.6 g) in dimethylformamide (100 ml) was added dicyclohexylcarbodiimide (2.3 g), and the mixture was stirred at room temperature for 13 hours. Under reduced pressure, the solvent was evaporated, and to the residue was ethyl acetate. The mixture was washed with potassium hydrogensulfate solution and water, and to the mixture was added 1N sodium hydroxide solution. The aqueous layer was washed with diethylether and neutralized with 1N hydrochloric acid, and the mixture was extracted with ethyl acetate. The organic layer was washed with water and saturated brine, dried with magnesium sulfate and concentrated under reduced pressure to give oil of 5-(3-chlorothiophen-2-yl)-2-(1-hydroxyethylidene)-cyclohexane-1,3-dione (2.2 g).

$^1$H-NMR(CDCl$_3$) δ: 2.65 (3H,s), 2.66 (1H,dd,J=12,16 Hz), 2.85 (1H,dd,J=12,18 Hz), 2.89 (1H,ddd,J=2,5,16 Hz), 3.03 (1H,ddd,J=2,5,18 Hz), 3.71–3.91 (1H,m), 6.92 (1H,q,J=5 Hz), 7.20 (1H,d,J=5 Hz).

Reference Example 121

A solution of 5-(3-chlorothiophen-2-yl)-2-(1-hydroxyethylidene)-cyclohexane-1,3-dione (2.2 g) and hydrazine hydrate (0.45 g) in ethanol (60 ml) was refluxed for 2 hours. Under reduced pressure, the solvent was evaporated, and the residue was recrystallized from ethyl acetate-hexane to give colorless crystals of 6-(3-chlorothiophen-2-yl)-3-methyl-4,5,6,7-tetrahydroindazol-4-one (1.3 g).

mp. 163–165° C.

$^1$H-NMR(CDCl$_3$) δ: 2.59 (3H,s), 2.70 (1H,dd,J=11,17 Hz), 2.86 (1H,dd,J=4,17 Hz), 2.96 (1H,dd,J=11,16 Hz), 3.29 (1H,dd,J=4,16 Hz), 3.84–4.03 (1H,m), 6.91 (1H,d,J=5 Hz), 7.18 (1H,d,J=5 Hz).

Reference Example 122

A solution of 5-(2,5-dichlorophenyl)-cyclohexane-1,3-dione (5.0 g) and ammonium acetate (4.5 g) in ethanol (100 ml) was refluxed for 20.5 hours. Under reduced pressure, the solvent was evaporated, and the residue was washed with water and toluene and dried to give crystals, which were dissolved in ethanol (50 ml) and toluene (150 ml). To the solution were added 3-oxobutylaldehydedimethylacetal (6.1 g) and powdery 85% potassium hydroxide (1.0 g), and the mixture was refluxed. To the mixture was added powdery 85% potassium hydroxide (0.21 g), 30 minutes later; were added powdery 85% potassium hydroxide (0.21 g) and 3-oxobutylaldehydedimethylacetal(0.24 g), 1 hour later; and powdery 85% potassium hydroxide (0.21 g), 1.5 hours later; and then the mixture was refluxed for 1.5 hours. Under reduced pressure, the solvent was evaporated, and to the residue was added ethyl acetate. The mixture was washed with water and saturated brine, dried with magnesium sulfate and concentrated under reduced pressure, and the residue was purified with silica gel column chromatography (EtOAc/hexane). The resulting crystals were recrystallized from ethyl acetate-hexane to give 7-(2,5-dichlorophenyl)-4-methyl-5,6,7,8-tetrahydroquinolin-5-one (3.7 g) as crystals.

mp. 116–117° C.

$^1$H-NMR(CDCl$_3$) δ: 2.72 (3H,s), 2.80 (1H,dd,J=12,16 Hz), 3.00 (1H,ddd,J=2,4,17 Hz), 3.26 (1H,dd,J=12,17 Hz), 3.46 (1H,ddd,J=2,4,16 Hz), 3.83–4.04 (1H,m), 7.12 (1H,d,J=5 Hz), 7.21 (1H,dd,J=2,8 Hz), 7.31 (1H,d,J=2 Hz), 7.36 (1H,d,J=8 Hz), 8.50 (1H,d,J=5 Hz).

Reference Example 123

To a solution of 7-(3-chlorothiophen-2-yl)-4-methyl-5,6,7,8-tetrahydroquinolin-5-one (0.74 g) in ethyl acetate (10 ml) were added pyridine (0.21 g) and sulfuryl chloride (1.1 g) at room temperature, and the mixture was stirred at the same temperature for 3 hours. To the reaction solution was added ethyl acetate, and the mixture was washed with sodium hydrogen carbonate solution, water and saturated brine, dried with magnesium sulfate and concentrated under reduced pressure. The residue was purified with silica gel column chromatography (EtOAc/hexane) to give 7-(3,5-dichlorothiophen-2-yl)-4-methyl-5,6,7,8-tetrahydroquinolin-5-one (0.56 g).

mp. 109–111° C.

$^1$H-NMR(CDCl$_3$) δ: 2.68 (3H,s), 2.76 (1H,dd,J=12,16 Hz), 3.04 (1H,ddd,J=2,4,17 Hz), 3.24 (1H,dd,J=11,17 Hz), 3.51 (1H,ddd,J=2,4,17 Hz), 3.82–3.99 (1H,m), 6.76 (1H,s), 7.11 (1H,d,J=5 Hz), 8.49 (1H,d,J=5 Hz).

Reference Example 124

To a solution of 2,5-dichlorothiophene (100.0 g) and dichloromethylmethylether (165.3 g) in dichloromethane (800 ml) was added dropwise a solution of titanium tetrachloride (272.7 g) in dichloromethane (160 ml) at −10 to −15° C. taking 50 minutes, and at the same temperature, the mixture was stirred for 30 minutes. The reaction solution was poured into ice, and the organic layer was washed with water, sodium hydrogen carbonate solution, water and saturated brine, and dried with magnesium sulfate. Under reduced pressure, the solvent was evaporated to give 2,5-dichloro-3-formylthiophene (115.0 g) as oil. To a mixture of acetone (1000 ml), sodium hydroxide (28.6 g) and water (1200 ml) was added at 0° C. a solution of 2,5-dichloro-3-formylthiophene (58.6 g) in acetone (200 ml) for 1.5 hours, and the mixture was stirred at the same temperature for 1 hour. Under reduced pressure, acetone was evaporated, and the crystals were filtered, washed with water and dried to give 4-(2,5-dichlorothiophen-3-yl)-3-buten-2-one (136.6 g). To a solution of 20% sodium ethoxide in ethanol (211 g) was added diethyl malonate (99.3 g) at room temperature, and then 4-(2,5-dichlorothiophen-3-yl)-3-buten-2-one (136.6 g) little by little. The mixture was stirred at room temperature for 30 minutes, heated for 2 hours while stirring, and cooled. The solvent was evaporated, and to the residue was added water. The aqueous layer was washed with ethyl acetate and concentrated, to which was added 2M sodium hydroxide (340 ml). The mixture was stirred at 100° C. for 2 hours and cooled. To the mixture was added 2.5M sulfuric acid (340 ml) for 15 minutes, and the mixture was stirred at 100° C. for 1.5 hours. The mixture was cooled, and precipitated crystals were filtered and washed with ethyl acetate-isopropylether (1:4) and isopropylether to give 5-(2,5-dichlorothiophen-3-yl)cyclohexane-1,3-dione (78.9 g) as colorless crystals.

mp 200° C. (decomp.)

$^1$H-NMR(CDCl$_3$) δ: 2.36–2.61 (4H, m), 3.42–3.62 (1H, m), 5.51 (1H, s), 6.76 (1H, s), 8.0–12.5 (1H, br).

Reference Example 125

A solution of 5-(2,5-dichlorothiophen-3-yl)cyclohexane-1,3-dione (42.0 g) and ammonium acetate (36.9 g) in ethanol (840 ml) was refluxed for 12 hours. Under reduced pressure, the solvent was evaporated, and to the residue was added water. The crystals were filtered, washed with toluene and dried to give 1-amino-5-(2,5-dichlorothiophen-3-yl) cyclohexen-3-one (40.3 g). To a solution of 1-amino-5-(2, 5-dichlorothiophen-3-yl)cyclohexen-3-one (37.0 g) in ethanol (700 ml) and toluene (1400 ml) were added 3-oxobutylaldehydedimethylacetal (46.6 g) and powdery potassium hydroxide (7.7 g), and the mixture was refluxed. To the mixture was added powdery potassium hydroxide (1.6 g) 30 minutes later; powdery potassium hydroxide (1.6 g) and 3-oxobutylaldehydedimethylacetal (3.7 g) 1 hour later; and powdery potassium hydroxide (1.6 g) 1.5 hours later; and then the mixture was stirred at the same temperature for 2 hours. After the mixture was cooled, the solvent was evaporated under reduced pressure and to the residue was added ethyl acetate. The mixture was washed with water and saturated brine, and dried with magnesium sulfate. Under reduced pressure, ethyl acetate was evaporated, and the thus obtained oil containing crystals were subjected to silica gel column (EtOAc/hexane) to remove starting materials. The thus obtained crystals were recrystallized from ethyl acetate-hexane to give 7-(2,5-dichlorothiophen-3-yl)-4-methyl-5,6,7,8-tetrahydroquinolin-5-one (32.6 g).

mp. 138–140° C.

$^1$H-NMR(CDCl$_3$) δ: 2.70 (3H, s), 2.75 (1H, dd, J=12, 17 Hz), 2.93 (1H, ddd, J=2, 4, 16 Hz), 3.22 (1H, dd, J=11, 17 Hz), 3.39 (1H, ddd, J=2, 5, 17 Hz), 3.57–3.76 (1H, m), 6.72 (1H, s), 7.11 (1H, d, J=5 Hz), 8.50 (1H, d, J=5 Hz).

Reference Example 126

To a solution of 4-methyl-7-(3-thienyl)-5,6,7,8-tetrahydroquinolin-5-one (2.18 g) in acetic acid (10 ml) was added a solution of N-bromosuccinimide (2.32 g) in acetic acid (10 ml), and the mixture was stirred under argon atmosphere at room temperature for 20 hours. Under reduced pressure, the solvent was evaporated, and to the residue was added sodium hydrogen carbonate solution. The mixture was extracted with ethyl acetate, and the organic layer was concentrated under reduced pressure. The residue was purified with silica gel column chromatography to give 7-(2-bromothiophen-3-yl)-4-methyl-5,6,7,8-tetrahydroquinolin-5-one (1.74 g) as pale yellow crystals and 7-(2,5-dibromothiophen-3-yl)-4-methyl-5,6,7,8-tetrahydroquinolin-5-one (0.53 g) as pale yellow crystals.

7-(2-bromothiophen-3-yl)-4-methyl-5,6,7,8-tetrahydroquinolin-5-one mp84–85° C.

$^1$H-NMR(CDCl$_3$) δ: 2.71 (3H,s), 2.81 (1H,dd), 2.96 (1H, ddd), 3.28 (1H,dd), 3.42 (1H,ddd), 3.68 (1H,m), 6.88 (1H, d), 7.11 (1H,d), 7.31 (1H,d), 8.5 (1H,d).

7-(2,5-dibromothiophen-3-yl)-4-methyl-5,6,7,8-tetrahydroquinolin-5-one mp130–131° C.

$^1$H-NMR(CDCl$_3$) δ: 2.70 (3H,s), 2.75 (1H,dd), 2.93 (1H, ddd), 3.23 (1H,dd), 3.69 (1H,ddd), 3.64 (1H,m), 6.87 (1H, d), 7.12 (1H,d), 8.5 (1H,d).

Reference Example 127

To a solution of 5-(2,5-dichlorothiophen-3-yl) cyclohexane-1,3-dione (3.07 g), 4-dimethylaminopyridine (2.14 g) and dicyclohexylcarbodiimide (3.13 g) in dimethylformamide (10 ml) was added acetic acid (1.26 g), and the mixture was stirred at room temperature for 13 hours. To the mixture were added water (30 ml) and 2N hydrochloric acid (10 ml), and the mixture was extracted with ethyl acetate. The organic layer was extracted with 0.5N sodium hydroxide solution, and to the aqueous layer was added 2N hydrochloric acid to make the solution acidic. The solution was extracted with ethyl acetate, and the organic layer was washed with water. Under reduced pressure, the solvent was evaporated, and the residue was recrystallized from ethyl acetate-hexane to give 5-(2,5-dichlorothiophen-3-yl)-2-(1-hydroxyethylidene)cyclohexane-1,3-dione (2.5 g) as yellow crystals.

mp107–108° C.

$^1$H-NMR(CDCl$_3$) δ: 2.58–2.86 (7H,m), 3.45–3.62 (1H, m), 6.67 (1H,s).

Reference Example 128

A solution of 5-(2,5-dichlorothiophen-3-yl)-2-(1-hydroxyethylidene)cyclohexane-1,3-dione (2.48 g) and hydrazine hydrate (0.508 g) in ethanol (10 ml) was refluxed for 2 hours. Under reduced pressure, the solvent was evaporated, and to the residue was added water. The mixture was extracted with ethyl acetate, and the organic layer was washed with water and concentrated under reduced pressure. The residue was washed with diisopropylether to give 6-(2,5-dichlorothiophen-3-yl)-3-methyl-4,5,6,7-tetrahydroindazol-4-one (2.15 g) as pale yellow crystals.

mp.167–168° C.

$^1$H-NMR(CDCl$_3$) δ: 2.58–2.67 (5H,m), 2.87 (1H,dd), 3.12 (1H,dd), 3.56–3.73 (1H,m), 6.70 (1H,S).

Reference Example 129

A mixture of 5-(thiophen-3-yl)cyclohexane-1,3-dione (3.83 g), p-toluene sulfonylhydrazide (3.72 g) and ethanol (50 ml) was refluxed for 1 hour and cooled, and precipitated crystals were filtered and washed with ethanol to give 1-[2-(4-methylphenylsulfonyl)hydrazino]-5-(thiophen-3-yl)cyclohexen-3-one (4.5 g) as colorless crystals.

mp. 228–229° C. (decomp.)

$^1$H-NMR(DMSO-d$_6$) δ: 2.32–2.48 (7H,m), 3.12–3.29 (1H,m), 5.20 (1H,s), 7.09 (1H,dd), 7.21 (1H,d), 7.42 (2H,d), 7.46–7.49 (1H,m), 7.72 (2H,d), 8.74 (1H,broad), 9.81 (1H,s).

Reference Example 130

A mixture of 1-[2-(4-methylphenylsulfonyl)hydrazino]-5-(thiophen-3-yl)cyclohexen-3-one (3.62 g), anhydrous potassium carbonate (3.45 g), chloroacetone (1.15 g), sodium iodide (1 g), ethanol (50 ml) and 1,2-dimethoxyethane (20 ml) was stirred at 80° C. for 1 hour. Under reduced pressure, the solvent was evaporated, and the residue was extracted with ethyl acetate. The organic layer was concentrated, and the residue was purified with silica gel column chromatography. The resulting crystals were recrystallized from ethyl acetate-hexane to give 4-methyl-7-(thiophen-3-yl)-5,6,7,8-tetrahydrocinnolin-5-one (0.8 g) as yellow crystals.

mp. 125–126° C.

$^1$H-NMR(CDCl$_3$) δ: 2.68 (3H,s), 2.92 (1H,dd), 3.14 (1H, ddd), 3.48 (1H,dd), 3.60–3.74 (1H,m), 3.82 (1H,ddd), 7.08 (2H,d), 7.43–7.38 (1H,m), 9.13 (1H,s).

Reference Example 131

A mixture of 5-(2-chlorophenyl)cyclohexane-1,3-dione (5.5 g), p-toluene sulfonylhydrazide (4.6 g) and ethanol (70 ml) was refluxed for 70 minutes and cooled, and precipitated crystals were filtered and washed with ethanol to give 5-(2-chlorophenyl)-1-[2-(4-methylphenylsulfonyl)hydrazino]cyclohexen-3-one (7.2 g) as colorless crystals.

mp.235–236° C.

$^1$H-NMR(DMSO-d$_6$) δ: 2.24 (1H,dd), 2.40 (3H,s), 2.49–2.60 (3H,m), 3.44–3.60 (1H,m), 5.23 (1H,s), 7.23–7.34 (2H,m), 7.37–7.48 (4H,m), 7.71 (1H,d), 8.79 (1H,broad), 9.83 (1H,broad).

Reference Example 132

A mixture of 5-(2-chlorophenyl)-1-[2-(4-methylphenylsulfonyl)hydrazino]cyclohexen-3-one (1.17 g), anhydrous potassium carbonate (1.1 g), chloroacetone (0.335 g), sodium iodide (0.4 g), ethanol (7.5 ml) and 1,2-dimethoxyethane (7.5 ml) was stirred at 80° C. for 4 hours. Under reduced pressure, the solvent was evaporated, and the residue was extracted with ethyl acetate. The organic layer was concentrated, and the residue was purified with silica gel column chromatography to give 4-methyl-7-(2-chlorophenyl)-5,6,7,8-tetrahydrocinnolin-5-one (0.34 g) as pale yellow crystals.

mp. 108–109° C.

$^1$H-NMR(CDCl$_3$) δ: 2.71 (3H,s), 2.88 (1H,dd), 3.09 (1H, ddd), 3.49 (1H,dd), 3.79 (1H,ddd), 3.93–4.1 (1H,m), 7.22–7.35 (3H,m), 7.45 (1H,dd), 9.16 (1H,s).

Reference Example 133

A mixture of 5-(2,5-dichlorothiophen-3-yl)cyclohexane-1,3-dione (5.83 g), p-toluene sulfonylhydrazide (4.3 g) and ethanol (50 ml) was refluxed for 1.5 hours and cooled, and precipitated crystals were filtered and washed with ethanol to give 5-(2,5-dichlorothiophen-3-yl)-1-[2-(4-methylphenylsulfonyl)hydrazino]cyclohexen-3-one (8.5 g) as colorless crystals.

mp. 255–256° C. (decomp.)

$^1$H-NMR(DMSO-d$_6$) δ: 2.17 (1H,dd), 2.30–2.55 (6H,m), 3.15–3.31 (1H,m), 5.23 (1H,s), 7.20 (1H,s), 7.42 (2H,d), 7.71 (2H,d), 8.78 (1H,broad), 9.84 (1H,broad).

Reference Example 134

A mixture of 5-(2,5-dichlorothiophen-3-yl)-1-[2-(4-methylphenylsulfonyl)hydrazino]cyclohexen-3-one (1.33 g), anhydrous potassium carbonate (1.14 g), chloroacetone (0.4 g), sodium iodide (0.3 g), methanol (25 ml) and 1,2-dimethoxyethane (10 ml) was stirred at 80° C. for 3 hours. Under reduced pressure, the solvent was evaporated, and the residue was extracted with ethyl acetate. The organic layer was concentrated, and the residue was purified with silica gel column chromatography to give 7-(2,5-dichlorothiophen-3-yl)-4-methyl-5,6,7,8-tetrahydrocinnolin-5-one (0.51 g) as colorless crystals.

mp. 137–138° C.

$^1$H-NMR(CDCl$_3$) δ: 2.7 (3H,s), 2.81 (1H,ddd), 3.01 (1H, dd), 3.36 (1H,dd), 3.61–3.75 (2H,m), 6.74 (1H,s), 9.15 (1H,s).

Reference Example 135

A mixture of 5-(2-chlorophenyl)-1-[2-(4-methylphenylsulfonyl)hydrazino]cyclohexen-3-one (1.56 g), anhydrous potassium carbonate (0.72 g), 1-bromobutan-2-one (0.785 g) and methanol (30 ml) was stirred at room temperature for 2.5 hours. To the mixture was added anhydrous potassium carbonate (0.72 g), and the mixture was stirred at room temperature 1.5 hours and refluxed for 30 minutes. Under reduced pressure, the solvent was evaporated, and the residue was extracted with ethyl acetate. The organic layer was concentrated, and the residue was purified with silica gel column chromatography to give 7-(2-chlorophenyl)-4-ethyl-5,6,7,8-tetrahydrocinnolin-5-one (0.492 g) as oil.

$^1$H-NMR(CDCl$_3$) δ: 1.31 (3H,t), 2.89 (1H,dd), 3.04–3.37 (3H,m), 3.44 (1H,dd), 3.78 (1H,ddd), 3.93–4.07 (1H,m), 7.2–7.34 (3H,s), 7.45 (1H,dd), 9.19 (1H,s).

Reference Example 136

A mixture of 5-(2,5-dichlorothiophen-3-yl)cyclohexane-1,3-dione (5.26 g), 4-methoxyphenylsulfonylhydrazide (4.04 g) and ethanol (50 ml) was refluxed for 3 hours and cooled, and precipitated crystals were filtered and washed with ethanol to give 5-(2,5-dichlorothiophen-3-yl)-1-[2-(4-methoxyphenylsulfonyl)hydrazino]cyclohexen-3-one (7.1 g) as pale yellow crystals.

mp. 241–242° C. (decomp.)

¹H-NMR(DMSO-d₆) δ: 2.16 (1H,dd), 2.33–2.60 (3H,m), 3.15–3.35 (1H,m), 3.85 (3H,s), 5.22 (1H,s), 7.14 (2H,d), 7.21 (1H,s), 7.75 (2H,d), 8.78 (1H,broad), 9.75 (1H,broad).

Reference Example 137

To a mixture of 5-(2,5-dichlorothiophen-3-yl)-1-[2-(4-methoxyphenylsulfonyl)hydrazino]cyclohexen-3-one (1.79 g), anhydrous potassium carbonate (0.718 g) and methanol (30 ml) was added under ice-cooling 1-bromobutan-2-one (0.785 g), and the mixture was stirred at room temperature for 2 hours. To the mixture was added anhydrous potassium carbonate (1.2 g), and the mixture was stirred for 2 hours. Under reduced pressure, the solvent was evaporated, and the residue was extracted with ethyl acetate. The organic layer was concentrated, and the residue was purified with silica gel column chromatography to give 7-(2,5-dichlorothiophen-3-yl)-4-ethyl-5,6,7,8-tetrahydrocinnolin-5-one (0.26 g) as oil.

¹H-NMR(CDCl₃) δ: 1.29 (3H,t), 2.8 (1H,dd), 3.0 (1H,ddd), 3.13 (2H,), 3.36 (1H,dd), 3.6–3.76 (2H,m), 6.73 (1H,s), 9.18 (1H,s).

Reference Example 138

A mixture of 5-(2-chlorophenyl)-1-[2-(4-methylphenylsulfonyl)hydrazino]cyclohexen-3-one (1.35 g), anhydrous potassium carbonate (1.19 g), 2-bromoacetophenone (0.893 g) and methanol (30 ml) was stirred at 80° C. for 3 hours. Under reduced pressure, the solvent was evaporated, and the residue was extracted with ethyl acetate. The organic layer was concentrated, and the residue was purified with silica gel column chromatography to give 7-(2-chlorophenyl)-4-phenyl-5,6,7,8-tetrahydrocinnolin-5-one (0.46 g) as oil.

¹H-NMR(CDCl₃) δ: 2.90 (1H,dd), 3.07 (1H,ddd), 3.52 (1H,dd), 3.88 (1H,ddd), 4.0–4.17 (1H,m), 7.22–7.38 (5H,s), 7.43–7.53 (4H,m), 9.20 (1H,s).

Reference Example 139

To a mixture of 5-(2-chlorophenyl)-1-[2-(4-methylphenylsulfonyl)hydrazino]cyclohexen-3-one (2.74 g), anhydrous potassium carbonate (1.26 g) and methanol (30 ml) was added at room temperature 1-bromo-3,3,3-trifluoropropan-2-one (1.74 g), and the mixture was stirred at the same temperature for 0.5 hours. To the mixture was added anhydrous potassium carbonate (1.26 g), and the mixture was refluxed for 1 hour. Under reduced pressure, the solvent was evaporated, and the residue was extracted with ethyl acetate. The organic layer was concentrated, and the residue was dissolved in acetic acid (20 ml). To the solution was added concentrated sulfuric acid (1 ml), and the mixture was refluxed for 20 minutes. To the reaction solution was added water (120 ml), and the mixture was concentrated under reduced pressure. The residue was extracted with ethyl acetate, and the organic layer was washed with sodium hydrogen carbonate solution and concentrated. The residue was purified with silica gel column chromatography to give 7-(2-chlorophenyl)-4-trifluoromethyl-5,6,7,8-tetrahydrocinnolin-5-one (1.02 g) as oil.

¹H-NMR(CDCl₃) δ: 3.01 (1H,dd), 3.2 (1H,ddd), 3.57 (1H,dd), 3.98 (1H,ddd), 4.0–4.16 (1H,m), 7.26–7.5 (4H,m), 9.64 (1H,s).

Reference Example 140

To a mixture of 5-(2,5-dichlorothiophen-3-yl)-1-[2-(4-methylphenylsulfonyl)hydrazino]cyclohexen-3-one (2.0 g), anhydrous potassium carbonate (0.9 g) and methanol (20 ml) was added, under ice-cooling, 1-bromo-3,3,3-trifluoropropan-2-one (1.24 g), and the mixture was stirred at the same temperature for 0.5 hours. To the mixture was added anhydrous potassium carbonate (1.2 g), and the mixture was refluxed for 2 hours. Under reduced pressure, the solvent was evaporated, and the residue was extracted with ethyl acetate. The organic layer was concentrated, and the residue was dissolved in acetic acid (15 ml). To the solution was added concentrated sulfuric acid (0.6 ml), and the mixture was refluxed for 30 minutes. To the reaction solution was added water (120 ml), and the mixture was concentrated under reduced pressure. The residue was extracted with ethyl acetate, and the organic layer was washed with sodium hydrogen carbonate solution and concentrated. The residue was purified with silica gel column chromatography to give 7-(2,5-dichlorothiophen-3-yl)-4-trifluoromethyl-5,6,7,8-tetrahydrocinnolin-5-one (0.867 g) as oil.

¹H-NMR(CDCl₃) δ: 2.92 (1H,dd), 3.11 (1H,ddd), 3.49 (1H,dd), 3.67–3.83 (1H,m), 3.87 (1H,ddd), 6.76 (1H,s), 9.64 (1H,s).

Reference Example 141

A mixture of 1-amino-5-(thiophen-3-yl)cyclohexen-3-one (4.75 g) and methyl acetoacetate (10 g) was stirred at 170° C. for 18 hours and cooled, and to the mixture was added ethyl acetate. Precipitated crystals were filtered and washed with ethyl acetate to give 4-methyl-7-(thiophen-3-yl)-1,2,5,6,7,8-hexahydroquinoline-2,5-dione (1.4 g) as yellow crystals.

mp300° C. or more

¹H-NMR(DMSO-d₆) δ: 2.4 (3H,s), 2.6–2.8 (2H,m), 3.05 (2H,d), 3.4–3.6 (1H,m), 6.05 (1H,s), 7.13 (1H,dd), 7.28 (1H,d), 7.52 (1H,dd), 12.03 (1H,broad).

Reference Example 142

To a solution of 4-methyl-7-(thiophen-3-yl)-1,2,5,6,7,8-hexahydroquinoline-2,5-dione (0.518 g) in dimethylformamide (5 ml) was added at room temperature 60% sodium hydride (0.08 g) and then was added methyl iodide (0.3 ml), and the mixture was stirred at room temperature for 4 hours. Under reduced pressure, the solvent was evaporated, and the residue was extracted with ethyl acetate. The organic layer was washed with water and concentrated under reduced pressure. The resulting crystals were washed with ethyl acetate to give 1,4-dimethyl-7-(thiophen-3-yl)-1,2,5,6,7,8-hexahydroquinoline-2,5-dione (0.405 g) as colorless crystals.

mp156–157° C.

¹H-NMR(DMSO-d₆) δ: 2.53 (3H,s), 2.72 (1H,dd), 2.88 (1H,ddd), 2.99 (1H,dd), 3.3 (1H,ddd), 3.46–3.65 (1H,m), 3.58 (3H,s), 6.33 (1H,s), 7.06 (1H,dd), 7.1–7.12 (1H,m), 7.39 (1H,dd).

Reference Example 143

To a solution of 1,4-dimethyl-7-(thiophen-3-yl)-1,2,5,6,7,8-hexahydroquinoline-2,5-dione (0.518 g) and pyridine (0.216 g) in ethyl acetate (20 ml) was added at room temperature sulfuryl chloride (0.405 g), and the mixture was stirred at the same temperature for 0.5 hours. To the reaction solution was added water, and the mixture was extracted with ethyl acetate. The organic layer was concentrated under reduced pressure, and the residue was purified with silica gel column chromatography to give 3-chloro-7-(2- chlorothiophen-3-yl)-1,4-dimethyl-1,2,5,6,7,8-hexahydroquinoline-2,5-dione (0.195 g) as colorless crystals.

mp175–176° C.

$^1$H-NMR(DMSO-$d_6$) δ:2.72 (3H,s), 2.71–2.81 (2H,m), 2.94 (1H,dd), 3.21 (1H,dd), 3.6–3.75 (1H,m), 3.65 (3H,s), 6.88 (1H,d), 7.19 (1H,d).

Reference Example 144

A mixture of 1-amino-5-(2-chlorophenyl)cyclohexen-3-one (6.66 g) and methyl acetoacetate (5.8 g) was stirred at 170° C. for 2.5 hours, and to the mixture was added methyl acetoacetate (3 g). The mixture was stirred for 1.5 hours and cooled, and precipitated crystals were filtered and washed with ethanol to give 7-(2-chlorophenyl)-4-methyl-1,2,5,6,7,8-hexahydroquinoline-2,5-dione (0.42 g) as pale yellow crystals.

mp290–291° C.

$^1$H-NMR(DMSO-$d_6$) δ: 2.43 (3H,s), 2.51–2.62 (1H,m), 2.78–3.24 (3H,m), 3.74–3.87 (1H,m), 6.08 (1H,s), 7.28–7.51 (4H,d), 12.60 (1H,broad).

Working Example 106
(Production of Compound 108)

In methanol (390 ml) was suspended (±)-7-(2,5-dichlorothiophen-3-yl)-5-guanidinoimino-4-methyl-5,6,7,8-tetrahydroquinoline hydrochloride (39.0 g), and to the suspension was added dropwise a solution of 28% sodium methoxide in methanol. The mixture was stirred at 50° C. for 1 hour. Under reduced pressure, the mixture was concentrated, and the obtained crystals were washed with water and dried to give (±)-7-(2,5-dichlorothiophen-3-yl)-5-guanidinoimino-4-methyl-5,6,7,8-tetrahydroquinoline (Compound 108) (32.8 g).

mp.250–251° C.

Elemental Analysis for $C_{15}H_{15}Cl_2N_5S.0.2H_2O$

Calcd. C,48.45; H,4.17; N,18.83.

Found C,48.38; H,4.40; N,18.74.

$^1$H-NMR(CD$_3$OD) δ: 2.70 (3H, s), 2.74 (1H, dd, J=13, 18 Hz), 3.02–3.08 (2H, m), 3.13–3.38 (2H, m), 6.97 (1H, s), 7.19 (1H, d, J=5 Hz), 8.14 (1H, d, J=5 Hz).

Working Example 107
(Production of Compounds 109–110)

Using CHIRALPAK AD (eluent: hexane-ethanol), (±)-7-(2,5-dichlorothiophen-3-yl)-4-methyl-5,6,7,8-tetrahydroquinolin-5-one (1.0 g) was subjected to optical resolution to give (−)-7-(2,5-dichlorothiophen-3-yl)-4-methyl-5,6,7,8-tetrahydroquinolin-5-one (0.40 g) and (±)-7-(2,5-dichlorothiophen-3-yl)-4-methyl-5,6,7,8-tetrahydroquinolin-5-one (0.41 g).

In ethanol (10 ml) was dissolved (−)-7-(2,5-dichlorothiophen-3-yl)-4-methyl-5,6,7,8-tetrahydroquinolin-5-one (0.35 g), and to the mixture were added aminoguanidine hydrochloride (0.15 g), concentrated hydrochloric acid (0.28 ml) and water (0.28 ml). The mixture was refluxed for 4 hours, and under reduced pressure, the solvent was evaporated. The residue was dissolved in water, and the mixture was washed with ethyl acetate and concentrated under reduced pressure. The residue was heated in a little amount of ethanol, and the solution was cooled. Precipitated crystals were filtered off, and the mother liquor was concentrated to give crystals, which were recrystallized from water to give (−)-7-(2,5-dichlorothiophen-3-yl)-5-guanidinoimino-4-methyl-5,6,7,8-tetrahydroquinoline hydrochloride (Compound 109) (0.47 g) as colorless crystals.

Elemental Analysis for $C_{15}H_{15}C_{12}N_5S.2HCl.H_2O$

Calcd. C,39.23; H,4.17; N,15.25; Cl,30.88.

Found C,39.06; H,4.31; N,15.25; Cl,30.69.

$^1$H-NMR(DMSO-$d_6$) was agreed with that of Compound 102.

In ethanol (10 ml) was dissolved (+)-7-(2,5-dichlorothiophen-3-yl)-4-methyl-5,6,7,8-tetrahydroquinolin-5-one (0.36 g), and to the mixture were added aminoguanidine hydrochloride (0.15 g), concentrated hydrochloric acid (0.29 ml) and water (0.29 ml). The mixture was refluxed for 4 hours, and under reduced pressure, the solvent was evaporated. The residue was dissolved in water, and the mixture was washed with ethyl acetate and concentrated under reduced pressure. The residue was heated in a little amount of ethanol, and the solution was cooled. Precipitated crystals were filtered off, and the mother liquor was concentrated to give crystals, which were recrystallized from water to give (+)-7-(2,5-dichlorothiophen-3-yl)-5-guanidinoimino-4-methyl-5,6,7,8-tetrahydroquinoline hydrochloride (Compound 110) (0.46 g) as colorless crystals.

Elemental Analysis for $C_{15}H_{15}C_{12}N_5S.2HCl.0.5H_2O$

Calcd. C,40.02; H,4.03; N,15.56.

Found C,39.69; H,4.17; N,15.50.

$^1$H-NMR(DMSO-$d_6$) was agreed with that of Compound 102.

Working Example 108
(Production of Compounds 111–113)

To a solution of (±)-7-(2,5-dichlorothiophen-3-yl)-5-guanidinoimino-4-methyl-5,6,7,8-tetrahydroquinoline (17.4 g) in ethanol (200 ml) was added a solution of L-pyroglutamic acid (4.0 g) in ethanol (20 ml), at 80° C., and the mixture was gradually cooled to the room temperature and stirred at room temperature for 6 hours. The crystals were filtered and washed with ethanol to give (+)-7-(2,5-dichlorothiophen-3-yl)-5-guanidinoimino-4-methyl-5,6,7,8-tetrahydroquinoline L-pyroglutamate (11.0 g). Said crystals were suspended in methanol (200 ml), and to the mixture was added a solution of 28% sodium methoxide in methanol (4.2 ml). Under reduced pressure, the solvent was evaporated to give crystals, which were washed with water, dried and recrystallized from ethanol. To the crystals was added ethanol (30 ml), and then methanesulfonic acid (3.4 g). The mixture was heated to give a homogenous solution and cooled, and precipitated crystals were filtered to give (+)-7-(2,5-dichlorothiophen-3-yl)-5-guanidinoimino-4-methyl-5,6,7,8-tetrahydroquinoline methanesulfonate (Compound 111) (8.5 g, 99.9% ee).

mp. 225–229° C.

Elemental Analysis for $C_{15}H_{15}Cl_2N_5S.2MeSO_3H$

Calcd. C,36.43; H,4.14; N,12.49; Cl,12.65.

Found C,36.61; H,4.14; N,12.39; Cl,12.57.

$^1$H-NMR(DMSO-$d_6$) δ: 2.41 (6H, s), 2.70–2.94 (1H, m), 2.86 (3H, s), 2.97–3.26 (2H, m), 3.27–3.57 (2H, m), 7.2–8.4 (4H, br), 7.41 (1H, s), 7.82 (1H, d, J=6 Hz), 8.65 (1H, d, J=6 Hz), 10.80 (1H, s).

To the mother liquor obtained by the separation treatment with L-pyroglutamic acid and washing solution was added a solution of 28% sodium methoxide in methanol (3 ml), and the mixture was concentrated and washed with water to give (−)-isomer rich crystals (9.3 g, 78.5% ee), which were recrystallized from ethanol to give (−)-7-(2,5-dichlorothiophen-3-yl)-5-guanidinoimino-4-methyl-5,6,7,8-tetrahydroquinoline (Compound 112) (7.6 g,99.2% ee). (This compound was confirmed to be S-isomer (absolute configuration), according to X-ray crystal structure analysis.)

mp.129–133° C.

$^1$H-NMR(CD$_3$OD) was agreed with that of Compound 108.

To (−)-7-(2,5-dichlorothiophen-3-yl)-5-guanidinoimino-4-methyl-5,6,7,8-tetrahydroquinoline (6.4 g) was added ethanol (50 ml) and methanesulfonic acid (3.1 g) to give a homogenous solution, and the solution was concentrated to give crystals, which were recrystallized from ethanol to give (−)-7-(2,5-dichlorothiophen-3-yl)-5-guanidinoimino-4-methyl-5,6,7,8-tetrahydroquinoline methanesulfonate (Compound 113) (8.1 g,99.5% ee).

mp. 229–231° C.

Elemental Analysis for C$_{15}$H$_{15}$Cl$_2$N$_5$S.2MeSO$_3$H

Calcd. C,36.43; H,4.14; N,12.49; Cl,12.65.

Found C,36.50; H,4.06; N,12.34; Cl,12.62.

$^1$H-NMR(DMSO-d$_6$) was agreed with that of Compound 111.

Working Example 109
(Production of Compound 114)

To a solution of (−)-7-(2,5-dichlorothiophen-3-yl)-5-guanidinoimino-4-methyl-5,6,7,8-tetrahydroquinoline (0.8 g) in ethanol (20 ml) was added methanesulfonic acid (0.37 g), and the mixture was concentrated under reduced pressure. To the residue was added water (1 ml), and the mixture was concentrated to precipitate crystals, which were filtered and washed with ethanol. The thus obtained crystals were dried to give (−)-7-(2,5-dichlorothiophen-3-yl)-5-guanidinoimino-4-methyl-5,6,7,8-tetrahydroquinoline methanesulfonate monohydrate (Compound 114) (1.0 g).

mp. 239–241° C.

Elemental Analysis for C$_{15}$H$_{15}$Cl$_2$N$_5$S.2MeSO$_3$H.H$_2$O

Calcd. C,35.29; H,4.36; N,12.11.

Found C,35.11; H,4.27; N,12.15.

$^1$H-NMR(DMSO-d$_6$) δ: 2.41 (6H, s), 2.70–2.94 (1H, m), 2.86 (3H, s), 2.97–3.26 (2H, m), 3.27–3.57 (2H, m), 7.2–8.4 (4H, br), 7.40 (1H, s), 7.83 (1H, d, J=6 Hz), 8.65 (1H, d, J=6 Hz), 10.79 (1H, s).

Working Example 110
(Production of Compound 115)

To a solution of (−)-7-(2,5-dichlorothiophen-3-yl)-5-guanidinoimino-4-methyl-5,6,7,8-tetrahydroquinoline (0.8 g) in ethanol (20 ml) was added 0.5M sulfuric acid (3.9 ml), and the mixture was concentrated under reduced pressure to give crystals, which were recrystallized from water and washed with ethanol to give (−)-7-(2,5-dichlorothiophen-3-yl)-5-guanidinoimino-4-methyl-5,6,7,8-tetrahydroquinoline sulfurate (Compound 115) (0.8 g).

mp. 239–242° C.

Elemental Analysis for C$_{15}$H$_{15}$Cl$_2$N$_5$S.H$_2$SO$_4$.0.5H$_2$O

Calcd. C,37.90; H,3.82; N,14.73.

Found C,37.87; H,3.88; N,14.56.

$^1$H-NMR(DMSO-d$_6$) δ: 2.40–3.6 (5H, m), 2.64 (3H, s), 7.0–8.0 (4H, br), 7.37 (1H, s), 7.24 (1H, d, J=5 Hz), 8.32 (1H, d, J=5 Hz), 10.58 (1H, br).

Working Example 111
(Production of Compound 116)

To a solution of (−)-7-(2,5-dichlorothiophen-3-yl)-5-guanidinoimino-4-methyl-5,6,7,8-tetrahydroquinoline (0.8 g) in ethanol (20 ml) was added 1.7M nitric acid (2.3 ml), and the mixture was concentrated under reduced pressure to give crystals, which were recrystallized from water to give (−)-7-(2,5-dichlorothiophen-3-yl)-5-guanidinoimino-4-methyl-5,6,7,8-tetrahydroquinoline nitrate (Compound 116) (0.92 g).

mp. 167° C. (decomp.)

Elemental Analysis for C$_{15}$H$_{15}$Cl$_2$N$_5$S.HNO$_3$.0.5H$_2$O

Calcd. C,35.79; H,3.60; N,19.48.

Found C,35.56; H,3.58; N,19.39.

$^1$H-NMR(DMSO-d$_6$) δ: 2.69–3.21 (3H, m), 2.83 (3H, s), 3.26–3.63 (2H, m), 7.2–8.0 (4H, br), 7.40 (1H, s), 7.77 (1H, d, J=6 Hz), 8.64 (1H, d, J=6 Hz), 10.61 (1H, s).

Working Example 112
(Production of Compound 117)

A mixture of 6-(2-chlorophenyl)-3-methyl-4,5,6,7-tetrahydrobenzothiophene-4-one (0.07 g), aminoguanidine hydrochloride (0.034 g), concentrated hydrochloric acid (0.063 ml), water (0.063 ml) and ethanol (10 ml) was refluxed for 4 hours. Under reduced pressure, the solvent was evaporated, and the residue was recrystallized from ethanol to give 6-(2-chlorophenyl)-4-guanidinoimino-3-methyl-4,5,6,7-tetrahydrobenzothiophene hydrochloride (Compound 117) (80 mg) as colorless crystals.

mp. 246° C. (decomp.)

Elemental Analysis for C$_{16}$H$_{16}$N$_4$S.HCl.0.5H$_2$O

Calcd. C,50.80; H,5.06; N,14.81.

Found C,50.60; H,4.85; N,15.01.

$^1$H-NMR(DMSO-d$_6$) δ: 2.45 (3H,s), 2.73 (1H,dd,J=12,17 Hz), 3.0–3,20 (3H,m), 3.56–3.77 (1H,m), 6.9–8.1 (4H,br), 7.03 (1H,s), 7.25–7.66 (4H,m), 10.77 (1H,s).

Working Example 113
(Production of Compound 118)

A mixture of 4-methyl-7-(2-thiazolyl)-5,6,7,8-tetrahydroquinolin-5-one (0.68 g), aminoguanidine hydrochloride (0.37 g), concentrated hydrochloric acid (0.7 ml), water (0.7 ml) and ethanol (25 ml) was refluxed for 5 hours. Under reduced pressure, the solvent was evaporated, and to the residue was added water. The mixture was washed with ethyl acetate. Under reduced pressure, the solvent was evaporated, and the residue was recrystallized from ethanol-water to give 5-guanidinoimino-4-methyl-7-(2-thiazolyl)-5,6,7,8-tetrahydroquinoline hydrochloride (Compound 118) (0.9 g) as colorless crystals.

mp. 282° C. (decomp.)

Elemental Analysis for C$_{14}$H$_{16}$N$_6$S.3HCl

Calcd. C,41.04; H,4.67; N,20.51.

Found C,41.13; H,4.63; N,20.74.

$^1$H-NMR(DMSO-d$_6$) δ: 2.88 (3H,s), 3.19 (1H,dd,J=9,18 Hz), 3.37 (1H,dd,J=5,17 Hz), 3.46–3.80 (2H,m), 3.80–4.2 (1H,m), 7.69 (1H,d,J=3 Hz), 7.6–8.5 (4H,br), 7.74 (1H,d, J=3 Hz), 7.89 (1H,d,J=6 Hz), 8.68 (1H,d,J=6 Hz), 11.69 (1H,s).

Working Example 114
(Production of Compound 119)

A mixture of 6-(3-chloro-2-thienyl)-3-methyl-4,5,6,7-tetrahydroindazol-4-one (1.2 g), aminoguanidine hydrochloride (0.6 g), concentrated hydrochloric acid (1.1 ml), water (1.1 ml) and ethanol (50 ml) was refluxed for 3 hours. Under reduced pressure, the solvent was evaporated, and the residue was washed with ethanol to give 6-(3-chloro-2-thienyl)-4-guanidinoimino-3-methyl-4,5,6,7-tetrahydroindazole hydrochloride (Compound 119) (1.2 g) as colorless crystals.

mp. 204° C. (decomp.)

Elemental Analysis for C$_{13}$H$_{15}$ClN$_6$S.2HCl

Calcd. C,39.46; H,4.33; N,21.24.

Found C,39.49; H,4.31; N,21.06.

$^1$H-NMR(DMSO-d$_6$) δ: 2.48 (3H,s), 2.69 (1H,dd,J=10,17 Hz), 2.85 (1H,dd,J=10,16 Hz), 3.0–3.2 (2H,m), 3.62–3.81 (1H,m), 6.9–8.4 (4H,br), 7.04 (1H,d,J=5 Hz), 7.56 (1H,d, J=5 Hz), 11.04 (1H,s).

Working Example 115
(Production of Compound 120)

A mixture of 7-(2,5-dichlorophenyl)-4-methyl-5,6,7,8-tetrahydroquinolin-5-one (1.0 g), aminoguanidine hydrochloride (0.43 g), concentrated hydrochloric acid (0.82 ml), water (0.82 ml) and ethanol (30 ml) was refluxed for 6 hours. Under reduced pressure, the solvent was evaporated. To the residue was added water, and the mixture was washed with ethyl acetate. Under reduced pressure, the solvent was evaporated, and the residue recrystallized from water to give 7-(2,5-dichlorophenyl)-5-guanidinoimino-4-methyl-5,6,7,8-tetrahydroquinoline hydrochloride (Compound 120) (1.3 g) as colorless crystals.

mp. 300° C. or more

Elemental Analysis for $C_{17}H_{17}Cl_2N_5.2HCl.0.5H_2O$

Calcd. C,45.97; H,4.54; N,15.77.

Found C,46.21; H,4.53; N,15.88.

$^1$H-NMR(DMSO-$d_6$) δ: 2.83–3.03 (1H,m), 2.88 (3H,s), 3.14–3.77 (4H,m), 7.43 (1H,dd,J=2,9 Hz), 7.5–8.4 (4H,br), 7.55 (1H,d,J=9 Hz), 7.76 (1H,d,J=2 Hz), 7.83 (1H,d,J=5 Hz), 8.63 (1H,d,J=5 Hz), 11.51 (1H,s).

Working Example 116
(Production of Compound 121)

A mixture of 7-(3,5-dichlorothiophen-2-yl)-4-methyl-5,6,7,8-tetrahydroquinolin-5-one (0.5 g), aminoguanidine hydrochloride (0.21 g), concentrated hydrochloric acid (0.4 ml), water (0.4 ml) and ethanol (15 ml) was refluxed for 4 hours. Under reduced pressure, the solvent was evaporated. To the residue was added water, and the mixture was washed with ethyl acetate. Under reduced pressure, the solvent was evaporated, and the residue was recrystallized from water. The resulting crystals were washed with ethanol to give 7-(3,5-dichlorothiophen-2-yl)-5-guanidinoimino-4-methyl-5,6,7,8-tetrahydroquinoline hydrochloride (Compound 121) (0.40 g) as colorless crystals.

mp. 184–187° C.

Elemental Analysis for $C_{15}H_{15}Cl_2N_5S.2HCl.0.5H_2O$

Calcd. C,40.02; H,4.03; N,15.56.

Found C,40.35; H,3.94; N,15.68.

$^1$H-NMR(DMSO-$d_6$) δ: 2.72–2.94 (1H,m), 2.83 (3H,s), 3.20–4.0 (4H,m), 7.24 (1H,s), 7.75 (1H,d,J=6 Hz), 7.87 (4H,br), 8.60 (1H,d,J=6 Hz), 11.47 (1H,s).

Working Example 117
(Production of Compound 122)

To a solution of 7-(3-methyl-2-thienyl)-4-methyl-5,6,7,8-tetrahydroquinolin-5-one (0.38 g) in ethyl acetate (10 ml) were added pyridine (0.023 g) and sulfuryl chloride (0.3 g) at room temperature, and the mixture was stirred at the same temperature for 4 hours. To the reaction solution was added sodium hydrogen carbonate solution, and the organic layer was washed with water and saturated brine, dried with magnesium sulfate and concentrated under reduced pressure. The residue was purified with silica gel column chromatography (EtOAc/hexane) to give 7-(5-chloro-3-methyl-2-thienyl)-4-methyl-5,6,7,8-tetrahydroquinolin-5-one (0.32 g), which was dissolved in ethanol (20 ml). To the solution were added aminoguanidine hydrochloride (0.15 g), concentrated hydrochloric acid (0.27 ml) and water (0.27 ml), and the mixture was refluxed for 7 hours. Under reduced pressure, the solvent was evaporated. To the residue was added water, and the mixture was washed with ethyl acetate. Under reduced pressure, the solvent was evaporated, and the residue was recrystallized from ethanol to give 7-(5-chloro-3-methyl-2-thienyl)-5-guanidinoimino-4-methyl-5,6,7,8-tetrahydroquinoline hydrochloride (Compound 122) (0.32 g) as colorless crystals.

mp. 193–196° C.

Elemental Analysis for $C_{16}H_{18}ClN_5S.2HCl.H_2O$

Calcd. C,43.79; H,5.05; N,15.96.

Found C,44.05; H,5.13; N,15.96.

$^1$H-NMR(CD$_3$OD) δ: 2,20 (3H,s), 2.85 (1H,dd,J=11,17 Hz), 2.98 (3H,s), 3.26–3.54 (3H,m), 3.72–3.92 (1H,m), 6.77 (1H,s), 7.91 (1H,d,J=6 Hz), 8.59 (1H,d,J=6 Hz).

Working Example 118
(Production of Compound 123)

To a mixture of 7-(2-bromothiophen-3-yl)-4-methyl-5,6,7,8-tetrahydroquinolin-5-one (0.12 g) and aminoguanidine hydrochloride (45 mg) were added ethanol (2 ml) and concentrated hydrochloric acid (0.05 ml), and the mixture was stirred at 90° C. for 13 hours and cooled. Precipitated crystals were filtered, washed with ethanol and dried to give 7-(2-bromothiophen-3-yl)-5-guanidinoimino-4-methyl-5,6,7,8-tetrahydroquinoline hydrochloride (Compound 123) (0.14 g) as pale yellow crystals.

mp243–245° C.

Elemental Analysis for $C_{15}H_{16}N_5BrS.2HCl$ Calcd. C,39.93; H,4.02; N,15.52. Found C,39.88; H,4.08; N,15.40.

$^1$H-NMR(DMSO-$d_6$) δ: 2.87 (4H,m), 3.13 (1H,dd), 3.39 (3H,m), 7.25 (1H,d), 7.70 (1H,d), 7.82 (1H,d), 7.92 (4H, broad), 8.64 (1H,d), 11.38 (1H,broad).

Working Example 119
(Production of Compound 124)

To a mixture of 7-(2,5-dibromothiophen-3-yl)-4-methyl-5,6,7,8-tetrahydroquinolin-5-one (0.08 g) and aminoguanidine hydrochloride (24 mg) were added ethanol (1 ml) and concentrated hydrochloric acid (0.04 ml), and the mixture was stirred at 90° C. for 12 hours and cooled. Precipitated crystals were filtered, washed with ethanol and dried to give 7-(2,5-dibromothiophen-3-yl)-5-guanidinoimino-4-methyl-5,6,7,8-tetrahydroquinoline hydrochloride (Compound 124) (0.09 g) as pale yellow crystals.

mp272–273° C.

Elemental Analysis for $C_{15}H_{15}N_5Br_2S.2HCl$ Calcd. C,33.99; H,3.23; N,13.21. Found C,33.99; H,3.33; N,13.12.

$^1$H-NMR(DMSO-$d_6$) δ: 2.84 (4H,m), 3.10 (1H,dd), 3.33 (3H,m), 7.49 (1H,s), 7.77 (1H,d), 7.86 (4H,broad), 8.62 (1H,d), 11.31 (1H,broad).

Working Example 120
(Production of Compound 125)

To a mixture of 7-(2-bromothiophen-3-yl)-4-methyl-5,6,7,8-tetrahydroquinolin-5-one (0.245 g) and 1-amino-3-hydroxyguanidine p-toluenesulfonate (262 mg) were added ethanol (3 ml) and concentrated hydrochloric acid (0.1 ml), and the mixture was stirred at 90° C. for 2 hours. Under reduced pressure, the solvent was evaporated, and to the residue was added 0.2N sodium hydroxide solution (20 ml). The mixture was extracted with a mixture of ethyl acetate (20 ml) and tetrahydrofuran (20 ml). The organic layer was washed with 0.2N sodium hydroxide solution (20 ml) and water, to which was added 2N hydrochloric acid (0.8 ml). The mixture was concentrated, and to the residue was added ethanol (3 ml). The mixture was stirred at 90° C. for 3 hours and cooled, and precipitated crystals were filtered, washed with ethanol and dried to give 7-(2-bromothiophen-3-yl)-5-(1-hydroxyguanidin-3-yl)imino-4-methyl-5,6,7,8-tetrahydroquinoline hydrochloride (Compound 125) (0.215 g) as pale yellow crystals.

mp197–198° C.

Elemental Analysis for $C_{15}H_{16}N_5BrOS.2HCl$ Calcd. C,38.56; H,3.88; N,14.99. Found C,38.81; H,4.16; N,15.05.

$^1$H-NMR(DMSO-$d_6$) δ: 2.87 (4H,m), 3.07–3.46 (4H,m), 7.23 (1H,d), 7.69 (1H,d), 7.79 (1H,d), 8.38 (2H,broad), 8.62 (1H,d), 10.40 (1H,broad), 11.12 (1H,broad)11.34 (1H, broad).

Working Example 121
(Production of Compound 126)

To a mixture of 7-(2,5-dibromothiophen-3-yl)-4-methyl-5,6,7,8-tetrahydroquinolin-5-one (0.07 g) and 1-amino-3-hydroxyguanidine p-toluenesulfonate (58 mg) were added ethanol (1.5 ml) and concentrated hydrochloric acid (0.04 ml), and the mixture was stirred at 90° C. for 2 hours. Under reduced pressure, the solvent was evaporated, and to the residue was added 0.2N sodium hydroxide solution (10 ml). The mixture was extracted with ethyl acetate (30 ml) and tetrahydrofuran (20 ml). The organic layer was washed with water, to which was added concentrated hydrochloric acid (0.02 ml). The mixture was concentrated, and to the residue was added ethanol (1 ml). To the solution was added ether (0.2 ml), and the mixture was stirred for 3 hours. Precipitated crystals were filtered, washed with a mixture of ethanol/ether and dried to give 7-(2,5-dibromothiophen-3-yl)-5-(1-hydroxyguanidin-3-yl)imino-4-methyl-5,6,7,8-tetrahydroquinoline hydrochloride (Compound 126) (0.27 g) as pale yellow crystals.

mp194–196° C. (decomp.).

Elemental Analysis for $C_{15}H_{15}N_5Br_2OS.2HCl$ Calcd. C,33.71; H,3.71; N,12.28 Found C,38.79; H,3.47; N,12.13

$^1$H-NMR(DMSO-$d_6$) δ: 2.70–2.90 (4H,m), 3.04–3.40 (4H,m), 7.48 (1H,s), 7.70 (1H,d), 8.30 (2H,broad), 8.57 (1H,d), 10.35 (1H,broad), 11.09 (1H,broad), 11.19 (1H,broad).

Working Example 122
(Production of Compound 127)

To a mixture of 6-(2,5-dichlorothiophen-3-yl)-3-methyl-4,5,6,7-tetrahydroindazol-4-one (0.3 g) and aminoguanidine hydrochloride (122 mg) were added ethanol (5 ml) and concentrated hydrochloric acid (0.1 ml), and the mixture was refluxed for 4 hours and cooled. Precipitated crystals were filtered, washed with ethanol and dried to give 6-(2,5-dichlorothiophen-3-yl)-4-guanidinoimino-3-methyl-4,5,6,7-tetrahydroindazole hydrochloride (Compound 127) (0.41 g) as pale yellow crystals.

mp300° C. or more.

Elemental Analysis for $C_{13}H_{14}N_6Cl_2S.2HCl$ Calcd. C,36.84; H,4.07; N,18.86. Found C,36.84; H,4.92; N,18.96.

$^1$H-NMR(DMSO-$d_6$) δ:2.45 (3H,s), 2.62 (1H,dd), 2.75–3.05 (3H,m), 3.20–3.40 (1H,m)7.33 (1H,s), 7.41 (4H,broad), 10.86 (1H,s).

Working Example 123
(Production of Compound 128)

To a mixture of 6-(2,5-dichlorothiophen-3-yl)-3-methyl-4,5,6,7-tetrahydroindazol-4-one (0.211 g) and 1-amino-3-hydroxyguanidine hydrochloride (102 mg) were added ethanol (4 ml) and concentrated hydrochloric acid (0.1 ml), and the mixture was stirred at 90° C. for 4 hours. Under reduced pressure, the solvent was evaporated, and to the residue was added ethanol (2 ml). Precipitated crystals were filtered, washed with ethanol and dried to give 6-(2,5-dichlorothiophen-3-yl)-4-(1-hydroxyguanidin-3-yl)imino-3-methyl-4,5,6,7-tetrahydroindazole hydrochloride (Compound 128) (0.225 g) as pale yellow crystals.

mp190–192° C. (decomp.).

Elemental Analysis for $C_{13}H_{14}N_6Cl_2OS.2HCl$ Calcd. C,34.30; H,3.76; N,18.46. Found C,34.14; H,3.75; N,18.46.

$^1$H-NMR(DMSO-$d_6$) δ: 2.46 (3H,s), 2.61 (1H,dd), 2.84–3.03 (3H,m), 3.20–3.40 (1H,m), 7.32 (1H,s), 7.92 (2H,broad), 10.10 (1H,broad), 10.60 (1H,broad), 10.77 (1H,broad).

Working Example 124
(Production of Compound 129)

To a mixture of 7-(2-chlorophenyl)-4-methyl-5,6,7,8-tetrahydrocinnolin-5-one (0.218 g) and aminoguanidine hydrochloride (94 mg) were added ethanol (5 ml) and concentrated hydrochloric acid (0.1 ml), and the mixture was refluxed for 1.5 hours and cooled. Precipitated crystals were filtered, washed with ethanol and dried to give 7-(2-chlorophenyl)-5-guanidinoimino-4-methyl-5,6,7,8-tetrahydrocinnoline hydrochloride (Compound 129) (0.255 g) as crystals.

mp241–243° C.

Elemental Analysis for $C_{16}H_{17}N_6Cl.2HCl$ Calcd. C,47.84; H,4.77; N,20.92. Found C,47.82; H,4.61; N,20.98.

$^1$H-NMR(DMSO-$d_6$) δ: 2.78 (3H,s), 2.91 (1H,dd), 3.21–3.34 (1H,m), 3.40–3.56 (2H,m), 3.61–3.78 (1H,m), 7.31–7.52 (3H,m), 7.67 (1H,dd), 8.00 (4H,broad), 9.32 (1H,s).

Working Example 125
(Production of Compound 130)

To a mixture of 4-methyl-7-(thiophen-3-yl)-5,6,7,8-tetrahydrocinnolin-5-one (0.195 g) and aminoguanidine hydrochloride (94 mg) were added ethanol (5 ml) and concentrated hydrochloric acid (0.1 ml), and the mixture was refluxed for 1.5 hours and cooled. Precipitated crystals were filtered, washed with ethanol and dried to give 5-guanidinoimino-4-methyl-7-(thiophen-3-yl)-5,6,7,8-tetrahydrocinnoline hydrochloride (Compound 130) (0.26 g) as colorless crystals.

mp278–280° C. (decomp.).

Elemental Analysis for $C_{14}H_{16}N_6S.2HCl$ Calcd. C,43.98; H,5.01; N,21.98. Found C,43.73; H,4.91; N,21.12.

$^1$H-NMR(DMSO-$d_6$) δ: 2.79 (3H,s), 2.94 (1H,dd), 3.24–3.61 (4H,m)), 7.27 (1H,d), 7.52–7.59 (2H,m), 8.07 (4H,broad), 9.34 (1H,s), 11.97 (1H,broad).

Working Example 126
(Production of Compound 131)

To a mixture of 7-(2,5-dichlorothiophen-3-yl)-4-methyl-5,6,7,8-tetrahydrocinnolin-5-one (0.203 g) and aminoguanidine hydrochloride (80 mg) were added ethanol (6 ml) and concentrated hydrochloric acid (0.1 ml), and the mixture was refluxed for 1.5 hours and cooled. Precipitated crystals were filtered, washed with ethanol and dried to give 7-(2,5-dichlorothiophen-3-yl)-5-guanidinoimino-4-methyl-5,6,7,8-tetrahydrocinnoline hydrochloride (Compound 131) (0.25 g) as crystals.

mp300° C. or more.

Elemental Analysis for $C_{14}H_{14}N_6Cl_2S.2HCl$ Calcd. C,38.03; H,3.65; N,19.01. Found C,38.15; H,3.49; N,19.03.

$^1$H-NMR(DMSO-$d_6$) δ: 2.73 (3H,s), 2.89 (1H,dd), 3.12 (1H,broad), 3.24–3.41 (3H,m), 7.40 (1H,s), 7.95 (2H,broad), 9.27 (1H,s), 11.57 (1H,broad).

Working Example 127
(Production of Compound 132)

To a mixture of 7-(2-chlorophenyl)-4-phenyl-5,6,7,8-tetrahydrocinnolin-5-one (0.230 g) and aminoguanidine hydrochloride (84 mg) were added ethanol (5 ml) and concentrated hydrochloric acid (0.1 ml), and the mixture was refluxed for 14 hours. Under reduced pressure, the solvent was evaporated, and to the residue was added water (10 ml). Precipitated crystals were filtered and dissolved in water (10 ml), and to the solution was added 0.2N sodium hydroxide solution (5 ml). The mixture was extracted with ethyl acetate, and the organic layer was washed with water, to which was added methanesulfonic acid (100 mg). The mixture was concentrated under reduced pressure, and to the residue was added acetone (10 ml). The resulting crystals were filtered, washed with acetone and dried to give 7-(2-chlorophenyl)-5-guanidinoimino-4-phenyl-5,6,7,8-tetrahydrocinnoline methanesulfonate (Compound 132) (0.120 g) as crystals.

mp276–278° C. (decomp.).

Elemental Analysis for $C_{23}H_{19}N_6Cl\cdot 2CH_3SO_3H$ Calcd. C,47.02; H,4.72; N,14.30. Found C,47.22; H,4.68; N,14.03.

$^1$H-NMR(DMSO-$d_6$) δ: 2.37 (6H,s), 2.78 (1H,dd), 3.07 (1H,dd), 3.35–3.60 (2H,m), 3.75–3.90 (1H,m), 7.32–7.52 (8H,m), 7.55 (4H,broad), 7.67 (1H,s), 9.12 (1H,s), 10.84 (1H,broad).

Working Example 128
(Production of Compound 133)

To a mixture of 7-(2-chlorophenyl)-4-ethyl-5,6,7,8-tetrahydrocinnolin-5-one (0.287 g) and aminoguanidine hydrochloride (122 mg) were added ethanol (5 ml) and concentrated hydrochloric acid (0.1 ml), and the mixture was refluxed for 1.5 hours. Under reduced pressure, the solvent was evaporated, and to the residue were water (15 ml) and 2N sodium hydroxide solution. Precipitated crystals were filtered, washed with water and ethanol, dried and dissolved in acetone (25 ml), and to the solution was added methanesulfonic acid (130 mg). The reaction solution was concentrated under reduced pressure, and the residue was recrystallized from methanol-acetone to give 7-(2-chlorophenyl)-5-guanidinoimino-4-ethyl-5,6,7,8-tetrahydrocinnoline methanesulfonate (Compound 133) (0.292 g) as colorless crystals.

mp244–245° C. (decomp.).

Elemental Analysis for $C_{17}H_{19}N_6Cl\cdot 2CH_3SO_3H$ Calcd. C,42.65; H,5.09; N,15.71. Found C,42.62; H,4.97; N,15.51.

$^1$H-NMR(DMSO-$d_6$) δ: 1.28 (3H,t), 2.38 (6H,s), 2.80 (1H,dd), 3.09–3.26 (4H,m), 3.53 (1H,dd), 3.55–3.70 (1H,m), 7.32–7.53 (3H,m), 7.65 (1H,dd), 7.75 (2H,broad), 9.30 (1H,s), 10.85 (1H,broad).

Working Example 129
(Production of Compound 134)

To a mixture of 7-(2,5-dichlorothiophen-3-yl)-4-ethyl-5,6,7,8-tetrahydrocinnolin-5-one (0.195 g) and aminoguanidine hydrochloride (73 mg) were added ethanol (3 ml) and concentrated hydrochloric acid (0.1 ml), and the mixture was refluxed for 1 hour. Under reduced pressure, the solvent was evaporated, and the residue was dissolved in water (10 ml). The solution was washed with ether, and insoluble materials were filtered off. To the filtrate was added potassium carbonate to make the solution alkaline, and the mixture was extracted with a mixture of ethyl acetate-tetrahydrofuran. The organic layer was washed with water. Under reduced pressure, the solvent was evaporated, and the residue was dissolved in a mixture of acetone-methanol. To the solution was added methanesulfonic acid (120 mg), and precipitated crystals were filtered, washed with acetone and dried to give 7-(2,5-dichlorothiophen-3-yl)-4-ethyl-5-guanidinoimino-5,6,7,8-tetrahydrocinnoline methanesulfonate (Compound 134) (0.206 g) as colorless crystals.

mp241–242° C. (decomp.).

Elemental Analysis for $C_{17}H_{16}N_6Cl_2S\cdot 2CH_3SO_3H$ Calcd. C,35.48; H,4.20; N,14.60. Found C,35.67; H,4.14; N,14.39.

$^1$H-NMR(DMSO-$d_6$) δ: 1.25 (3H,t), 2.37 (6H,s), 2.80 (1H,dd), 3.02 (1H,dd), 3.11–3.39 (4H,m), 3.79–3.97 (1H,m), 7.40 (1H,s), 7.68 (4H,broad), 9.24 (1H,s), 10.79 (1H,broad).

Working Example 130
(Production of Compound 135)

To a solution of 7-(2,5-dichlorothiophen-3-yl)-4-trifluoromethyl-5,6,7,8-tetrahydrocinnolin-5-one (0.443 g) and aminoguanidine hydrochloride (167 mg) in ethanol (10 ml) were added methanesulfonic acid (0.2 ml) and benzene (10 ml), and the mixture was refluxed for 1.5 hours. Under reduced pressure, the solvent was evaporated, and to the residue was added sodium hydrogen carbonate solution to make the solution alkaline. The mixture was extracted with ethyl acetate, and the organic layer was washed with water and concentrated under reduced pressure. The residue was washed with isopropylether and diethylether and dried to give 7-(2,5-dichlorothiophen-3-yl)-5-guanidinoimino-4-trifluoromethyl-5,6,7,8-tetrahydrocinnoline (Compound 135) (0.160 g) as colorless crystals.

mp265–266° C. (decomp.).

$^1$H-NMR(DMSO-$d_6$) δ: 2.67 (1H,dd), 3.18–3.45 (4H,m), 6.28 (2H,broad), 7.28 (1H,s), 9.27 (1H,s).

Working Example 131
(Production of Compound 136)

To a solution of 7-(2-chlorophenyl)-4-trifluoromethyl-5,6,7,8-tetrahydrocinnolin-5-one (0.335 g) and aminoguanidine hydrochloride (165 mg) in ethanol (10 ml) were added methanesulfonic acid (0.3 ml) and benzene (10 ml), and the mixture was refluxed for 80 minutes. Under reduced pressure, the solvent was evaporated, and to the residue was added sodium hydrogen carbonate solution to make the solution alkaline. The mixture was extracted with ethyl acetate, and the organic layer was washed with water and concentrated under reduced pressure. The residue was dissolved in acetone, and to the solution was added methanesulfonic acid (0.15 ml). Precipitated crystals were filtered, washed with acetone and dried to give 7-(2-chlorophenyl)-5-guanidinoimino-4-trifluoromethyl-5,6,7,8-tetrahydrocinnoline methanesulfonate (Compound 136) (0.240 g) as yellow crystals.

mp207–208° C.

$^1$H-NMR(DMSO-$d_6$) δ: 2.43 (6H,s), 2.90 (1H,dd), 3.17 (1H,dd), 3.41–3.85 (3H,m), 7.31–7.53(3H,m), 7.65 (1H,d), 8.00 (4H,broad), 9.64 (1H,s), 11.31 (1H,broad).

Working Example 132
(Production of Compound 137)

To a mixture of 1,4-dimethyl-7-(thiophen-3-yl)-1,2,5,6,7,8-hexahydroquinoline-2,5-dione (0.1 g) and aminoguanidine hydrochloride (41 mg) were added ethanol (3 ml) and 2N hydrochloric acid (0.2 ml), and the mixture was refluxed for 4 hours and concentrated under reduced pressure. To the residue was added ethanol (1 ml), and precipitated crystals were filtered, washed with ethanol and dried to give 1,4-dimethyl-5-guanidinoimino-7-(thiophen-3-yl)-1,2,5,6,7,8-hexahydroquinolin-2-one hydrochloride (Compound 137) (0.125 g) as colorless crystals.

mp156–157° C.

$^1$H-NMR(DMSO-$d_6$) δ: 2.45 (3H,s), 2.6 (1H,dd), 2.91 (1H,dd), 3.18–3.33 (3H,m), 3.51 (3H,s), 6.27 (1H,s), 7.3 (1H,dd), 7.5–7.56 (6H,m), 11.10 (1H,s).

Working Example 133
(Production of Compound 138)

To a mixture of 4-methyl-7-(thiophen-3-yl)-1,2,5,6,7,8-hexahydroquinoline-2,5-dione (0.155 g) and aminoguanidine hydrochloride (73 mg) were added 2-ethoxyethanol (2 ml) and 2N hydrochloric acid (0.3 ml), and the mixture was stirred at 125° C. for 13 hours and cooled. Precipitated crystals were filtered, washed with ethanol and dried to give 5-guanidinoimino-4-methyl-7-(thiophen-3-yl)-1,2,5,6,7,8-hexahydroquinolin-2-one hydrochloride (Compound 138) (0.093 g) as colorless crystals.

mp300° C. or more.

Elemental Analysis for $C_{15}H_{17}N_5OS \cdot 2HCl \cdot H_2O$ Calcd. C,44.34; H,5.21; N,17.24. Found C,44.36; H,5.24; N,17.34.

$^1$H-NMR(DMSO-$d_6$) δ: 2.47 (3H,S), 2.64 (1H,dd), 2.77–2.97 (2H,m), 3.08–3.35 (2H,m), 6.16 (1H,s), 7.20 (1H,dd), 7.40 (1H,dd), 7.49 (4H,broad), 7.54 (1H,dd), 10.98 (1H,s).

Working Example 134
(Production of Compound 139)

To a mixture of 7-(2-chlorophenyl)-4-methyl-1,2,5,6,7,8-hexahydroquinoline-2,5-dione (0.144 g) and aminoguanidine hydrochloride (61 mg) were added 2-ethoxyethanol (2.5 ml) and concentrated hydrochloric acid (0.1 ml), and the mixture was stirred at 135° C. for 1 hour and cooled. Precipitated crystals were filtered, washed with methanol and dried to give 7-(2-chlorophenyl)-5-guanidinoimino-4-methyl-1,2,5,6,7,8-hexahydroquinolin-2-one hydrochloride (Compound 139) (0.15 g) as colorless crystals.

mp300° C. or more.

Elemental Analysis for $C_{17}H_{18}ClN_5O \cdot 2HCl$ Calcd. C,49.00; H,4.84; N,16.81. Found C,49.04; H,4.89; N,16.84.

$^1$H-NMR(DMSO-$d_6$) δ: 2.49 (3H,S), 2.66 (1H,dd), 2.83 (1H,dd), 2.97–3.13 (2H,m), 3.45–3.60 (1H,m), 6.20 (1H,s), 7.29–7.61 (8H,m), 10.88 (1H,s).

Working Example 135
(Production of Compound 140)

To a mixture of 3-chloro-7-(2-chlorothiophen-3-yl)-1,4-dimethyl-1,2,5,6,7,8-hexahydroquinoline-2,5-dione (0.098 g) and aminoguanidine hydrochloride (32 mg) were added 2-ethoxyethanol (1.5 ml) and concentrated hydrochloric acid (0.05 ml), and the mixture was stirred at 135° C. for 1 hour and cooled. Precipitated crystals were filtered, washed with methanol and dried to give 3-chloro-7-(2-chlorothiophen-3-yl)-5-guanidinoimino-1,4-dimethyl-1,2,5,6,7,8-hexahydroquinolin-2-one hydrochloride (Compound 140) (0.04 g) as crystals.

mp218–219° C.

Elemental Analysis for $C_{16}H_{17}N_5ClOS \cdot HCl \cdot 0.5H_2O$ Calcd. C,43.30; H,4.32; N,15.78. Found C,43.38; H,4.44; N,15.76.

$^1$H-NMR(DMSO-$d_6$) δ: 2.6 (3H,s), 2.65 (1H,d), 2.94–3.1 (3H,m), 3.2–3.45 (1H,m), 3.56 (3H,s), 7.25 (1H,d), 7.5 (3H,broad), 7.54 (1H,d), 7.86 (1H,broad), 10.72 (1H,broad).

Reference Example 145

A mixture of 5-(2-chlorophenyl)-1-[2-(4-methylphenylsulfonyl)hydrazino]cyclohexen-3-one (2.0 g), 2-bromo-4'-chloroacetophenone (1.6 g), anhydrous potassium carbonate (1.8 g) and ethanol (50 ml) was refluxed for 13 hours. Under reduced pressure, the solvent was evaporated, and the residue was extracted with ethyl acetate. The organic layer was concentrated, and the residue was purified with silica gel column chromatography. The resulting crystals were recrystallized from ethyl acetate-hexane to give 7-(2-chlorophenyl)-4-(4-chlorophenyl)-5,6,7,8-tetrahydrocinnolin-5-one (0.2 g) as colorless crystals.

mp163–166° C.

$^1$H-NMR(CDCl$_3$) δ: 2.90 (1H,dd), 3.06 (1H,ddd), 3.5 (1H,dd), 3.86 (1H,ddd), 3.98–4.20 (1H,m), 6.8–8.2 (4H,br), 7.16–7.52 (8H,m), 9.14 (1H,s).

Reference Example 146

To a solution of 1-amino-5-(2-chlorophenyl)cyclohexen-3-one (2.0 g) in acetonitrile (50 ml) was added phenyl isothiocyanate (1.2 g), and the mixture was refluxed for 15 hours. Under reduced pressure, the solvent was evaporated, and to the residue were added ethanol (20 ml) and hydrazine hydrate (0.55 g). The mixture was refluxed for 1 hour, and under reduced pressure, the solvent was evaporated. The residue was washed with ethyl acetate to give yellow crystals of 6-(2-chlorophenyl)-3-phenylamino-4,5,6,7-tetrahydroindazol-4-one (0.8 g).

mp272° C. (decomp.).

$^1$H-NMR(DMSO-$d_6$) δ: 2.46–2.57 (1H,m), 2.87 (1H,dd, J=12,16 Hz), 3.02–3.17 (2H,m), 3.8–4.1 (1H,m), 6.8–6.92 (1H,m), 7.2–7.66 (8H,m), 8.01 (1H,br), 12.53 (1H,br).

Reference Example 147

A solution of 5-(2-chlorophenyl)-cyclohexane-1,3-dione (1.0 g), hydrazine hydrochloride (0.31 g) in ethanol (10 ml) was refluxed for 3 hours. To the solution was added benzaldehyde (1.5 g), and the mixture was refluxed for 4 days. Under reduced pressure, the solvent was evaporated, and the residue was purified with silica gel column chromatography to give crystals, which were recrystallized from ethyl acetate-hexane to give 6-(2-chlorophenyl)-3-phenyl-4,5,6,7-tetrahydroindazol-4-one (0.06 g) as crystals.

mp218–222° C.

$^1$H-NMR(CDCl$_3$) δ: 2.76–2.88 (2H,m), 3.02 (1H,dd,J=11,16 Hz), 3.29 (1H,dd,J=,4,16 Hz), 3.96–4.15 (1H,m), 7.18–7.58 (8H,m), 7.92–8.04 (2H,m).

Reference Example 148

To a solution of 5-(2-chlorophenyl)cyclohexane-1,3-dione (1.0 g), 4-dimethylaminopyridine (0.82 g) and methoxyacetic acid (0.73 g) in dimethylformamide (40 ml) was added dicyclohexylcarbodiimide (1.0 g), and the mixture was stirred at room temperature for 3 days. Under reduced pressure, the solvent was evaporated, and to the residue was added ethyl acetate. Insoluble materials were filtered off, and the organic layer was extracted with 1N sodium hydroxide solution. To the aqueous layer was added 1N hydrochloric acid to make the solution acidic, and the mixture was extracted with ethyl acetate. The organic layer was washed with water and saturated brine, and dried with magnesium sulfate. Under reduced pressure, the solvent was evaporated to give 5-(2-chlorophenyl)-2-(1-hydroxy-2-methoxyethylidene)cyclohexane-1,3-dione (0.86 g) as oil.

$^1$H-NMR(CDCl$_3$) δ: 2.44–3.2 (5H,m), 3.51 (3H,s), 3.78–3.98 (1H,m), 4.76 (2H,s), 7.1–7.44 (4H,m).

Reference Example 149

A solution of 5-(2-chlorophenyl)-2-(1-hydroxy-2-methoxyethylidene)cyclohexane-1,3-dione (0.4 g) and hydrazine hydrate (0.072 g) in ethanol (15 ml) was refluxed for 1 hour. Under reduced pressure, the solvent was evaporated, and the residue was purified with silica gel column chromatography to give 6-(2-chlorophenyl)-3-methoxymethyl-4,5,6,7-tetrahydroindazol-4-one (0.1 g) as oil.

$^1$H-NMR(CDCl$_3$) δ: 2.56–2.84 (2H,m), 2.96 (1H,dd,J=6, 16 Hz), 3.24 (1H,dd,J=4,16 Hz), 3.49 (3H,s), 3.88–4.1 (1H,m), 4.85 (2H,s), 7.02–7.43 (4H,S), 8.0 (1H,br).

Reference Example 150

To a solution of 5-(2-chlorophenyl)-2-(1-hydroxyethylidene)cyclohexane-1,3-dione (0.5 g) and benzylhydrazine 2 hydrochloride (0.39 g) in ethanol (30 ml) was added triethylamine (0.42 g), and the mixture was refluxed for 2.5 hours. Under reduced pressure, the solvent was evaporated, and the residue was dissolved in ethyl acetate. The organic layer was washed with water and saturated brine, dried with magnesium sulfate and concentrated under reduced pressure, and the residue was purified with silica gel column chromatography (ethyl acetate-hexane). The resulting crystals were recrystallized from ethyl acetate-hexane to give 1-benzyl-6-(2-chlorophenyl)-3-methyl-4,5,6,7-tetrahydroindazol-4-one (0.37 g) as colorless crystals.

mp108–109° C.

$^1$H-NMR(CDCl$_3$) δ: 2.52 (3H,s), 2.61–2.84 (3H,m), 3.11 (1H,dd,J=5,16 Hz), 3.86–4.08 (1H,m), 5.12–5.33 (2H,m), 7.08–7.43 (9H,m).

Reference Example 151

A solution of 5-(2-chlorophenyl)-2-(1-hydroxyethylidene)cyclohexane-1,3-dione (1.0 g) and phenylhydrazine (0.43 g) in ethanol (20 ml) was refluxed for 2 hours. Under reduced pressure, the solvent was evaporated, and the resulting crystals were recrystallized from ethyl acetate-hexane to give 6-(2-chlorophenyl)-3-methyl-2-phenyl-4,5,6,7-tetrahydroindazol-4-one (0.97 g) as colorless crystals.

mp153–154° C.

$^1$H-NMR(CDCl$_3$) δ: 2.59 (3H,s), 2.74 (1H,dd,J=3,16 Hz), 2.88 (1H,dd,J=11,16 Hz), 3.07 (1H,dd,J=11,16 Hz), 3.22 (1H,dd,J=3,16 Hz), 3.93–4.13 (1H,m), 7.16–7.64 (9H,m).

Reference Example 152

To a suspension of 60% sodium hydride (0.041 g, washed with hexane thrice) in dimethylformamide (10 ml) was added a solution of 6-(2-chlorophenyl)-3-methyl-4,5,6,7-tetrahydroindazol-4-one (0.4 g) in dimethylformamide (2 ml), and the mixture was stirred at room temperature for 40 minutes. To the mixture was added 2-phenylethyl bromide (0.30 g), and the mixture was stirred at the same temperature for 18 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (ethyl acetate-hexane) to give 6-(2-chlorophenyl)-3-methyl-1-(2-phenylethyl)-4,5,6,7-tetrahydroindazol-4-one (0.22 g) as colorless crystals and 6-(2-chlorophenyl)-3-methyl-2-(2-phenylethyl)-4,5,6,7-tetrahydroindazol-4-one (0.2 g) as oil.

6-(2-chlorophenyl)-3-methyl-1-(2-phenylethyl)-4,5,6,7-tetrahydroindazol-4-one mp132–134° C.

$^1$H-NMR(CDCl$_3$) δ: 2.12 (1H,dd,J=5,16 Hz), 2.37–2.65 (3H,m), 2.53 (3H,s), 3.09 (2H,t,J=6 Hz), 3.57–3.83 (1H,m), 4.12–4.23 (2H,m), 6.86–7.97 (2H,m), 7.05–7.37 (7H,m).

6-(2-chlorophenyl)-3-methyl-2-(2-phenylethyl)-4,5,6,7-tetrahydroindazol-4-one $^1$H-NMR(CDCl$_3$) δ: 2.19 (3H,s), 2.66–2.74 (2H,m), 2.93 (1H,dd,J=11,16 Hz), 3.12 (2H,t,J=7 Hz), 3.19 (1H,dd,J=4,16 Hz), 3.84–4.03 (1H,m), 4.22 (2H,t,J=7 Hz), 6.99–7.18 (2H,m), 7.12–7.43 (7H,m).

Reference Example 153

To a suspension of 60% sodium hydride (0.068 g, washed with hexane thrice) in dimethylformamide (10 ml) was added a solution of 6-(2-chlorophenyl)-3-methyl-4,5,6,7-tetrahydroindazol-4-one (0.4 g) in dimethylformamide (2 ml) at 0° C., and the mixture was stirred at room temperature for 40 minutes. To the mixture was added 3-phenylpropyl bromide (0.32 g), and the mixture was stirred at the same temperature for 19 hours. Under reduced pressure, the solvent was evaporated, and the residue was dissolved in ethyl acetate. The solution was washed with water and saturated brine, dried with magnesium sulfate and concentrated under reduced pressure, and the residue was purified with silica gel column chromatography (ethyl acetate-hexane) to give 6-(2-chlorophenyl)-3-methyl-1-(3-phenylpropyl)-4,5,6,7-tetrahydroindazol-4-one (0.20 g) as colorless crystals and 6-(2-chlorophenyl)-3-methyl-2-(3-phenylpropyl)-4,5,6,7-tetrahydroindazol-4-one (0.26 g) as oil.

6-(2-chlorophenyl)-3-methyl-1-(2-phenylpropyl)-4,5,6,7-tetrahydroindazol-4-one mp100–101° C.

$^1$H-NMR(CDCl$_3$) δ: 2.06–2.24 (2H,m), 2.50 (3H,s), 2.55–2.82 (5H,m), 2.99 (1H,dd,J=5,16 Hz), 3.84–4.07 (1H, m), 3.98 (2H,t,J=7 Hz), 7.07–7.32 (8H,m), 7.36–7.43 (1H, m).

6-(2-chlorophenyl)-3-methyl-2-(2-phenylpropyl)-4,5,6,7-tetrahydroindazol-4-one $^1$H-NMR(CDCl$_3$) δ: 2.08–2.32 (2H,m), 2.49 (3H,s), 2.5–2.7 (4H,m), 2.88 (1H,dd,J=11,16 Hz), 3.16 (1H,dd,J=4, 16 Hz), 3.84–4.17 (3H,m), 7.08–7.44 (9H,m).

Reference Example 154

In benzene (4 ml) was dissolved 7-(2-chlorophenyl)-4-methyl-5,6,7,8-tetrahydroquinolin-5-one (272 mg), and to the solution was added m-chloroperbenzoic acid (267 mg). The mixture was stirred at room temperature for 1 hour, and to the mixture were added ethyl acetate (70 ml), saturated sodium hydrogen carbonate solution (30 ml) and sodium nitrite (100 mg). The mixture was shaken, and the separated upper layer was washed with water and concentrated under reduced pressure. The residue was washed with ethyl acetate and dried to give 7-(2-chlorophenyl)-4-methyl-5,6,7,8-tetrahydroquinolin-5-one-1-oxide (205 mg) as pale yellow crystals.

mp225–226° C.

$^1$H-NMR(CDCl$_3$) δ: 2.68 (3H,s), 2.88–3.15 (3H,m), 3.84–4.05 (2H,m), 7.12 (1H,d), 7.20–7.36 (3H,m), 7.42 (1H,dd), 8.33 (1H,d).

Reference Example 155

In benzene (15 ml) was dissolved 7-(2,5-dichlorothiophen-3-yl)-4-methyl-5,6,7,8-tetrahydroquinolin-5-one (1.09 g), and to the solution was added m-chloroperbenzoic acid (0.963 g). The mixture was stirred at room temperature for 1 hour, and to the mixture were added ethyl acetate (150 ml), saturated sodium hydrogen carbonate solution (200 ml) and sodium nitrite(200 mg). The mixture was shaken, and the separated upper layer was washed with water and concentrated under reduced pressure. The residue was washed with a mixture of isopropylether and ethyl acetate (2:1) to give 7-(2,5-dichlorothiophen-3-yl)-4-methyl-5,6,7,8-tetrahydroquinolin-5-one-1-oxide (1.04 g) as yellow crystals.

mp169–170° C. (recrystallized from ethyl acetate-hexane to give).

¹H-NMR(CDCl₃) δ: 2.67 (3H,s), 2.78 (1H,dd), 2.86–3.09 (2H,m), 3.54–3.70 (1H,m), 3.82 (1H,ddd), 6.74 (1H,s), 7.13 (1H,d), 8.33 (1H,d).

Reference Example 156

In benzene (10 ml) was dissolved 7-(2-chlorophenyl)-4-methyl-5,6,7,8-tetrahydrocinnolin-5-one (1.54 g), and to the solution was added m-chloroperbenzoic acid (1.72 g). The mixture was stirred at room temperature for 1 hour, and to the mixture were added ethyl acetate (300 ml), saturated sodium hydrogen carbonate solution (300 ml) and sodium nitrite (500 mg). The mixture was shaken, and the separated upper layer was washed with water and concentrated under reduced pressure. The residue was purified with silica gel column chromatography to give 7-(2-chlorophenyl)-4-methyl-5,6,7,8-tetrahydrocinnolin-5-one-1-oxide (478 mg) as pale yellow crystals.

mp154–155° C. (recrystallized from ethyl acetate-hexane to give).

¹H-NMR(CDCl₃) δ: 2.63 (3H,s), 2.85–3.01 (2H,m), 3.08 (1H,dd), 3.89–4.06 (1H,m), 3.74 (1H,dd), 7.25–7.47 (4H, m), 8.37,(1H,s)

At the same time, 7-(2-chlorophenyl)-4-methyl-5,6,7,8-tetrahydrocinnolin-5-one-2-oxide (296 mg) was obtained as pale yellow crystals.

mp167–168° C. (recrystallized from ethyl acetate-hexane to give).

¹H-NMR(CDCl₃) δ: 2.66 (3H,s), 2.85 (1H,dd), 3.03 (1H, ddd), 3.20 (1H,dd), 3.41 (1H,ddd), 3.91–4.07 (1H,m), 7.25–7.47 (4H,m), 7.95 (1H,s).

Reference Example 157

A mixture of 5-(2,5-dichlorophenyl)cyclohexene-1,3-dione (1.19 g), p-toluenesulfonylhydrazide (0.86 g) and ethanol (15 ml) was refluxed for 2.5 hours and cooled, and precipitated crystals were filtered and washed with ethanol to give 5-(2,5-dichlorophenyl)-1-[2-(4-methylphenylsulfonyl)hydrazino]cyclohexan-3-one (1.67 g) as colorless crystals.

mp256–257° C. (decomp.).

¹H-NMR(DMSO-d₆) δ:2.23 (1H, dd), 2.40 (3H, s), 2.45–2.65 (3H, m), 3.40–3.55 (1H, m), 5.23 (1H, s), 7.32–7.56 (5H, m), 7.71 (2H, d), 8.00 (1H, br), 9.85 (1H, s).

Reference Example 158

To a mixture of 5-(2,5-dichlorophenyl)-1-[2-(4-methylphenylsulfonyl)hydrazino]cyclohexen-3-one (1.65 g), anhydrous potassium carbonate (0.696 g), methanol (10 ml) and 1,2-dimethoxyethane (8 ml) were added under ice-cooling 1-chloropropan-2-one (0.465 g) and sodium iodide (0.15 g), and the mixture was stirred at room temperature for 2 hours. To the mixture was added anhydrous potassium carbonate (0.64 g), and the mixture was stirred for 3 hours at 80° C. Under reduced pressure, the solvent was evaporated, and to the residue was added ethyl acetate (70 ml) and water (30 ml). The mixture was shaken, and the separated upper layer was washed with water and concentrated under reduced pressure. The residue was purified with silica gel column chromatography to give 7-(2,5-dichlorophenyl)-4-methyl-5,6,7,8-tetrahydrocinnolin-5-one (0.253 g) as yellowish brown oil.

¹H-NMR(CDCl₃) δ: 2.71 (3H, s), 2.84 (1H, dd), 3.08 (1H, ddd), 3.39 (1H, dd), 3.77 (1H, ddd), 3.87–4.04 (1H, m), 7.22–7.41 (3H, m), 9.16 (1H, s).

Reference Example 159

A solution of 5-(2-chloro-5-methylphenyl)cyclohexane-1,3-dione (3.0 g) and ammonium acetate (2.9 g) in ethanol (50 ml) was refluxed for 13 hours. Under reduced pressure, the solvent was evaporated, and precipitated crystals were washed with water and toluene, and dried to give 1-amino-5-(2-chloro-5-methylphenyl)cyclohexen-3-one (2.9 g).

In ethanol (70 ml) and toluene (120 ml) was dissolved 1-amino-5-(2-chloro-5-methylphenyl)cyclohexen-3-one (2.9 g), and to the solution were added 3-oxobutylaldehydedimethylacetal (4.1 g) and powdery potassium hydroxide (0.5 g). The mixture was refluxed, and to the mixture was added powdery potassium hydroxide (0.14 g), 30 minutes later; were added powdery potassium hydroxide (0.14 g) and 3-oxobutylaldehydedimethylacetal (0.33 g), 1 hour later; and was added powdery potassium hydroxide (0.14 g), 1.5 hours later. The mixture was refluxed at the same temperature 2 hours and cooled. Under reduced pressure, the solvent was evaporated, and to the residue was added ethyl acetate. The organic layer was washed with water and saturated brine, and dried with magnesium sulfate. Under reduced pressure, ethyl acetate was evaporated, and the residue was purified with silica gel column (ethyl acetate-hexane). The resulting crystals were recrystallized from ethyl acetate-hexane to give 7-(2-chloro-5-methylphenyl)-4-methyl-5,6,7,8-tetrahydroquinolin-5-one (2.3 g).

mp123–124° C.

¹H-NMR(CDCl₃) δ: 2.35 (3H,s), 2.71 (3H,s), 2.82 (1H, dd,J=12,17 Hz), 3.01 (1H,ddd,J=2,4,17 Hz), 3.28 (1H,dd,J= 12,17 Hz), 3.46 (1H,ddd,J=2,4,17 Hz), 3.84–4.04 (1H,m), 6.94–7.17 (3H,m), 7.24–7.34 (1H,m), 8.50 (1H,d,J=5 Hz).

Reference Example 160

A solution of 5-(2-fluoro-5-methylphenyl)cyclohexane-1,3-dione (1.5 g) and ammonium acetate (1.6 g) in ethanol (23 ml) was refluxed for 20 hours. Under reduced pressure, the solvent was evaporated, and precipitated crystals were washed with water and toluene, and dried to give 1-amino-5-(2-fluoro-5-methylphenyl)cyclohexen-3-one (1.3 g).

In ethanol (35 ml) and toluene (60 ml) was dissolved 1-amino-5-(2-fluoro-5-methylphenyl)cyclohexen-3-one (1.3 g), and to the solution were added 3-oxobutylaldehydedimethylacetal (2.0 g) and powdery potassium hydroxide (0.32 g). The mixture was refluxed, and to the mixture was added powdery potassium hydroxide (0.07 g), 30 minutes later; were added powdery potassium hydroxide (0.07 g) and 3-oxobutylaldehydedimethylacetal (0.16 g), 1 hour later; and was added powdery potassium hydroxide (0.07 g), 1.5 hours later. The mixture was stirred at the same temperature for 2 hours and cooled. Under reduced pressure, the solvent was evaporated, and to the residue was added ethyl acetate. The organic layer was washed with water and saturated brine, and dried with magnesium sulfate. Under reduced pressure, ethyl acetate was evaporated, and the residue was purified with silica gel column (ethyl acetate-hexane). The resulting crystals were recrystallized from ethyl acetate-hexane to give 7-(2-fluoro-5-methylphenyl)-4-methyl-5,6,7,8-tetrahydroquinolin-5-one (1.3 g).

mp92–94° C.

¹H-NMR(CDCl₃) δ: 2.33 (3H,s), 2.71 (3H,s), 2.82–3.04 (2H,m), 3.3–3.5 (2H,m), 3.6–3.84 (1H,m), 6.88–7.17 (4H, m), 8.50 (1H,d,J=5 Hz).

Reference Example 161

A solution of 5-(5-chloro-2-methylphenyl)cyclohexane-1,3-dione (2.9 g) and ammonium acetate (2.8 g) in ethanol (50 ml) was refluxed for 14 hours. Under reduced pressure, the solvent was evaporated, and the residue was dissolved in ethyl acetate, and the mixture was washed with water and saturated brine, and dried with magnesium sulfate. Under reduced pressure, the solvent was evaporated to give 1-amino-5-(5-chloro-2-methylphenyl)cyclohexen-3-one, which was dissolved in a mixture of ethanol (70 ml) and toluene (120 ml). To the mixture were added 3-oxobutylaldehydedimethylacetal (4.1 g) and powdery potassium hydroxide (0. 57 g), and the mixture was refluxed. To the mixture was added powdery potassium hydroxide (0.14 g) 30 minutes later; powdery potassium hydroxide (0.14 g) and 3-oxobutylaldehydedimethylacetal (0.33 g) 1 hour later; and powdery potassium hydroxide (0.14 g) 1.5 hours later, and then the mixture was stirred at the same temperature for 2 hours and cooled. Under reduced pressure, the solvent was evaporated, and to the residue was added ethyl acetate. The organic layer was washed with water and saturated brine, and dried with magnesium sulfate. Under reduced pressure ethyl acetate was evaporated, and the residue was subjected to silica gel column (ethyl acetate-hexane) to give crystals, which were recrystallized from diisopropylether to give 7-(5-chloro-2-methylphenyl)-4-methyl-5,6,7,8-tetrahydroquinolin-5-one (1.1 g).

mp125–127° C.

$^1$H-NMR(CDCl$_3$) δ: 2.33 (3H, s), 2.72 (3H, s), 2.82–2.96 (2H, m), 3.16–3.46 (2H, m), 3.55–3.74 (1H, m), 7.08–7.33 (4H, m), 8.50 (1H, d, J=5 Hz).

Reference Example 162

A solution of 5-(5-fluoro-2-methylphenyl)cyclohexane-1,3-dione (3.0 g) and ammonium acetate (3.1 g) in ethanol (50 ml) was refluxed for 14 hours. Under reduced pressure, the solvent was evaporated, and the residue was dissolved in ethyl acetate. The mixture was washed with water and saturated brine, and dried with magnesium sulfate. Under reduced pressure, the solvent was evaporated to give 1-amino-5-(5-fluoro-2-methylphenyl)cyclohexen-3-one, which was dissolved in ethanol (70 ml) and toluene (120 ml). To the mixture were added 3-oxobutylaldehydedimethylacetal (4.1 g) and powdery potassium hydroxide (0.57 g), and the mixture was refluxed. To the mixture was added powdery potassium hydroxide (0.14 g) 30 minutes later; powdery potassium hydroxide (0.14 g) and 3-oxobutylaldehydedimethylacetal (0.33 g) 1 hour later; and powdery potassium hydroxide (0.14 g) 1.5 hours later. Then, the mixture was stirred at the same temperature for 2 hours and cooled. Under reduced pressure, the solvent was evaporated, and to the residue was added ethyl acetate. The organic layer was washed with water and saturated brine, and dried with magnesium sulfate. Under reduced pressure, ethyl acetate was evaporated, and the residue was subjected to silica gel column (ethyl acetate-hexane) to give crystals, which were recrystallized from ethyl acetate-hexane to give 7-(5-fluoro-2-methylphenyl)-4-methyl-5,6,7,8-tetrahydroquinolin-5-one (1.5 g).

mp113–114° C.

$^1$H-NMR(CDCl$_3$) δ: 2.33 (3H, s), 2.71 (3H, s), 2.78–2.98 (2H, m), 3.24 (1H, dd, J=11, 16 Hz), 3.28–3.44 (1H, m), 3.55–3.74 (1H, m), 6.82–7.04 (2H, m), 7.12 (1H, d, J=5 Hz), 7.07–7.22 (2H, m), 8.50 (1H, d, J=5 Hz).

Reference Example 163

A solution of 5-(5-chloro-2-methoxyphenyl)cyclohexane-1,3-dione (5.0 g) and ammonium acetate (4.6 g) in ethanol (100 ml) was refluxed for 20 hours. Under reduced pressure, the solvent was evaporated, and the residue was dissolved in ethyl acetate. The solution was washed with water and saturated brine, and dried with magnesium sulfate. Under reduced pressure, the solvent was evaporated to give 1-amino-5-(5-chloro-2-methoxyphenyl)cyclohexen-3-one, which was dissolved in ethanol (120 ml) and toluene (210 ml). To the solution were added 3-oxobutylaldehydedimethylacetal (6.5 g) and powdery potassium hydroxide (0.92 g), and the mixture was refluxed. To the mixture was added powdery potassium hydroxide (0.19 g), 30 minutes later; were added powdery potassium hydroxide (0.19 g) and 3-oxobutylaldehydedimethylacetal (0.52 g), 1 hour later; and was added powdery potassium hydroxide (0.19 g), 1.5 hours later, and the mixture was stirred at the same temperature for 2 hours and cooled. Under reduced pressure, the solvent was evaporated, and to the residue was added ethyl acetate. The organic layer was washed with water and saturated brine, and dried with magnesium sulfate. Under reduced pressure, ethyl acetate was evaporated, and the residue was purified with silica gel column (ethyl acetate-hexane) to give 7-(5-chloro-2-methoxyphenyl)-4-methyl-5,6,7,8-tetrahydroquinolin-5-one (2.2 g) as colorless crystals.

mp131–133° C.

$^1$H-NMR(CDCl$_3$) δ: 2.71 (3H,s), 2.84 (1H,dd,J=11,17 Hz), 2.88–3.03 (1H,m), 3.28 (1H,dd,J=11,17 Hz), 3.41 (1H, ddd,J=2,5,17 Hz), 3.71–3.92 (1H,m), 3.82 (3H,s), 6.83 (1H, d,J=8 Hz), 7.1 (1H,d,J=5 Hz), 7.16–7.30 (2H,m), 8.49 (1H,d,J=5 Hz).

Reference Example 164

A mixture of 5-(5-fluoro-2-methoxy)cyclohexane-1,3-dione (9.5 g) and ammonium acetate (8 g) in ethanol (80 ml) was refluxed for 1.5 hours. The reaction solution was concentrated under reduced pressure, and to the residue were added water (100 ml) and ethyl acetate (150ml). The mixture was shaken, and the separated upper layer was washed with water and concentrated under reduced pressure. The residue was washed with ethyl acetate and dried to give 1-amino-5-(5-fluoro-2-methoxyphenyl)cyclohexan-3-one (8.45 g).

mp 163–163° C.

$^1$H-NMR(DMSO-d$_6$) δ: 2.14 (1H,dd), 2.28–2.63 (3H,m), 3.43–3.59 (1H,m), 3.79 (3H,s), 5.00 (1H,s), 6.40 (1H,br), 6.98–7.15 (3H,m).

Reference Example 165

To a mixture of 1-amino-5-(5-fluoro-2-methoxyphenyl)cyclohexan-3-one (4.5 g), 1,1-dimethoxy-3-butanone (7 ml), toluene (70 ml) and ethanol (30 ml), while stirring at 110–115° C., was added granulated potassium hydroxide (1.3 g). Soon after potassium hydroxide had been dissolved, granulated potassium hydroxide (1 g) was added to the solution. With 30 minutes intervals, granulated potassium hydroxide (0.25 g) was added thrice to the solution. To the mixture was added 1,1-dimethoxy-3-butanone (3 ml), 2 hours after the reaction had started. To the mixture was added granulated potassium hydroxide (0.25 g), and the mixture was stirred for 1 hour under the same conditions. The reaction solution was concentrated under reduced pressure, and to the residue was added water (30 ml) and ethyl acetate (150 ml). The mixture was shaken and the separated upper layer was washed with water, to which was added concentrated hydrochloric acid (1.6 ml). The mixture was concentrated under reduced pressure, and the residue was washed with a little amount of ethanol and dried to give 7-(5-fluoro-2-methoxyphenyl)-4-methyl-5,6,7,8-tetrahydroquinolin-5-one hydrochloride (3.34 g).

mp174–175° C.

¹H-NMR(DMSO-d$_6$) δ: 2.74–2.84 (4H,m), 3.10 (1H,dd), 3.35–3.60 (2H,m), 3.81–4.00 (4H,m), 7.00–7.23 (3H,m), 7.76 (1H,d), 8.77 (1H,d).

Reference Example 166

To 7-(5-fluoro-2-methoxyphenyl)-4-methyl-5,6,7,8-tetrahydroquinolin-5-one hydrochloride (2.13 g) were added water (20 ml), anhydrous potassium carbonate (1.5 g) and ethyl acetate (50 ml). The mixture was shaken, and the separated upper layer was concentrated under reduced pressure. The residue was dissolved in dichloromethane (15 ml), and to the solution was added dropwise a solution of 1M-boron tribromide-dichloromethane (21 ml), while stirring in ice-cooling bath. The bath was removed, and the mixture was stirred for 2 hours, and poured onto ice-water. To the mixture was added excess amount of sodium hydrogen carbonate solution, and the mixture was extracted with ethyl acetate. The extract was concentrated under reduced pressure, and the residue was purified with silica gel column chromatography to give 7-(5-fluoro-2-hydroxyphenyl)-4-methyl-5,6,7,8-tetrahydroquinolin-5-one (0.773 g).

mp222–224° C.

¹H-NMR(CDCl$_3$-CD$_3$OD) δ: 2.71 (3H,s), 2.84–3.03 (2H, m), 3.30 (1H,dd), 3.46 (1H,dd), 3.73–3.87 (1H,m), 6.72–6.90 (3H,m), 7.14 (1H,d), 8.44 (1H,d).

Reference Example 167

A solution of 5-(5-chloro-2-fluorophenyl)cyclohexane-1,3-dione (2 g) and ammonium acetate (1.9 g) in ethanol (15 ml) was refluxed for 15 hours. The reaction solution was concentrated under reduced pressure, and to the residue were added water (30 ml) and ethyl acetate (150 ml). The mixture was shaken, and the separated upper layer was washed with water and concentrated under reduced pressure. The residue was washed with ethyl acetate and dried to give 1-amino-5-(5-chloro-2-fluorophenyl)cyclohexan-3-one (1.45 g) as yellow crystals.

mp233–234° C.

¹H-NMR(DMSO-d$_6$) δ:2.20 (1H, dd), 2.34–2.53 (2H, m), 2.64 (1H, dd), 3.39–3.55 (1H, m), 5.02 (1H, s), 6.88 (1H, br), 7.19–7.50 (3H, m).

Reference Example 168

To a mixture of 1-amino-5-(5-chloro-2-fluorophenyl)cyclohexan-3-one (1.33 g), 1,1-dimethoxy-3-butanone (2 ml), toluene (20 ml) and ethanol (9 ml) was added granulated potassium hydroxide (0.4 g) at 110–115° C. while stirring. Just after potassium hydroxide was dissolved, granulated potassium hydroxide (0.3 g) was added to the mixture. With 30 minutes intervals, granulated potassium hydroxide (0.1 g) was added three times to the mixture. To the mixture was added 1,1-dimethoxy-3-butanone (1ml) 2 hours after the reaction had started, and then granulated potassium hydroxide (0.1 g) was added to the mixture. The mixture was stirred for 1 hour under the same conditions. The reaction solution was concentrated under reduced pressure, and to the residue was added water (30 ml) and ethyl acetate (100 ml). The mixture was shaken and the separated upper layer was washed with water. To the mixture was added concentrated hydrochloric acid (0.5 ml). The mixture was concentrated under reduced pressure, and the residue washed with a little amount of ethanol and dried to give 7-(5-chloro-2-fluorophenyl)-4-methyl-5,6,7,8-tetrahydroquinolin-5-one hydrochloride (1.05 g).

mp179–180° C.

¹H-NMR(DMSO-d$_6$) δ:2.79–2.90 (4H, m), 3.16 (1H, dd), 3.43–3.69 (2H, m), 3.82–3.98 (1H, m), 7.26–7.47 (2H, m), 7.59 (1H, dd), 7.75 (1H, d), 8.77 (1H, d).

Reference Example 169

A mixture of 7-(3-chlorothiophen-2-yl)-4-methyl-5,6,7,8-tetrahydroquinolin-5-one (7.07 g), ethyleneglycol (6.2 g) and p-toluenesulfonic acid (6.9 g) in toluene (200 ml) was refluxed for 15 hours, with separating water, and to the reaction solution were added ethyl acetate (150 ml) and saturated sodium hydrogen carbonate solution (200 ml). The mixture was shaken, and the separated upper layer was washed with water and concentrated under reduced pressure. The residue was purified with silica gel column chromatography to give 7-(3-chlorothiophen-2-yl)-4-methyl-5,6,7,8-tetrahydroquinolin-5-one-ethyleneacetal(7.3 g) as colorless crystals.

mp117–1180° C. (recrystallized from ethyl acetate-hexane to give).

¹H-NMR(CDCl$_3$) δ: 1.96 (1H,t), 2.45–2.55 (4H,m)3.09 (1H,dd), 3.36 (1H,ddd), 3.64–3.80 (1H,m)4.15–4.37 (4H, m), 6.93 (1H,d), 7.08 (1H,d), 7.18 (1H,d), 8.36 (1H,d).

Reference Example 170

In tetrahydrofuran (16 ml) was dissolved 7-(3-chlorothiophen-2-yl)-4-methyl-5,6,7,8-tetrahydroquinolin-5-one ethyleneacetal (1.61 g), and to the solution was added at −60° C. or less a solution of 1.6M butyllithium in hexane (35 ml), while stirring. The mixture was stirred at −60° C. or less for 0.5 hours, and to the mixture was added methyl iodide (1 ml) under the same conditions. The cooling bath was removed, and the mixture was stirred for 13 hours. To the reaction solution were added water (80 ml), ethyl acetate (125 ml) and hexane (100 ml). The mixture was shaken, and the separated upper layer was washed with sodium nitrite solution and water, and concentrated under reduced pressure to give pale green syrup (1.47 g), which was dissolved in 1,2-dimethoxyethane (12 ml). To the solution was added 2N hydrochloric acid (6 ml), and the mixture was stirred at 110° C. for 2 hours. Under reduced pressure, the reaction solution was concentrated, and the residue was washed with ethanol and dried to give 7-(3-chloro-5-methylthiophen-2-yl)-4-methyl-5,6,7,8-tetrahydroquinolin-5-one hydrochloride (1.03 g) as pale yellow crystals.

mp192–193° C.

¹H-NMR(DMSO-d6) δ: 2.41 (3H,s), 2.77 (3H,s), 2.94–2.98 (2H,m), 3.44 (1H,dd), 3.59 (1H,dd), 3.90–4.08 (1H,m), 6.78 (1H,s), 7.72 (1H,d), 8.76 (1H,d).

Reference Example 171

A mixture of 5-(2-chloro-5-methylphenyl)cyclohexane-1,3-dione (2.37 g), p-toluene sulfonylhydrazide (2 g) and ethanol (20 ml) was refluxed for 3.5 hours and cooled, and precipitated crystals were filtered to give 5-(2-chloro-5-methylphenyl)-1-[2-(4-methylphenylsulfonyl)hydrazino]cyclohexen-3-one (3.67 g) as pale yellow crystals.

mp 256–257° C. (decomp.).

¹H-NMR(DMSO-d$_6$) δ: 2.21 (1H,dd), 2.29 (3H,s), 2.36–2.50 (6H,m), 3.42–3.57 (1H,m), 5.24 (1H,s), 7.07 (1H,dd), 7.28 (1H,s), 7.30 (1H,d), 7.42 (2H,d), 7.72 (2H,d), 8.78 (1H,br), 9.83 (1H,br).

Reference Example 172

A mixture of 5-(2-chloro-5-methylphenyl)-1-[2-(4-methylphenylsulfonyl)hydrazino]cyclohexen-3-one (2.03 g), anhydrous potassium carbonate (1.73 g) and methanol (20 ml) was stirred at room temperature for 30 minutes, and to the mixture were added 1,2-dimethoxyethane (10 ml) and bromoacetone (0.891 g). The mixture was stirred at 80° C. for 4.5 hours. Under reduced pressure, the solvent was evaporated, and to the residue were added ethyl acetate (200 ml) and water (30 ml). The mixture was shaken, and the separated upper layer was washed with water and concentrated under reduced pressure. The residue was purified with silica gel column chromatography to give 7-(2-chloro-5-methylphenyl)-4-methyl-5,6,7,8-tetrahydrocinnolin,-5-one (0.804 g) as brown crystals.

mp65–70° C.

$^1$H-NMR(CDCl3) δ: 2.36 (3H,s), 2.71 (3H,s), 2.86 (1H, dd), 3.07 (1H,ddd), 3.41 (1H,dd), 3.76 (1H,ddd), 3.88–4.03 (1H,m), 7.06 (1H,dd), 7.13 (1H,s), 7.32 (1H,dd), 9.15 (1H, s).

Reference Example 173

A mixture of 5-(5-fluoro-2-methylphenyl)cyclohexene-1,3-dione (2.2 g), p-toluenesulfonylhydrazide (2 g) and ethanol (20 ml) was refluxed for 2.5 hours and cooled, and precipitated crystals were filtered and washed with ethanol to give 5-(3-fluoro-6-methylphenyl)-1-[2-(4-methylphenylsulfonyl)hydrazino]cyclohexan-3-one (1.64 g) as colorless crystals.

mp 241–242° C. (decomp.).

$^1$H-NMR(DMSO-d$_6$) δ: 2.15 (1H, dd), 2.24 (3H, s), 2.27–2.60 (6H, m), 3.20–3.37 (1H, m), 5.23 (1H, s), 6.88–6.98 (1H, m), 7.12–7.22 (2H, m), 7.42 (2H, d), 7.72 (2H, d), 8.73 (1H, br), 9.82 (1H, br).

Reference Example 174

To a mixture of 5-(5-fluoro-2-methylphenyl)-1-[2-(4-methylphenylsulfonyl)hydrazino]cyclohexen-3-one (1.63 g), anhydrous potassium carbonate (1.45 g), methanol (20 ml) and 1,2-dimethoxyethane (10 ml) was added under ice-cooling 1-bromopropan-2-one (0.75 g), and the mixture was stirred at room temperature for 2 hours and then at 80° C. for 5 hours. Under reduced pressure, the solvent was evaporated, and to the residue were added ethyl acetate (70 ml) and water (30 ml). The mixture was shaken, and the separated upper layer was washed with water and concentrated under reduced pressure. The residue was purified with silica gel column chromatography to give 7-(5-fluoro-2-methylphenyl)-4-methyl-5,6,7,8-tetrahydrocinnolin-5-one (0.265 g) as yellowish brown crystals.

mp 127–128° C.

$^1$H-NMR(CDCl$_3$) δ: 2.34 (3H, s), 2.71 (3H, s), 2.85 (1H, dd), 2.98 (1H, ddd), 3.36 (1H, dd), 3.62–3.77 (2H, m), 6.87–7.02 (2H, m), 7.20 (1H, dd), 9.16 (1H,s).

Reference Example 175

A mixture of 5-(5-chloro-2-fluorophenyl)cyclohexane-1,3-dione (2.04 g), p-toluenesulfonylhydrazide (1.67 g) and ethanol (15 ml) was refluxed for 2.5 hours and cooled, and precipitated crystals were filtered and washed with ethanol to give 5-(5-chloro-2-fluorophenyl)-1-[2-(4-methylphenylsulfonyl)hydrazino]cyclohexen-3-one (2.08 g) as colorless crystals.

mp 244–245° C. (decomp.).

$^1$H-NMR(DMSO-d$_6$) δ: 2.23 (1H, dd), 2.40 (3H, s), 2.43–2.60 (3H, m), 3.32–3.47 (1H, m), 5.23 (1H, s), 7.19–7.49 (5H, m), 7.72 (2H, d), 8.79 (1H, br), 9.85 (1H, s).

Reference Example 176

To a mixture of 5-(5-chloro-2-fluorophenyl)-1-[2-(4-methylphenylsulfonyl)hydrazino]cyclohexen-3-one (2.0 g), anhydrous potassium carbonate (1.68 g), methanol (20 ml) and 1,2-dimethoxyethane (10 ml) was added under ice-cooling 1-bromopropan-2-one (0.87 g), and the mixture was stirred for 2 hours at room temperature, and then for 6 hours at 80° C. Under reduced pressure, the solvent was evaporated, and to the residue was added ethyl acetate (70 ml) and water (30 ml). The mixture was shaken, and the separated upper layer was washed with water and concentrated under reduced pressure. The residue was purified with silica gel column chromatography to give 7-(5-chloro-2-fluorophenyl)-4-methyl-5,6,7,8-tetrahydrocinnolin-5-one (0.338 g) as yellowish brown crystals.

mp 124–125° C. (recrystallized from ethyl acetate-hexane).

$^1$H-NMR(CDCl$_3$) δ: 2.71 (3H, s), 2.93 (1H, dd), 3.05 (1H, ddd), 3.48 (1H, dd), 3.68–3.85 (2H, m), 7.02–7.10 (1H, m), 7.24–7.31 (2H, m), 9.16 (1H, s).

Reference Example 177

To a solution of 5-(2,5-dichlorophenyl)cyclohexane-1,3-dione (1.5 g), 4-dimethylaminopyridine (1.1 g) and acetic acid (0.63 g) in dimethylformamide (60 ml) was added dicyclohexylcarbodiimide (1.3 g), and the mixture was stirred at room temperature for 36 hours. Under reduced pressure, the solvent was evaporated, and the residue was dissolved in ethyl acetate. The solution was extracted with 1N sodium hydroxide solution, and the aqueous layer was filtered. Insoluble materials were filtered off, and the filtrate was neutralized with 1N hydrochloric acid and extracted with ethyl acetate. The organic layer was washed with water and saturated brine, and dried with magnesium sulfate. Under reduced pressure, the solvent was evaporated to give 5-(2,5-dichlorophenyl)-2-(1-hydroxyethylidene)cyclohexane-1,3-dione (1.4 g), which was dissolved in ethanol (30 ml). To the solution was added hydrazine hydrate (0.26 g), and the mixture was refluxed for 30 minutes. Under reduced pressure, the solvent was evaporated, and the residue was dissolved in ethyl acetate. The organic layer was washed with water and saturated brine, and dried with magnesium sulfate. Under reduced pressure, the solvent was evaporated, and the residue was purified with silica gel column chromatography (ethyl acetate-hexane) to give 6-(2,5-dichlorophenyl)-3-methyl-4,5,6,7-tetrahydroindazol-4-one (1.2 g) as colorless crystals.

mp184–186° C.

$^1$H-NMR(CDCl$_3$) δ: 2.60 (3H,s), 2.66–2.82 (2H,m), 2.92 (1H,dd,J=12,16 Hz), 3.20 (1H,dd,J=4,16 Hz), 3.83–4.03 (1H,m), 7.16–7.37 (4H,m).

Reference Example 178

In water (500 ml) was dissolved sodium hydroxide (4.0 g), and to the mixture was added acetone (100 ml), and then 2,5-dichlorobenzaldehyde (15.9 g). The mixture was stirred at room temperature for 1 hour, and acetone was evaporated under reduced pressure. The residue was extracted with ethyl acetate, and the organic layer was washed with water and saturated brine, and concentrated under reduced pressure to give 4-(2,5-dichlorophenyl)-3-buten-2-one (19.0 g).

To a solution of 20% sodium ethoxide in ethanol (6.2 g) were added at room temperature ethanol (150 ml) and diethyl malonate (14.6 g), and then added little by little 4-(2,5-dichlorophenyl)-3-buten-2-one (19.0 g). The mixture was stirred at room temperature for 30 minutes, refluxed for 2 hours and cooled. The solvent was evaporated, and to the residue was added water. The aqueous layer was washed with ethyl acetate and concentrated, and to the residue was added 2M sodium hydroxide (50 ml). The mixture was refluxed for 2 hours and cooled, and to the mixture was added 2.5M sulfuric acid (50 ml) for 15 minutes. The mixture was refluxed for 1.5 hours and cooled, and precipitated crystals were filtered and washed with water and toluene to give 5-(2,5-dichlorophenyl)cyclohexane-1,3-dione (9.9 g) as colorless crystals.

mp187° C. (decomp.).

$^1$H-NMR(CDCl$_3$) δ: 2.42–2.70 (4H, m), 3.71–3.89 (1H, m), 5.54 (1H, s), 7.16–7.43 (3H, m).

Reference Example 179

In water (100 ml) was dissolved sodium hydroxide (3.0 g), and to the solution was added acetone (80 ml) and then was added dropwise a solution of 5-chloro-2-methoxybenzaldehyde (11.8 g) in acetone (30 ml). The reaction solution was stirred at room temperature for 2 hours, and acetone was evaporated under reduced pressure. The residue was extracted with ethyl acetate, and the organic layer was washed with water and saturated brine and concentrated under reduced pressure. The residue was purified with silica gel column chromatography to give 4-(5-chloro-2-methoxyphenyl)-3-buten-2-one (6.8 g).

To a solution of 20% sodium ethoxide in ethanol (2.3 g) was added at room temperature diethyl malonate (5.4 g) and then was added little by little 4-(5-chloro-2-methoxyphenyl)-3-buten-2-one (6.8 g), and the reaction mixture was stirred at room temperature for 30 minutes, refluxed for 2 hours and cooled. The solvent was evaporated, and to the residue was added water. The aqueous layer was washed with ethyl acetate and concentrated. To the residue was added 2M sodium hydroxide (18 ml), and the mixture was refluxed for 2 hours and cooled. To the mixture was added 2.5M sulfuric acid (18 ml) for 15 minutes, and the mixture was refluxed for 15 minutes, cooled and extracted with ethyl acetate. The organic layer was washed with water and saturated brine, and dried with magnesium sulfate. Under reduced pressure, the solvent was evaporated to give 5-(5-chloro-2-methoxyphenyl)cyclohexane-1,3-dione (7.3 g) as amorphous.

$^1$H-NMR(CDCl$_3$) δ: 2.5–2.95 (4H,m), 3.4–3.88 (1H,m), 3.80 (3H,s), 5.61 (1H,s), 6.38 (1H,br), 6.77–7.28 (3H,m).

Reference Example 180

To a solution of 2-bromo-4-fluorotoluene (16.0 g) in anhydrous tetrahydrofuran was added dropwise at −78° C. a solution of 1.6M butyllithium in hexane (55.5 ml), and the mixture was stirred at the same temperature for 30 minutes. To the mixture was added dropwise a solution of dimethylformamide (6.8 g) in tetrahydrofuran (20 ml), and the mixture was allowed to stand to warm up to 0° C. To the reaction solution was added ice-water, and the reaction solution was extracted with ethyl acetate. The organic layer was washed with water and saturated brine and dried with magnesium sulfate. Under reduced pressure, the solvent was evaporated to give oil of 5-fluoro-2-methylbenzaldehyde (11.5 g).

To a mixture of acetone (80 ml), sodium hydroxide (3.7 g) and water (100 ml) was added dropwise at room temperature a solution of 5-fluoro-2-methylbenzaldehyde (11.5 g) in acetone (30 ml), and the mixture was stirred at the same temperature for 1 hour. Under reduced pressure, acetone was evaporated, and the residue was extracted with ethyl acetate. The organic layer was washed with water and saturated brine, and concentrated under reduced pressure to give 4-(5-fluoro-2-methylphenyl)-3-buten-2-one (13.4 g).

To a solution of 20% sodium ethoxide in ethanol (5.9 g) was added at room temperature diethyl malonate (14.0 g), and then added little by little 4-(5-fluoro-2-methylphenyl)-3-buten-2-one (13.4 g), and the mixture was stirred at room temperature for 30 minutes and then for 2 hours while heating, and cooled. The solvent was evaporated, and to the residue was added water. The aqueous layer was washed with ethyl acetate and concentrated. To the residue was added 2M sodium hydroxide (46 ml), and the mixture was refluxed for 2 hours and cooled. To the mixture was added 2.5M sulfuric acid (46 ml) for 10 minutes, and the mixture was refluxed for 30 minutes and cooled. Precipitated crystals were filtered and washed with water and isopropylether to give 5-(5-fluoro-2-methylphenyl)cyclohexane-1,3-dione (8.6 g) as colorless crystals.

mp175–176° C.

$^1$H-NMR(CDCl$_3$) δ: 2.30 (3H, s), 2.27–2.56 (4H, m), 2.5–4.3 (1H, br), 3.44–3.63 (1H, m), 5.55 (1H, s), 6.77–7.01 (2H, m), 7.09–7.17 (1H, m).

Reference Example 181

To a solution of 4-fluorotoluene (21.5 g) and dichloromethylmethylether (56.1 g) in dichloromethane (160 ml) was added dropwise at room temperature a solution of titanium tetrachloride (92.6 g) in dichloromethane (50 ml), and the mixture was stirred at the same temperature for 5 hours. The reaction solution was poured into ice, and the organic layer was washed with water, sodium hydrogen carbonate solution, water and saturated brine, and dried with magnesium sulfate. Under reduced pressure, the solvent was evaporated to give oil of a mixture of 2-fluoro-5-methylbenzaldehyde and 5-fluoro-2-methylbenzaldehyde (about 1:7) (28.1 g).

To a mixture of acetone (160 ml), sodium hydroxide (6.4 g) and water (200 ml) was added dropwise at 0° C. a mixture of 2-fluoro-5-methylbenzaldehyde and 5-fluoro-2-methylbenzaldehyde (about 1:7) (28.1 g) in acetone (40 ml), and the mixture was stirred at the same temperature for 1 hour. To the mixture was added 1N hydrochloric acid (160 ml), and acetone was evaporated under reduced pressure. The residue was extracted with ethyl acetate, and the organic layer was washed with water and saturated brine and concentrated under reduced pressure. The residue was purified with silica gel column chromatography (ethyl acetate-hexane) to give 4-(2-fluoro-5-methylphenyl)-3-buten-2-one (18.2 g).

To a solution of 20% sodium ethoxide in ethanol (1.4 g) was added at room temperature diethyl malonate (3.3 g) and then was added little by little 4-(2-fluoro-5-methylphenyl)-3-buten-2-one (3.5 g), and the reaction mixture was stirred at room temperature for 30 minutes, refluxed for 2 hours and cooled. The solvent was evaporated, and to the residue was added water. The aqueous layer was washed with ethyl acetate and concentrated. To the residue was added 2M sodium hydroxide (11 ml), and the mixture was refluxed for 2 hours and cooled. To the mixture was added 2.5M sulfuric acid (11 ml) for 5 minutes, and the mixture was refluxed for 30 minutes and cooled. Precipitated crystals were filtered, washed with water and isopropylether to give 5-(2-fluoro-5-methylphenyl)cyclohexane-1,3-dione (1.6 g) as colorless crystals.

mp174° C. (decomp.).

$^1$H-NMR(CDCl$_3$-DMSO-d$_6$) δ: 2.31 (3H,s), 2.47–2.93 (4H,m), 3.48–3.68 (1H,m), 5.56 (1H,s), 6.77–7.30 (1H,br), 6.86–7.07 (3H,m).

Reference Example 182

To a solution of 4-chlorotoluene (25.0 g) and dichloromethylmethylether (45.4 g) in dichloromethane (160 ml) was added dropwise at room temperature a solution of titanium tetrachloride (74.9 g) in dichloromethane (40 ml), and the mixture was stirred at the same temperature for 15 hours. The reaction solution was poured into ice, and the organic layer was washed with water, sodium hydrogen carbonate solution, water and saturated brine, and dried with magnesium sulfate. Under reduced pressure, the solvent was evaporated, and the residue was subjected to silica gel column chromatography (ethyl acetate-hexane) to give oil of crude 2-chloro-5-methylbenzaldehyde (18.3 g) and 5-chloro-2-methylbenzaldehyde (4.1 g), respectively.

To a mixture of acetone (160 ml), sodium hydroxide (2.6 g) and water (160 ml) was added dropwise at 0° C. a solution of crude 2-chloro-5-methylbenzaldehyde (18.3 g) in acetone (30 ml), and the mixture was stirred at the same temperature for 1 hour. Under reduced pressure, acetone was evaporated, and the residue was extracted with ethyl acetate. The organic layer was washed with water and saturated brine, and concentrated under reduced pressure to give 4-(2-chloro-5-methylphenyl)-3-buten-2-one (18.9 g) as oil.

To a solution of 20% sodium ethoxide in ethanol (4.3 g) was added at room temperature diethyl malonate (10.1 g), and then added little by little 4-(2-chloro-5-methylphenyl)-3-buten-2-one (18.9 g). The mixture was stirred at room temperature for 30 minutes, refluxed for 2 hours and cooled. The solvent was evaporated, and to the residue was added water. The aqueous layer was washed with ethyl acetate and concentrated. To the residue was added 2M sodium hydroxide (33 ml), and the mixture was refluxed for 2 hours and cooled. To the mixture was added 2.5M sulfuric acid (33 ml) for 15 minutes, and the mixture was refluxed for 30 minutes and cooled. Precipitated crystals were filtered and washed with water and isopropylether to give 5-(2-chloro-5-methylphenyl)cyclohexane-1,3-dione (7.8 g) as colorless crystals.

mp186–188° C.

$^1$H-NMR(CDCl$_3$) δ: 2.33 (3H, s), 2.38–2.72 (4H, m), 3.2–5.4 (1H, br), 3.73–3.93 (1H, m), 5.55 (1H, s), 7.01 (1H, d, J=8 Hz), 7.03 (1H, s), 7.26 (1H, d, J=8 Hz).

To a mixture of acetone (80 ml), sodium hydroxide (1.2 g) and water (80 ml) was added dropwise at 0° C. a solution of 5-chloro-2-methylbenzaldehyde (4.1 g) in acetone (10 ml), and the mixture was stirred at the same temperature for 1 hour. Under reduced pressure, acetone was evaporated, and the residue was extracted with ethyl acetate. The organic layer was washed with water and saturated brine, and concentrated under reduced pressure to give 4-(5-chloro-2-methylphenyl)-3-buten-2-one (5.5 g) as oil.

To a solution of 20% sodium ethoxide in ethanol (9.5 g) was added at room temperature diethyl malonate (4.5 g) and then added little by little 4-(5-chloro-2-methylphenyl)-3-buten-2-one (5.5 g). The mixture was stirred at room temperature for 30 minutes, refluxed for 2 hours and cooled. The solvent was evaporated, and to the residue was added water. The aqueous layer was washed with ethyl acetate and concentrated. To the residue was added 2M sodium hydroxide (15 ml), and the mixture was refluxed for 2 hours and cooled. To the mixture was added 2.5M sulfuric acid (15 ml) for 15 minutes, and the mixture was refluxed for 30 minutes and cooled. Precipitated crystals were filtered and washed with water and isopropylether to give 5-(5-chloro-2-methylphenyl)cyclohexane-1,3-dione (2.9 g) as colorless crystals.

mp180–181° C.

$^1$H-NMR(CDCl$_3$-DMSO-d$_6$) δ: 2.31 (3H, s), 2.35–2.84 (4H, m), 3.37–3.73 (1H, m), 5.56 (1H, s), 6.9–7.43 (1H, br), 7.08–7.26 (3H, m).

Reference Example 183

In water (200 ml) was dissolved sodium hydroxide (3 g), and to the solution was added acetone (80 ml) and then was added dropwise a solution of 5-fluoro-2-methoxybenzaldehyde (10 g) in acetone (25 ml). The reaction solution was stirred at room temperature for 4 hours, and acetone was evaporated under reduced pressure. The residue was extracted with ethyl acetate, and the organic layer was washed with water and saturated brine and concentrated under reduced pressure to give 4-(5-fluoro-2-methoxyphenyl)-3-buten-2-one (13 g).

To a solution of 20% sodium ethoxide in ethanol (21.4 g) was added at room temperature diethyl malonate (11.2 g) and then was added little by little 4-(5-fluoro-2-methoxyphenyl)-3-buten-2-one (13 g), and the reaction mixture was stirred at room temperature for 30 minutes, refluxed for 2 hours and cooled. The solvent was evaporated, and to the residue was added water. The aqueous layer was washed with ethyl acetate and concentrated. To the residue was added 2M sodium hydroxide (50 ml), and the mixture was refluxed for 2 hours and cooled. To the mixture was added 2.5M sulfuric acid (50 ml) for 15 minutes, and the mixture was refluxed for 15 minutes and cooled. Precipitated crystals were washed with ethyl acetate to give 5-(5-fluoro-2-methoxyphenyl)cyclohexane-1,3-dione (9.6 g) as pale yellow crystals.

mp160–161° C.

$^1$H-NMR(DMSO-d$_6$) δ: 2.3–2.66 (4H,m), 3.5–3.66 (1H, m), 3.80 (3H,s), 5.29 (1H,s), 6.96–7.17 (3H,m), 11.20 (1H, br).

Reference Example 184

To a solution of 1.6M butyllithium in hexane (32 ml) was added anhydrous tetrahydrofuran (100 ml), and then added dropwise 2,2,6,6-tetramethylpiperidine (8.4 ml) at −70° C. or less. To the mixture was added dropwise a solution of 1-chloro-4-fluorobenzene (6.5 g) in anhydrous tetrahydrofuran (20 ml), and the mixture was stirred at −70° C. or less for 2 hours. To the mixture was added dropwise a solution of dimethylformamide (6.5 g) in tetrahydrofuran (15 ml), and the mixture was allowed to stand to warm up to 0° C. The reaction solution was poured into ice-water and extracted with ethyl acetate. The organic layer was washed with water and saturated brine, and dried with magnesium sulfate. Under reduced pressure, the solvent was evaporated to give oil of 5-chloro-2-fluorobenzaldehyde (5.1 g).

To a mixture of acetone (22 ml), sodium hydroxide (0.83 g) and water (55 ml) was added dropwise at room temperature a solution of 5-chloro-2-fluorobenzaldehyde (3.5 g) in acetone (20 ml), and the mixture was stirred at the same temperature for 15 hours. Under reduced pressure, acetone was evaporated, and the residue was extracted with ethyl acetate. The organic layer was washed with water and saturated brine, and concentrated under reduced pressure to give 4-(5-chloro-2-fluorophenyl)-3-buten-2-one (4.3 g).

To a solution of 20% sodium ethoxide in ethanol (7.4 g) was added at room temperature diethyl malonate (3.6 g), and then added little by little 4-(5-chloro-2-fluorophenyl)-3-buten-2-one (4.3 g). The mixture was stirred at room temperature for 30 minutes and then for 2 hours while heating, and cooled. The solvent was evaporated, and to the residue was added water. The aqueous layer was washed with ethyl acetate and concentrated. To the residue was added 2M sodium hydroxide (17 ml), and the mixture was refluxed for 1 hour and cooled. To the mixture was added 2.5M sulfuric acid (17 ml) for 10 minutes, and the mixture was refluxed for 30 minutes and cooled. Precipitated crystals were filtered and washed with water and isopropylether to give 5-(5-chloro-2-fluorophenyl)cyclohexane-1,3-dione (4.1 g) as pale yellow crystals.

mp176–177° C.

$^1$H-NMR(DMSO-d$_6$) δ: 2.33–2.72 (4H, m), 3.43–3.65 (1H, m), 5.30 (1H, s), 7.18–7.39 (2H, m), 7.47–7.52 (1H, m), 10.78 (1H, br).

Working Example 136
(Production of Compounds 141–142)

To a solution of (±)-7-(2,5-dichlorophenyl)-5-guanidinoimino-4-methyl-5,6,7,8-tetrahydroquinoline hydrochloride (3.0 g) in methanol (50 ml) was added a solution of 28% sodium methoxide in methanol (2.7 g), and the mixture was stirred at 50° C. for 1 hour. Under reduced pressure, the solvent was evaporated, and to the residue was added water. Precipitated crystals were washed with water and dried to give (±)-7-(2,5-dichlorophenyl)-5-guanidinoimino-4-methyl-5,6,7,8-tetrahydroquinoline.

To a solution of (±)-7-(2,5-dichlorophenyl)-5-guanidinoimino-4-methyl-5,6,7,8-tetrahydroquinoline (2.3 g) in ethanol (10 ml) was added a solution of L-pyroglutamic acid (0.81 g) in ethanol (5 ml) at 80° C., and the mixture was gradually cooled to room temperature and stirred for 6 hours. The resulting crystals were filtered and washed with ethanol to give (+)-7-(2,5-dichlorophenyl)-5-guanidinoimino-4-methyl-5,6,7,8-tetrahydroquinoline L-pyroglutamate (1.61 g). Said crystals were recrystallized from ethanol and suspended in methanol, and to the suspension was added a solution of 28% sodium methoxide in methanol (0.5 g). Under reduced pressure, the solvent was evaporated. The resulting crystals were washed with water, dried, recrystallized from acetonitrile and dissolved in ethanol (10 ml). To the solution was added methanesulfonic acid (0.12 g), and the mixture was concentrated. The resulting crystals were recrystallized from ethanol to give (+)-7-(2,5-dichlorophenyl)-5-guanidinoimino-4-methyl-5,6,7,8-tetrahydroquinoline methanesulfonate (Compound 141) (0.25 g,99.8%ee).

mp. 248° C. (decomp.).

Elemental Analysis for $C_{17}H_{17}Cl_2N_5 \cdot 2MeSO_3H$ Calcd. C,41.16; H,4.54; N,12.63; Cl,12.79. Found C,41.16; H,4.42; N,12.40; Cl,12.51.

$^1$H-NMR(DMSO-d$_6$) δ: 2.38 (6H,s), 2.58–2.96 (1H,m), 2.73 (3H,s), 2.97–4.2 (4H,m), 7.2–8.4 (4H,br), 7.38–7.80 (4H,m), 8.45 (1H,d,J=6 Hz), 10.64 (1H,s).

To the mother liquor separated with L-pyroglutamic acid and washing solution was added a solution of 28% sodium methoxide in methanol (1.5 g), and the mixture was concentrated. The residue was washed with water to give (−)-isomer rich crystals (1.9 g), which was dissolved in ethanol (10 ml). To the solution was added D-pyroglutamic acid (0.68 g), and the mixture was heated to give a homogenous solution, which was concentrated. The residue was recrystallized from ethanol to give (−)-7-(2,5-dichlorophenyl)-5-guanidinoimino-4-methyl-5,6,7,8-tetrahydroquinoline D-pyroglutamate (1.0 g). Said crystals were suspended in methanol, and to the suspension was added a solution of 28% sodium methoxide in methanol (0.8 g). Under reduced pressure, the solvent was evaporated. The resulting crystals were washed with water, dried and dissolved in ethanol (10 ml). To the solution was added methanesulfonic acid (0.41 g), and the mixture was concentrated. The resulting crystals were recrystallized from ethanol to give (−)-7-(2,5-dichlorophenyl)-5-guanidinoimino-4-methyl-5,6,7,8-tetahydroquinoline methanesulfonate (Compound 142) (0.31 g, 99.0%ee).

mp. 258° C. (decomp.).

Elemental Analysis for $C_{17}H_{17}Cl_2N_5 \cdot 2MeSO_3H$ Calcd. C,41.16; H,4.54; N,12.63; Cl,12.79. Found C,40.97; H,4.55; N,12.31; Cl,12.71.

$^1$H-NMR(DMSO-d$_6$) agreed with that of Compound 141.

Working Example 137
(Production of Compounds 143–144)

To a solution of (±)-7-(3,5-dichlorothiophen-2-yl)-5-guanidinoimino-4-methyl-5,6,7,8-tetrahydroquinoline hydrochloride (3.0 g) in methanol (30 ml) was added a solution of 28% sodium methoxide in methanol (3 g), and the mixture was stirred at 50° C. for 1 hour. Under reduced pressure, the solvent was evaporated, and to the residue was added water. Precipitated crystals were washed with water and dried to give (±)-7-(3,5-dichlorothiophen-2-yl)-5-guanidinoimino-4-methyl-5,6,7,8-tetrahydroquinoline.

To a solution of (±)-7-(3,5-dichlorothiophen-2-yl)-5-guanidinoimino-4-methyl-5,6,7,8-tetrahydroquinoline (1.6 g) in ethanol (10 ml) was added a solution of L-pyroglutamic acid (0.56 g) in ethanol (2 ml) at 80° C., and the mixture was gradually cooled to room temperature and stirred at room temperature for 6 hours. The resulting crystals were filtered and washed with ethanol to give (+)-7-(3,5-dichlorothiophen-2-yl)-5-guanidinoimino-4-methyl-5,6,7,8-tetrahydroquinoline L-pyroglutamate (1.2 g). Said crystals were recrystallized from ethanol and suspended in methanol, and to the suspension was added a solution of 28% sodium methoxide in methanol (0.6 g). Under reduced pressure, the solvent was evaporated. The resulting crystals were washed with water, dried and dissolved in ethanol (10 ml). To the solution was added methanesulfonic acid (0.098 g), and the mixture was concentrated. The resulting crystals were recrystallized from ethanol to give (+)-7-(3,5-dichlorothiophen-2-yl)-5-guanidinoimino-4-methyl-5,6,7,8-tetrahydroquinoline methanesulfonate (Compound 143) (0.1 g,99.6%ee).

mp.168–172° C.

Elemental Analysis for $C_{15}H_{15}Cl_2N_5S \cdot 2MeSO_3H$ Calcd. C,36.43; H,4.14; N,12.49. Found C,36.54; H,4.10; N,12.66.

$^1$H-NMR(DMSO-d$_6$) δ: 2.37 (6H,s), 2.67–2.92 (1H,m), 2.80 (3H,s), 3.02–4.12 (4H,m), 7.24 (1H,s), 7.4–8.1 (4H,br), 7.68 (1H,d,J=5 Hz), 8.58 (1H,d,J=5 Hz), 10.72 (1H,s).

To the mother liquor separated with L-pyroglutamic acid and washing solution was added a solution of 28% sodium methoxide in methanol (0.8 g), and the mixture was concentrated.

The residue was washed with water to give (−)-isomer rich crystals (1.3 g), which was dissolved in ethanol. To the solution was added D-pyroglutamic acid (0.46 g), and the mixture was heated to give a homogenous solution, which was cooled. Precipitated crystals were filtered to give (−)-7-(3,5-dichlorothiophen-2-yl)-5-guanidinoimino-4-methyl-5,6,7,8-tetrahydroquinoline D-pyroglutamate. Said crystals were suspended in methanol, and to the suspension was added a solution of 28% sodium methoxide in methanol (0.8 g). Under reduced pressure, the solvent was evaporated. The resulting crystals were washed with water, dried and dissolved in ethanol (10 ml). To the solution was added methanesulfonic acid (0.32 g), and the mixture was concentrated. The resulting crystals were recrystallized from ethanol to give (−)-7-(3,5-dichlorothiophen-2-yl)-5-guanidinoimino-4-methyl-5,6,7,8-tetrahydroquinoline methanesulfonate (Compound 144) (0.39 g,99.6%ee).

mp. 172–176° C.

Elemental Analysis for $C_{15}H_{15}Cl_2N_5S.2MeSO_3H$ Calcd. C,36.43; H,4.14; N,12.49. Found C,36.63; H,3.94; N,12.32.

$^1$H-NMR(DMSO-$d_6$) was agreed with that of Compound 143.

Working Example 138
(Production of Compound 145)

To a solution of 7-(2-chlorophenyl)-4-(4-chlorophenyl)-5,6,7,8-tetrahydrocinnolin-5-one (0.18 g) and aminoguanidine hydrochloride (65 mg) in ethanol (10 ml) were added concentrated hydrochloric acid (0.12 ml) and water (0.12 ml), and the mixture was refluxed for 6 hours. Under reduced pressure, the solvent was evaporated, and to the residue was added sodium hydrogen carbonate solution to make the solution alkaline. The mixture was extracted with ethyl acetate, and the organic layer was washed with water and concentrated under reduced pressure. The residue was purified with silica gel column chromatography (ethyl acetate-methanol). The resulting crystals were dissolved in 1N hydrochloric acid (1 ml), and the solution was concentrated. The residue was recrystallized from ethanol-ethyl acetate to give 7-(2-chlorophenyl)-4-(4-chlorophenyl)-5-guanidinoimino-5,6,7,8-tetrahydrocinnoline hydrochloride (Compound 145) (0.13 g) as colorless crystals.

mp196° C. (decomp.).

$^1$H-NMR(DMSO-$d_6$) δ: 2.72–3.01 (1H,m), 3.06–3.28 (1H,m), 3.3–3.52 (2H,m), 3.72–3.99 (1H,m), 6.0–8.6 (4H, broad), 7.28–7.77 (8H,s), 9.12 (1H,s), 11.62 (1H,s).

Working Example 139
(Production of Compound 146)

A mixture of 6-(2-chlorophenyl)-3-phenylamino-4,5,6,7-tetrahydroindazol-4-one (0.4 g), aminoguanidine hydrochloride (0.16 g), concentrated hydrochloric acid (0.31 ml), water (0.31 ml) and ethanol (20 ml) was refluxed for 6 hours. Under reduced pressure, the solvent was evaporated, and to the residue was added sodium hydrogen carbonate solution to make the solution alkaline. The mixture was extracted with ethylacetate, and the organic layer was washed with water and concentrated under reduced pressure. The residue was dissolved in ethanol, and to the solution was added 1N hydrochloric acid (5 ml) and concentrated. Precipitated crystals were recrystallized from ethanol to give 6-(2-chlorophenyl)-4-guanidinoimino-3-phenylamino-4,5,6,7-tetrahydroindazole hydrochloride (Compound 146) (0.23 g) as colorless crystals.

mp. 208–210° C.

$^1$H-NMR(DMSO-$d_6$) δ: 2.72 (1H,dd), 2.86–3.16 (3H,m), 3.6–3.9 (1H,m), 6.6–8.5 (4H,br), 6.84 (1H,t), 7.20–7.63 (9H,m), 10.68 (1H,s).

Working Example 140
(Production of Compound 147)

A mixture of 6-(2-chlorophenyl)-3-phenyl-4,5,6,7-tetrahydroindazol-4-one (0.05 g), aminoguanidine hydrochloride (0.021 g), concentrated hydrochloric acid (0.039 ml), water (0.039 ml) and ethanol (5 ml) was refluxed for 5 hours. Under reduced pressure, the solvent was evaporated, and the residue was recrystallized from ethanol to give 6-(2-chlorophenyl)-4-guanidinoimino-3-phenyl-4,5,6,7-tetrahydroindazole hydrochloride (Compound 147) (0.04 g) as colorless crystals.

mp. 185° C. (decomp.).

$^1$H-NMR(DMSO-$d_6$) δ: 2.73 (1H,dd,J=12,16 Hz), 2.96–3.12 (3H,m), 3.6–3.9 (1H,m), 6.6–8.4 (4H,br), 7.16–7.8 (9H,m), 10.97 (1H,s).

Working Example 141
(Production of Compound 148)

A mixture of 6-(2-chlorophenyl)-3-methoxymethyl-4,5,6,7-tetrahydroindazol-4-one (0.1 g), aminoguanidine hydrochloride (0.046 g), concentrated hydrochloric acid (0.086 ml), water (0.086 ml) and ethanol (10 ml) was refluxed for 5 hours. Under reduced pressure, the solvent was evaporated, and to the residue was added sodium hydrogen carbonate solution to make the solution alkaline. The mixture was extracted with ethyl acetate, and the organic layer was washed with water and concentrated under reduced pressure. The residue was dissolved in 1N hydrochloric acid (1ml), and the solution was concentrated. The resulting crystals were recrystallized from ethanol-ethyl acetate to give 6-(2-chlorophenyl)-4-guanidinoimino-3-methoxymethyl-4,5,6,7-tetrahydroindazole hydrochloride (Compound 148) (0.06 g) as colorless crystals.

mp. 210–212° C.

Elemental Analysis for $C_{16}H_{19}ClN_6O.2HCl$ Calcd. C,45.78; H,5.04; N,20.02. Found C,45.70; H,5.08; N,19.89.

$^1$H-NMR(DMSO-$d_6$) δ: 2.69 (1H,dd,J=12,16 Hz), 2.89–3.12 (3H,m), 3.3 (3H,s), 3.51–3.76 (1H,m), 4.69 (2H, s), 6.9–8.4 (4H,br), 7.26–7.65 (4H,m), 10.97 (1H,s).

Working Example 142
(Production of Compound 149)

A mixture of 1-benzyl-6-(2-chlorophenyl)-3-methyl-4,5,6,7-tetrahydroindazol-4-one (0.3 g), aminoguanidine hydrochloride (0.11 g), concentrated hydrochloric acid (0.21 ml), water (0.21 ml) and ethanol (20 ml) was refluxed for 18 hours. Under reduced pressure, the solvent was evaporated, and the resulting crystals were recrystallized from ethanol-water to give 1-benzyl-6-(2-chlorophenyl)-4-guanidinoimino-3-methyl-4,5,6,7-tetrahydroindazole hydrochloride (Compound 149) (0.37 g) as colorless crystals.

mp.151–153° C.

Elemental Analysis for $C_{22}H_{23}ClN_6.2HCl.0.5H_2O$ Calcd. C,58.41; H,5.57; N,18.58. Found C,58.73; H,5.46; N,18.39.

$^1$H-NMR(DMSO-$d_6$) δ: 2.41 (3H,s), 2.69 (1H,dd), 2.81–3.74 (4H,m), 5.14–5.36 (2H,m), 6.8–7.65 (4H,br), 7.08–7.63 (9H,m), 10.70 (1H,s).

Working Example 143
(Production of Compound 150)

A mixture of 6-(2-chlorophenyl)-3-methyl-2-phenyl-4,5,6,7-tetrahydroindazol-4-one (0.6 g), aminoguanidine hydrochloride (0.24 g), concentrated hydrochloric acid (0.45 ml), water (0.45 ml) and ethanol (20 ml) was refluxed for 12 hours. Under reduced pressure, the solvent was evaporated, and the resulting crystals were recrystallized from ethanol-water to give 6-(2-chlorophenyl)-4-guanidinoimino-3-methyl-2-phenyl-4,5,6,7-tetrahydroindazole hydrochloride (Compound 150) (0.73 g) as colorless crystals.

mp.192–194° C.

Elemental Analysis for $C_{21}H_{21}ClN_6.HCl.H_2O$ Calcd. C,56.38; H,5.41: N,18.79. Found C,56.57; H,5.41; N,18.76.

$^1$H-NMR(DMSO-$d_6$) δ: 2.52 (3H,s), 2.73 (1H,dd), 2.95 (1H,dd), 3.0–3.2 (1H,m), 3.25–3.52 (1H,m), 3.57–3.8 (1H, m), 6.8–8.4 (4H,br), 7.26–7.75 (9H,m), 10.9 (1H,br).

Working Example 144
(Production of Compound 151)

A mixture of 6-(2-chlorophenyl)-3-methyl-1-(2-phenylethyl)-4,5,6,7-tetrahydroindazol-4-one (0.15 g), aminoguanidine hydrochloride (0.055 g), concentrated hydrochloric acid (0.1 ml), water (0.1 ml) and ethanol (15 ml) was refluxed for 12 hours. Under reduced pressure, the solvent was evaporated, and the resulting crystals were recrystallized from ethanol to give 6-(2-chlorophenyl)-4-guanidinoimino-3-methyl-1-(2-phenylethyl)-4,5,6,7-tetrahydroindazole hydrochloride (Compound 151) (0.07 g) as colorless crystals.

mp.152–154° C.

$^1$H-NMR(DMSO-d$_6$) δ: 2.33–2.7 (3H,m), 2.42 (3H,s), 2.83–2.92 (1H,m), 3.01 (2H,t), 3.28–3.55 (1H,m), 4.21 (2H,m), 6.2–8.4 (4H,br), 6.97–7.5 (9H,m), 10.72 (1H,s).

Working Example 145
(Production of Compound 152)

A mixture of 6-(2-chlorophenyl)-3-methyl-2-(2-phenylethyl)-4,5,6,7-tetrahydroindazol-4-one (0.20 g), aminoguanidine hydrochloride (0.073 g), concentrated hydrochloric acid (0.14 ml), water (0.14 ml) and ethanol (15 ml) was refluxed for 12 hours. Under reduced pressure, the solvent was evaporated, and the resulting crystals were recrystallized from ethanol to give 6-(2-chlorophenyl)-4-guanidinoimino-3-methyl-2-(2-phenylethyl)-4,5,6,7-tetrahydroindazole hydrochloride (Compound 152) (0.17 g) as colorless crystals.

mp.185° C. (decomp.).

Elemental Analysis for $C_{23}H_{25}ClN_6 \cdot HCl \cdot 0.5H_2O$ Calcd. C,59.23; H,5.83; N,18.02. Found C,59.36; H,5.75; N,17.89.

$^1$H-NMR(DMSO-d$_6$) δ: 2.30 (3H,s), 2.66 (1H,dd), 2.8–3.15 (3H,m), 3.06 (2H,t), 3.5–3.7 (1H,m), 4.27 (2H,t), 6.2–8.0 (4H,br), 7.05–7.63 (9H,m), 10.71 (1H,s).

Working Example 146
(Production of Compound 153)

A mixture of 6-(2-chlorophenyl)-3-methyl-1-(3-phenylpropyl)-4,5,6,7-tetrahydroindazol-4-one (0.11 g), aminoguanidine hydrochloride (0.048 g), concentrated hydrochloric acid (0.073 ml), water (0.073 ml) and ethanol (10 ml) was refluxed for 8 hours. Under reduced pressure, the solvent was evaporated, and the resulting crystals were recrystallized from ethanol to give 6-(2-chlorophenyl)-4-guanidinoimino-3-methyl-1-(3-phenylpropyl)-4,5,6,7-tetrahydroindazole hydrochloride (Compound 153) (0.12 g) as colorless crystals.

mp.210° C. (decomp.).

Elemental Analysis for $C_{24}H_{27}ClN_6 \cdot HCl \cdot 0.5H_2O$ Calcd. C,60.00; H,6.08; N,17.49. Found C,60.11, H,6.00; N,17.65.

$^1$H-NMR(DMSO-d$_6$) δ: 1.92–2.13 (2H,m), 2.3–2.76 (3H, m), 2.4 (3H,s), 2.8–3.1 (3H,m), 3.53–3.74 (1H,m), 3.83–4.16 (2H,m), 6.6–8.4 (4H,br), 7.08–7.65 (9H,m), 10.81 (1H,s).

Working Example 147
(Production of Compound 154)

A mixture of 6-(2-chlorophenyl)-3-methyl-2-(3-phenylpropyl)-4,5,6,7-tetrahydroindazol-4-one (0.25 g), aminoguanidine hydrochloride (0.11 g), concentrated hydrochloric acid (0.16 ml), water (0.16 ml) and ethanol (15 ml) was refluxed for 8 hours. Under reduced pressure, the solvent was evaporated, and the resulting crystals were recrystallized from ethanol-water to give 6-(2-chlorophenyl)-4-guanidinoimino-3-methyl-2-(3-phenylpropyl)-4,5,6,7-tetrahydroindazole hydrochloride (Compound 154) (0.24 g) as colorless crystals.

mp.170–180° C.

Elemental Analysis for $C_{24}H_{27}ClN_6 \cdot HCl \cdot 0.5H_2O$ Calcd. C,60.00; H,6.08; N,17.49. Found C,60.35; H,5.85; N,17.38.

$^1$H-NMR(DMSO-d$_6$) δ: 1.96–2.17 (2H,m), 2.38–2.77 (3H,m), 2.51 (3H,s), 2.8–3.12 (3H,m), 3.2–3.74 (1H,m), 3.93–4.23 (2H,m), 6.6–8.4 (4H,br), 7.13–7.63 (9H,m), 10.74 (1H,s).

Working Example 148
(Production of Compound 155)

To a mixture of 7-(2,5-dichlorothiophen-3-yl)-4-methyl-5,6,7,8-tetrahydrocinnolin-5-one (145 mg) and 1-amino-3-hydroxyguanidine hydrochloride (61 mg) were added ethanol (3 ml) and concentrated hydrochloric acid (0.05 ml), and the mixture was stirred at 90° C. for 1.5 hours. The reaction solution was concentrated under reduced pressure, and the residue was recrystallized from ethanol-acetone to give 7-(2,5-dichlorothiophen-3-yl)-5-(1-hydroxyguanidin-3-yl)imino-4-methyl-5,6,7,8-tetrahydrocinnoline hydrochloride (Compound 155) (80 mg) as whitish gray crystals.

mp 176–178° C.

Elemental Analysis for $C_{14}H_{16}N_6Cl_2OS \cdot 2HCl \cdot 0.5H_2O$ Calcd. C,35.99; H,3.57; N,17.99. Found C,35.90; H,3.84; N,17.72.

$^1$H-NMR(DMSO-d$_6$) δ: 2.77 (3H,S), 2.84–3.42 (5H,m), 7.40 (1H,S), 8.49 (2H,br), 9.31 (1H,s), 11.27 (1H,br), 11.73 (1H,br).

Working Example 149
(Production of Compound 156)

To a mixture of 7-(2-chlorophenyl)-4-methyl-5,6,7,8-tetrahydrocinnolin-5-one (101 mg) and 1-amino-3-hydroxyguanidine hydrochloride (48 mg) were added ethanol (2 ml) and concentrated hydrochloric acid (0.05 ml), and the mixture was stirred at 90° C. for 1.5 hours. The reaction solution was concentrated under reduced pressure, and the residue was washed with ethanol and dried to give 7-(2-chlorophenyl)-5-(1-hydroxyguanidin-3-yl)imino-4-methyl-5,6,7,8-tetrahydrocinnoline hydrochloride (Compound 156) (110 mg) as gray white crystals.

mp210° C. (decomp.).

$^1$H-NMR(DMSO-d$_6$) δ: 2.76 (3H,S), 2.88 (1H,dd), 3.23 (1H,ddd), 3.36–3.68 (3H,m), 7.31–7.54 (3H,m), 7.63 (1H, dd), 8.45 (2H,br), 9.27 (1H,s), 11.20 (1H,br), 11.58 (1H,br).

Working Example 150
(Production of Compound 157)

To a mixture of 7-(2-chlorophenyl)-4-methyl-5,6,7,8-tetrahydroquinolin-5-one-1-oxide (0.23 g) and aminoguanidine hydrochloride (100 mg) were added ethanol (6 ml) and concentrated hydrochloric acid (0.1 ml), and the mixture was refluxed for 3 hours. The reaction solution was cooled to room temperature, and the resulting crystals were filtered and dried to give 7-(2-chlorophenyl)-5-guanidinoimino-4-methyl-5,6,7,8-tetrahydroquinoline-1-oxide hydrochloride (Compound 157) (220 mg) as colorless crystals.

mp202–203° C.

Elemental Analysis for $C_{17}H_{18}N_5Cl \cdot HCl \cdot H_2O$ Calcd. C,51.27; H,5.31; N,17.58. Found C,51.02; H,5.29; N,17.34.

$^1$H-NMR(DMSO-d$_6$) δ: 2.61 (3H,s), 2.74–2.96 (2H,m), 3.18 (1H,br), 3.45–3.65 (2H,m), 7.27–7.51 (4H,m), 7.60 (1H,d), 7.74 (4H,br), 8.23 (1H,d), 11.20 (1H,br).

Working Example 151
(Production of Compound 158)

To a mixture of 7-(2,5-dichlorothiophen-3-yl)-4-methyl-5,6,7,8-tetrahydroquinolin-5-one-1-oxide (426 mg) and aminoguanidine hydrochloride (159 mg) were added ethanol (8 ml) and concentrated hydrochloric acid (0.15 ml), and the mixture was stirred at 105° C. for 2 hours. The reaction solution was cooled to room temperature, and the resulting crystals were filtered and dried to give 7-(2,5-dichlorothiophen-3-yl)-5-guanidinoimino-4-methyl-5,6,7,8-tetrahydroquinoline-1-oxide hydrochloride (Compound 158) (480 mg) as colorless crystals.

mp300° C. or more.

$^1$H-NMR(DMSO-d$_6$) δ: 2.61 (3H,s), 2.69–3.60 (5H,m), 7.31 (1H,d), 7.38 (1H,s), 7.69 (4H,br), 8.27 (1H,d), 11.10 (1H,br).

Working Example 152
(Production of Compound 159)

To a mixture of 7-(2-chlorophenyl)-4-methyl-5,6,7,8-tetrahydrocinnolin-5-one-1-oxide (173 mg) and aminoguanidine hydrochloride (73 mg) were added ethanol (4 ml) and concentrated hydrochloric acid (0.07 ml), and the mixture was stirred at 90° C. (bath temperature) for 3.5 hours. The reaction solution was cooled to room temperature, and the resulting crystals were filtered and dried to give 7-(2-chlorophenyl)-5-guanidinoimino-4-methyl-5,6,7,8-tetrahydrocinnolin-1-oxide hydrochloride (Compound 159) (195 mg) as colorless crystals.

mp283–284° C.

$^1$H-NMR(DMSO-d$_6$) δ: 2.59 (3H,s), 2.83 (1H,dd), 2.94 (1H,dd), 3.18–3.25 (1H,m), 3.26–3.48 (1H,m), 3.50–3.70 (1H,m), 7.30–7.63 (4H,m), 7.89 (4H,br), 8.50 (1H,s)11.57 (1H,br).

Working Example 153
(Production of Compound 160)

To a mixture of 7-(2-chlorophenyl)-4-methyl-5,6,7,8-tetrahydrocinnolin-5-one-2-oxide (116 mg) and aminoguanidine hydrochloride (49 mg) were added ethanol (3 ml) and concentrated hydrochloric acid (0.05 ml), and the mixture was stirred at 100° C. (bath temperature) for 3 hours. The reaction solution was cooled to room temperature, and the resulting crystals were filtered and dried to give 7-(2-chlorophenyl)-5-guanidinoimino-4-methyl-5,6,7,8-tetrahydrocinnolin-2-oxide hydrochloride (Compound 160) (116 mg) as colorless crystals.

mp249–250° C.

$^1$H-NMR(DMSO-d$_6$) δ: 2.61 (3H,s), 2.78 (1H,dd), 2.89–2.97 (1H,m), 3.08–3.22 (1H,m), 3.28 (1H,d), 3.53–3.73 (1H,m), 7.30–7.63 (4H,m), 7.74 (4H,br), 8.35 (1H,s), 11.00 (1H,br).

Working Example 154
(Production of Compound 161)

To a mixture of 7-(2,5-dichlorophenyl)-4-methyl-5,6,7,8-tetrahydrocinnolin-5-one (246 mg) and aminoguanidine hydrochloride (98 mg) were added ethanol (5 ml) and concentrated hydrochloric acid (0.1 ml), and the mixture was stirred at 110° C. (bath temperature) for 1.5 hours. The reaction solution was cooled to room temperature, and the crystals were filtered and dried to give 7-(2,5-dichlorophenyl)-5-guanidinoimino-4-methyl-5,6,7,8-tetrahydrocinnoline hydrochloride (Compound 161) (215 mg) as gray white crystals.

mp256–258° C.

Elemental Analysis for $C_{16}H_{16}N_6Cl_2.2HCl$ Calcd. C,44.06; H,4.16; N,19.27. Found C,43.98; H,4.18; N,19.13.

$^1$H-NMR(DMSO-d$_6$) δ: 2.74 (3H, s), 2.93 (1H, dd), 3.15–3.70 (4H, m), 7.44 (1H, dd), 7.56 (1H, d), 7.77 (1H, d), 7.96 (4H, br), 9.28 (1H, s), 11.59 (1H, br).

Working Example 155
(Production of Compound 162)

To a solution of 7-(2-chloro-5-methylphenyl)-4-methyl-5,6,7,8-tetrahydroquinolin-5-one (1.1 g) and aminoguanidine hydrochloride (0.51 g) in ethanol (30 ml) were added concentrated hydrochloric acid (0.96 ml) and water (0.96 ml), and the mixture was refluxed for 5 hours. Under reduced pressure, the solvent was evaporated, and precipitated crystals were recrystallized from ethanol to give 7-(2-chloro-5-methylphenyl)-5-guanidinoimino-4-methyl-5,6,7,8-tetrahydroquinoline hydrochloride (Compound 162) (1.5 g) as colorless crystals.

mp240–243° C.

Elemental Analysis for $C_{18}H_{20}N_5Cl.2HCl.0.3H_2O$ Calcd. C,51.45; H,5.42; N,16.67. Found C,51.60; H,5.68; N,16.53.

$^1$H-NMR(DMSO-d$_6$) δ: 2.35 (3H,s), 2.77–3.04 (1H,m), 2.91 (3H,s), 3.15–3.33 (1H,m), 3.39–3.75 (3H,m), 7.16 (1H,d,J=8 Hz), 7.36 (1H,d,J=8 Hz), 7.48 (1H,s), 7.5–8.4 (4H,br), 7.86 (1H,d,J=6 Hz), 8.65 (1H,d,J=6 Hz), 11.44 (1H,s).

Working Example 156
(Production of Compound 163)

To a solution of 7-(2-fluoro-5-methylphenyl)-4-methyl-5,6,7,8-tetrahydroquinolin-5-one (1.1 g) and aminoguanidine hydrochloride (0.54 g) in ethanol (30 ml) were added concentrated hydrochloric acid (1.0 ml) and water (1.0 ml), and the mixture was refluxed for 7 hours. Under reduced pressure, the solvent was evaporated, and the residue was dissolved in water. The solution was washed with ethyl acetate, and to the aqueous layer was added sodium hydrogen carbonate solution to make the solution alkaline. The mixture was extracted with ethyl acetate, and the organic layer was washed with water and saturated brine, dried with magnesium sulfate and concentrated under reduced pressure. The residue was dissolved in ethanol, and to the solution was added 1N hydrochloric acid (10 ml). The mixture was concentrated, and precipitated crystals were recrystallized from ethanol to give 7-(2-fluoro-5-methylphenyl)-5-guanidinoimino-4-methyl-5,6,7,8-tetrahydroquinoline hydrochloride (Compound 163) (1.4 g) as colorless crystals.

mp230–235° C.

Elemental Analysis for $C_{18}H_{20}FN_5.2HCl$ Calcd. C,54.28; H,5.57; N,17.58. Found C,54.10; H,5.50; N,17.27.

$^1$H-NMR(DMSO-d$_6$) δ: 2.32 (3H,s), 2.75–3.02 (1H,m), 2.87 (3H,s), 3.21 (1H,dd,J=4,18 Hz), 3.31–3.63 (3H,m), 7.06–7.27 (2H,m), 7.4 (1H,d,J=7 Hz), 7.5–8.4 (4H,br), 7.84 (1H,d,J=6 Hz), 8.63 (1H,d,J=6 Hz), 11.54 (1H,s).

Working Example 157
(Production of Compound 164)

To a solution of 7-(5-chloro-2-methylphenyl)-4-methyl-5,6,7,8-tetrahydroquinolin-5-one (1.0 g) and aminoguanidine hydrochloride (0.46 g) in ethanol (30 ml) were added concentrated hydrochloric acid (0.9 ml) and water (0.9 ml), and the mixture was refluxed for 5 hours. Under reduced pressure, the solvent was evaporated, and the residue was dissolved in water. The mixture was washed with ethyl acetate, and to the aqueous layer was added sodium hydrogen carbonate solution to make it alkaline. The solution was extracted with ethyl acetate, and the organic layer was washed with water and saturated brine, and dried with magnesium sulfate. Under reduced pressure, the solution was concentrated, and the residue was dissolved in ethanol. To the solution was added 1N hydrochloric acid (10 ml), and the mixture was concentrated. Precipitated crystals were recrystallized from ethanol to give 7-(5-chloro-2- methylphenyl)-5-guanidinoimino-4-methyl-5,6,7,8-tetrahydroquinoline hydrochloride (Compound 164) (1.4 g) as colorless crystals.

mp215–220° C.

Elemental Analysis for $C_{18}H_{20}N_5Cl.2HCl.0.3H_2O$ Calcd. C,51.45; H,5.42; N,16.67. Found C,51.49; H,5.57; N,16.44.

$^1$H-NMR(DMSO-d$_6$) δ: 2.32 (3H, s), 2.68–3.03 (1H, m), 2.87 (3H, s), 3.13–3.65 (4H, m), 7.12–7.38 (2H, m), 7.54 (1H, s), 7.6–8.45 (4H, br), 7.87 (1H, d, J=6 Hz), 8.66 (1H, d, J=6 Hz), 11.48 (1H, s).

Working Example 158
(Production of Compound 165)

To a solution of 7-(5-fluoro-2-methylphenyl)-4-methyl-5,6,7,8-tetrahydroquinolin-5-one (1.1 g) and aminoguanidine hydrochloride (0.54 g) in ethanol (30 ml) were added concentrated hydrochloric acid (1.0 ml) and water (1.0 ml), and the mixture was refluxed for 6 hours. Under reduced pressure, the solvent was evaporated, and the residue was dissolved in water. The mixture was washed with ethyl acetate, and to the aqueous layer was added sodium hydrogen carbonate solution to make it alkaline. The solution was extracted with ethyl acetate, and the organic layer was washed with water and saturated brine, dried with magnesium sulfate and concentrated under reduced pressure. The residue was dissolved in ethanol, and to the mixture was added 1N hydrochloric acid (10 ml). The mixture was concentrated, and precipitated crystals were recrystallized from ethanol to give 7-(5-fluoro-2-methylphenyl)-5-guanidinoimino-4-methyl-5,6,7,8-tetrahydroquinoline hydrochloride (Compound 165) (1.4 g) as colorless crystals.

mp202–205° C.

Elemental Analysis for $C_{18}H_{20}N_5F.2HCl.0.5H_2O$ Calcd. C,53.08; H,5.69; N,17.19. Found C,53.33; H,5.87; N,16.94.

$^1$H-NMR(DMSO-d$_6$) δ: 2.31 (3H, s), 2.72–3.03 (1H, m), 2.90 (3H, s), 3.13–3.57 (4H, m), 6.93–7.06 (1H, m), 7.17–7.4 (2H, m), 7.5–8.4 (4H, br), 7.85 (1H, d, J=6 Hz), 8.65 (1H, d, J=6 Hz), 11.39 (1H, s).

Working Example 159
(Production of Compound 166)

To a solution of 7-(5-chloro-2-methoxyphenyl)-4-methyl-5,6,7,8-tetrahydroquinolin-5-one (1.0 g) and aminoguanidine hydrochloride (0.44 g) in ethanol (30 ml) were added a concentrated hydrochloric acid (0.83 ml) and water (0.83 ml), and the mixture was refluxed for 7 hours. Under reduced pressure, the solvent was evaporated, and the residue was dissolved in water. The solution was washed with ethyl acetate, and to the aqueous layer was added sodium hydrogen carbonate solution to make the solution alkaline. The mixture was extracted with ethyl acetate, and the organic layer was washed with water and saturated brine, dried with magnesium sulfate and concentrated under reduced pressure. The residue was dissolved in ethanol, and to the solution was added 1N hydrochloric acid (10 ml). The mixture was concentrated. And precipitated crystals were recrystallized from ethanol to give 7-(5-chloro-2-methoxyphenyl)-5-guanidinoimino-4-methyl-5,6,7,8-tetrahydroquinoline hydrochloride (Compound 166) (1.2 g) as colorless crystals.

mp205–209° C.

Elemental Analysis for $C_{18}H_{20}N_5OCl.2HCl.0.5H_2O$ Calcd. C,48.96; H,5.30; N,15.86. Found C,49.18; H,5.38; N,15.50.

$^1$H-NMR(DMSO-d$_6$) δ: 2.73–2.97 (1H,m), 2.85 (3H,s), 3.07–3.65 (4H,m), 3.82 (3H,s), 7.09 (1H,d,J=9 Hz), 7.35 (1H,dd,J=3,9 Hz), 7.47 (1H,d,J=3 Hz), 7.63–8.25 (4H,br), 7.79 (1H,d,J=6 Hz), 8.6 (1H,d,J=6 Hz), 11.38 (1H,s).

Working Example 160
(Production of Compound 167)

To a solution of 1M boron tribromide in dichloromethane (12.3 ml) was added dropwise a solution of 7-(5-chloro-2-methoxyphenyl)-4-methyl-5,6,7,8-tetrahydroquinolin-5-one (1.2 g) in dichloromethane (30 ml) at 0° C. The reaction solution was stirred at room temperature for 1.5 hours, and to the solution were added ice and sodium hydrogen carbonate solution. The mixture was extracted with ethyl acetate, and the organic layer was washed with water and saturated brine, and dried with sodium sulfate. Under reduced pressure, the solvent was evaporated to give 7-(5-chloro-2-hydroxyphenyl)-4-methyl-5,6,7,8-tetrahydroquinolin-5-one.

To 7-(5-chloro-2-hydroxyphenyl)-4-methyl-5,6,7,8-tetrahydroquinolin-5-one were added aminoguanidine hydrochloride (0.53 g), ethanol (30 ml), concentrated hydrochloric acid (1.0 ml) and water (1.0 ml), and the mixture was refluxed for 4 hours. Under reduced pressure, the solvent was evaporated, and the residue was dissolved in water. The solution was washed with ethyl acetate, and to the aqueous layer was added sodium hydrogen carbonate solution to make the solution alkaline. The solution was extracted with ethyl acetate, and the organic layer was washed with water and saturated brine, dried with magnesium sulfate and concentrated under reduced pressure. The residue was dissolved in ethanol, and to the solution was added 1N hydrochloric acid (10 ml). The mixture was concentrated, and precipitated crystals were recrystallized from ethanol to give 7-(5-chloro-2-hydroxyphenyl)-5-guanidinoimino-4-methyl-5,6,7,8-tetrahydroquinoline hydrochloride (Compound 167) (1.1 g) as colorless crystals.

mp202° C. (decomp.)

Elemental Analysis for $C_{17}H_{18}N_5OCl.2HCl.0.5H_2O$ Calcd. C,47.96; H,4.97; N,16.45. Found C,48.01; H,5.00; N,16.28.

$^1$H-NMR(DMSO-d$_6$) δ: 2.76–3.0 (1H,m), 2.89 (3H,s), 3.06–3.57 (4H,m), 6.96 (1H,d,J=8 Hz), 7.16 (1H,dd,J=2,8 Hz), 7.36 (1H,d,J=2 Hz), 7.4–8.5 (4H,br), 7.86 (1H,d,J=6 Hz), 8.64 (1H,d,J=6 Hz), 10.22 (1H,br), 11.42 (1H,s).

Working Example 161
(Production of Compound 168)

To a mixture of 7-(5-fluoro-2-methoxyphenyl)-4-methyl-5,6,7,8-tetrahydroquinolin-5-one hydrochloride (1.2 g) and aminoguanidine hydrochloride (0.477 g) were added ethanol (15 ml) and concentrated hydrochloric acid (0.1 ml), and the mixture was stirred at 110° C. (bath temperature) for 2 hours. The reaction solution was cooled to room temperature, and the resulting crystals were filtered and dried to give 7-(5-fluoro-2-methoxyphenyl)-5-guanidinoimino-4-methyl-5,6,7,8-tetrahydroquinoline hydrochloride (Compound 168) (1.4 g) as colorless crystals.

mp300° C. or more.

Elemental Analysis for $C_{18}H_{20}N_5OF.2HCl$ Calcd. C,52.18; H,5.35; N,16.90. Found C,51.98; H,5.22; N,16.90.

$^1$H-NMR(DMSO-d$_6$) δ: 2.77–2.92 (4H,m), 3.16 (1H,dd), 3.33–3.61 (3H,m), 3.81 (3H,s), 7.01–7.15 (2H,m), 7.28–7.33 (1H,m), 7.82 (1H,d), 7.91 (4H,br), 8.62 (1H,d), 11.42 (1H,br).

Working Example 162
(Production of Compound 169)

To a mixture of 7-(5-fluoro-2-hydroxyphenyl)-4-methyl-5,6,7,8-tetrahydroquinolin-5-one (0.75 g) and aminoguanidine hydrochloride (0.333 g) were added ethanol (8 ml) and concentrated hydrochloric acid (0. 5 ml), and the mixture was stirred at 110° C. (bath temperature) for 2.5 hours. The reaction solution was cooled to room temperature, and the resulting crystals were filtered and dried to give 7-(5-fluoro-2-hydroxyphenyl)-5-guanidinoimino-4-methyl-5,6,7,8-tetrahydroquinoline hydrochloride (Compound 169) (1 g) as pale yellow crystals.

mp264–266° C.

Elemental Analysis for $C_{17}H_{18}N_5OF \cdot 2HCl$ Calcd. C,51.01; H,5.04; N,17.50. Found C,50.71; H,5.06; N,17.59.

$^1$H-NMR(DMSO-$d_6$) δ: 2.78–2.92 (4H,m), 3.09–3.23 (1H,m), 3.26–3.60 (3H,m), 6.88–7.00 (2H,m), 7.17 (1H,dd), 7.80 (1H,d), 7.81 (4H,br), 8.62 (1H,d), 9.80 (1H,br), 11.24 (1H,s).

Working Example 163
(Production of Compound 170)

To a solution of 2-chloro-5-fluorotoluene (5.0 g) in acetic anhydride (40 ml) was added dropwise under ice-cooling concentrated sulfuric acid (40 ml), and then added dropwise a solution of anhydrous chromic acid (9.3 g) in acetic anhydride (40 ml) for 2 hours. The mixture was stirred at the same temperature for 1 hour, poured into ice-water and extracted with diethylether. The organic layer was washed with sodium carbonate solution, water and saturated brine and dried with magnesium sulfate. Under reduced pressure, the solvent was evaporated, and the residue was dissolved in tetrahydrofuran (10 ml). To the mixture were added water (4 ml) and concentrated sulfuric acid (4 ml), and the mixture was stirred at 100° C. for 30 minutes and cooled. The reaction solution was extracted with ethyl acetate. The organic layer was washed with sodium carbonate solution, water and saturated brine and dried with magnesium sulfate. Under reduced pressure, the solvent was evaporated to give the residue, which was subjected to silica gel column chromatography to give 2-chloro-5-fluorobenzaldehyde (1.6 g).

The similar reaction was repeated to give 2-chloro-5-fluorobenzaldehyde (1.2 g).

In water (55 ml) was dissolved sodium hydroxide (0.78 g), and to the mixture was added acetone (55 ml), and then added dropwise a solution of 2-chloro-5-fluorobenzaldehyde (2.8 g) in acetone (10 ml). The reaction solution was stirred at room temperature for 2 hours, and acetone was evaporated under reduced pressure. The residue was extracted with ethyl acetate, and the organic layer was washed with water and saturated brine, and concentrated under reduced pressure to give 4-(2-chloro-5-fluorophenyl)-3-buten-2-one (0.24 g).

To a solution of 20% sodium ethoxide in ethanol (0.43 g) was added at room temperature diethyl malonate (0.2 g), and then added little by little 4-(2-chloro-5-fluorophenyl)-3-buten-2-one (0.24 g). The mixture was stirred at room temperature for 30 minutes, refluxed for 2 hours and cooled, and the solvent was evaporated. The residue was dissolved in water, and the aqueous layer was washed with ethyl acetate and concentrated. To the reside was added 2M sodium hydroxide (0.7 ml), and the mixture was refluxed for 2 hours cooled. To the mixture was added 2.5M sulfuric acid (0.7 ml), and the mixture was refluxed for 15 minutes. The mixture was extracted with ethyl acetate, and the organic layer was washed with water and saturated brine and dried with magnesium sulfate. Under reduced pressure, the solvent was evaporated to give 5-(2-chloro-5-fluorophenyl)cyclohexane-1,3-dione (0.17 g) as oil.

A solution of 5-(5-chloro-2-fluorophenyl)cyclohexane-1,3-dione (0.17 g) and ammonium acetate (0.16 g) in ethanol (10 ml) was refluxed for 12 hours. Under reduced pressure, the solvent was evaporated, and to the residue was added ethyl acetate. The organic layer was washed with sodium carbonate solution, water and saturated brine and dried with magnesium sulfate. Under reduced pressure, the solvent was evaporated, and the residue was dissolved in ethanol (3.5 ml) and toluene (6 ml). To the mixture were added 3-oxobutylaldehydedimethylacetal (0.21 g) and powdery potassium hydroxide (34 mg), and the mixture was refluxed. To the mixture was added powdery potassium hydroxide (0.07 g) 30 minutes later; powdery potassium hydroxide (0.07 g) and 3-oxobutylaldehydedimethylacetal (17 mg) 1 hour later; and powdery potassium hydroxide (0.07 g) 1.5 hours later. Then, the mixture was stirred at the same temperature for 2 hours and cooled. Under reduced pressure, the solvent was evaporated, and the residue was extracted with ethyl acetate. The organic layer was washed with water and saturated brine and dried with magnesium sulfate. Under reduced pressure, ethyl acetate was evaporated, and the residue was subjected to silica gel column chromatography(ethyl acetate-hexane) to give 7-(2-chloro-5-fluorophenyl)-4-methyl-5,6,7,8-tetrahydroquinolin-5-one.

To a solution of 7-(2-chloro-5-fluorophenyl)-4-methyl-5,6,7,8-tetrahydroquinolin-5-one in ethanol (10 ml) were added aminoguanidine hydrochloride (0.041 g), concentrated hydrochloric acid (0.078 ml) and water (0.078 ml), and the mixture was refluxed for 4 hours. Under reduced pressure, the solvent was evaporated, and to the residue was added water. The aqueous layer was washed with ethyl acetate, and to the aqueous layer was added sodium hydrogen carbonate solution to make it alkaline. The solution was extracted with ethyl acetate, and the organic layer was washed with water and saturated brine, dried with magnesium sulfate, and concentrated under reduced pressure. The residue was dissolved in 1N hydrochloric acid (1 ml) and concentrated to give crystals, which were recrystallized from ethanol-ethyl acetate to give 7-(2-chloro-5-fluorophenyl)-5-guanidinoimino-4-methyl-5,6,7,8-tetrahydroquinoline hydrochloride (Compound 170) (0.05 g) as colorless crystals.

mp. 268° C. (decomp.).

$^1$H-NMR(DMSO-$d_6$) δ: 2.76–3.05 (1H, m), 2.84 (3H, s), 3.13–3.75 (4H, m), 7.0–8.4 (4H, br), 7.2–7.34 (1H, m), 7.52–7.66 (2H, m), 7.76 (1H, d, J=6 Hz), 8.6 (1H, d, J=6 Hz), 11.36 (1H, s).

Working Example 164
(Production of Compound 171)

To a solution of 7-(5-chloro-2-fluorophenyl)-4-methyl-5,6,7,8-tetrahydroquinolin-5-one hydrochloride (0.6 g) and aminoguanidine hydrochloride (0.233 g) in ethanol (10 ml) was added concentrated hydrochloric acid (0.1 ml), and the mixture was stirred at 110° C. (bath temperature) for 2 hours. The reaction solution was cooled to room temperature, and the crystals were filtered and dried to give 7-(5-chloro-2-fluorophenyl)-5-guanidinoimino-4-methyl-5,6,7,8-tetrahydroquinoline hydrochloride (Compound 171) (0.6 g) as colorless crystals.

mp 300° C. or more.

Elemental Analysis for $C_{16}H_{16}N_6ClF \cdot 2HCl$ Calcd. C,45.79; H,4.32; N,20.02. Found C,45.74; H,4.36; N,19.88.

$^1$H-NMR(DMSO-$d_6$) δ: 2.88 (3H, s), 2.95 (1H, dd), 3.23 (1H, dd), 3.39–3.70 (3H, m), 7.26–7.48 (2H, m), 7.70 (1H, dd), 7.85 (1H, d), 7.96 (4H, br), 8.63 (1H, d), 11.60 (1H, s).

Working Example 165
(Production of Compound 172)

To a mixture of 7-(3-chloro-5-methylthiophen-2-yl)-4-methyl-5,6,7,8-tetrahydroquinolin-5-one hydrochloride (1 g) and aminoguanidine hydrochloride (0.366 g) were added ethanol (12 ml) and concentrated hydrochloric acid (0.1 ml), and the mixture was stirred at 110° C. (bath temperature) for 3 hours. The reaction solution was cooled to room temperature, and the resulting crystals were filtered and dried to give 7-(3-chloro-5-methylthiophen-2-yl)-5-guanidinoimino-4-methyl-5,6,7,8-tetrahydroquinoline hydrochloride (Compound 172) (1.17 g) as colorless crystals.

mp198–200° C.

$^1$H-NMR(DMSO-d$_6$) δ: 2.42 (3H,s), 2.79 (1H,dd), 2.85 (3H,s), 3.26 (1H,dd), 3.40–3.46 (2H,m), 3.64–3.78 (1H,m), 6.80 (1H,s), 7.80 (1H,d), 8.91 (4H,br), 8.62 (1H,d), 11.46 (1H,br).

Working Example 166
(Production of Compound 173)

To a mixture of 7-(2-chloro-5-methylphenyl)-4-methyl-5,6,7,8-tetrahydrocinnolin-5-one (0.4 g) and aminoguanidine hydrochloride (0.164 g) were added ethanol (8 ml) and concentrated hydrochloric acid (0.15 ml), and the mixture was stirred at 110° C. (bath temperature) for 1.5 hours. The reaction solution was cooled to room temperature, and the resulting crystals were filtered and dried to give 7-(2-chloro-5-methylphenyl)-5-guanidinoimino-4-methyl-5,6,7,8-tetrahydrocinnoline hydrochloride (Compound 173) (0.261 g) as blue white crystals.

mp240–242° C.

$^1$H-NMR(DMSO-d$_6$) δ: 2.34 (3H,s), 2.76 (3H,s), 2.88 (1H,dd), 3.13–3.66 (4H,m), 7.16 (1H,d), 7.37 (1H,d), 7.49 (1H,s), 7.97 (4H,br), 9.30 (1H,s), 11.57 (1H,br).

Working Example 167
(Production of Compound 174)

To a solution of 7-(5-fluoro-2-methylphenyl)-4-methyl-5,6,7,8-tetrahydrocinnolin-5-one (0.265 g) and aminoguanidine hydrochloride (0.12 g) in ethanol (3 ml) was added concentrated hydrochloric acid (0.15 ml), and the mixture was stirred at 110° C. (bath temperature) for 3.5 hours. The reaction solution was cooled to room temperature, and the crystals were filtered and dried to give 7-(5-fluoro-2-methylphenyl)-5-guanidinoimino-4-methyl-5,6,7,8-tetrahydrocinnoline hydrochloride (Compound 174) (0.33 g) as blue gray crystals.

mp240° C. (decomp.).

$^1$H-NMR(DMSO-d$_6$) δ: 2.30 (3H, s), 2.73–2.90 (4H, m), 3.17–3.50 (4H, m), 6.96–7.06 (1H, m), 7.21–7.36 (2H, m), 8.02 (4H, br), 9.35 (1H, s), 11.66 (1H, s).

Working Example 168
(Production of Compound 175)

To a mixture of 7-(5-chloro-2-fluorophenyl)-4-methyl-5,6,7,8-tetrahydrocinnolin-5-one (0.33 g) and aminoguanidine hydrochloride (0.133 g) in ethanol (4 ml) was added concentrated hydrochloric acid (0.1 ml), and the mixture was stirred at 110° C. (bath) for 2 hours. The reaction solution was cooled to room temperature, and the crystals were filtered and dried to give 7-(5-chloro-2-fluorophenyl)-5-guanidinoimino-4-methyl-5,6,7,8-tetrahydrocinnoline hydrochloride (Compound 175) (0.345 g) as blue gray crystals.

mp 300° C. or more.

Elemental Analysis for $C_{16}H_{16}N_6ClF \cdot 2HCl$ Calcd. C,45.79; H,4.32; N,20.02. Found C,45.74; H,4.36; N,19.88.

$^1$H-NMR(DMSO-d$_6$) δ: 2.77 (3H, s), 2.96 (1H, dd), 3.17–3.60 (4H, m), 7.27–7.48 (2H, m), 7.71 (1H, dd), 8.03 (4H, br), 9.33 (1H, s), 11.78 (1H, br).

Working Example 169
(Production of Compound 176)

To a solution of 6-(2,5-dichlorophenyl)-3-methyl-4,5,6,7-tetrahydroindazol-4-one hydrochloride (1.1 g), aminoguanidine hydrochloride (0.49 g) in ethanol (30 ml) were added concentrated hydrochloric acid (0.9 ml) and water (0.9 ml), and the mixture was refluxed for 5 hours. Under reduced pressure, the solvent was evaporated, and the residue was dissolved in water. The solution was washed with ethyl acetate, and the aqueous layer was concentrated under reduced pressure. Precipitated crystals were recrystallized from ethanol-water to give 6-(2,5-dichlorophenyl)-4-guanidinoimino-3-methyl-4,5,6,7-tetrahydroindazole hydrochloride (Compound 176) (1.2 g) as colorless crystals.

mp287° C. (decomp.).

$^1$H-NMR(DMSO-d$_6$) δ: 2.35–3.22 (4H,m), 2.48 (3H,s), 3.40–3.68 (1H,m), 6.6–8.4 (4H,br), 7.39 (1H,dd,J=2,8 Hz), 7.54 (1H,d,J=8 Hz), 7.72 (1H,d,J=2 Hz), 10.9 (1H,s).

For example, Na—H exchange inhibitor (e.g., a pharmaceutical composition for treating ischemic cardiac disease, etc. such as myocardial infarction, arrhythmia, etc., etc.) of the present invention, which comprises a compound of the formula (I) or a salt thereof as an active ingredient, can be produced according to the following formulations:

Formulation Example 1

Capsule

| | |
|---|---|
| (1) Compound 64 obtained in Working Example 63 | 30 mg |
| (2) lactose | 60 mg |
| (3) fine crystalline cellulose | 9 mg |
| (4) magnesium stearate | 1 mg |
| 1 capsule | 100 mg |

(1), (2), (3) and ½ of (4) are mixed and then granulated. To the granules is added the remainder of (4), and the whole is filled into a gelatin capsule.

Formulation Example 2

Tablet

| | |
|---|---|
| (1) Compound 64 obtained in Working Example 63 | 30 mg |
| (2) lactose | 48 mg |
| (3) corn starch | 18 mg |
| (3) fine crystalline cellulose | 3.5 mg |
| (5) magnesium stearate | 0.5 mg |
| 1 tablet | 100 mg |

(1), (2), (3), ⅔ of (4) and ½ of (5) are mixed and then granulated. To the granules are added the remainders of (4) and (5), followed by subjecting the mixture to compression molding.

Formulation Example 3

Compound 64 obtained in Working Example 63 (500 mg) is dissolved in distilled water for injection (Japanese Pharmacopoeia) 50 ml, and to the solution is added the distilled water to make the whole volume 100 ml. The solution is filtered under sterile conditions. Each 1 ml of the solution is filled into a vial for injection under sterile conditions, subjected to freeze-drying and kept airtight.

Formulation Example 4

Compound 64 obtained in Working Example 63 (5 g) is dissolved in distilled water for injection (Japanese Pharmacopoeia) 50 ml, and to the solution is added the distilled water to make the whole volume 100 ml. The solution is filtered under sterile conditions. Each 1 ml of the solution is filled into a vial for injection under sterile conditions, subjected to freeze-drying and kept airtight.

Test Example 1

Male Wistar rats (350–450 g) were anesthetized with sodium pentobarbital (50 mg/kg, i.p.). Using a disposable syringe pre-filled with 1.5 ml of 3.8% citric acid solution, 8.5 ml of blood was collected from the abdominal aorta. The blood was centrifuged at 3000 rpm for 5 seconds to obtain platelet rich plasma (PRP). The number of platelets in the PRP was counted by an automatic hemocytometer (Sysmex 2500, TOA Medical Electronics). The PRP was diluted with physiological saline to make the concentration of $40 \times 10^4$ platelets per 1 µl. A platelet aggregometer (Hematoracer, Niko Bioscience) was used for measurement of the platelet swelling. 200 µl of the PRP was poured into a cuvette and 600 µl of sodium propionate solution (Na propionate 135, glucose 10, Hepes 20, $CaCl_2$ 1, $MgCl_2$ 1; Units: mM; pH6.7) was added while stirring at 37° C. The change in the light transmittance of PRP which was an indicator of the platelet swelling was recorded on a plotter. The test compound was added 3 minutes before addition of the sodium propionate solution. The test compounds were dissolved in dimethyl-sulfoxide (DMSO). The final concentration of DMSO was adjusted to 1%. The values obtained 1 minute after addition of the sodium propionate solution were subjected to analysis. The rate of inhibition of the test compounds on the increase of the light transmittance was calculated designating the difference obtained between the treatments with 1% DMSO and HOE-642 ($10^{-5}$M), which is represented by the following formula and a known Na—H exchange inhibitor, as 100%. results are shown as percentage inhibition in Table 1. From these results, it is clear that the compound of the present invention inhibit Na—H exchange.

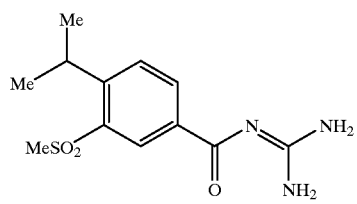

HOE-642

TABLE 1

| Compound No. | n | Inhibition Rate (%) [$10^{-7}$ M] |
|---|---|---|
| 6 | 5 | 86 |
| 21 | 3 | 72 |
| 27 | 3 | 76 |
| 48 | 5 | 70 |
| 59 | 3 | 72 |
| 61 | 3 | 78 |
| 64 | 3 | 86 |
| 68 | 3 | 70 |
| 70 | 3 | 81 |
| 73 | 3 | 76 |
| 74 | 3 | 98 |
| 79 | 3 | 77 |
| 80 | 3 | 75 |
| 93 | 3 | 69 |
| 109 | 5 | 91 |
| 113 | 3 | 100 |

TABLE 1-continued

| Compound No. | n | Inhibition Rate (%) [$10^{-7}$ M] |
|---|---|---|
| 119 | 3 | 100 |
| 123 | 3 | 81 |
| 127 | 3 | 98 |
| 128 | 3 | 78 |
| 129 | 3 | 80 |
| 131 | 3 | 88 |
| 133 | 3 | 87 |
| 134 | 3 | 83 |

Industrial Applicability

The present invention is to provide Na—H exchange inhibitor which is useful for treating ischemic cardiac disease, etc. such as myocardial infarction, arrhythmia, etc.

What is claimed is:

1. A compound of the formula:

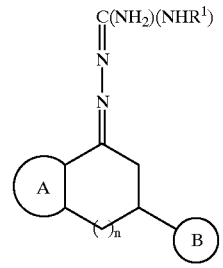

wherein the ring A is a 5- to 6-membered aromatic heterocyclic ring selected from the group consisting of pyridine, pyridazine, pyrrole, pyrazole, furan, thiophene, isoxazole and pyrimidine, wherein a ring nitrogen atom may be oxidized and wherein said ring is unsubstituted or substituted with 1 to 4 substituents selected from the group consisting of
  (1) a halogen atom,
  (2) a hydroxy group,
  (3) a nitro group,
  (4) a cyano group,
  (5) a $C_{1-6}$ alkyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
  (6) a $C_{2-6}$ alkenyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
  (7) a $C_{2-6}$ alkynyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
  (8) a $C_{7-10}$ aralkyl group optionally substituted with 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
  (9) a $C_{1-6}$ alkoxy group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,

(10) a $C_{1-6}$ alkylthio group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,

(11) an amino group optionally substituted with 1 to 2 substituents selected from the group consisting of $C_{1-6}$ alkyl, $C_{1-6}$ alkoxy, halogeno $C_{1-6}$ alkyl, $C_{3-6}$ cycloalkyl, hydroxy group, carbamoyl, phenyl, phenyl-$C_{1-6}$ alkyl, $C_{1-6}$ alkanoyl, $C_{3-6}$ cycloalkyl-carbonyl, benzoyl, phenyl-$C_{2-6}$ alkanoyl, $C_{1-6}$ alkoxy-carbonyl, phenoxycarbonyl, phenyl-$C_{1-6}$ alkoxy-carbonyl, $C_{1-6}$ alkylsulfinyl, $C_{3-6}$ cycloalkylsulfinyl, phenylsulfinyl, $C_{1-6}$ alkylsulfonyl, $C_{3-6}$ cycloalkylsulfonyl and $C_{1-6}$ alkoxysulfonyl, or a cyclic amino group selected from the group consisting of pyrrolidino, piperidino, morpholino and thiomorpholino, each of the optionally substituted amino groups and cyclic amino groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(12) an optionally esterified or amidated carboxyl group selected from the group consisting of a $C_{1-6}$ alkoxy-carbonyl group, a $C_{3-6}$ cycloalkoxy-carbonyl, a phenyl-$C_{1-6}$ alkoxy-carbonyl, a nitroxy-$C_{1-6}$ alkoxy-carbonyl, a carbamoyl, an N-mono-$C_{1-6}$ alkylcarbamoyl, an N,N-di-$C_{1-6}$ alkylcarbamoyl, a $C_{3-6}$ cycloalkyl-carbamoyl, a phenyl-$C_{1-6}$ alkyl-carbamoyl, a nitroxy-$C_{1-6}$ alkylamino-carbonyl, a cyclic aminocarbonyl and an anilinocarbonyl, each of the optionally esterified or amidated carboxyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(13) an optionally substituted sulfonyl group selected from the group consisting of $C_{1-6}$ alkylsulfonyl, a $C_{3-6}$ cycloalkylsulfonyl, a phenyl-$C_{1-6}$ alkylsulfonyl, a lower ($C_{1-6}$) alkoxysulfonyl, a $C_{3-6}$ cycloalkyloxysulfonyl, a phenyl-$C_{1-6}$ alkoxysulfonyl, a sulfamoyl, a $C_{1-6}$ alkylaminosulfonyl, a $C_{3-6}$ cycloalkylaminosulfonyl, a phenyl-$C_{1-6}$ alkylaminosulfonyl, morpholinosulfonyl, piperidinosulfonyl, pyrrolidinosulfonyl, thiomorpholinosulfonyl, a nitroxy-$C_{1-6}$ alkylamino-sulfonyl and an anilinosulfonyl, each of the optionally sulfonyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(14) an optionally substituted acyl group selected from the group consisting of a $C_{1-6}$ alkyl-carbonyl, a $C_{3-6}$ cycloalkyl-carbonyl, benzoyl, a $C_{1-6}$ alkylsulfinyl, a $C_{3-6}$ cycloalkylsulfinyl, phenylsulfinyl, a $C_{1-6}$ alkylsulfonyl, a $C_{3-6}$ cycloalkylsulfonyl and phenylsulfonyl, each of the optionally substituted acyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group, hydroxy and a halogeno $C_{1-6}$ alkoxy group, and

(15) a phenyl group an optionally substituted with 1 to 3 substituents selected from the group consisting of a halogen atom, hydroxy group, nitro group, cyano group, a $C_{1-6}$ alkyl group, halogeno $C_{1-6}$ alkyl group, a $C_{1-6}$ alkoxy group and halogeno $C_{1-6}$ alkoxy group, or two adjoining two substituents forming a divalent hydrocarbon group, said divalent hydrocarbon group selected from the group consisting of —CH=CH—CH=CH—, —CH=CH—CH$_2$—CH$_2$—, —CH$_2$—CH=CH—CH$_2$—, —CH=CH—CH$_2$— and —(CH$_2$)$_a$—, wherein a is 3 or 4, said divalent hydrocarbon group being optionally substituted with 1 to 3 substituents selected from the group consisting of a $C_{1-6}$ alkyl group, a halogen atom, a $C_{1-6}$ alkoxy group, a halogeno $C_{1-6}$ alkyl group, a halogeno $C_{1-6}$ alkoxy group, a $C_{1-6}$ alkoxy-carbonyl group, a cyano group, a nitro group and a hydroxy group;

the ring B is a 5- to 6-membered aromatic homocyclic ring or a 5- to 6- membered aromatic heterocyclic ring selected from the group consisting of pyridine, pyrrole, furan, thiophene and benzene, wherein a ring nitrogen atom may be oxidized and said ring being unsubstituted or substituted with 1 to 4 substituents selected from the group consisting of (1) a halogen atom,
(2) a hydroxy group,
(3) a nitro group,
(4) a cyano group,
(5) a $C_{1-6}$ alkyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(6) a $C_{2-6}$ alkenyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(7) a $C_{2-6}$ alkynyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(8) a $C_{7-10}$ aralkyl group optionally substituted with 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
(9) a $C_{1-6}$ alkoxy group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(10) a $C_{1-6}$ alkylthio group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(11) an amino group optionally substituted with 1 to 2 substituents selected from the group consisting of $C_{1-6}$ alkyl, $C_{1-6}$ alkoxy, halogeno $C_{1-6}$ alkyl, $C_{3-6}$ cycloalkyl, hydroxy group, carbamoyl, phenyl, phenyl-$C_{1-6}$ alkyl, $C_{1-6}$ alkanoyl, $C_{3-6}$ cycloalkyl-carbonyl, benzoyl, phenyl-$C_{2-6}$ alkanoyl, $C_{1-6}$ alkoxy-carbonyl, phenoxycarbonyl, phenyl-$C_{1-6}$ alkoxy-carbonyl, $C_{1-6}$ alkylsulfinyl, $C_{3-6}$ cycloalkylsulfinyl, phenylsulfinyl, $C_{1-6}$ alkylsulfonyl, $C_{3-6}$ cycloalkylsulfonyl and $C_{1-6}$ alkoxysulfonyl, or a cyclic amino group selected from the group consisting of pyrrolidino, piperidino, morpholino and thiomorpholino, each of the optionally substituted amino groups and cyclic amino groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(12) an optionally esterified or amidated carboxyl group selected from the group consisting of a $C_{1-6}$ alkoxy-carbonyl group, a $C_{3-6}$ cycloalkoxy-carbonyl, a phenyl-$C_{1-6}$ alkoxy-carbonyl, a nitroxy-$C_{1-6}$ alkoxy-carbonyl, a carbamoyl, an N-mono-$C_{1-6}$ alkylcarbamoyl, an N,N-di-$C_{1-6}$ alkylcarbamoyl, a $C_{3-6}$ cycloalkyl-carbamoyl, a phenyl-$C_{1-6}$ alkyl-carbamoyl, a nitroxy-$C_{1-6}$ alkylamino-carbonyl, a cyclic aminocarbonyl and an anilinocarbonyl, each of the optionally esterified or amidated carboxyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(13) an optionally substituted sulfonyl group selected from the group consisting of $C_{1-6}$ alkylsulfonyl, a $C_{3-6}$ cycloalkylsulfonyl, a phenyl-$C_{1-6}$ alkylsulfonyl, a lower ($C_{1-6}$) alkoxysulfonyl, a $C_{3-6}$ cycloalkyloxysulfonyl, a phenyl-$C_{1-6}$ alkoxysulfonyl, a sulfamoyl, a $C_{1-6}$ alkylaminosulfonyl, a $C_{3-6}$ cycloalkylaminosulfonyl, a phenyl-$C_{1-6}$ alkylaminosulfonyl, morpholinosulfonyl, piperidinosulfonyl, pyrrolidinosulfonyl, thiomorpholinosulfonyl, a nitroxy-$C_{1-6}$ alkylamino-sulfonyl and an anilinosulfonyl, each of the optionally sulfonyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(14) an optionally substituted acyl group selected from the group consisting of a $C_{1-6}$ alkyl-carbonyl, a $C_{3-6}$ cycloalkyl-carbonyl, benzoyl, a $C_{1-6}$ alkylsulfinyl, a $C_{3-6}$ cycloalkylsulfinyl, phenylsulfinyl, a $C_{1-6}$ alkylsulfonyl, a $C_{3-6}$ cycloalkylsulfonyl and phenylsulfonyl, each of the optionally acyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group, hydroxy and a halogeno $C_{1-6}$ alkoxy group, and

(15) a phenyl group an optionally substituted with 1 to 3 substituents selected from the group consisting of a halogen atom, hydroxy group, nitro group, cyano group, a $C_{1-6}$ alkyl group, halogeno $C_{1-6}$ alkyl group, a $C_{1-6}$ alkoxy group and halogeno $C_{1-6}$ alkoxy group, or two adjoining substituents forming a divalent hydrocarbon group selected from the group consisting of —CH=CH—CH=CH—, —CH=CH—CH$_2$—CH$_2$—, —CH$_2$—CH=CH—CH$_2$—, —CH=CH—CH$_2$— and —(CH$_2$)$_a$— wherein a is 3 or 4, said divalent hydrocarbon group is optionally substituted with 1 to 3 substituents selected from the group consisting of a $C_{1-6}$ alkyl group, a halogen atom, a $C_{1-6}$ alkoxy group, a halogeno $C_{1-6}$ alkyl group, a halogeno $C_{1-6}$ alkoxy group, a $C_{1-6}$ alkoxy-carbonyl group, a cyano group, a nitro group and a hydroxy group;

$R^1$ is a hydrogen atom, a hydroxy group or a $C_{1-6}$ alkyl group, and n is 0 or 1, or a salt thereof.

2. A pro-drug of a compound of claim 1 or a salt thereof.

3. A compound of claim 1, of the formula:

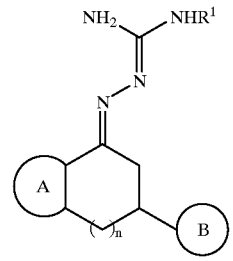

wherein A, B, $R^1$ and n are as defined in claim 1, or a salt thereof.

4. A compound of claim 1, of the formula:

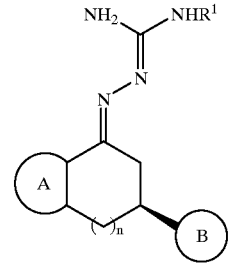

wherein A, B, $R^1$ and n are as defined in claim 1, or a salt thereof.

5. A compound according to claim 1, wherein $R^1$ is a hydrogen atom.

6. A compound according to claim 1, wherein n is 1.

7. (S)-(−)-7-(2,5-dichlorothiophen-3-yl)-5-guanidinoimino-4-methyl-5,6,7,8-tetrahydroquinoline or a salt thereof.

8. (±)-7-(2,5-dichlorothiophen-3-yl)-5-guanidinoimino-4-methyl-5,6,7,8-tetrahydroquinoline or a salt thereof.

9. (S)-(−)-7-(2-chlorophenyl)-5-guanidinoimino-4-methyl-5,6,7,8-tetrahydroquinoline or a salt thereof.

10. (±)-7-(2-chlorophenyl)-5-guanidinoimino-4-methyl-5,6,7,8-tetrahydroquinoline or a salt thereof.

11. (±)-7-(2,5-dichlorophenyl)-5-guanidinoimino-4-methyl-5,6,7,8-tetrahydrocinnoline or a salt thereof.

12. (±)-7-(5-chloro-2-methylphenyl)-5-guanidinoimino-4-methyl-5,6,7,8-tetrahydroquinoline or a salt thereof.

13. (±)-7-(5-fluoro-2-methylphenyl)-5-guanidinoimino-4-methyl-5,6,7,8-tetrahydroquinoline or a salt thereof.

14. (±)-7-(2-chloro-5-fluorophenyl)-5-guanidinoimino-4-methyl-5,6,7,8-tetrahydroquinoline or a salt thereof.

15. (±)-7-(5-chloro-2-fluorophenyl)-5-guanidinoimino-4-methyl-5,6,7,8-tetrahydroquinoline or a salt thereof.

16. (±)-7-(5-fluoro-2-methylphenyl)-5-guanidinoimino-4-methyl-5,6,7,8-tetrahydrocinnoline or a salt thereof.

17. (±)-7-(5-chloro-2-fluorophenyl)-5-guanidinoimino-4-methyl-5,6,7,8-tetrahydrocinnoline or a salt thereof.

18. A pharmaceutical composition comprising
    a compound as claimed in claim 1 or a salt thereof, and
    a pharmaceutically acceptable excipient, carrier or diluent.

19. A method for inhibiting Na—H exchange in a mammal which comprises administering to said mammal an effective amount of the compound as claimed in claim 1 or a salt thereof.

20. A method for treating ischemic cardiac disease in a mammal comprising administering to said mammal an effective amount of a compound of claim 1 or a salt thereof.

21. A method for treating cardiac insufficiency in a mammal comprising administering to said mammal an effective amount of a compound of claim 1 or a salt thereof.

22. A method for producing a compound of the formula (I):

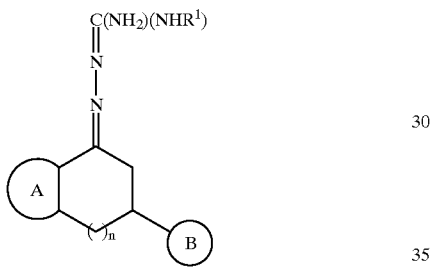

wherein the ring A is a 5- to 6-membered aromatic heterocyclic ring selected from the group consisting of pyridine, pyridazine, pyrrole, pyrazole, furan, thiophene, isoxazole and pyrimidine, wherein a ring nitrogen atom may be oxidized and wherein said ring is unsubstituted or substituted with 1 to 4 substituents selected from the group consisting of (1) a halogen atom,
(2) a hydroxy group,
(3) a nitro group,
(4) a cyano group,
(5) a $C_{1-6}$ alkyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(6) a $C_{2-6}$ alkenyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(7) a $C_{2-6}$ alkynyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(8) a $C_{7-10}$ aralkyl group optionally substituted with 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
(9) a $C_{1-6}$ alkoxy group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(10) a $C_{1-6}$ alkylthio group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(11) an amino group optionally substituted with 1 to 2 substituents selected from the group consisting of $C_{1-6}$ alkyl, $C_{1-6}$ alkoxy, halogeno $C_{1-6}$ alkyl, $C_{3-6}$ cycloalkyl, hydroxy group, carbamoyl, phenyl, phenyl-$C_{1-6}$ alkyl, $C_{1-6}$ alkanoyl, $C_{3-6}$ cycloalkyl-carbonyl, benzoyl, phenyl-$C_{2-6}$ alkanoyl, $C_{1-6}$ alkoxy-carbonyl, phenoxycarbonyl, phenyl-$C_{1-6}$ alkoxy-carbonyl, $C_{1-6}$ alkylsulfinyl, $C_{3-6}$ cycloalkylsulfinyl, phenylsulfinyl, $C_{1-6}$ alkylsulfonyl, $C_{3-6}$ cycloalkylsulfonyl and $C1-6$ alkoxysulfonyl,
or a cyclic amino group selected from the group consisting of pyrrolidino, piperidino, morpholino and thiomorpholino,
each of the optionally substituted amino groups and cyclic amino groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
(12) an optionally esterified or amidated carboxyl group selected from the group consisting of a $C_{1-6}$ alkoxy-carbonyl group, a $C_{3-6}$ cycloalkoxy-carbonyl, a phenyl-$C_{1-6}$ alkoxy-carbonyl, a nitroxy-$C_{1-6}$ alkoxy-carbonyl, a carbamoyl, a N-mono-$C_{1-6}$ alkylcarbamoyl, a N,N-di-$C_{1-6}$ alkylcarbamoyl, a $C_{3-6}$ cycloalkyl-carbamoyl, a phenyl-$C_{1-6}$ alkyl-carbamoyl, a nitroxy-$C_{1-6}$ alkylamino-carbonyl, a cyclic aminocarbonyl and an anilinocarbonyl,
each of the optionally esterified or amidated carboxyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
(13) an optionally substituted sulfonyl group selected from the group consisting of $C_{1-6}$ alkylsulfonyl, a $C_{3-6}$ cycloalkylsulfonyl, a phenyl-$C_{1-6}$ alkylsulfonyl, a lower ($C_{1-6}$) alkoxysulfonyl, a $C_{3-6}$ cycloalkyloxysulfonyl, a phenyl-$C_{1-6}$ alkoxysulfonyl, a sulfamoyl, a $C_{1-6}$ alkylaminosulfonyl, a $C_{3-6}$ cycloalkylaminosulfonyl, a phenyl-$C_{1-6}$ alkylaminosulfonyl, morpholinosulfonyl, piperidinosulfonyl, pyrrolidinosulfonyl, thiomorpholinosulfonyl, a nitroxy-$C_{1-6}$ alkylamino-sulfonyl and an anilinosulfonyl,
each of the optionally sulfonyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
(14) an optionally substituted acyl group selected from the group consisting of a $C_{1-6}$ alkyl-carbonyl, a $C_{3-6}$ cycloalkyl-carbonyl, benzoyl, a $C_{1-6}$ alkylsulfinyl, a $C_{3-6}$ cycloalkylsulfinyl, phenylsulfinyl, a $C_{1-6}$ alkylsulfonyl, a $C_{3-6}$ cycloalkylsulfonyl and phenylsulfonyl, each of the optionally substituted acyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group, hydroxy and a halogeno $C_{1-6}$ alkoxy group, and

(15) a phenyl group an optionally substituted with 1 to 3 substituents selected from the group consisting of a halogen atom, hydroxy group, nitro group, cyano group, a $C_{1-6}$ alkyl group, halogeno $C_{1-6}$ alkyl group, a $C_{1-6}$ alkoxy group and halogeno $C_{1-6}$ alkoxy group, or two adjoining two substituents forming a divalent hydrocarbon group, said divalent hydrocarbon group selected from the group consisting of —CH=CH—CH=CH—, —CH=CH—CH$_2$—CH$_2$—, —CH$_2$—CH=CH—CH$_2$—, —CH=CH—CH$_2$— and —(CH$_2$)$_a$—, wherein a is 3 or 4, said divalent hydrocarbon group being optionally substituted with 1 to 3 substituents selected from the group consisting of a $C_{1-6}$ alkyl group, a halogen atom, a $C_{1-6}$ alkoxy group, a halogeno $C_{1-6}$ alkyl group, a halogeno $C_{1-6}$ alkoxy group, a $C_{1-6}$ alkoxy-carbonyl group, a cyano group, a nitro group and a hydroxy group;

the ring B is a 5- to 6-membered aromatic homocyclic ring or a 5- to 6-membered aromatic heterocyclic ring selected from the group consisting of pyridine, pyrrole, furan, thiophene and benzene, wherein a ring nitrogen atom may be oxidized and said ring being unsubstituted or substituted with 1 to 4 substituents selected from the group consisting of (1) a halogen atom,
(2) a hydroxy group,
(3) a nitro group,
(4) a cyano group,
(5) a $C_{1-6}$ alkyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(6) a $C_{2-6}$ alkenyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(7) a $C_{2-6}$ alkynyl group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(8) a $C_{7-10}$ aralkyl group optionally substituted with 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,
(9) a $C_{1-6}$ alkoxy group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(10) a $C_{1-6}$ alkylthio group optionally substituted with 1 to 3 substituents selected from the group consisting of a halogen atom, a hydroxy group, a nitro group, a cyano group, a $C_{1-6}$ alkoxy group and a halogeno $C_{1-6}$ alkoxy group,
(11) an amino group optionally substituted with 1 to 2 substituents selected from the group consisting of $C_{1-6}$ alkyl, $C_{1-6}$ alkoxy, halogeno $C_{1-6}$ alkyl, $C_{3-6}$ cycloalkyl, hydroxy group, carbamoyl, phenyl, phenyl-$C_{1-6}$ alkyl, $C_{1-6}$ alkanoyl, $C_{3-6}$ cycloalkyl-carbonyl, benzoyl, phenyl-$C_{2-6}$ alkanoyl, $C_{1-6}$ alkoxy-carbonyl, phenoxycarbonyl, phenyl-$C_{1-6}$ alkoxy-carbonyl, $C_{1-6}$ alkylsulfinyl, $C_{3-6}$ cycloalkylsulfinyl, phenylsulfinyl, $C_{1-6}$ alkylsulfonyl, $C_{3-6}$ cycloalkylsulfonyl and $C_{1-6}$ alkoxysulfonyl, or a cyclic amino group selected from the group consisting of pyrrolidino, piperidino, morpholino and thiomorpholino, each of the optionally substituted amino groups and cyclic amino groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(12) an optionally esterified or amidated carboxyl group selected from the group consisting of a $C_{1-6}$ alkoxy-carbonyl group, a $C_{3-6}$ cycloalkoxy-carbonyl, a phenyl-$C_{1-6}$ alkoxy-carbonyl, a nitroxy-$C_{1-6}$ alkoxy-carbonyl, a carbamoyl, a N-mono-$C_{1-6}$ alkylcarbamoyl, a N,N-di-$C_{1-6}$ alkylcarbamoyl, a $C_{3-6}$ cycloalkyl-carbamoyl, a phenyl-$C_{1-6}$ alkyl-carbamoyl, a nitroxy-$C_{1-6}$ alkylamino-carbonyl, a cyclic aminocarbonyl and an anilinocarbonyl, each of the optionally esterified or amidated carboxyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(13) an optionally substituted sulfonyl group selected from the group consisting of $C_{1-6}$ alkylsulfonyl, a $C_{3-6}$ cycloalkylsulfonyl, a phenyl-$C_{1-6}$ alkylsulfonyl, a lower ($C_{1-6}$) alkoxysulfonyl, a $C_{3-6}$ cycloalkyloxysulfonyl, a phenyl-$C_{1-6}$ alkoxysulfonyl, a sulfamoyl, a $C_{1-6}$ alkylaminosulfonyl, a $C_{3-6}$ cycloalkylaminosulfonyl, a phenyl-$C_{1-6}$ alkylaminosulfonyl, morpholinosulfonyl, piperidinosulfonyl, pyrrolidinosulfonyl, thiomorpholinosulfonyl, a nitroxy-$C_{1-6}$ alkylamino-sulfonyl and an anilinosulfonyl, each of the optionally sulfonyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group and a halogeno $C_{1-6}$ alkoxy group,

(14) an optionally substituted acyl group selected from the group consisting of a $C_{1-6}$ alkyl-carbonyl, a $C_{3-6}$ cycloalkyl-carbonyl, benzoyl, a $C_{1-6}$ alkylsulfinyl, a $C_{3-6}$ cycloalkylsulfinyl, phenylsulfinyl, a $C_{1-6}$ alkylsulfonyl, a $C_{3-6}$ cycloalkylsulfonyl and phenylsulfonyl, each of the optionally acyl groups optionally having 1 to 3 substituents selected from the group consisting of a halogen atom, a hydroxy group, a nitro group, a cyano group, a $C_{1-6}$ alkyl group, a halogeno $C_{1-6}$ alkyl group, a $C_{1-6}$ alkoxy group, hydroxy and a halogeno $C_{1-6}$ alkoxy group, and

(15) a phenyl group an optionally substituted with 1 to 3 substituents selected from the group consisting of a halogen atom, hydroxy group, nitro group, cyano group, a $C_{1-6}$ alkyl group, halogeno $C_{1-6}$ alkyl group, a $C_{1-6}$ alkoxy group and halogeno $C_{1-6}$ alkoxy group, or two adjoining substituents forming a divalent hydrocarbon group selected from the group consisting of —CH=CH—CH=CH—, —CH=CH—CH$_2$—CH$_2$—, —CH$_2$—CH=CH—CH$_2$—, —CH=CH—CH$_2$— and —(CH$_2$)$_a$—
wherein a is 3 or 4, said divalent hydrocarbon group is optionally substituted with 1 to 3 substituents selected from the group consisting of a $C_{1-6}$ alkyl group, a halogen atom, a $C_{1-6}$ alkoxy group, a halogeno $C_{1-6}$ alkyl group, a halogeno $C_{1-6}$ alkoxy group, a $C_{1-6}$ alkoxy-carbonyl group, a cyano group, a nitro group and a hydroxy group;

$R^1$ is a hydrogen atom, a hydroxy group or a $C_{1-6}$ alkyl group, and n is 0 or 1, or a salt thereof; comprising reacting a compound of the formula (II):

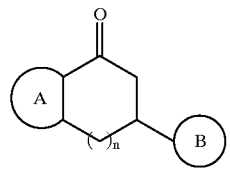

(II)

wherein A, B and n are as defined above, or a salt thereof with a compound of the formula (III):

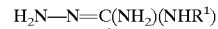

H$_2$N—N=C(NH$_2$)(NHR$^1$)

wherein $R^1$ is as defined above, or a salt thereof.

23. A compound of the formula:

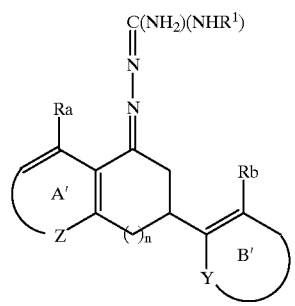

wherein

Ra is an optionally halogenated $C_{1-6}$ alkyl group or an optionally halogenated $C_{1-6}$ alkoxy group;

the ring A' is pyridine, pyrazole, pyrrole or furan optionally substituted with an optionally halogenated $C_{1-6}$ alkyl group or an optionally halogenated $C_{1-6}$ alkoxy group;

Z is an oxygen atom or a nitrogen atom;

Rb is a halogen atom, an optionally halogenated $C_{1-6}$ alkyl group, a hydroxy group or an optionally halogenated $C_{1-6}$ alkoxy group;

the ring B' is benzene or thiophene optionally substituted with a halogen atom, an optionally halogenated $C_{1-6}$ alkyl group, a hydroxy group or an optionally halogenated $C_{1-6}$ alkoxy group;

Y is a carbon atom or a sulfur atom;

$R^1$ is a hydrogen atom, a hydroxy group or a $C_{1-6}$ alkyl group, and n is 0 or 1, or a salt thereof.

* * * * *